United States Patent
Claremon et al.

(10) Patent No.: US 10,829,481 B2
(45) Date of Patent: Nov. 10, 2020

(54) BENZIMIDAZOLE DERIVATIVES AS MODULATORS OF ROR-GAMMA

(71) Applicant: Vitae Pharmaceuticals, LLC, Madison, NJ (US)

(72) Inventors: David A. Claremon, Maple Glen, PA (US); Lawrence Wayne Dillard, Yardley, PA (US); Yi Fan, Doylestown, PA (US); Stephen D. Lotesta, Burlington, NJ (US); Suresh B. Singh, Kendall Park, NJ (US); Colin M. Tice, Maple Glen, PA (US); Wei Zhao, North Potomac, MD (US); Linghang Zhuang, Chalfont, PA (US)

(73) Assignee: Vitae Pharmaceuticals, LLC, Madison, NJ (US)

( * ) Notice: Subject to any disclaimer, the term of this patent is extended or adjusted under 35 U.S.C. 154(b) by 0 days.

(21) Appl. No.: 16/073,503

(22) PCT Filed: Jan. 27, 2017

(86) PCT No.: PCT/US2017/015220
§ 371 (c)(1),
(2) Date: Jul. 27, 2018

(87) PCT Pub. No.: WO2017/132432
PCT Pub. Date: Aug. 3, 2017

(65) Prior Publication Data
US 2019/0352286 A1    Nov. 21, 2019

Related U.S. Application Data

(60) Provisional application No. 62/320,893, filed on Apr. 11, 2016, provisional application No. 62/288,487, filed on Jan. 29, 2016.

(51) Int. Cl.
*C07D 405/14*    (2006.01)
*C07D 405/10*    (2006.01)

(52) U.S. Cl.
CPC ......... *C07D 405/14* (2013.01); *C07D 405/10* (2013.01)

(58) Field of Classification Search
CPC ................ C07D 405/10; C07D 405/14
See application file for complete search history.

(56) References Cited

U.S. PATENT DOCUMENTS

| | | |
|---|---|---|
| 5,238,950 A | 8/1993 | Clader et al. |
| 5,272,158 A | 12/1993 | Hartman et al. |
| 5,326,760 A | 7/1994 | McElroy et al. |
| 5,364,869 A | 11/1994 | De |
| 5,389,631 A | 2/1995 | Claremon et al. |
| 5,571,774 A | 11/1996 | Hamprecht et al. |
| 5,719,144 A | 2/1998 | Hartman et al. |
| 5,770,590 A | 6/1998 | Natsugari et al. |
| 5,786,352 A | 7/1998 | Natsugari et al. |
| 5,959,116 A | 9/1999 | Hamprecht et al. |
| 6,103,659 A | 8/2000 | Pasenok et al. |
| 6,166,219 A * | 12/2000 | Yamasaki ............ C07D 209/08 548/309.4 |
| 6,177,443 B1 | 1/2001 | Madsen et al. |
| 6,348,032 B1 | 2/2002 | Sperl et al. |
| 6,358,978 B1 | 3/2002 | Ritzeler et al. |
| 6,417,207 B1 | 7/2002 | Garvey et al. |
| 6,444,617 B1 | 9/2002 | Takaishi et al. |
| 6,489,315 B1 | 12/2002 | Natsugari et al. |
| 6,512,117 B1 | 1/2003 | Harclerode et al. |
| 6,770,666 B2 | 8/2004 | Hashimoto et al. |
| 7,112,600 B1 | 9/2006 | Hashimoto et al. |
| 7,115,752 B2 | 10/2006 | Lesieur et al. |
| 7,183,318 B2 | 2/2007 | Lesieur et al. |
| 7,244,730 B2 | 7/2007 | Suzuki et al. |
| 7,732,616 B2 | 6/2010 | Marlow et al. |

(Continued)

FOREIGN PATENT DOCUMENTS

| | | |
|---|---|---|
| CA | 2031684 A1 | 6/1991 |
| CA | 2134192 A1 | 5/1995 |

(Continued)

OTHER PUBLICATIONS

Babu et al., Emerging therapeutic strategies in COPD. Drug Discov Today. Mar. 2015;20(3):371-9.
Bendele et al., Animal models of arthritis: relevance to human disease. Toxicol Pathol. Jan.-Feb. 1999;27(1):134-42.
Bendele, Animal models of rheumatoid arthritis. J Musculoskelet Neuronal Interact. Jun. 2001;1(4):377-85.
Campochiaro, The complexity of animal model generation for complex diseases. JAMA. Feb. 17, 2010;303(7):657-8.
Center for Disease Control, Classification of Diseases and Injuries. ICD-9-CM Tabular List of Diseases (FY03). 748 pages, accessed online Sep. 10, 2015.

(Continued)

*Primary Examiner* — Alicia L Otton
(74) *Attorney, Agent, or Firm* — McCarter & English, LLP; Steven G. Davis; Michael J. DeGrazia

(57) ABSTRACT

Provided are novel compounds of Formula I: pharmaceutically acceptable salts thereof, and pharmaceutical compositions thereof, which are useful in the treatment of diseases and disorders mediated by RORγ. Also provided are pharmaceutical compositions comprising the novel compounds of Formula I and methods for their use in treating one or more inflammatory, metabolic, autoimmune and other diseases or disorders.

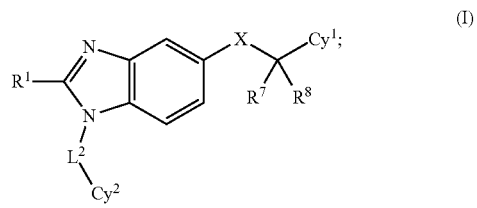

(I)

22 Claims, 7 Drawing Sheets
Specification includes a Sequence Listing.

(56) References Cited

U.S. PATENT DOCUMENTS

| | | |
|---|---|---|
| 7,750,021 B2 | 7/2010 | Mi et al. |
| 8,389,739 B1 | 3/2013 | Thacher et al. |
| 8,399,477 B2 | 3/2013 | Alisi et al. |
| 8,415,351 B2 | 4/2013 | Wagner et al. |
| 9,266,886 B2 | 2/2016 | Lotesta et al. |
| 9,481,674 B1 | 11/2016 | Claremon et al. |
| 9,624,217 B2 | 4/2017 | Claremon et al. |
| 9,663,515 B2 | 5/2017 | Claremon et al. |
| 9,796,710 B2 | 10/2017 | Claremon et al. |
| 9,868,748 B2 | 1/2018 | Claremon et al. |
| 10,047,085 B2 | 8/2018 | Claremon et al. |
| 10,087,184 B2 | 10/2018 | Claremon et al. |
| 2002/0132817 A1 | 9/2002 | Natsugari et al. |
| 2003/0050320 A1 | 3/2003 | Hashimoto et al. |
| 2004/0002424 A1 | 1/2004 | Minn et al. |
| 2004/0038973 A1 | 2/2004 | Nahra et al. |
| 2005/0004204 A1 | 1/2005 | Suzuki et al. |
| 2005/0020593 A1 | 1/2005 | Mailliet et al. |
| 2005/0234065 A1 | 10/2005 | Hulin |
| 2006/0135557 A1 | 6/2006 | Nan et al. |
| 2007/0032497 A1 | 2/2007 | Hashimoto et al. |
| 2007/0112038 A1 | 5/2007 | Marlow et al. |
| 2007/0258887 A1 | 11/2007 | Tamagnan et al. |
| 2008/0277622 A1 | 11/2008 | Deshpande et al. |
| 2008/0287462 A1 | 11/2008 | Chessari et al. |
| 2009/0036423 A1 | 2/2009 | Pan et al. |
| 2009/0076275 A1 | 3/2009 | Bolin et al. |
| 2009/0233945 A9 | 9/2009 | Chessari et al. |
| 2009/0258871 A1 | 10/2009 | Jitsuoka et al. |
| 2009/0270405 A1 | 10/2009 | Cook, II et al. |
| 2010/0099684 A1 | 4/2010 | Cook, II et al. |
| 2011/0070193 A1 | 3/2011 | Wagner et al. |
| 2011/0189167 A1 | 8/2011 | Flynn et al. |
| 2011/0313003 A1 | 12/2011 | Shi et al. |
| 2012/0077840 A1 | 3/2012 | Turner et al. |
| 2012/0115903 A1 | 5/2012 | Frank et al. |
| 2012/0245163 A1 | 9/2012 | Gomtsyan et al. |
| 2012/0322837 A1 | 12/2012 | Maeba et al. |
| 2013/0143870 A1 | 6/2013 | Grauert et al. |
| 2013/0150347 A1 | 6/2013 | Rudolf et al. |
| 2014/0163001 A1 | 6/2014 | Yamamoto et al. |
| 2014/0228409 A1 | 8/2014 | Yamamoto et al. |
| 2016/0122345 A1 | 5/2016 | Claremon et al. |
| 2017/0081327 A1 | 3/2017 | Claremon et al. |
| 2017/0260180 A1 | 9/2017 | Claremon et al. |
| 2018/0222860 A1 | 8/2018 | Claremon et al. |
| 2018/0222902 A1 | 8/2018 | Claremon et al. |
| 2018/0370968 A1 | 12/2018 | Claremon et al. |
| 2019/0322687 A1 | 10/2019 | Claremon et al. |
| 2020/0062707 A1 | 2/2020 | Claremon et al. |
| 2020/0079767 A1 | 3/2020 | Claremon et al. |

FOREIGN PATENT DOCUMENTS

| | | |
|---|---|---|
| CA | 2352612 A1 | 6/2000 |
| CA | 2524027 A1 | 12/2004 |
| CN | 1424770 A | 6/2003 |
| CN | 1869036 A | 11/2006 |
| CN | 101225070 A | 7/2008 |
| CN | 101455661 A | 6/2009 |
| CN | 102180780 A | 9/2011 |
| CN | 104024239 A | 9/2014 |
| DE | 4343922 A1 | 6/1995 |
| DE | 1446396 A1 | 7/1995 |
| EP | 254951 A2 | 2/1988 |
| EP | 321368 A1 | 6/1989 |
| EP | 468187 A2 | 1/1992 |
| EP | 520277 A2 | 12/1992 |
| EP | 520573 A1 | 12/1992 |
| EP | 540334 A1 | 5/1993 |
| EP | 655439 A2 | 5/1995 |
| EP | 733632 A1 | 9/1996 |
| EP | 1178048 A1 | 2/2002 |
| EP | 2327704 A1 | 6/2011 |
| FR | 2725946 A1 | 4/1996 |
| FR | 2926554 A1 | 7/2009 |
| GB | 2276384 A | 9/1994 |
| JP | H06-236056 A | 8/1994 |
| JP | H11-43489 A | 2/1999 |
| JP | 2000-007661 A | 1/2000 |
| JP | 2003-171380 A | 6/2003 |
| JP | 2003-531894 A | 10/2003 |
| JP | 2004-203791 A | 7/2004 |
| JP | 2015-124178 A | 7/2015 |
| WO | 1990/09787 A1 | 9/1990 |
| WO | 1994/00119 A1 | 1/1994 |
| WO | 1994/24712 A1 | 10/1994 |
| WO | 1995/11680 A1 | 5/1995 |
| WO | 1995/17397 A1 | 6/1995 |
| WO | 1996/26187 A1 | 8/1996 |
| WO | 1997/32832 A1 | 9/1997 |
| WO | 1998/40385 A1 | 9/1998 |
| WO | 1998/42666 A1 | 10/1998 |
| WO | 1999/47132 A2 | 9/1999 |
| WO | 1999/58495 A1 | 11/1999 |
| WO | 1999/58496 A1 | 11/1999 |
| WO | 2000/032192 A1 | 6/2000 |
| WO | 2000/067754 A1 | 11/2000 |
| WO | 2001/005790 A1 | 1/2001 |
| WO | 2001/09076 A2 | 2/2001 |
| WO | 2001/047883 A1 | 7/2001 |
| WO | 2001/051128 A1 | 7/2001 |
| WO | 2001/083445 A1 | 11/2001 |
| WO | 2002/38107 A2 | 5/2002 |
| WO | 2002/081443 A1 | 10/2002 |
| WO | 2002/081447 A1 | 10/2002 |
| WO | 2002/081463 A1 | 10/2002 |
| WO | 2002/085855 A1 | 10/2002 |
| WO | 2002/094833 A1 | 11/2002 |
| WO | 2003/008421 A1 | 1/2003 |
| WO | 2003/029252 A1 | 4/2003 |
| WO | 2003/029254 A1 | 4/2003 |
| WO | 2003/043991 A1 | 5/2003 |
| WO | 2003/062241 A1 | 7/2003 |
| WO | 2003/066055 A1 | 8/2003 |
| WO | 2003/070710 A1 | 8/2003 |
| WO | 2003/076440 A1 | 9/2003 |
| WO | 2003/104216 A1 | 12/2003 |
| WO | 2004/014365 A1 | 2/2004 |
| WO | 2004/026871 A1 | 4/2004 |
| WO | 2004/042029 A2 | 5/2004 |
| WO | 2004/065351 A1 | 8/2004 |
| WO | 2004/089897 A1 | 10/2004 |
| WO | 2004/103309 A2 | 12/2004 |
| WO | 2004/108133 A2 | 12/2004 |
| WO | 2004/111010 A1 | 12/2004 |
| WO | 2004/113330 A1 | 12/2004 |
| WO | 2005/005392 A1 | 1/2005 |
| WO | 2005/011601 A2 | 2/2005 |
| WO | 2005/023806 A2 | 3/2005 |
| WO | 2005/025504 A2 | 3/2005 |
| WO | 2005/028480 A2 | 3/2005 |
| WO | 2005/039564 A1 | 5/2005 |
| WO | 2005/051301 A2 | 6/2005 |
| WO | 2005/060958 A1 | 7/2005 |
| WO | 2005/063296 A2 | 7/2005 |
| WO | 2005/097129 A5 | 10/2005 |
| WO | 2005/100334 A1 | 10/2005 |
| WO | 2005/117890 A2 | 12/2005 |
| WO | 2006/032631 A1 | 3/2006 |
| WO | 2006/062981 A2 | 6/2006 |
| WO | 2006/065842 A2 | 6/2006 |
| WO | 2006/074428 A2 | 7/2006 |
| WO | 2006/082001 A1 | 8/2006 |
| WO | 2006/092731 A1 | 9/2006 |
| WO | 2006/109085 A1 | 10/2006 |
| WO | 2007/007054 A1 | 1/2007 |
| WO | 2007/022280 A1 | 2/2007 |
| WO | 2007/036733 A1 | 4/2007 |
| WO | 2007/036734 A1 | 4/2007 |
| WO | 2007/050124 A1 | 5/2007 |
| WO | 2007/084451 A1 | 7/2007 |
| WO | 2007/084455 A1 | 7/2007 |
| WO | 2007/084815 A2 | 7/2007 |

(56) References Cited

FOREIGN PATENT DOCUMENTS

| | | |
|---|---|---|
| WO | 2007/087231 A2 | 8/2007 |
| WO | 2007/097931 A2 | 8/2007 |
| WO | 2007/101224 A2 | 9/2007 |
| WO | 2007/107545 A1 | 9/2007 |
| WO | 2007/109596 A2 | 9/2007 |
| WO | 2007/131982 A2 | 11/2007 |
| WO | 2008/006479 A1 | 1/2008 |
| WO | 2008/010964 A1 | 1/2008 |
| WO | 2008/013963 A2 | 1/2008 |
| WO | 2008/044027 A2 | 4/2008 |
| WO | 2008/044029 A1 | 4/2008 |
| WO | 2008/044041 A1 | 4/2008 |
| WO | 2008/044045 A1 | 4/2008 |
| WO | 2008/044054 A2 | 4/2008 |
| WO | 2008/048991 A2 | 4/2008 |
| WO | 2008/073865 A2 | 6/2008 |
| WO | 2008/083070 A1 | 7/2008 |
| WO | 2008/086161 A1 | 7/2008 |
| WO | 2008/132155 A2 | 11/2008 |
| WO | 2008/135524 A2 | 11/2008 |
| WO | 2008/135526 A1 | 11/2008 |
| WO | 2008/149163 A2 | 12/2008 |
| WO | 2009/004496 A2 | 1/2009 |
| WO | 2009/013299 A2 | 1/2009 |
| WO | 2009/026248 A2 | 2/2009 |
| WO | 2009/049154 A1 | 4/2009 |
| WO | 2009/050228 A2 | 4/2009 |
| WO | 2009/052319 A1 | 4/2009 |
| WO | 2009/052320 A1 | 4/2009 |
| WO | 2009/068463 A2 | 6/2009 |
| WO | 2009/073788 A1 | 6/2009 |
| WO | 2009/083526 A1 | 7/2009 |
| WO | 2009/097972 A1 | 8/2009 |
| WO | 2009/112445 A1 | 9/2009 |
| WO | 2009/112678 A2 | 9/2009 |
| WO | 2009/112826 A1 | 9/2009 |
| WO | 2009/112839 A1 | 9/2009 |
| WO | 2009/124755 A1 | 10/2009 |
| WO | 2009/131926 A1 | 10/2009 |
| WO | 2009/144450 A1 | 12/2009 |
| WO | 2010/003022 A1 | 1/2010 |
| WO | 2010/021878 A1 | 2/2010 |
| WO | 2010/033350 A1 | 3/2010 |
| WO | 2010/056194 A1 | 5/2010 |
| WO | 2010/056195 A1 | 5/2010 |
| WO | 2010/077680 A2 | 7/2010 |
| WO | 2010/086311 A1 | 8/2010 |
| WO | 2011/078143 A1 | 6/2011 |
| WO | 2011/090473 A1 | 7/2011 |
| WO | 2011/094545 A2 | 8/2011 |
| WO | 2011/107248 A1 | 9/2011 |
| WO | 2011/140936 A1 | 11/2011 |
| WO | 2011/146358 A1 | 11/2011 |
| WO | 2011/159297 A1 | 12/2011 |
| WO | 2012/019015 A2 | 2/2012 |
| WO | 2012/027965 A1 | 3/2012 |
| WO | 2012/028100 A1 | 3/2012 |
| WO | 2012/031197 A1 | 3/2012 |
| WO | 2012/043505 A1 | 4/2012 |
| WO | 2012/062462 A1 | 5/2012 |
| WO | 2012/064744 A2 | 5/2012 |
| WO | 2012/100732 A1 | 8/2012 |
| WO | 2012/100734 A1 | 8/2012 |
| WO | 2012/106995 A1 | 8/2012 |
| WO | 2012/125521 A1 | 9/2012 |
| WO | 2012/136296 A1 | 10/2012 |
| WO | 2012/139775 A1 | 10/2012 |
| WO | 2013/000994 A1 | 1/2013 |
| WO | 2013/019621 A1 | 2/2013 |
| WO | 2013/019626 A1 | 2/2013 |
| WO | 2013/019635 A1 | 2/2013 |
| WO | 2013/019653 A1 | 2/2013 |
| WO | 2013/019682 A1 | 2/2013 |
| WO | 2013/029338 A1 | 3/2013 |
| WO | 2013/045431 A1 | 4/2013 |
| WO | 2013/064231 A1 | 5/2013 |
| WO | 2013/067036 A1 | 5/2013 |
| WO | 2013/078233 A1 | 5/2013 |
| WO | 2013/078240 A1 | 5/2013 |
| WO | 2013/079223 A1 | 6/2013 |
| WO | 2013/083741 A1 | 6/2013 |
| WO | 2013/087739 A1 | 6/2013 |
| WO | 2013/092460 A1 | 6/2013 |
| WO | 2013/092939 A1 | 6/2013 |
| WO | 2013/092941 A1 | 6/2013 |
| WO | 2013/096496 A2 | 6/2013 |
| WO | 2013/100027 A1 | 7/2013 |
| WO | 2013/159095 A1 | 10/2013 |
| WO | 2013/160418 A1 | 10/2013 |
| WO | 2013/160419 A1 | 10/2013 |
| WO | 2013/166013 A1 | 11/2013 |
| WO | 2013/169588 A1 | 11/2013 |
| WO | 2013/169704 A2 | 11/2013 |
| WO | 2013/169864 A2 | 11/2013 |
| WO | 2013/171729 A2 | 11/2013 |
| WO | 2013/178362 A1 | 12/2013 |
| WO | 2014/008214 A1 | 1/2014 |
| WO | 2014/009447 A1 | 1/2014 |
| WO | 2014/026327 A1 | 2/2014 |
| WO | 2014/026328 A1 | 2/2014 |
| WO | 2014/026329 A1 | 2/2014 |
| WO | 2014/026330 A1 | 2/2014 |
| WO | 2014/028589 A2 | 2/2014 |
| WO | 2014/028591 A2 | 2/2014 |
| WO | 2014/028597 A2 | 2/2014 |
| WO | 2014/028600 A2 | 2/2014 |
| WO | 2014/028669 A1 | 2/2014 |
| WO | 2014/044738 A1 | 3/2014 |
| WO | 2014/062938 A1 | 4/2014 |
| WO | 2014/086894 A1 | 6/2014 |
| WO | 2014/179564 A1 | 11/2014 |
| WO | 2015/038503 A1 | 3/2015 |
| WO | 2015/083130 A1 | 6/2015 |
| WO | 2015/100420 A1 | 7/2015 |
| WO | 2015/101928 A1 | 7/2015 |
| WO | 2015/114157 A1 | 8/2015 |
| WO | 2015/116904 A1 | 8/2015 |
| WO | 2015/144480 A1 | 10/2015 |
| WO | 2015/144605 A1 | 10/2015 |
| WO | 2015/144609 A1 | 10/2015 |
| WO | 2015/144803 A1 | 10/2015 |
| WO | 2015/159233 A1 | 10/2015 |
| WO | 2016/061160 A1 | 4/2016 |
| WO | 2016/064970 A1 | 4/2016 |
| WO | 2016/144351 A1 | 9/2016 |
| WO | 2017/024018 A1 | 2/2017 |
| WO | 2017/087608 A1 | 5/2017 |
| WO | 2017/132432 A1 | 8/2017 |

OTHER PUBLICATIONS

Chaichian et al., Targeted Therapies in Systemic Lupus Erythematosus: A State-of-the-Art Review. J Clin Cell Immunol. 2013;S6:8 pages.

Chiba, Emerging Therapeutic Strategies in Alzheimer's Disease. InTech, retrieved online at: http://dx.doi.org/10.5772/55293. Chapter 9, pp. 181-225, (2013).

Cyr et al., Recent progress on nuclear receptor RORgamma modulators. Bioorganic & Medicinal Chemistry Letters. 2016;26:4387-4393.

Damia et al., Contemporary pre-clinical development of anticancer agents—What are the optimal preclinical models? European Journal of Cancer. 2009;45:2768-2781.

Edwards et al., Molecular genetics of AMD and current animal models. Angiogenesis. 2007;10(2):119-32.

Elborn, Cystic fibrosis. The Lancet. Retrieved online at: http://dx.doi.org/10.1016/S0140-6736(16)00576-6. 13 pages. Apr. 29, 2016.

Flowers et al., How we treat chronic graft-versus-host disease. Blood. Jan. 22, 2015;125(4):606-15.

Fries et al., O-divinylbenzene and naphthalene. Ber Dtsch Chem Ges B. 1936;69:715-22.

(56) References Cited

OTHER PUBLICATIONS

Galiè et al., Guidelines for the diagnosis and treatment of pulmonary hypertension: the Task Force for the Diagnosis and Treatment of Pulmonary Hypertension of the European Society of Cardiology (ESC) and the European Respiratory Society (ERS), endorsed by the International Society of Heart and Lung Transplantation (ISHLT). Eur Heart J. Oct. 2009;30(20):2493-537.

Hackam et al., Translation of research evidence from animals to humans. JAMA. Oct. 11, 2006;296(14):1731-2.

Healthline, Overview. Retrieved online at: http://www.healthline.com/health/inflammatory-bowel-disease. 7 pages. (2005-2015).

Hynes et al., The discovery of (R)-2-(sec-butylamino)-N-(2-methyl-5-(methylcarbamoyl)phenyl) thiazole-5-carboxamide (BMS-640994)—A potent and efficacious p38alpha MAP kinase inhibitor. Bioorg Med Chem Lett. Mar. 15, 2008;18(6):1762-7.

Johnson et al., Relationships between drug activity in NCI preclinical in vitro and in vivo models and early clinical trials. Br J Cancer. May 18, 2001;84(10)1424-31.

Jordan, Tamoxifen: a most unlikely pioneering medicine. Nat Rev Drug Discov. Mar. 2003;2(3):205-13.

Lamotte et al. Discovery of novel indazole derivatives as dual angiotensin II antagonists and partial PPAR? agonists. Bioorg Med Chem Lett. Feb. 15, 2014;24(4):1098-103.

Ledford, US cancer institute to overhaul tumour cell lines. Nature. Feb. 25, 2016;530(7591):391.

Lim et al., Age-related macular degeneration. Lancet. May 5, 2012;379(9827):1728-38.

Lutz et al., Overview of Animal Models of Obesity. Curr Protoc Pharmacol. Sep. 2012 Chapter: Unit 5.61. 22 pages.

Maddur et al., Th17 cells: biology, pathogenesis of autoimmune and inflammatory diseases, and therapeutic strategies. Am J Pathol. Jul. 2012;181(1):8-18.

Makrilakis, Pathophysiology of Type 2 diabetes. Diabetes in Clinical Practice: Questions and Answers from Case Studies. John Wiley & Sons, Ltd. Chapter 3, pp. 43-58, (2006).

Marcoux et al., Annulation of ketones with vinamidinium hexafluorophosphate salts: an efficient preparation of trisubstituted pyridines. Org Lett. Jul. 27, 2000;2(15):2339-41.

Ocana et al., Preclinical development of molecular-targeted agents for cancer. Nat Rev Clin Oncol. 2011;8:200-209.

Pilz et al., Modem multiple sclerosis treatment—what is approved, what is on the horizon. Drug Discov Today. Dec. 2008;13(23-24):1013-25.

Quinby, Conventional Therapy. Psoriasis and Psoriatic Arthritism. An Integrated Approach. Kenneth B. Gordon (Ed.), Springer-Verlag, Berlin Heidelberg. Chapter 9, pp. 134-184, (2005).

Sangshetti et al., Antileishmanial drug discovery: comprehensive review of the last 10 years. RSC Adv. 2015;5:32376-32415.

Schlecker et al., Regioselective Metalation of Pyridinylcarbamates and Pyridinecarboxamides with (2,2,6,6-Tetramethylpiperidino)magnesium Chloride. J Org Chem. 1995;60:8414-8416.

Schlecker et al., Regioselective Monometalation of 2,5-Pyridinedicarboxamides with (2,2,6,6-Tetramethylpiperidino)magnesium Chloride (TMPMgCl). Liebigs Ann. 1995;8:1441-1446.

Sharma et al., Cell line-based platforms to evaluate the therapeutic efficacy of candidate anticancer agents. Nat Rev Cancer. Apr. 2010;10(4):241-53.

Sime et al., Discovery of GSK1997132B a novel centrally penetrant benzimidazole PPAR? partial agonist. Bioorg Med Chem Lett. Sep. 15, 2011;21(18):5568-72.

University of Cambridge, Alzheimer's disease and tauopathy. John van Geest Centre for Brain Repair, School of Clinical Medicine. 1 page, (2016).

Vickers et al., The utility of animal models to evaluate novel anti-obesity agents. Br J Pharmacol. Oct. 2011;164(4):1248-62.

Vourloumis et al., Solid-phase synthesis of benzimidazole libraries biased for RNA targets. Tetrahedron Letters. 2003;44:2807-2811.

Wang et al., Structure-Based Design of Tetrahydroisoquinoline-7-carboxamides as Selective Discoidin Domain Receptor 1 (DDR1) Inhibitors. J Med Chem. Jun. 23, 2016;59(12):5911-6.

Yan et al., Quality control in combinatorial chemistry: determination of the quantity, purity, and quantitative purity of compounds in combinatorial libraries. J Comb Chem. Sep.-Oct. 2003;5(5):547-59.

Co-pending U.S. Appl. No. 15/776,836, filed May 17, 2018.

Co-pending U.S. Appl. No. 16/110,224, filed Aug. 23, 2018.

Co-pending U.S. Appl. No. 16/115,860, filed Aug. 29, 2018.

Fries et al., o-Divinylbenzol and Naphtalin. Annalen der Chemie. 1937;533:72-92.

Ito et al., A medium-term rat liver bioassay for rapid in vivo detection of carcinogenic potential of chemicals. Cancer Sci. Jan. 2003;94(1):3-8.

Schonherr et al., Profound Methyl Effects in Drug Discovery and a Call for New C—H Methylation Reactions. Angew Chem Int Ed. 2013;52:12256-67.

STN Registry No. 1030136-78-7, 2H-Indazole-6-carboxamide, 1 page, (2020).

STN Registry No. 1030136-78-7, 2H-Indazole-6-carboxamide, N-[(4-chlorophenyl)methyl]-2-[{4-methoxyphenyl) methyl]. Jun. 24, 2008.

STN Registry No. 1115530-36-3, Thieno[2,3-d]pyrimidine-6-carboxamide, N-[(2-bromophenyl)methyl]-4-(4-ethyl-1-piperazinyl)-5-methyl. Mar. 4, 2009.

STN Registry No. 1141899-39-9, 6-Isoquinolinecarboxamide, N-((2,4-dichlorophenyl)methyl)-1,2,3,4-tetrahydro-2-(4-(methylamino)-6-phenyl-1,3,5-triazine-2-yl). May 1, 2009.

STN Registry No. 1346976-76-8, 2H-Indazole-6-carboxamide, 2-[2-[5-(aminocarbonyl)-1H-pyrazol-1-yl]-ethyl]-N-[(3-chlorophenyl)methyl], Dec. 1, 2011.

STN Registry No. 926926-48-9, 6-Isoquinolinecarboxamide, N-(cyclopropylmethyl)-2-(6,7-dimethoxy-4-quinazolinyl)-1,2,3,4-tetrahydro. Mar. 18, 2007.

Copending U.S. Appl. No. 16/506,518, filed Jul. 9, 2019.

Copending U.S. Appl. No. 16/751,739, filed Jan. 24, 2020.

Copending U.S. Appl. No. 16/633,334, filed Jan. 23, 2020.

Copending U.S. Appl. No. 16/633,335, filed Jan. 23, 2020.

* cited by examiner

SEQUENCE LISTING

```
<160> NUMBER OF SEQ ID NOS: 2

<210> SEQ ID NO 1
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
aaagtaggtc a                                                          11

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 2

His His His His His His
1               5
```

BENZIMIDAZOLE DERIVATIVES AS MODULATORS OF ROR-GAMMA

RELATED APPLICATIONS

This application is a 35 U.S.C. § 371 national stage filing of International Application No. PCT/US2017/015220, filed Jan. 27, 2017, which claims priority to U.S. Provisional Application No. 62/288,487, filed Jan. 29, 2016 and U.S. Provisional Application No. 62/320,893, filed Apr. 11, 2016, the contents of each of which are incorporated herein by reference.

TECHNICAL FIELD

The present disclosure is directed to novel retinoic acid receptor-related orphan receptor gamma ("RORγ" or "ROR-gamma") modulators, processes for their preparation, pharmaceutical compositions containing these modulators, and their use in the treatment of inflammatory, metabolic, autoimmune and other diseases mediated by RORγ.

BACKGROUND

Retinoic acid receptor-related orphan receptors (RORs) are a subfamily of transcription factors in the steroid hormone nuclear receptor superfamily (Jetten & Joo (2006) Adv. Dev. Biol. 2006, 16, 313-355). The ROR family consists of ROR alpha (RORα), ROR beta (RORβ) and ROR gamma (RORγ), each encoded by a separate gene (in human: RORA, RORB and RORC, respectively; in mouse: rora, rorb and rorc, respectively). RORs contain four principal domains shared by the majority of nuclear receptors: an N-terminal domain, a highly conserved DNA-binding domain (DBD) consisting of two zinc finger motifs, a hinge domain, and a ligand binding domain (LBD). Each ROR gene generates several isoforms, differing only in their N-terminal domains. RORγ has two isoforms: RORγ1 and RORγ2 (also known as RORγt). RORγ refers to RORγ1 and/or RORγt. RORγ1 is expressed in a variety of tissues including thymus, muscle, kidney and liver, but RORγt is exclusively expressed in the cells of the immune system, has a critical role in thymopoiesis and the development of several secondary lymphoid tissues, and is a key regulator of Th17 cell differentiation (Jetten, 2009, Nucl. Recept. Signal., 7:e003, doi:10.1621/nrs.07003, Epub 2009 Apr. 3).

Th17 cells are a subset of T helper cells which preferentially produce the pro-inflammatory cytokines IL-17A, IL-17F, IL-21 and IL-22. Th17 cells and their effector molecules, such as IL-17, IL-21, IL-22, GM-CSF and CCL20, are associated with the pathogenesis of several autoimmune and inflammatory diseases, such as rheumatoid arthritis, systemic lupus erythematosus, multiple sclerosis, psoriasis, inflammatory bowel disease, allergy and asthma (Maddur et al., 2012, Am. J. Pathol., 181:8-18). Recent findings support a role for IL17 and Th17 cells in the pathogenesis of acne (Thiboutot et al., 2014, J. Invest. Dermatol., 134(2):307-10, doi: 10.1038/jid.2013.400; Agak et al., 2014, J. Invest. Dermatol., 134(2):366-73, doi: 10.1038/jid.2013.334, Epub 2013 Aug. 7). Th17 cells are also potent inducers of inflammation associated with endometriosis, a chronic inflammatory disease (Hirata et al., 2010, Endocrinol., 151:5468-5476; Hirata et al., 2011, Fertil Steril., July; 96(1):113-7, doi: 10.1016/j.fertnstert.2011.04.060, Epub 2011 May 20). Additionally, Th17 cells have a key role in the mouse autoimmune models of experimental autoimmune encephalomyelitis (EAE), collagen-induced arthritis (CIA) and adjuvant-induced arthritis (AIA) (Bedoya et al., 2013, Clin. Dev. Immunol., 2013: 986789. Epub 2013 Dec. 26. Th17 cells are activated during inflammatory and autoimmune disease processes and are responsible for recruiting other inflammatory cell types, particularly neutrophils, to mediate pathology in target tissues (Miossec & Kolls, 2012, Nature Rev., 11:763-776; Korn et al., 2009, Annu. Rev. Immunol., 27:485-517). Aberrant Th17 cell function has been implicated in a variety of autoimmune diseases, including multiple sclerosis and rheumatoid arthritis. Autoimmune disease is believed to arise from the disruption of the equilibrium between effector and regulatory T cells (Solt et al., 2012, ACS Chem. Biol., 7:1515-1519, Epub 2012 Jul. 9). The importance of RORγt to Th17 cell differentiation and the pathogenic role of Th17 cells is evidenced by the fact that RORγt-deficient mice have very few Th17 cells and have a reduction in severity of EAE (Ivanov et al., 2006, Cell, 126:1121-1133).

Recently, IL-17-producing neutrophils have been identified as promoting inflammation leading to both microbial clearance and IL-17-associated tissue damage in the cornea and other tissues (Taylor et al., 2014, J. Immunol, 192:3319-3327; Taylor et al., 2014, Nat. Immunol., 15:143-151), supporting a role for compounds that inhibit RORγ activity in the treatment of corneal ulcers and other diseases and disorders associated with IL-17 expressing neutrophils.

Circadian rhythms are daily cycles of behavioral and physiological changes that are regulated by endogenous circadian clocks. A number of studies have established links between nuclear receptor (including RORγ) function and expression, the circadian regulatory circuitry, and the regulation of various physiological processes (Jetten (2009) op. cit.).

Obstructive sleep apnea syndrome (OSAS) is a chronic inflammatory disease regulated by T lymphocytes. OSAS patients have a significant increase in peripheral Th17 cell frequency, IL-17 and RORγt levels (Ye et al., 2012, Mediators Inflamm., 815308, doi: 10.1155/2012/815308, Epub 2012 Dec. 31).

A number of studies have provided evidence of a role of RORs in cancer. Mice deficient in the expression of RORγ exhibit a high incidence of thymic lymphomas that metastasize frequently to liver and spleen. High expression of Th17-associated genes (including RORγ) and high levels of Th17 cells in the tumor microenvironment has been shown to correlate with a poor prognosis in various cancers, including lung, gastric, breast and colon cancer (Tosolini et al., 2011, Cancer Res., 71:1263-1271, doi: 10.1158/0008-5472.CAN-10-2907, Epub 2011 Feb. 8; Su et al., 2014, Immunol. Res., 58:118-124, doi: 10.1007/s12026-013-8483-y, Epub 2014 Jan. 9; Carmi et al., 2011, J. Immunol., 186:3462-3471, doi: 10.4049/jimmunol. 1002901, Epub 2011 Feb. 7; Chen et al., 2013, Histopathology, 63:225-233, doi: 10.1111/his.12156, Epub 2013 Jun. 6). Recent evidence also shows that RORγ is overexpressed and amplified in metastatic castration-resistant prostate cancer tumors, and that RORγ antagonists suppressed tumor growth in multiple androgen receptor-expressing xenograft prostate cancer models. See e.g., Nature Medicine, Mar. 28, 2016, advance online publication, doi: 10.1038/nm.4070.

RORγ has also been identified to have a regulatory role in lipid/glucose homeostasis, and has been implicated in metabolic syndrome, obesity (Meissburger et al., 2011, EMBO Mol. Med., 3:637-651), hepatosteatosis, insulin resistance and diabetes.

Further support for the role of RORγ in the pathogenesis of inflammatory, metabolic, circadian effect, cancer, and autoimmune diseases and disorders can be found in the following references: Chang et al., 2012, J. Exp. Pharmacol., 4:141-148; Jetten et al., 2013, Frontiers Endocrinol., 4:1-8; Huh & Littman, 2012, Eur. J. Immunol., 42:2232-2237; Martinez et al., 2008, Ann. N.Y. Acad. Sci., 1143:188-211; Pantelyushin et al., 2012, J. Clin. Invest., 122:2252-2256; Jetten & Ueda, 2002, Cell Death Differen., 9:1167-1171; Solt et al., 2010, Curr. Opin. Lipidol., 21:204-211.

In light of the role that RORγ plays in disease pathogenesis, inhibition of RORγ activity and Th17 cell differentiation and activity, including IL17 production, is of significant therapeutic benefit. Compounds that inhibit RORγ activity and hence have utility in the treatment of e.g., inflammatory, autoimmune, metabolic, circadian effect, cancer, and other diseases mediated by RORγ are described in WO 2014/179564 and WO 2015/116904. However, there is a continuing need for the development of new and improved drugs that modulate RORγ and are useful in the treatment of disease.

SUMMARY

It has now been found that compounds described herein, and pharmaceutically acceptable compositions thereof, are effective modulators of RORγ (see e.g., Table 3. Such compounds include those of Formula I:

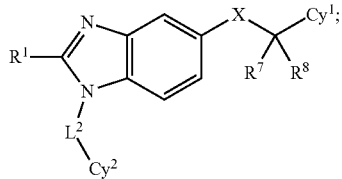

or a pharmaceutically acceptable salt thereof, wherein each of $Cy^1$, $Cy^2$, $L^2$, $R^1$, $R^7$, $R^8$, and X are as defined and described herein.

The provided compounds can be used alone (i.e., as a monotherapy) or in combination with one or more other therapeutic agent effective for treating any of the indications described herein.

DETAILED DESCRIPTION OF CERTAIN EMBODIMENTS

1. General Description of Compounds

Figure 1:
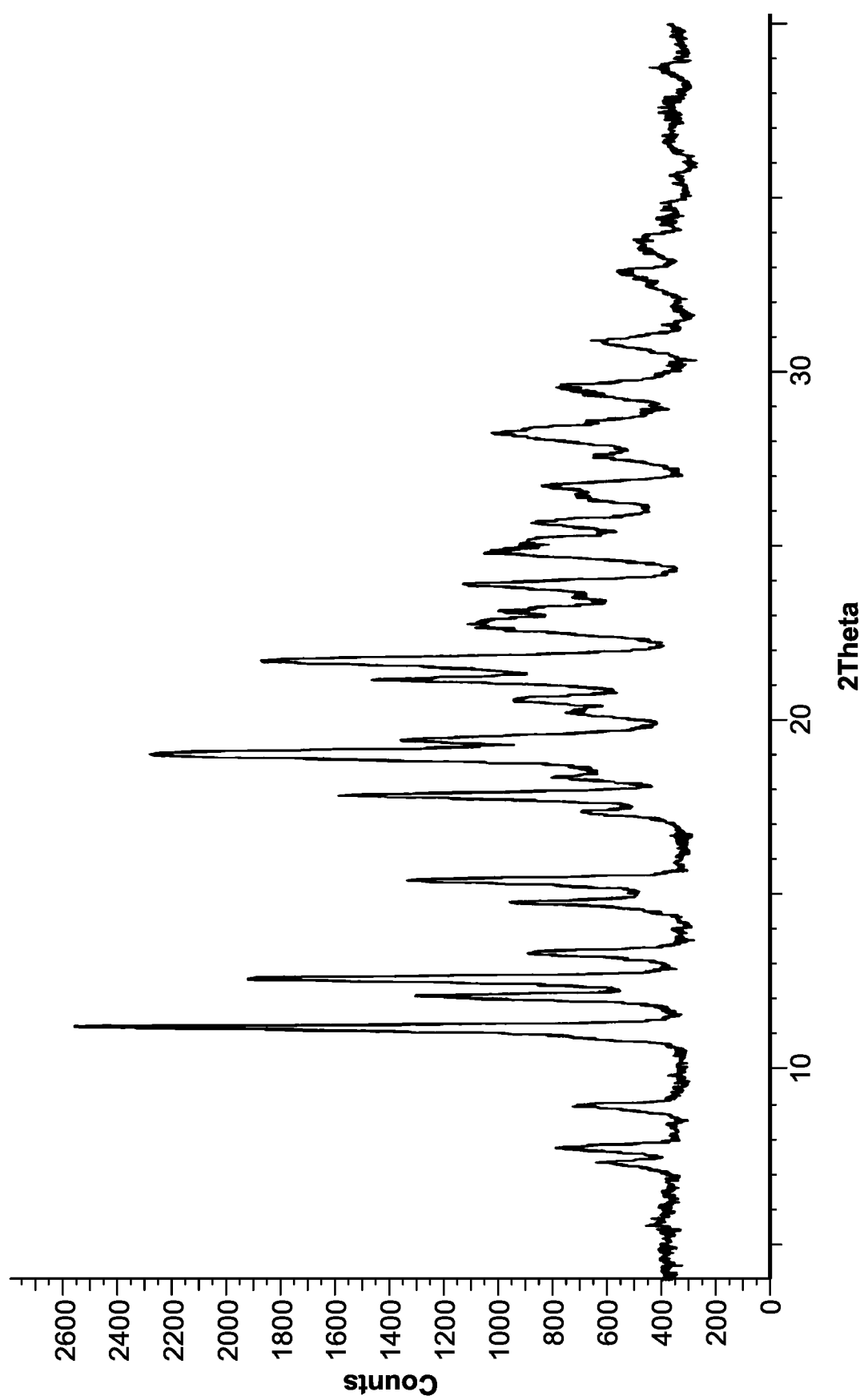
FIG. 1 depicts a powder X-ray diffractogram of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide (I-130.1) HCl salt.

In certain embodiments, the present disclosure provides a compound of Formula I:

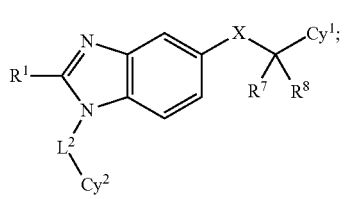

or a pharmaceutically acceptable salt thereof, wherein
X is —C(O)NH— or —NHC(O)—;
$R^1$ is $(C_1-C_4)$alkyl —C(=O)$OR^c$, halo$(C_1-C_4)$alkyl, $(C_1-C_4)$alkoxy, halo$(C_1-C_4)$alkoxy, —$NR^dR^e$, monocyclic heterocyclyl, or monocyclic cycloalkyl, wherein said $(C_1-C_4)$ alkyl is optionally substituted with —$OR^c$, said monocyclic heterocyclyl is optionally substituted with $(C_1-C_4)$alkyl or =O, and said monocyclic cycloalkyl is optionally substituted with —C(=O)$OR^c$, —CN, or one or more halo;
$L^2$ is $CH_2$, CHMe, or cyclopropyl;
$Cy^1$ is aryl, heteroaryl, heterocyclyl, or cycloalkyl, each of which is optionally substituted with 1 to 3 groups independently selected from $R^5$;
$Cy^2$ is aryl, heteroaryl, or heterocyclyl, each of which is optionally substituted with 1 to 3 groups independently selected from $R^6$;
$R^5$ and $R^6$ are each independently selected from halo, —CN, —$OR^c$, —$NR^dR^e$, —$S(O)_kR^b$, —$NR^cS(O)_2R^c$, —$S(O)_2NR^dR^e$, —C(=O)$OR^c$, —OC(=O)$OR^c$, —OC(=O)$R^c$, —OC(=S)$OR^c$, —C(=S)$OR^c$, —OC(=S)$R^c$, —C(=O)$NR^dR^e$, —$NR^cC(=O)R^c$, —C(=S)$NR^dR^e$, —$NR^cC(=S)R^c$, —$NR^cC(=O)OR^c$, —OC(=O)$NR^dR^e$, —$NR^c(C=S)OR^c$, —OC(=S)$NR^dR^e$, —$NR^cC(=O)$ $NR^dR^e$, —$NR^c(C=S)NR^dR^e$, —C(=S)$R^c$, —C(=O)$R^c$, oxo, $(C_1-C_6)$alkyl, cycloalkyl, —$(CH_2)_{1-4}$-cycloalkyl, heterocyclyl, —$(CH_2)_{1-4}$-heterocyclyl, aryl, —NHC(=O)-heterocyclyl, —NHC(=O)-cycloalkyl, —$(CH_2)_{1-4}$-aryl, heteroaryl and —$(CH_2)_{1-4}$-heteroaryl, wherein the alkyl, cycloalkyl, heterocyclyl, aryl or heteroaryl portion present in each of said $(C_1-C_6)$alkyl, cycloalkyl, —$(CH_2)_{1-4}$-cycloalkyl, heterocyclyl, —$(CH_2)_{1-4}$-heterocyclyl, aryl, —$(CH_2)_{1-4}$-aryl, heteroaryl and —$(CH_2)_{1-4}$-heteroaryl substituent for $R^5$ and $R^6$ are further optionally substituted with one or more halo, OR$^c$, —NO$_2$, —CN, —NR$^c$C(=O)R$^c$, —NR$^d$R$^e$, —S(O)$_k$R$^b$, —C(=O)OR$^c$, —C(=O)NR$^d$R$^e$, —C(=O)R$^c$, (C$_1$-C$_3$)alkyl, halo(C$_1$-C$_3$)alkyl, (C$_1$-C$_3$)alkoxy(C$_1$-C$_3$)alkyl, (C$_1$-C$_3$)alkoxy, or halo(C$_1$-C$_3$)alkoxy;

R$^7$ and R$^8$ are each independently hydrogen, OR$^c$, —C(=O)OR$^c$, monocyclic heterocyclyl, halophenyl, or (C$_1$-C$_3$)alkyl, wherein the (C$_1$-C$_3$)alkyl is optionally substituted with OR$^c$, —NR$^d$R$^e$, —O(C$_1$-C$_3$)alkyl-C(=O)OR$^c$, —C(=O)OR$^c$, —C(=O)NR$^d$R$^e$, or halophenyl;

k is 0, 1 or 2;

each R$^b$ is independently selected from hydrogen and (C$_1$-C$_3$)alkyl optionally substituted with OH, —O(C$_1$-C$_3$)alkyl, —C(O)O(C$_1$-C$_3$)alkyl, —C(O)NH$_2$, —C(O)NH(C$_1$-C$_3$)alkyl, or —C(O)N((C i-C$_3$)alkyl)$_2$;

each R$^c$ is independently selected from hydrogen and (C$_1$-C$_3$)alkyl optionally substituted with one or more halo; and each R$^d$ and R$^e$ is independently selected from hydrogen and (C$_1$-C$_3$)alkyl.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The term "haloalkyl" or "halocycloalkyl" include mono, poly, and perhaloalkyl groups where the halogens are independently selected from fluorine, chlorine, and bromine.

The term "cycloalkyl" refers to a cyclic hydrocarbon having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. It will be understood that when specified, optional substituents on a cycloalkyl or cycloaliphatic group may be present on any substitutable position and, include, e.g., the position at which the cycloalkyl or cycloaliphatic group is attached.

The term "aryl" used alone or as part of a larger moiety as in "aralkyl", "aralkoxy", or "aryloxyalkyl", refers to an aromatic carbocyclic ring system having, unless otherwise specified, a total of 6 to 10 ring members. The term "aryl" may be used interchangeably with the term "aryl ring", "aryl group", "aryl moiety," or "aryl radical". In certain embodiments, "aryl" refers to an aromatic ring system which includes, but is not limited to, phenyl (abbreviated as "Ph"), naphthyl and the like. It will be understood that when specified, optional substituents on an aryl group may be present on any substitutable position and, include, e.g., the position at which the aryl is attached.

The term "heteroaryl" used alone or as part of a larger moiety as in "heteroarylalkyl", "heteroarylalkoxy", or "heteroarylaminoalkyl", refers to a 5- to 12-membered aromatic radical containing 1-4 heteroatoms selected from N, O, and S. The term "heteroaryl" may be used interchangeably with the terms "heteroaryl ring", "heteroaryl group", or "heteroaromatic". A heteroaryl group may be mono- or bi-cyclic. Monocyclic heteroaryl includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, Bi-cyclic heteroaryls include groups in which a monocyclic heteroaryl ring is fused to one or more aryl or heteroaryl rings. Nonlimiting examples include indolyl, benzoxazolyl, benzooxodiazolyl, indazolyl, benzimidazolyl, benzthiazolyl, quinolyl, quinazolinyl, quinoxalinyl, pyrrolopyridinyl, pyrrolopyrimidinyl, pyrrolopyridinyl, thienopyridinyl, thienopyrimidinyl, indolizinyl, purinyl, naphthyridinyl, and pteridinyl. It will be understood that when specified, optional substituents on a heteroaryl group may be present on any substitutable position and, include, e.g., the position at which the heteroaryl is attached.

The term "heterocyclyl" means a 4- to 12-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. A heterocyclyl group may be mono- or bicyclic. Examples of monocyclic saturated or partially unsaturated heterocyclic radicals include, without limitation, tetrahydrofuranyl, tetrahydrothienyl, tetrahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. Bi-cyclic heterocyclyl groups include, e.g., unsaturated heterocyclic radicals fused to another unsaturated heterocyclic radical, cycloalkyl, or aromatic or heteroaryl ring, such as for example, benzodioxolyl, dihydrobenzodioxinyl, 6,7-dihydro-5H-pyrrolo[2,1-c][1,2,4]triazolyl, 5,6,7,8-tetrahydroimidazo[1,2-a]pyridinyl, 1,2-dihydroquinolinyl, dihydrobenzofuranyl, tetrahydronaphthyridine, indolinone, dihydropyrrolotriazole, quinolinone, dioxaspirodecane. It will be understood that when specified, optional substituents on a heterocyclyl group may be present on any substitutable position and, include, e.g., the position at which the heterocyclyl is attached.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

As used herein, a hyphen ("-") at the beginning or end of a recited group designates the point at which a recited group is attached to a defined group. For example, —SO$_2$—(C$_1$-C$_3$)alkyl-(C$_2$-C$_6$)cycloalkyl means that the group is attached via the sulfonyl.

"Racemate" or "racemic mixture" means a compound of equimolar quantities of two enantiomers, wherein such mixtures exhibit no optical activity, i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. When a disclosed compound is named or depicted by structure without indicating a particular geometric isomer form, it is to be understood that the name or structure encompasses one geometric isomer free of other geometric isomers, mixtures of geometric isomers, or mixtures of all geometric isomers.

The compounds of the herein may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomer is at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound, or mixtures enriched in one enantiomer relative to its corresponding optical isomer.

When a disclosed compound is named or depicted by structure without indicating the stereochemistry and e.g., the compound has more than one chiral center (e.g., at least two chiral centers), it is to be understood that the name or structure encompasses one stereoisomer free of other stereoisomers, mixtures of stereoisomers, or mixtures of stereoisomers in which one or more stereoisomers is enriched relative to the other stereoisomer(s). For example, the name or structure may encompass one stereoisomer free of other diastereomers, mixtures of stereoisomers, or mixtures of stereoisomers in which one or more diastereomers is enriched relative to the other diastereomer(s).

The compounds of the herein may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present disclosure provides a compound of Formula I:

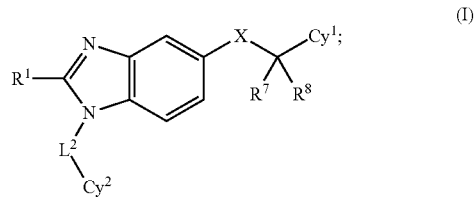

or a pharmaceutically acceptable salt thereof, wherein the variables are as described above.

In a second embodiment, $Cy^2$ in Formula I is heteroaryl or heterocyclyl, each of which are optionally substituted with 1 to 3 groups independently selected from $R^6$, wherein the remaining variables are as described above for Formula I.

In a third embodiment, $Cy^2$ in Formula I is bi-cyclic heterocyclyl or bi-cyclic heteroaryl, each of which are optionally substituted with 1 to 3 groups independently selected from $R^6$, wherein the remaining variables are as described above for Formula I and the second embodiment.

In a fourth embodiment, $Cy^2$ in Formula I is selected from:

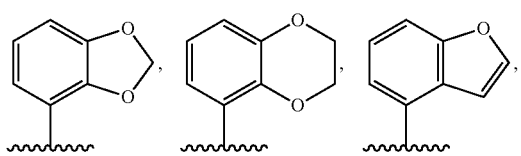

-continued

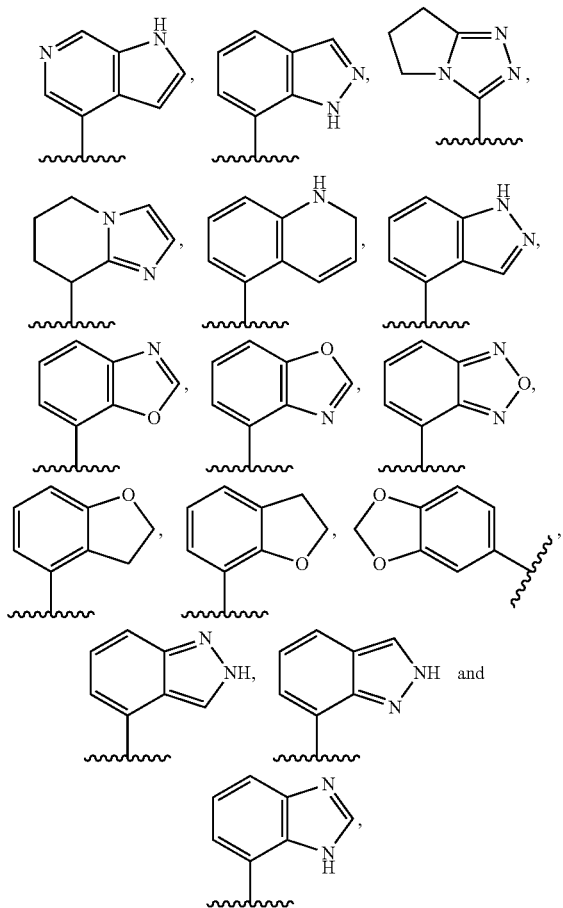

each of which are optionally substituted with 1 to 3 groups independently selected from $R^6$, wherein the remaining variables are as described above for Formula I and the second or third embodiment.

In a fifth embodiment, $Cy^2$ in Formula I is selected from:

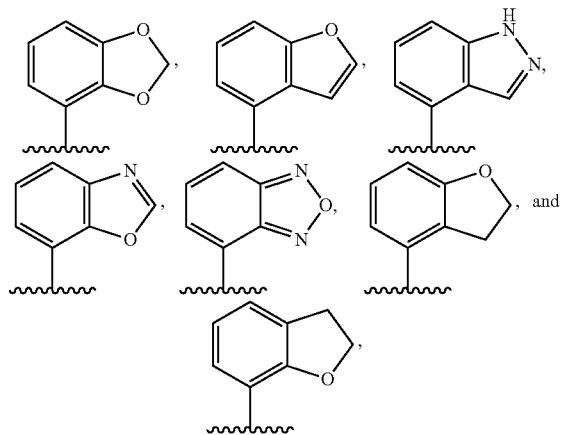

each of which are optionally substituted with 1 to 3 groups independently selected from $R^6$, wherein the remaining variables are as described above for Formula I and the second, third, or fourth embodiment.

In a sixth embodiment, $Cy^2$ in Formula I is

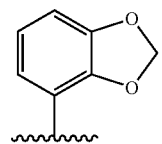 [SMILES: *c1cccc2c1OCO2]

optionally substituted with 1 to 3 groups independently selected from $R^6$, wherein the remaining variables are as described above for Formula I and the second, third, fourth, or fifth embodiment.

In a seventh embodiment, $Cy^2$ in Formula I is a monocyclic heteroaryl optionally substituted with 1 to 3 groups independently selected from $R^6$, wherein the remaining variables are as described above for Formula I and the second embodiment.

In an eighth embodiment, $Cy^2$ in Formula I is pyridyl or pyrimindinyl, each of which are optionally substituted with 1 to 3 groups independently selected from $R^6$, wherein the remaining variables are as described above for Formula I and the second or seventh embodiment.

In a ninth embodiment, $Cy^2$ in Formula I is phenyl, optionally substituted with 1 to 3 groups independently selected from $R^6$, wherein the remaining variables are as described above for Formula I.

In a tenth embodiment, $L^2$ in Formula I is $CH_2$ or CHMe, wherein the remaining variables are as described above for Formula I and the first, second, third, fourth, fifth, sixth, seventh, eighth, or ninth embodiment.

In an eleventh embodiment, the compound of Formula I is of the Formula II:

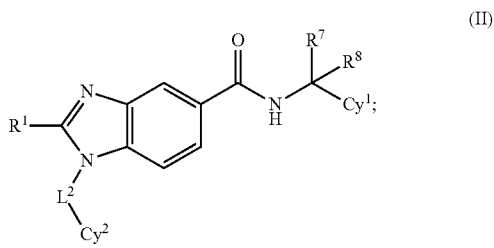

(II)

or a pharmaceutically acceptable salt thereof, wherein the remaining variables are as described above for Formula I and the first, second, third, fourth, fifth, sixth, seventh, eighth, ninth, or tenth embodiment.

In a twelfth embodiment, the compound of Formula I is of the Formula III:

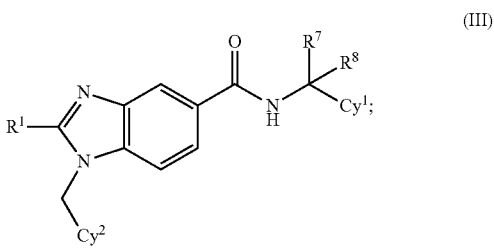

(III)

or a pharmaceutically acceptable salt thereof, wherein the remaining variables are as described above for Formula I and the first, second, third, fourth, fifth, sixth, seventh, eighth, ninth, tenth, or eleventh embodiment.

In a thirteenth embodiment, the compound of Formula I is of the Formula IV:

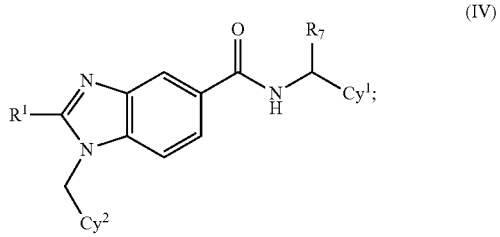

or a pharmaceutically acceptable salt thereof, wherein the remaining variables are as described above for Formula I and the first, second, third, fourth, fifth, sixth, seventh, eighth, ninth, tenth, eleventh, or twelfth embodiment.

In a fourteenth embodiment, the compound of Formula I is of the Formula V:

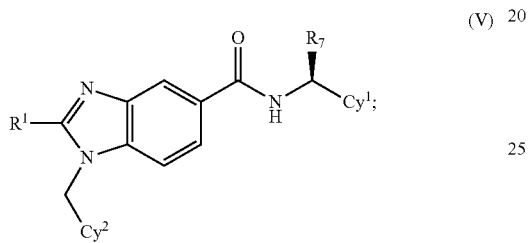

or a pharmaceutically acceptable salt thereof, wherein the remaining variables are as described above for Formula I and the first, second, third, fourth, fifth, sixth, seventh, eighth, ninth, tenth, eleventh, twelfth, or thirteenth embodiment.

In a fifteenth embodiment, $Cy^1$ in Formulae I to V is selected from aryl, monocyclic heteroaryl, and monocyclic heterocyclyl, each of which are optionally substituted with 1 to 3 groups independently selected from $R^5$, wherein the remaining variables are as described above for Formula I and the first, second, third, fourth, fifth, sixth, seventh, eighth, ninth, tenth, eleventh, twelfth, thirteenth, or fourteenth embodiment.

In a sixteenth embodiment, $Cy^1$ in Formulae I to V is selected from phenyl, pyridyl, and piperidinyl, each of which are optionally substituted with 1 to 3 groups independently selected from $R^5$, wherein the remaining variables are as described above for Formula I and the first, second, third, fourth, fifth, sixth, seventh, eighth, ninth, tenth, eleventh, twelfth, thirteenth, fourteenth, or fifteenth embodiment.

In a seventeenth embodiment, $Cy^1$ in Formulae I to V is phenyl or pyridyl optionally substituted with 1 to 3 groups independently selected from $R^5$, wherein the remaining variables are as described above for Formula I and the first, second, third, fourth, fifth, sixth, seventh, eighth, ninth, tenth, eleventh, twelfth, thirteenth, fourteenth, fifteenth, or sixteenth embodiment.

In an eighteenth embodiment, $R^7$ in Formulae I to V is hydrogen, $OR^c$, or $(C_1\text{-}C_3)$alkyl optionally substituted with $OR^c$ or $NR^dR^e$; and $R^8$ when present is hydrogen, wherein the remaining variables are as described above for Formula I and the first, second, third, fourth, fifth, sixth, seventh, eighth, ninth, tenth, eleventh, twelfth, thirteenth, fourteenth, fifteenth, sixteenth, or seventeenth embodiment.

In a nineteenth embodiment, $R^7$ in Formulae I to V is hydrogen or $(C_1\text{-}C_3)$alkyl optionally substituted with $OR^c$; and $R^8$ when present is hydrogen, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, or eighteenth embodiment.

In a twentieth embodiment, $R^7$ in Formulae I to V is hydrogen or —$(C_1\text{-}C_3)$alkyl-OH; and $R^8$ when present is hydrogen, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, or nineteenth embodiment.

In a twenty-first embodiment, $R^1$ in Formulae I to V is selected from $(C_1\text{-}C_4)$alkyl, halo$(C_1\text{-}C_4)$alkyl, cyclobutyl, tetrahydrofuranyl, $(C_1\text{-}C_4)$alkoxy, —$N((C_1\text{-}C_3)$alkyl$)_2$, —$(C_1\text{-}C_3)$alkyl-O—$(C_1\text{-}C_2)$alkyl, —$C(O)O(C_1\text{-}C_2)$alkyl, and cyclopropyl, wherein said cyclobutyl and cyclopropyl are each optionally substituted with $C(=O)OMe$, —CN, or 1 to 3 halo, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment.

In a twenty-second embodiment, $R^1$ in Formulae I to V is selected from $(C_1\text{-}C_4)$alkyl, halo$(C_1\text{-}C_4)$alkyl, $(C_1\text{-}C_4)$alkoxy, cyclobutyl, and cyclopropyl, wherein said cyclobutyl and cyclopropyl are each optionally substituted with 1 to 3 halo, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, or twenty-first embodiment.

In a twenty-third embodiment, $R^1$ in Formulae I to V is halo$(C_1\text{-}C_4)$alkyl, cyclobutyl, or cyclopropyl, wherein said cyclobutyl and cyclopropyl are optionally substituted with 1 to 3 halo, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first or twenty-second embodiment.

In a twenty-fourth embodiment, $R^1$ in Formulae I to V is $CF_3$, $CHF_2$, cyclobutyl, or cyclopropyl, wherein said cyclobutyl and cyclopropyl are optionally substituted with 1 to 2 fluoro, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment.

In a twenty-fifth embodiment, $R^1$ in Formulae I to V is —$C(=O)OR^c$, $(C_1\text{-}C_4)$alkoxy, halo$(C_1\text{-}C_4)$alkoxy, —$NR^dR^e$, monocyclic heterocyclyl, or monocyclic cycloalkyl, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, or twenty-fourth embodiment.

In a twenty-sixth embodiment, $R^1$ in Formulae I to V is cyclobutyl, tetrahydrofuranyl, $(C_1\text{-}C_4)$alkoxy, —$N((C_1\text{-}C_3)$alkyl$)_2$, —$C(O)O(C_1\text{-}C_2)$alkyl, or cyclopropyl, wherein said cyclobutyl and cyclopropyl are each optionally substituted with $C(=O)OMe$, —CN, or 1 to 3 halo, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, or twenty-fifth embodiment.

In a twenty-seventh embodiment, $R^1$ in Formulae I to V is selected from $(C_1\text{-}C_4)$alkoxy, cyclobutyl, and cyclopropyl, wherein said cyclobutyl and cyclopropyl are each optionally substituted with 1 to 3 halo, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth embodiment.

In a twenty-eighth embodiment, $R^5$ in Formulae I to V is selected from halo, —CN, —$OR^c$, —$NR^dR^e$, —$NR^cS(O)_2 R^c$, —$S(O)_2NR^dR^e$, —C(=O)$OR^c$, —C(=O)$NR^dR^e$, —$NR^cC$(=O)$R^c$, —$NR^cC$(=O)$OR^c$, —OC(=S)$NR^dR^e$, —C(=O)$R^c$, —$SO_2R^b$, and $(C_1$-$C_4)$alkyl optionally substituted with 1 to 3 halo, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, or twenty-seventh embodiment.

In a twenty-ninth embodiment, $R^5$ in Formulae I to V is selected from —CN, —$S(O)_2NR^dR^e$ and —$SO_2R^b$, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, or twenty-eighth embodiment.

In a thirtieth embodiment, $R^5$ in Formulae I to V is selected from —$S(O)_2NR^dR^e$ and —$SO_2R^b$, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, or twenty-ninth embodiment.

In a thirty-first embodiment, $R^5$ in Formulae I to V is —$SO_2(C_1$-$C_3)$alkyl, —$SO_2NH_2$, —$SO_2NH(C_1$-$C_3)$alkyl, —$SO_2(C_1$-$C_3)$alkyl-OH, —$SO_2(C_1$-$C_3)$alkyl-C(O)O$(C_1$-$C_3)$ alkyl, —$SO_2(C_1$-$C_3)$alkyl-C(O)NH$(C_1$-$C_3)$alkyl, —$SO_2 (C_1$-$C_3)$alkyl-O$(C_1$-$C_3)$alkyl, and —$SO_2(C_1$-$C_3)$alkyl-C(O) $NH_2$, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, or thirtieth embodiment.

In a thirty-second embodiment, $R^5$ in Formulae I to V is —$SO_2(C_1$-$C_3)$alkyl or —$SO_2NH(C_1$-$C_3)$alkyl, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-first embodiment.

In a thirty-third embodiment, $R^6$ in Formulae I to V is selected from halo, —CN, —$OR^c$, —$NR^dR^e$, —$NR^cS(O)_2 R^c$, —$S(O)_2NR^dR^e$, —C(=O)$OR^c$, —OC(=O)$OR^c$, —OC (=O)$R^c$, —C(=O)$NR^dR^e$, —$NR^cC$(=O)$R^c$, —C(=S) $NR^dR^e$, —$NR^cC$(=S)$R^c$, —$NR^cC$(=O)$OR^c$, —OC(=O) $NR^dR^e$, —$NR^c$(C=S)$OR^c$, —OC(=S)$NR^dR^e$, —$NR^cC$ (=O)$NR^dR^e$, —$NR^c$(C=S)$NR^dR^e$, —C(=S)$R^c$, —C(=O) $R^c$, —$SO_2R^b$, and $(C_1$-$C_4)$alkyl optionally substituted with 1 to 3 halo, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, or twenty-second embodiment.

In a thirty-fourth embodiment, $R^6$ in Formulae I to V is selected from halo, —CN, —$OR^c$, $(C_1$-$C_4)$alkyl and $(C_1$-$C_4)$alkyl optionally substituted with 1 to 3 halo, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, twenty-second, or twenty-third embodiment.

In a thirty-fifth embodiment, $R^6$ in Formulae I to V is selected from halo, —CN, —$OR^c$, and $(C_1$-$C_3)$alkyl; and $R^c$ is $(C_1$-$C_3)$alkyl, wherein the remaining variables are as described above for Formula I and the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, twenty-second, twenty-third, or twenty-fourth embodiment.

In a thirty-sixth embodiment, the compound of Formula I is of the Formula VI:

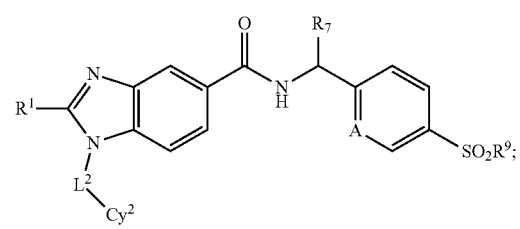

(VI)

or a pharmaceutically acceptable salt thereof, wherein A is N or CH; $R^1$ is $(C_1$-$C_4)$alkyl, halo$(C_1$-$C_4)$alkyl, or cycloalkyl optionally substituted with 1 to 3 halo; $L^2$ is $CH_2$ or CHMe; $Cy^2$ is bi-cyclic heterocyclyl or bi-cyclic heteroaryl, each of which are optionally substituted with 1 to 3 groups independently selected from halo, $(C_1$-$C_4)$alkyl, and $(C_1$-$C_4)$ alkoxy, wherein said $(C_1$-$C_4)$alkyl and $(C_1$-$C_4)$alkoxy are optionally substituted with 1 to 3 halo; $R^7$ is hydrogen or —$CH_2OH$; and $R^9$ is —$NH(C_1$-$C_4)$alkyl, $(C_1$-$C_4)$alkyl, or $(C_1$-$C_4)$alkyl substituted with OH.

In a thirty-seventh embodiment, the compound of Formula I is of the Formula VII:

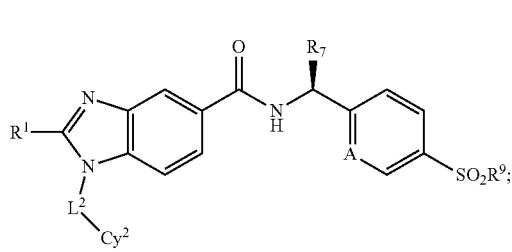

(VII)

or a pharmaceutically acceptable salt thereof, wherein the remaining variables are as described above for Formula I and the thirty-sixth embodiment.

In a thirty-eighth embodiment, the compound of Formula I is of the Formula VIII:

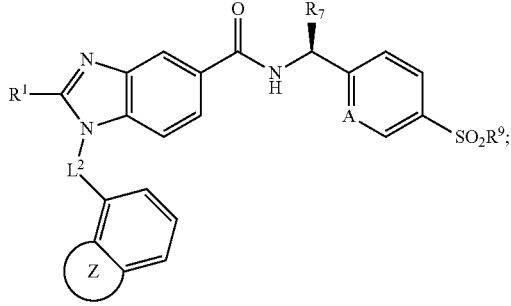

(VIII)

or a pharmaceutically acceptable salt thereof, wherein Z is a 5- or 6-membered heterocyclyl ring having one or more heteroatoms selected from oxygen or nitrogen; and wherein Z is optionally substituted with ($C_1$-$C_4$)alkyl or 1 to 3 halo, and wherein the remaining variables are as described above for Formula I and the thirty-sixth or thirty-seventh embodiment.

In a thirty-ninth embodiment, the compound of Formula I is of the Formula IX or X:

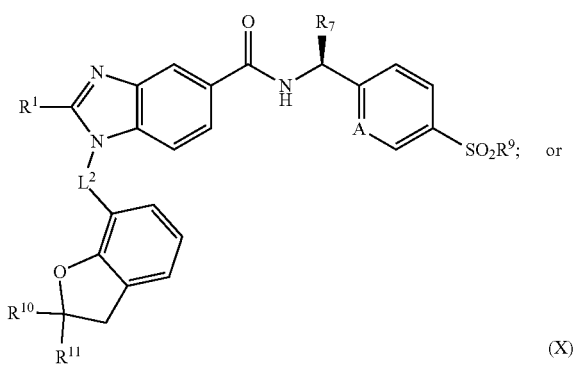

(IX)

(X)

or a pharmaceutically acceptable salt thereof, wherein $R^{10}$ and $R^{11}$ are each independently hydrogen, ($C_1$-$C_3$)alkyl, or halo, wherein the remaining variables are as described above for Formula I and the thirty-sixth, thirty-seventh, or thirty-eighth embodiment.

In a fortieth embodiment, the compound of Formula I is of the Formula XI:

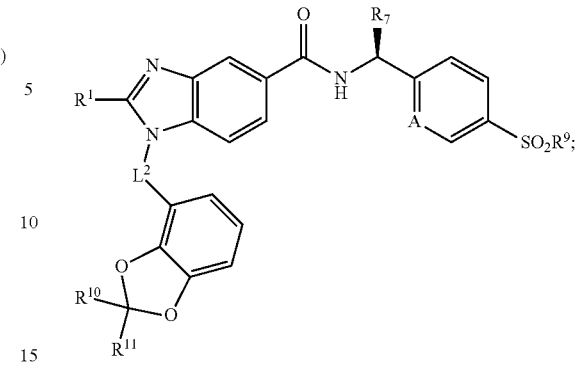

(XI)

or a pharmaceutically acceptable salt thereof, wherein $R^{10}$ and $R^{11}$ are each independently hydrogen or halo, wherein the remaining variables are as described above for Formula I and the thirty-sixth, thirty-seventh, thirty-eighth, or thirty-ninth embodiment.

In a forty-first embodiment, $R^{10}$ and $R^{11}$ in Formulae IX to XI are each halo, wherein the remaining variables are as described above for Formula I and the thirty-sixth, thirty-seventh, thirty-eighth, thirty-ninth, or fortieth embodiment.

In a forty-second embodiment, $R^{10}$ and $R^{11}$ in Formulae IX to XI are each fluoro, wherein the remaining variables are as described above for Formula I and the thirty-sixth, thirty-seventh, thirty-eighth, thirty-ninth, fortieth, or forty-first embodiment.

In a forty-third embodiment, $R^1$ in Formulae VI to XI is halo($C_1$-$C_4$)alkyl, cyclopropyl, or cyclobutyl, wherein said cyclopropyl and cyclobutyl are each optionally substituted with 1 to 3 halo, wherein the remaining variables are as described above for Formula I and the thirty-sixth, thirty-seventh, thirty-eighth, thirty-ninth, fortieth, forty-first, or forty-second embodiment.

In a forty-fourth embodiment, $R^1$ in Formulae VI to XI is $CF_3$, $CHF_2$, or cyclobutyl, wherein the remaining variables are as described above for Formula I and the thirty-sixth, thirty-seventh, thirty-eighth, thirty-ninth, fortieth, forty-first, forty-second, or forty-third embodiment.

In a forty-fifth embodiment, $R^9$ in Formulae VI to XI is ($C_1$-$C_3$)alkyl, wherein the remaining variables are as described above for Formula I and the thirty-sixth, thirty-seventh, thirty-eighth, thirty-ninth, fortieth, forty-first, forty-second, forty-third, or forty-fourth embodiment.

In a forty-sixth embodiment, $L^2$ in Formulae VI to XI is $CH_2$, wherein the remaining variables are as described above for Formula I and the thirty-sixth, thirty-seventh, thirty-eighth, thirty-ninth, fortieth, forty-first, forty-second, forty-third, forty-fourth, or forty-fifth embodiment.

In a forty-sixth embodiment, $R^7$ in Formulae VI to XI is —$CH_2OH$; and A is N, wherein the remaining variables are as described above for Formula I and the thirty-sixth, thirty-seventh, thirty-eighth, thirty-ninth, fortieth, forty-first, forty-second, forty-third, forty-fourth, forty-fifth, or forty-sixth embodiment.

In a forty-seventh embodiment, the compound of Formula I is of the Formula XII:

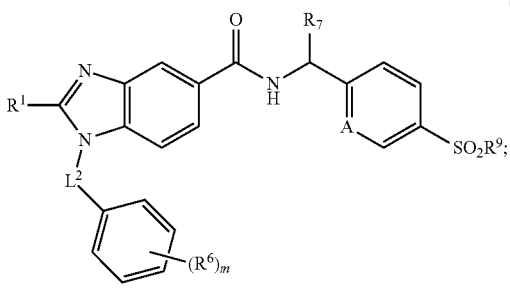

(XII)

or a pharmaceutically acceptable salt thereof, wherein

A is N or CH;

$R^1$ is $(C_1-C_4)$alkyl, halo$(C_1-C_4)$alkyl, cyclobutyl optionally substituted with 1 to 3 halo, or cyclopropyl optionally substituted with 1 to 3 halo;

$L^2$ is $CH_2$ or CHMe;

each $R^6$ is independently selected from halo, —CN, —$OR^c$, $(C_1-C_4)$alkyl and $(C_1-C_4)$alkyl substituted with halo; m is 1 or 2;

$R^7$ is hydrogen or —$CH_2OH$; and $R^9$ is —$NH(C_1-C_4)$alkyl, $(C_1-C_4)$alkyl, or $(C_1-C_4)$alkyl substituted with OH.

In a forty-eighth embodiment, the compound of Formula I is selected from any one of the compounds in Table 1 or a pharmaceutically acceptable salt thereof.

TABLE 1

| Cpd No | Name |
|---|---|
| I-1 | N-(1-((2,2-difluorobenzo[d][1,3]dioxol-4-yl)methyl)-2-(trifluoromethyl)-1H-benzo[d]imidazol-5-yl)-2-(4-(ethylsulfonyl)phenyl)acetamide |
| I-2 | N-(1-((2,2-difluorobenzo[d][1,3]dioxol-4-yl)methyl)-2-(trifluoromethyl)-1H-benzo[d]imidazol-5-yl)-2-(4-(methylsulfonyl)phenyl)acetamide |
| I-3 | N-(1-((2,2-difluorobenzo[d][1,3]dioxol-4-yl)methyl)-2-(trifluoromethyl)-1H-benzo[d]imidazol-5-yl)-2-(4-((2-hydroxyethyl)sulfonyl)phenyl)acetamide |
| I-4 | N-(1-((2,2-difluorobenzo[d][1,3]dioxol-4-yl)methyl)-2-(trifluoromethyl)-1H-benzo[d]imidazol-5-yl)-2-(4-((2-methoxyethyl)sulfonyl)phenyl)acetamide |
| I-5 | N-(1-((2,2-difluorobenzo[d][1,3]dioxol-4-yl)methyl)-2-(trifluoromethyl)-1H-benzo[d]imidazol-5-yl)-2-(4-(N-methylsulfamoyl)phenyl)acetamide |
| I-6 | 2-(4-cyanophenyl)-N-(1-((2,2-difluorobenzo[d][1,3]dioxol-4-yl)methyl)-2-(trifluoromethyl)-1H-benzo[d]imidazol-5-yl)acetamide |
| I-7 | ethyl 2-(4-(2-((1-((2,2-difluorobenzo[d][1,3]dioxol-4-yl)methyl)-2-(trifluoromethyl)-1H-benzo[d]imidazol-5-yl)amino)-2-oxoethyl)phenyl)acetate |
| I-8 | 2-(4-(2-((1-((2,2-difluorobenzo[d][1,3]dioxol-4-yl)methyl)-2-(trifluoromethyl)-1H-benzo[d]imidazol-5-yl)amino)-2-oxoethyl)phenyl)acetic acid |
| I-9 | N-(2-cyclopropyl-1-((2,2-difluorobenzo[d][1,3]dioxol-4-yl)methyl)-1H-benzo[d]imidazol-5-yl)-2-(4-(ethylsulfonyl)phenyl)acetamide |
| I-10 | N-(1-((2,2-difluorobenzo[d][1,3]dioxol-4-yl)methyl)-2-(trifluoromethyl)-1H-benzo[d]imidazol-5-yl)-2-(1-(methylsulfonyl)piperidin-4-yl)acetamide |
| I-11.1 | (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide |
| I-11.2 | (S)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide |
| I-12 | (R)-2-cyclopropyl-1-((2,2-difluorobenzo[d][1,3]dioxol-4-yl)methyl)-N-(1-(4-(ethylsulfonyl)phenyl)-2-hydroxyethyl)-1H-benzo[d]imidazole-5-carboxamide |
| I-13 | (R)-2-cyclobutyl-1-((2,2-difluorobenzo[d][1,3]dioxol-4-yl)methyl)-N-(1-(4-(ethylsulfonyl)phenyl)-2-hydroxyethyl)-1H-benzo[d]imidazole-5-carboxamide |
| I-14 | (R)-1-((2,2-difluorobenzo[d][1,3]dioxol-4-yl)methyl)-2-(1,1-difluoroethyl)-N-(1-(4-(ethylsulfonyl)phenyl)-2-hydroxyethyl)-1H-benzo[d]imidazole-5-carboxamide |
| I-15 | 1-((2,2-difluorobenzo[d][1,3]dioxol-4-yl)methyl)-N-((R)-1-(4-(ethylsulfonyl)phenyl)-2-hydroxyethyl)-2-((R)-tetrahydrofuran-2-yl)-1H-benzo[d]imidazole-5-carboxamide |
| I-16 | (R)-1-((2,2-difluorobenzo[d][1,3]dioxol-4-yl)methyl)-2-ethyl-N-(1-(4-(ethylsulfonyl)phenyl)-2-hydroxyethyl)-1H-benzo[d]imidazole-5-carboxamide |
| I-17 | (R)-1-((2,2-difluorobenzo[d][1,3]dioxol-4-yl)methyl)-2-(difluoromethyl)-N-(1-(4-(ethylsulfonyl)phenyl)-2-hydroxyethyl)-1H-benzo[d]imidazole-5-carboxamide |
| I-18 | (R)-1-((2,2-difluorobenzo[d][1,3]dioxol-4-yl)methyl)-N-(1-(4-(ethylsulfonyl)phenyl)-2-hydroxyethyl)-2-(1-fluorocyclopropyl)-1H-benzo[d]imidazole-5-carboxamide |
| I-19 | (R)-1-((2,2-difluorobenzo[d][1,3]dioxol-4-yl)methyl)-N-(1-(4-(ethylsulfonyl)phenyl)-2-hydroxyethyl)-2-(1-fluorocyclobutyl)-1H-benzo[d]imidazole-5-carboxamide |

TABLE 1-continued

| Cpd No | Name |
| --- | --- |
| I-20.1 | (R)-1-((2,2-difluorobenzo[d][1,3]dioxol-4-yl)methyl)-N-(2-hydroxy-1-(4-(methylsulfonyl)phenyl)ethyl)-2-(trifluoromethyl)-1H-benzo[d]imidazole-5-carboxamide |
| I-20.2 | (S)-1-((2,2-difluorobenzo[d][1,3]dioxol-4-yl)methyl)-N-(2-hydroxy-1-(4-(methylsulfonyl)phenyl)ethyl)-2-(trifluoromethyl)-1H-benzo[d]imidazole-5-carboxamide |
| I-21 | (R)-2-cyclopropyl-1-((2,2-difluorobenzo[d][1,3]dioxol-4-yl)methyl)-N-(2-hydroxy-1-(4-(methylsulfonyl)phenyl)ethyl)-1H-benzo[d]imidazole-5-carboxamide |
| I-22 | (R)-2-cyclobutyl-1-((2,2-difluorobenzo[d][1,3]dioxol-4-yl)methyl)-N-(2-hydroxy-1-(4-(methylsulfonyl)phenyl)ethyl)-1H-benzo[d]imidazole-5-carboxamide |
| I-23.1 | (R)-1-((2,2-difluorobenzo[d][1,3]dioxol-4-yl)methyl)-2-(difluoromethyl)-N-(2-hydroxy-1-(4-(methylsulfonyl)phenyl)ethyl)-1H-benzo[d]imidazole-5-carboxamide |
| I-23.2 | (S)-1-((2,2-difluorobenzo[d][1,3]dioxol-4-yl)methyl)-2-(difluoromethyl)-N-(2-hydroxy-1-(4-(methylsulfonyl)phenyl)ethyl)-1H-benzo[d]imidazole-5-carboxamide |
| I-24 | (R)-1-((2,2-difluorobenzo[d][1,3]dioxol-4-yl)methyl)-2-(1-fluorocyclopropyl)-N-(2-hydroxy-1-(4-(methylsulfonyl)phenyl)ethyl)-1H-benzo[d]imidazole-5-carboxamide |
| I-25 | 1-((2,2-difluorobenzo[d][1,3]dioxol-4-yl)methyl)-N-(4-(ethylsulfonyl)benzyl)-2-(trifluoromethyl)-1H-benzo[d]imidazole-5-carboxamide |
| I-26 | 2-cyclopropyl-1-((2,2-difluorobenzo[d][1,3]dioxol-4-yl)methyl)-N-(4-(ethylsulfonyl)benzyl)-1H-benzo[d]imidazole-5-carboxamide |
| I-27 | 1-((2,2-difluorobenzo[d][1,3]dioxol-4-yl)methyl)-N-(4-(ethylsulfonyl)benzyl)-2-(1-fluorocyclopropyl)-1H-benzo[d]imidazole-5-carboxamide |
| I-28 | 1-((2,2-difluorobenzo[d][1,3]dioxol-4-yl)methyl)-N-(4-(ethylsulfonyl)benzyl)-2-(methoxymethyl)-1H-benzo[d]imidazole-5-carboxamide |
| I-29 | 1-((2,2-difluorobenzo[d][1,3]dioxol-4-yl)methyl)-2-ethyl-N-(4-(ethylsulfonyl)benzyl)-1H-benzo[d]imidazole-5-carboxamide |
| I-30 | 2-(tert-butyl)-1-((2,2-difluorobenzo[d][1,3]dioxol-4-yl)methyl)-N-(4-(ethylsulfonyl)benzyl)-1H-benzo[d]imidazole-5-carboxamide |
| I-31 | 1-((2,2-difluorobenzo[d][1,3]dioxol-4-yl)methyl)-N-(4-(ethylsulfonyl)benzyl)-2-isopropyl-1H-benzo[d]imidazole-5-carboxamide |
| I-32 | 1-((2,2-difluorobenzo[d][1,3]dioxol-4-yl)methyl)-N-(4-(ethylsulfonyl)benzyl)-2-methyl-1H-benzo[d]imidazole-5-carboxamide |
| I-33 | 1-((2,2-difluorobenzo[d][1,3]dioxol-4-yl)methyl)-N-(4-(ethylsulfonyl)benzyl)-2-isobutyl-1H-benzo[d]imidazole-5-carboxamide |
| I-34 | 2-cyclopropyl-1-((2,2-difluorobenzo[d][1,3]dioxol-4-yl)methyl)-N-(4-(methylsulfonyl)benzyl)-1H-benzo[d]imidazole-5-carboxamide |
| I-35 | 2-cyclopropyl-1-((2,2-difluorobenzo[d][1,3]dioxol-4-yl)methyl)-N-(4-(N-methylsulfamoyl)benzyl)-1H-benzo[d]imidazole-5-carboxamide |
| I-36 | 2-cyclobutyl-1-((2,2-difluorobenzo[d][1,3]dioxol-4-yl)methyl)-N-(4-(ethylsulfonyl)benzyl)-1H-benzo[d]imidazole-5-carboxamide |
| I-37 | 1-((2,2-difluorobenzo[d][1,3]dioxol-4-yl)methyl)-2-(difluoromethyl)-N-(4-(ethylsulfonyl)benzyl)-1H-benzo[d]imidazole-5-carboxamide |
| I-38 | 1-((2,2-difluorobenzo[d][1,3]dioxol-4-yl)methyl)-2-(1,1-difluoroethyl)-N-(4-(ethylsulfonyl)benzyl)-1H-benzo[d]imidazole-5-carboxamide |
| I-39.1[a] | (R)-1-((2,2-difluorobenzo[d][1,3]dioxol-4-yl)methyl)-N-(4-(ethylsulfonyl)benzyl)-2-(tetrahydrofuran-2-yl)-1H-benzo[d]imidazole-5-carboxamide |
| I-39.2[b] | (S)-1-((2,2-difluorobenzo[d][1,3]dioxol-4-yl)methyl)-N-(4-(ethylsulfonyl)benzyl)-2-(tetrahydrofuran-2-yl)-1H-benzo[d]imidazole-5-carboxamide |
| I-40 | 1-((2,2-difluorobenzo[d][1,3]dioxol-4-yl)methyl)-2-(1-fluorocyclopropyl)-N-(4-(methylsulfonyl)benzyl)-1H-benzo[d]imidazole-5-carboxamide |
| I-41 | 1-((2,2-difluorobenzo[d][1,3]dioxol-4-yl)methyl)-2-(1-fluorocyclopropyl)-N-(4-((2-hydroxyethyl)sulfonyl)benzyl)-1H-benzo[d]imidazole-5-carboxamide |
| I-42 | 1-((2,2-difluorobenzo[d][1,3]dioxol-4-yl)methyl)-2-(1-fluorocyclopropyl)-N-(4-(N-methylsulfamoyl)benzyl)-1H-benzo[d]imidazole-5-carboxamide |
| I-43 | 1-((2,2-difluorobenzo[d][1,3]dioxol-4-yl)methyl)-N-(4-(ethylsulfonyl)benzyl)-2-(1-fluorocyclobutyl)-1H-benzo[d]imidazole-5-carboxamide |
| I-44 | 1-((2,2-difluorobenzo[d][1,3]dioxol-4-yl)methyl)-2-(difluoromethyl)-N-(4-((2-hydroxyethyl)sulfonyl)benzyl)-1H-benzo[d]imidazole-5-carboxamide |
| I-45 | 1-((2,2-difluorobenzo[d][1,3]dioxol-4-yl)methyl)-N-(4-((2-hydroxyethyl)sulfonyl)benzyl)-2-(trifluoromethyl)-1H-benzo[d]imidazole-5-carboxamide |

TABLE 1-continued

| Cpd No | Name |
|---|---|
| I-46 | 1-((2,2-difluorobenzo[d][1,3]dioxol-4-yl)methyl)-N-(4-(N-methylsulfamoyl)benzyl)-2-(trifluoromethyl)-1H-benzo[d]imidazole-5-carboxamide |
| I-47 | 2-cyclopropyl-1-((2,2-difluorobenzo[d][1,3]dioxol-4-yl)methyl)-N-(4-((2-hydroxyethyl)sulfonyl)benzyl)-1H-benzo[d]imidazole-5-carboxamide |
| I-48 | 1-((2,2-difluorobenzo[d][1,3]dioxol-4-yl)methyl)-N-(4-(methylsulfonyl)benzyl)-2-(trifluoromethyl)-1H-benzo[d]imidazole-5-carboxamide |
| I-49.1 and I-49.2[c] | (S)-1-((2,2-difluorobenzo[d][1,3]dioxol-4-yl)methyl)-N-(4-(ethylsulfonyl)benzyl)-2-(1-methoxyethyl)-1H-benzo[d]imidazole-5-carboxamide and (R)-1-((2,2-difluorobenzo[d][1,3]dioxol-4-yl)methyl)-N-(4-(ethylsulfonyl)benzyl)-2-(1-methoxyethyl)-1H-benzo[d]imidazole-5-carboxamide |
| I-50 | 1-((2,2-difluorobenzo[d][1,3]dioxol-4-yl)methyl)-2-(difluoromethyl)-N-(4-(methylsulfonyl)benzyl)-1H-benzo[d]imidazole-5-carboxamide |
| I-51 | 1-((2,2-difluorobenzo[d][1,3]dioxol-4-yl)methyl)-N-(4-sulfamoylbenzyl)-2-(trifluoromethyl)-1H-benzo[d]imidazole-5-carboxamide |
| I-52 | 1-((2,2-difluorobenzo[d][1,3]dioxol-4-yl)methyl)-N-(4-(propylsulfonyl)benzyl)-2-(trifluoromethyl)-1H-benzo[d]imidazole-5-carboxamide |
| I-53 | methyl 2-((4-((1-((2,2-difluorobenzo[d][1,3]dioxol-4-yl)methyl)-2-(trifluoromethyl)-1H-benzo[d]imidazole-5-carboxamido)methyl)phenyl)sulfonyl)acetate |
| I-54 | 1-((2,2-difluorobenzo[d][1,3]dioxol-4-yl)methyl)-N-(4-(ethylsulfonyl)benzyl)-2-(2-methoxypropan-2-yl)-1H-benzo[d]imidazole-5-carboxamide |
| I-55 | 1-((2,2-difluorobenzo[d][1,3]dioxol-4-yl)methyl)-N-(4-(ethylsulfonyl)benzyl)-2-methoxy-1H-benzo[d]imidazole-5-carboxamide |
| I-56 | 2-((1S,2R)-2-cyanocyclopropyl)-1-((2,2-difluorobenzo[d][1,3]dioxol-4-yl)methyl)-N-(4-(ethylsulfonyl)benzyl)-1H-benzo[d]imidazole-5-carboxamide |
| I-57 | 2-((1R,2R)-2-cyanocyclopropyl)-1-((2,2-difluorobenzo[d][1,3]dioxol-4-yl)methyl)-N-(4-(ethylsulfonyl)benzyl)-1H-benzo[d]imidazole-5-carboxamide |
| I-58 | methyl(1R,2R)-2-(1-((2,2-difluorobenzo[d][1,3]dioxol-4-yl)methyl)-5-((4-(ethylsulfonyl)benzyl)carbamoyl)-1H-benzo[d]imidazol-2-yl)cyclopropane-1-carboxylate |
| I-59 | (R)-1-((2,2-difluorobenzo[d][1,3]dioxol-4-yl)methyl)-N-(1-(4-(ethylsulfonyl)phenyl)-2-methoxyethyl)-2-(trifluoromethyl)-1H-benzo[d]imidazole-5-carboxamide |
| I-60 | (R)-2-cyclopropyl-1-((2,2-difluorobenzo[d][1,3]dioxol-4-yl)methyl)-N-(1-(4-(ethylsulfonyl)phenyl)-2-methoxyethyl)-1H-benzo[d]imidazole-5-carboxamide |
| I-61 | (R)-1-((2,2-difluorobenzo[d][1,3]dioxol-4-yl)methyl)-N-(1-(4-(ethylsulfonyl)phenyl)-2-methoxyethyl)-2-(1-fluorocyclopropyl)-1H-benzo[d]imidazole-5-carboxamide |
| I-62 | (R)-1-((2,2-difluorobenzo[d][1,3]dioxol-4-yl)methyl)-N-(1-(5-(ethylsulfonyl)pyridin-2-yl)-2-methoxyethyl)-2-(trifluoromethyl)-1H-benzo[d]imidazole-5-carboxamide |
| I-63 | 1-((2,2-difluorobenzo[d][1,3]dioxol-4-yl)methyl)-N-((5-(ethylsulfonyl)pyridin-2-yl)methyl)-2-(trifluoromethyl)-1H-benzo[d]imidazole-5-carboxamide |
| I-64 | 2-cyclopropyl-1-((2,2-difluorobenzo[d][1,3]dioxol-4-yl)methyl)-N-((5-(ethylsulfonyl)pyridin-2-yl)methyl)-1H-benzo[d]imidazole-5-carboxamide |
| I-65 | 2-cyclobutyl-1-((2,2-difluorobenzo[d][1,3]dioxol-4-yl)methyl)-N-((5-(ethylsulfonyl)pyridin-2-yl)methyl)-1H-benzo[d]imidazole-5-carboxamide |
| I-66 | 1-((2,2-difluorobenzo[d][1,3]dioxol-4-yl)methyl)-2-(1,1-difluoroethyl)-N-((5-(ethylsulfonyl)pyridin-2-yl)methyl)-1H-benzo[d]imidazole-5-carboxamide |
| I-67 | 1-((2,2-difluorobenzo[d][1,3]dioxol-4-yl)methyl)-N-((5-(ethylsulfonyl)pyridin-2-yl)methyl)-2-(1-fluorocyclopropyl)-1H-benzo[d]imidazole-5-carboxamide |
| I-68 | 1-((2,2-difluorobenzo[d][1,3]dioxol-4-yl)methyl)-2-(1-fluorocyclopropyl)-N-((5-(methylsulfonyl)pyridin-2-yl)methyl)-1H-benzo[d]imidazole-5-carboxamide |
| I-69 | 1-((2,2-difluorobenzo[d][1,3]dioxol-4-yl)methyl)-N-((5-(ethylsulfonyl)pyridin-2-yl)methyl)-2-(1-fluorocyclobutyl)-1H-benzo[d]imidazole-5-carboxamide |
| I-70 | 1-((2,2-difluorobenzo[d][1,3]dioxol-4-yl)methyl)-N-((5-(methylsulfonyl)pyridin-2-yl)methyl)-2-(trifluoromethyl)-1H-benzo[d]imidazole-5-carboxamide |

TABLE 1-continued

| Cpd No | Name |
|---|---|
| I-71 | 1-((2,2-difluorobenzo[d][1,3]dioxol-4-yl)methyl)-N-((1-(methylsulfonyl)piperidin-4-yl)methyl)-2-(trifluoromethyl)-1H-benzo[d]imidazole-5-carboxamide |
| I-72 | 2-cyclopropyl-1-((2,2-difluorobenzo[d][1,3]dioxol-4-yl)methyl)-N-((1-(methylsulfonyl)piperidin-4-yl)methyl)-1H-benzo[d]imidazole-5-carboxamide |
| I-73 | 1-((2,2-difluorobenzo[d][1,3]dioxol-4-yl)methyl)-2-(1-fluorocyclopropyl)-N-((1-(methylsulfonyl)piperidin-4-yl)methyl)-1H-benzo[d]imidazole-5-carboxamide |
| I-74 | methyl 2-((4-((1-((2,2-difluorobenzo[d][1,3]dioxol-4-yl)methyl)-2-(trifluoromethyl)-1H-benzo[d]imidazole-5-carboxamido)methyl)piperidin-1-yl)sulfonyl)acetate |
| I-75 | 1-((2,2-difluorobenzo[d][1,3]dioxol-4-yl)methyl)-N-((1-((2-(methylamino)-2-oxoethyl)sulfonyl)piperidin-4-yl)methyl)-2-(trifluoromethyl)-1H-benzo[d]imidazole-5-carboxamide |
| I-76 | methyl 2-(1-((2,2-difluorobenzo[d][1,3]dioxol-4-yl)methyl)-2-(trifluoromethyl)-1H-benzo[d]imidazole-5-carboxamido)-2-(1-(methylsulfonyl)piperidin-4-yl)acetate |
| I-77 | 1-((2,2-difluorobenzo[d][1,3]dioxol-4-yl)methyl)-N-((1-(N-methylsulfamoyl)piperidin-4-yl)methyl)-2-(trifluoromethyl)-1H-benzo[d]imidazole-5-carboxamide |
| I-78 | N-((1-((2-amino-2-oxoethyl)sulfonyl)piperidin-4-yl)methyl)-1-((2,2-difluorobenzo[d][1,3]dioxol-4-yl)methyl)-2-(trifluoromethyl)-1H-benzo[d]imidazole-5-carboxamide |
| I-79 | 2-cyclopropyl-1-((2,2-difluorobenzo[d][1,3]dioxol-4-yl)methyl)-N-((1-((2-(methylamino)-2-oxoethyl)sulfonyl)piperidin-4-yl)methyl)-1H-benzo[d]imidazole-5-carboxamide |
| I-80 | (R)-1-((2,3-dihydrobenzofuran-7-yl)methyl)-N-(1-(4-(ethylsulfonyl)phenyl)-2-hydroxyethyl)-2-(trifluoromethyl)-1H-benzo[d]imidazole-5-carboxamide |
| I-81 | (R)-1-(benzo[d][1,3]dioxol-4-ylmethyl)-N-(1-(4-(ethylsulfonyl)phenyl)-2-hydroxyethyl)-2-(trifluoromethyl)-1H-benzo[d]imidazole-5-carboxamide |
| I-82 | 1-(3,5-dimethoxybenzyl)-N-(4-(ethylsulfonyl)benzyl)-2-(trifluoromethyl)-1H-benzo[d]imidazole-5-carboxamide |
| I-83 | 1-(3-cyano-4-methoxybenzyl)-N-(4-(ethylsulfonyl)benzyl)-2-(trifluoromethyl)-1H-benzo[d]imidazole-5-carboxamide |
| I-84 | N-(4-(ethylsulfonyl)benzyl)-1-(4-(trifluoromethoxy)benzyl)-2-(trifluoromethyl)-1H-benzo[d]imidazole-5-carboxamide |
| I-85 | 1-(4-cyanobenzyl)-N-(4-(ethylsulfonyl)benzyl)-2-(trifluoromethyl)-1H-benzo[d]imidazole-5-carboxamide |
| I-86 | 1-((6,7-dihydro-5H-pyrrolo[2,1-c][1,2,4]triazol-3-yl)methyl)-N-(4-(ethylsulfonyl)benzyl)-2-(trifluoromethyl)-1H-benzo[d]imidazole-5-carboxamide |
| I-87 | N-(4-(ethylsulfonyl)benzyl)-1-((2-methyl-5,6,7,8-tetrahydroimidazo[1,2-a]pyridin-8-yl)methyl)-2-(trifluoromethyl)-1H-benzo[d]imidazole-5-carboxamide |
| I-88 | N-(4-(ethylsulfonyl)benzyl)-1-(3-methoxybenzyl)-2-(trifluoromethyl)-1H-benzo[d]imidazole-5-carboxamide |
| I-89 | N-(4-(ethylsulfonyl)benzyl)-1-((2-methoxypyridin-4-yl)methyl)-2-(trifluoromethyl)-1H-benzo[d]imidazole-5-carboxamide |
| I-90 | 1-(3-cyanobenzyl)-N-(4-(ethylsulfonyl)benzyl)-2-(trifluoromethyl)-1H-benzo[d]imidazole-5-carboxamide |
| I-91 | N-(4-(ethylsulfonyl)benzyl)-1-((2-oxo-1,2-dihydroquinolin-4-yl)methyl)-2-(trifluoromethyl)-1H-benzo[d]imidazole-5-carboxamide |
| I-92 | 1-(1-(3-cyanophenyl)cyclopropyl)-N-(4-(ethylsulfonyl)benzyl)-2-(trifluoromethyl)-1H-benzo[d]imidazole-5-carboxamide |
| I-93.1 | (S)-1-(1-(3-cyanophenyl)ethyl)-N-(4-(ethylsulfonyl)benzyl)-2-(trifluoromethyl)-1H-benzo[d]imidazole-5-carboxamide |
| I-93.2 | (R)-1-(1-(3-cyanophenyl)ethyl)-N-(4-(ethylsulfonyl)benzyl)-2-(trifluoromethyl)-1H-benzo[d]imidazole-5-carboxamide |
| I-94 | 1-(5-cyano-2-fluorobenzyl)-N-(4-(ethylsulfonyl)benzyl)-2-(trifluoromethyl)-1H-benzo[d]imidazole-5-carboxamide |
| I-95 | 1-(benzofuran-4-ylmethyl)-N-(4-(ethylsulfonyl)benzyl)-2-(trifluoromethyl)-1H-benzo[d]imidazole-5-carboxamide |
| I-96 | 1-((2,3-dihydrobenzofuran-7-yl)methyl)-N-(4-(ethylsulfonyl)benzyl)-2-(trifluoromethyl)-1H-benzo[d]imidazole-5-carboxamide |
| I-97 | 1-((1H-indazol-4-yl)methyl)-N-(4-(ethylsulfonyl)benzyl)-2-(trifluoromethyl)-1H-benzo[d]imidazole-5-carboxamide |
| I-98 | 1-(benzo[d][1,3]dioxol-4-ylmethyl)-N-(4-(ethylsulfonyl)benzyl)-2-(trifluoromethyl)-1H-benzo[d]imidazole-5-carboxamide |
| I-99 | methyl 3-((5-((4-(ethylsulfonyl)benzyl)carbamoyl)-2-(trifluoromethyl)-1H-benzo[d]imidazol-1-yl)methyl)benzoate |
| I-100 | 1-((1H-pyrrolo[2,3-c]pyridin-4-yl)methyl)-N-(4-(ethylsulfonyl)benzyl)-2-(trifluoromethyl)-1H-benzo[d]imidazole-5-carboxamide |
| I-101 | (R)-2-cyclopropyl-1-((2,2-dimethyl-2,3-dihydrobenzofuran-7-yl)methyl)-N-(1-(4-(ethylsulfonyl)phenyl)-2-hydroxyethyl)-1H-benzo[d]imidazole-5-carboxamide |

TABLE 1-continued

| Cpd No | Name |
|---|---|
| I-102 | (R)-2-cyclopropyl-1-((2,3-dihydrobenzofuran-7-yl)methyl)-N-(1-(4-(ethylsulfonyl)phenyl)-2-hydroxyethyl)-1H-benzo[d]imidazole-5-carboxamide |
| I-103 | 2-cyclopropyl-1-(3,5-dimethoxybenzyl)-N-(4-(ethylsulfonyl)benzyl)-1H-benzo[d]imidazole-5-carboxamide |
| I-104 | 2-cyclopropyl-N-(4-(ethylsulfonyl)benzyl)-1-(4-(trifluoromethoxy)benzyl)-1H-benzo[d]imidazole-5-carboxamide |
| I-105 | 2-cyclopropyl-1-((2,2-difluorobenzo[d][1,3]dioxol-5-yl)methyl)-N-(4-(ethylsulfonyl)benzyl)-1H-benzo[d]imidazole-5-carboxamide |
| I-106 | 2-cyclopropyl-N-(4-(ethylsulfonyl)benzyl)-1-(2-(trifluoromethoxy)benzyl)-1H-benzo[d]imidazole-5-carboxamide |
| I-107 | tert-butyl (R)-3-((2-cyclopropyl-5-((4-(ethylsulfonyl)benzyl)carbamoyl)-1H-benzo[d]imidazol-1-yl)methyl)pyrrolidine-1-carboxylate |
| I-108 | tert-butyl (R)-2-((2-cyclopropyl-5-((4-(ethylsulfonyl)benzyl)carbamoyl)-1H-benzo[d]imidazol-1-yl)methyl)pyrrolidine-1-carboxylate |
| I-109 | 2-cyclopropyl-N-(4-(ethylsulfonyl)benzyl)-1-(3-(trifluoromethoxy)benzyl)-1H-benzo[d]imidazole-5-carboxamide |
| I-110 | 2-cyclopropyl-N-(4-(ethylsulfonyl)benzyl)-1-(2-methoxy-3-(trifluoromethyl)benzyl)-1H-benzo[d]imidazole-5-carboxamide |
| I-111 | 2-cyclopropyl-N-(4-(ethylsulfonyl)benzyl)-1-((1-(2,2,2-trifluoroethyl)-1H-pyrazol-4-yl)methyl)-1H-benzo[d]imidazole-5-carboxamide |
| I-112 | 1-(3-cyanobenzyl)-2-cyclopropyl-N-(4-(ethylsulfonyl)benzyl)-1H-benzo[d]imidazole-5-carboxamide |
| I-113 | 2-cyclopropyl-1-(3-(difluoromethoxy)benzyl)-N-(4-(ethylsulfonyl)benzyl)-1H-benzo[d]imidazole-5-carboxamide |
| I-114 | 2-cyclopropyl-N-(4-(ethylsulfonyl)benzyl)-1-((1-(2,2,2-trifluoroethyl)-1H-pyrazol-3-yl)methyl)-1H-benzo[d]imidazole-5-carboxamide |
| I-115 | 2-cyclopropyl-N-(4-(ethylsulfonyl)benzyl)-1-(3-methoxy-5-(trifluoromethoxy)benzyl)-1H-benzo[d]imidazole-5-carboxamide |
| I-116 | (S)-2-cyclopropyl-1-(1-(2,2-difluorobenzo[d][1,3]dioxol-4-yl)ethyl)-N-(4-(ethylsulfonyl)benzyl)-1H-benzo[d]imidazole-5-carboxamide |
| I-117 | 2-cyclopropyl-N-(4-(ethylsulfonyl)benzyl)-1-((6-oxo-1-(2,2,2-trifluoroethyl)-1,6-dihydropyridin-3-yl)methyl)-1H-benzo[d]imidazole-5-carboxamide |
| I-118 | 2-cyclopropyl-1-((2,2-dimethyl-2,3-dihydrobenzofuran-7-yl)methyl)-N-(4-(ethylsulfonyl)benzyl)-1H-benzo[d]imidazole-5-carboxamide |
| I-119 | 2-cyclopropyl-1-(2,3-dimethoxybenzyl)-N-(4-(ethylsulfonyl)benzyl)-1H-benzo[d]imidazole-5-carboxamide |
| I-120 | 2-(4-((1-((2,2-difluorobenzo[d][1,3]dioxol-4-yl)methyl)-2-(trifluoromethyl)-1H-benzo[d]imidazole-5-carboxamido)methyl)cyclohexyl)acetic acid |
| I-121 | N-((1H-benzo[d][1,2,3]triazol-6-yl)methyl)-1-((2,2-difluorobenzo[d][1,3]dioxol-4-yl)methyl)-2-(trifluoromethyl)-1H-benzo[d]imidazole-5-carboxamide |
| I-122 | (R)-N-(1-(4-cyanophenyl)-2-hydroxyethyl)-1-((2,2-difluorobenzo[d][1,3]dioxol-4-yl)methyl)-2-(trifluoromethyl)-1H-benzo[d]imidazole-5-carboxamide |
| I-123 | (R)-1-((2,2-difluorobenzo[d][1,3]dioxol-4-yl)methyl)-N-(1-(4-(ethylsulfonyl)-2-fluorophenyl)-2-hydroxyethyl)-2-(trifluoromethyl)-1H-benzo[d]imidazole-5-carboxamide |
| I-124 | 1-(3,5-dimethoxybenzyl)-N-(4-((2-hydroxyethyl)sulfonyl)benzyl)-2-(trifluoromethyl)-1H-benzo[d]imidazole-5-carboxamide |
| I-125.1 | (S)-1-(1-(2,2-difluorobenzo[d][1,3]dioxol-4-yl)ethyl)-2-ethyl-N-(4-(ethylsulfonyl)benzyl)-1H-benzo[d]imidazole-5-carboxamide |
| I-125.2 | (R)-1-(1-(2,2-difluorobenzo[d][1,3]dioxol-4-yl)ethyl)-2-ethyl-N-(4-(ethylsulfonyl)benzyl)-1H-benzo[d]imidazole-5-carboxamide |
| I-126 | 1-((2,2-difluorobenzo[d][1,3]dioxol-4-yl)methyl)-N-(4-(ethylsulfonyl)-2-hydroxybenzyl)-2-(trifluoromethyl)-1H-benzo[d]imidazole-5-carboxamide |
| I-127 | methyl 2-((4-((1-((1H-indazol-4-yl)methyl)-2-(trifluoromethyl)-1H-benzo[d]imidazole-5-carboxamido)methyl)piperidin-1-yl)sulfonyl)acetate |
| I-128 | 1-(3,5-dimethoxybenzyl)-N-((5-(ethylsulfonyl)pyridin-2-yl)methyl)-2-(trifluoromethyl)-1H-benzo[d]imidazole-5-carboxamide |
| I-129 | 1-((2,2-difluorobenzo[d][1,3]dioxol-4-yl)methyl)-N-((4-oxo-1,4-dihydroquinolin-7-yl)methyl)-2-(trifluoromethyl)-1H-benzo[d]imidazole-5-carboxamide |
| I-130.1 | (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide |
| I-130.2 | (S)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide |
| I-131.1 | (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide |

TABLE 1-continued

| Cpd No | Name |
|---|---|
| I-131.2 | (S)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide |
| I-132.1 | (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide |
| I-132.2 | (S)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide |
| I-133.1 | (R)-2-cyclopropyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide |
| I-133.2 | (S)-2-cyclopropyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide |
| I-134.1 | (R)-1-((2,2-difluorobenzo[d][1,3]dioxol-4-yl)methyl)-N-(1-(5-(ethylsulfonyl)pyridin-2-yl)-2-hydroxyethyl)-2-(1-fluorocyclopropyl)-1H-benzo[d]imidazole-5-carboxamide |
| I-134.2 | (S)-1-((2,2-difluorobenzo[d][1,3]dioxol-4-yl)methyl)-N-(1-(5-(ethylsulfonyl)pyridin-2-yl)-2-hydroxyethyl)-2-(1-fluorocyclopropyl)-1H-benzo[d]imidazole-5-carboxamide |
| I-135 | (R)-1-((2,2-difluorobenzo[d][1,3]dioxol-4-yl)methyl)-N-(2-hydroxy-1-(5-(methylsulfonyl)pyridin-2-yl)ethyl)-2-(trifluoromethyl)-1H-benzo[d]imidazole-5-carboxamide |
| I-136 | N-(4-(ethylsulfonyl)benzyl)-1-(2-fluoro-3-methoxybenzyl)-2-(trifluoromethyl)-1H-benzo[d]imidazole-5-carboxamide |
| I-137 | N-(4-(ethylsulfonyl)benzyl)-1-((1-methyl-1H-indazol-7-yl)methyl)-2-(trifluoromethyl)-1H-benzo[d]imidazole-5-carboxamide |
| I-138 | N-(4-(ethylsulfonyl)benzyl)-1-((4-methyl-6-(trifluoromethyl)pyrimidin-2-yl)methyl)-2-(trifluoromethyl)-1H-benzo[d]imidazole-5-carboxamide |
| I-139 | N-(4-(ethylsulfonyl)benzyl)-1-((2-methyl-2H-indazol-7-yl)methyl)-2-(trifluoromethyl)-1H-benzo[d]imidazole-5-carboxamide |
| I-140 | 1-((1,2-dimethyl-1H-benzo[d]imidazol-7-yl)methyl)-N-(4-(ethylsulfonyl)benzyl)-2-(trifluoromethyl)-1H-benzo[d]imidazole-5-carboxamide |
| I-141 | N-(4-(ethylsulfonyl)benzyl)-1-((1-methyl-1H-indazol-4-yl)methyl)-2-(trifluoromethyl)-1H-benzo[d]imidazole-5-carboxamide |
| I-142 | 1-((1H-indazol-7-yl)methyl)-N-(4-(ethylsulfonyl)benzyl)-2-(trifluoromethyl)-1H-benzo[d]imidazole-5-carboxamide |
| I-143 | N-(4-(ethylsulfonyl)benzyl)-1-((2-methyl-2H-indazol-4-yl)methyl)-2-(trifluoromethyl)-1H-benzo[d]imidazole-5-carboxamide |
| I-144 | N-(4-(ethylsulfonyl)benzyl)-1-((6-oxo-1-(2,2,2-trifluoroethyl)-1,6-dihydropyridin-2-yl)methyl)-2-(trifluoromethyl)-1H-benzo[d]imidazole-5-carboxamide |
| I-145 | tert-butyl 4-((5-((4-(ethylsulfonyl)benzyl)carbamoyl)-2-(trifluoromethyl)-1H-benzo[d]imidazol-1-yl)methyl)piperidine-1-carboxylate |
| I-146 | N-(4-(ethylsulfonyl)benzyl)-1-((1-methyl-2-oxo-1,2-dihydropyridin-3-yl)methyl)-2-(trifluoromethyl)-1H-benzo[d]imidazole-5-carboxamide |
| I-147 | 1-(benzo[d]oxazol-4-ylmethyl)-N-(4-(ethylsulfonyl)benzyl)-2-(trifluoromethyl)-1H-benzo[d]imidazole-5-carboxamide |
| I-148 | 2-cyclopropyl-1-((2,3-dihydrobenzo[b][1,4]dioxin-5-yl)methyl)-N-(4-(ethylsulfonyl)benzyl)-1H-benzo[d]imidazole-5-carboxamide |
| I-149 | (R)-2-cyclopropyl-1-(1-(2,2-difluorobenzo[d][1,3]dioxol-4-yl)ethyl)-N-(4-(ethylsulfonyl)benzyl)-1H-benzo[d]imidazole-5-carboxamide |
| I-150 | 1-benzyl-N-(4-(ethylsulfonyl)benzyl)-2-methyl-1H-benzo[d]imidazole-5-carboxamide |
| I-151 | 1-(benzo[c][1,2,5]oxadiazol-4-ylmethyl)-N-(4-(ethylsulfonyl)benzyl)-2-(trifluoromethyl)-1H-benzo[d]imidazole-5-carboxamide |
| I-152 | 1-(benzo[d]oxazol-7-ylmethyl)-N-(4-(ethylsulfonyl)benzyl)-2-(trifluoromethyl)-1H-benzo[d]imidazole-5-carboxamide |
| I-153 | 2-cyclopropyl-N-(4-(ethylsulfonyl)benzyl)-1-(3-hydroxy-5-(trifluoromethoxy)benzyl)-1H-benzo[d]imidazole-5-carboxamide |
| I-154 | 2-cyclopropyl-1-(2,3-dihydroxybenzyl)-N-(4-(ethylsulfonyl)benzyl)-1H-benzo[d]imidazole-5-carboxamide |
| I-155 | N-(4-(ethylsulfonyl)benzyl)-1-((1-(2,2,2-trifluoroethyl)piperidin-4-yl)methyl)-2-(trifluoromethyl)-1H-benzo[d]imidazole-5-carboxamide |
| I-156 | (S)-2-cyclopropyl-N-(4-(ethylsulfonyl)benzyl)-1-((1-(2,2,2-trifluoroethyl)pyrrolidin-3-yl)methyl)-1H-benzo[d]imidazole-5-carboxamide |
| I-157 | (R)-2-cyclopropyl-N-(4-(ethylsulfonyl)benzyl)-1-((1-(2,2,2-trifluoroethyl)pyrrolidin-2-yl)methyl)-1H-benzo[d]imidazole-5-carboxamide |
| I-158 | N-(4-(ethylsulfonyl)benzyl)-1-((1-(5-fluoropyrimidin-2-yl)piperidin-4-yl)methyl)-2-(trifluoromethyl)-1H-benzo[d]imidazole-5-carboxamide |
| I-159 | (R)-2-cyclopropyl-N-(4-(ethylsulfonyl)benzyl)-1-((1-(5-fluoropyrimidin-2-yl)pyrrolidin-3-yl)methyl)-1H-benzo[d]imidazole-5-carboxamide |

TABLE 1-continued

| Cpd No | Name |
|---|---|
| I-160 | (R)-2-cyclopropyl-N-(4-(ethylsulfonyl)benzyl)-1-((1-(5-fluoropyrimidin-2-yl)pyrrolidin-2-yl)methyl)-1H-benzo[d]imidazole-5-carboxamide |
| I-161 | 2-((1-((2,2-difluorobenzo[d][1,3]dioxol-4-yl)methyl)-2-(trifluoromethyl)-1H-benzo[d]imidazole-5-carboxamido)methyl)-5-(ethylsulfonyl)pyridine 1-oxide |
| I-162 | 1-((2,2-difluorobenzo[d][1,3]dioxol-4-yl)methyl)-2-(dimethylamino)-N-(4-(ethylsulfonyl)benzyl)-1H-benzo[d]imidazole-5-carboxamide |
| I-163 | 1-((2,2-difluorobenzo[d][1,3]dioxol-4-yl)methyl)-N-((1-((2-hydroxyethyl)sulfonyl)piperidin-4-yl)methyl)-2-(trifluoromethyl)-1H-benzo[d]imidazole-5-carboxamide |
| I-164.1 and I-164.2[c] | (R)-1-((2,2-difluorobenzo[d][1,3]dioxol-4-yl)methyl)-N-(2-hydroxy-1-(1-(methylsulfonyl)piperidin-4-yl)ethyl)-2-(trifluoromethyl)-1H-benzo[d]imidazole-5-carboxamide and (S)-1-((2,2-difluorobenzo[d][1,3]dioxol-4-yl)methyl)-N-(2-hydroxy-1-(1-(methylsulfonyl)piperidin-4-yl)ethyl)-2-(trifluoromethyl)-1H-benzo[d]imidazole-5-carboxamide |
| I-165 | (S)-3-(1-((2,2-difluorobenzo[d][1,3]dioxol-4-yl)methyl)-2-(trifluoromethyl)-1H-benzo[d]imidazole-5-carboxamido)-3-(4-(ethylsulfonyl)phenyl)propanoic acid |
| I-166 | (R)-2-(2-(1-((2,2-difluorobenzo[d][1,3]dioxol-4-yl)methyl)-2-(trifluoromethyl)-1H-benzo[d]imidazole-5-carboxamido)-2-(4-(ethylsulfonyl)phenyl)ethoxy)acetic acid |
| I-167 | (S)-1-((2,2-difluorobenzo[d][1,3]dioxol-4-yl)methyl)-N-(1-(4-(ethylsulfonyl)phenyl)-3-(methylamino)-3-oxopropyl)-2-(trifluoromethyl)-1H-benzo[d]imidazole-5-carboxamide |
| I-168 | (S)-N-(3-amino-1-(4-(ethylsulfonyl)phenyl)-3-oxopropyl)-1-((2,2-difluorobenzo[d][1,3]dioxol-4-yl)methyl)-2-(trifluoromethyl)-1H-benzo[d]imidazole-5-carboxamide |
| I-169 | 1-((2,2-difluorobenzo[d][1,3]dioxol-4-yl)methyl)-N-(4-((2-(methylamino)-2-oxoethyl)sulfonyl)benzyl)-2-(trifluoromethyl)-1H-benzo[d]imidazole-5-carboxamide |
| I-170 | N-(1-((2,2-difluorobenzo[d][1,3]dioxol-4-yl)methyl)-2-(trifluoromethyl)-1H-benzo[d]imidazol-5-yl)-2-(4-(ethylsulfonyl)phenyl)-2-hydroxyacetamide |
| I-170.1 and I-170.2[c] | (S)-N-(1-((2,2-difluorobenzo[d][1,3]dioxol-4-yl)methyl)-2-(trifluoromethyl)-1H-benzo[d]imidazol-5-yl)-2-(4-(ethylsulfonyl)phenyl)-2-hydroxyacetamide and (R)-N-(1-((2,2-difluorobenzo[d][1,3]dioxol-4-yl)methyl)-2-(trifluoromethyl)-1H-benzo[d]imidazol-5-yl)-2-(4-(ethylsulfonyl)phenyl)-2-hydroxyacetamide |
| I-171 | 1-((2,2-difluorobenzo[d][1,3]dioxol-4-yl)methyl)-N-((4-methyl-1-(methylsulfonyl)-1,4-diazepan-5-yl)methyl)-2-(trifluoromethyl)-1H-benzo[d]imidazole-5-carboxamide |
| I-172 | 1-((2,3-dihydrobenzofuran-4-yl)methyl)-N-(4-(ethylsulfonyl)benzyl)-2-(trifluoromethyl)-1H-benzo[d]imidazole-5-carboxamide |
| I-173 | methyl 1-((2,2-difluorobenzo[d][1,3]dioxol-4-yl)methyl)-5-((4-(ethylsulfonyl)benzyl)carbamoyl)-1H-benzo[d]imidazole-2-carboxylate |
| I-174 | 1-((2,2-difluorobenzo[d][1,3]dioxol-4-yl)methyl)-N-(2-(4-(ethylsulfonyl)phenyl)-1,3-dihydroxypropan-2-yl)-2-(trifluoromethyl)-1H-benzo[d]imidazole-5-carboxamide |

[a]The compound was prepared from (R)-tetrahydrofuran-2-carboxylic acid but the integrity of the stereocenter in the product was not established.
[b]The compound was prepared from (S)-tetrahydrofuran-2-carboxylic acid but the integrity of the stereocenter in the product was not established.
[c]The isomers were separated by chromatography on a chiral column. The stereochemical configuration of the isomers was not determined.

Further provided is a crystalline hydrochloride salt form of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide (I-130.1). See Example 3 below.

In one aspect, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by at least three X-ray powder diffraction peaks at 2Θ angles selected from 11.20°, 12.60°, 17.86°, 19.04°, 21.12°, and 21.71°. Alternatively, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by at least four X-ray powder diffraction peaks at 2Θ angles selected from 11.20°, 12.60°, 17.86°, 19.04°, 21.12°, and 21.71°. In another alternative, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by at least five X-ray powder diffraction peaks at 2Θ angles selected from 11.20°, 12.60°, 17.86°, 19.04°, 21.12°, and 21.71°. In yet another alternative, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by X-ray powder diffraction peaks at 2Θ angles 11.20°, 12.60°, 17.86°, 19.04°, 21.12°, and 21.71°. In yet another embodiment, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by X-ray powder diffraction peaks at 2Θ angles selected from Table 2. In yet another embodiment, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by an X-ray powder diffraction pattern substantially similar to FIG. 1.

TABLE 2

| 2-Theta | d Value | Intensity | Rel. Intensity (%) |
|---|---|---|---|
| 7.31 | 12.08 | 235 | 12 |
| 7.75 | 11.4 | 433 | 22.1 |
| 8.95 | 9.87 | 386 | 19.7 |
| 10.86 | 8.14 | 304 | 15.5 |
| 11.2 | 7.879 | 1960 | 100 |
| 12.1 | 7.31 | 947 | 48.3 |
| 12.60 | 7.02 | 1590 | 81.2 |
| 13.43 | 6.63 | 576 | 29.4 |
| 14.79 | 5.98 | 634 | 32.4 |
| 15.42 | 5.74 | 964 | 49.2 |
| 17.39 | 5.10 | 349 | 17.8 |
| 17.90 | 4.96 | 1201 | 61.3 |
| 18.4 | 4.82 | 414 | 21.1 |
| 19.04 | 4.66 | 1887 | 96.3 |
| 19.44 | 4.56 | 959 | 48.9 |
| 20.27 | 4.38 | 282 | 14.4 |
| 20.60 | 4.31 | 532 | 27.1 |
| 21.19 | 4.19 | 1018 | 51.9 |
| 21.71 | 4.09 | 1456 | 74.3 |
| 22.79 | 3.90 | 693 | 35.4 |
| 23.14 | 3.84 | 529 | 27.0 |
| 23.90 | 3.72 | 725 | 37.0 |
| 24.86 | 3.58 | 614 | 31.3 |
| 25.11 | 3.54 | 511 | 26.1 |
| 25.67 | 3.47 | 511 | 26.1 |
| 26.46 | 3.37 | 307 | 15.6 |
| 26.71 | 3.33 | 464 | 23.7 |
| 27.59 | 3.23 | 270 | 13.8 |
| 28.26 | 3.16 | 604 | 30.8 |
| 29.55 | 3.02 | 398 | 20.3 |
| 30.86 | 2.90 | 285 | 14.5 |
| 31.34 | 2.85 | 49 | 2.5 |
| 32.90 | 2.72 | 182 | 9.3 |
| 33.62 | 2.66 | 138 | 7.0 |
| 33.68 | 2.67 | 137 | 7.0 |
| 33.83 | 2.65 | 138 | 7.0 |
| 33.81 | 2.65 | 119 | 6.0 |
| 34.84 | 2.57 | 57 | 2.9 |
| 38.75 | 2.32 | 118 | 6.0 |

In one aspect, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by at least three X-ray powder diffraction peaks at 2Θ angles selected from 11.20°, 12.60°, 17.86°, 19.04°, 21.19°, and 21.71°. Alternatively, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by at least four X-ray powder diffraction peaks at 2Θ angles selected from 11.20°, 12.60°, 17.86°, 19.04°, 21.19°, and 21.71°. In another alternative, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by at least five X-ray powder diffraction peaks at 2Θ angles selected from 11.20°, 12.60°, 17.86°, 19.04°, 21.19°, and 21.71°. In yet another alternative, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by X-ray powder diffraction peaks at 2Θ angles 11.20°, 12.60°, 17.86°, 19.04°, 21.19°, and 21.710. In yet another embodiment, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by X-ray powder diffraction peaks at 2Θ angles selected from Table 2-1.

TABLE 2-1

| 2-Theta | d Value | Intensity | Rel. Intensity (%) |
|---|---|---|---|
| 7.31 | 12.08 | 235 | 12.0 |
| 7.75 | 11.40 | 433 | 22.1 |
| 8.95 | 9.87 | 386 | 19.7 |
| 10.86 | 8.14 | 304 | 15.5 |
| 11.20 | 7.89 | 1960 | 100 |
| 12.10 | 7.31 | 947 | 48.3 |
| 12.60 | 7.02 | 1590 | 81.2 |
| 13.34 | 6.63 | 576 | 29.4 |
| 14.79 | 5.98 | 634 | 32.4 |
| 15.42 | 5.74 | 964 | 49.2 |
| 17.39 | 5.10 | 349 | 17.8 |
| 17.86 | 4.96 | 1201 | 61.3 |
| 18.40 | 4.82 | 414 | 21.1 |
| 19.04 | 4.66 | 1887 | 96.3 |
| 19.44 | 4.56 | 959 | 48.9 |
| 20.27 | 4.38 | 282 | 14.4 |
| 20.60 | 4.31 | 532 | 27.1 |
| 21.19 | 4.19 | 1018 | 51.9 |
| 21.71 | 4.09 | 1456 | 74.3 |
| 22.79 | 3.90 | 693 | 35.4 |
| 23.14 | 3.84 | 529 | 27.0 |
| 23.90 | 3.72 | 725 | 37.0 |
| 24.86 | 3.58 | 614 | 31.3 |
| 25.11 | 3.54 | 511 | 26.1 |
| 25.67 | 3.47 | 511 | 26.1 |
| 26.46 | 3.37 | 307 | 15.6 |
| 26.71 | 3.33 | 464 | 23.7 |
| 27.59 | 3.23 | 270 | 13.8 |
| 28.26 | 3.16 | 604 | 30.8 |
| 29.55 | 3.02 | 398 | 20.3 |
| 30.86 | 2.90 | 285 | 14.5 |
| 31.34 | 2.85 | 49 | 2.5 |
| 32.90 | 2.72 | 182 | 9.3 |
| 33.62 | 2.66 | 138 | 7.0 |
| 33.68 | 2.66 | 137 | 7.0 |
| 33.83 | 2.65 | 138 | 7.0 |
| 33.81 | 2.65 | 119 | 6.0 |
| 34.84 | 2.57 | 57 | 2.9 |
| 38.75 | 2.32 | 118 | 6.0 |

In one aspect, the crystalline HCl salt of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is at least 50% pure by weight, at least 75% pure by weight, at least 80% pure by weight, at least 90% pure by weight, at least 95% pure by weight, or at least 98% pure by weight.

Figure 2:
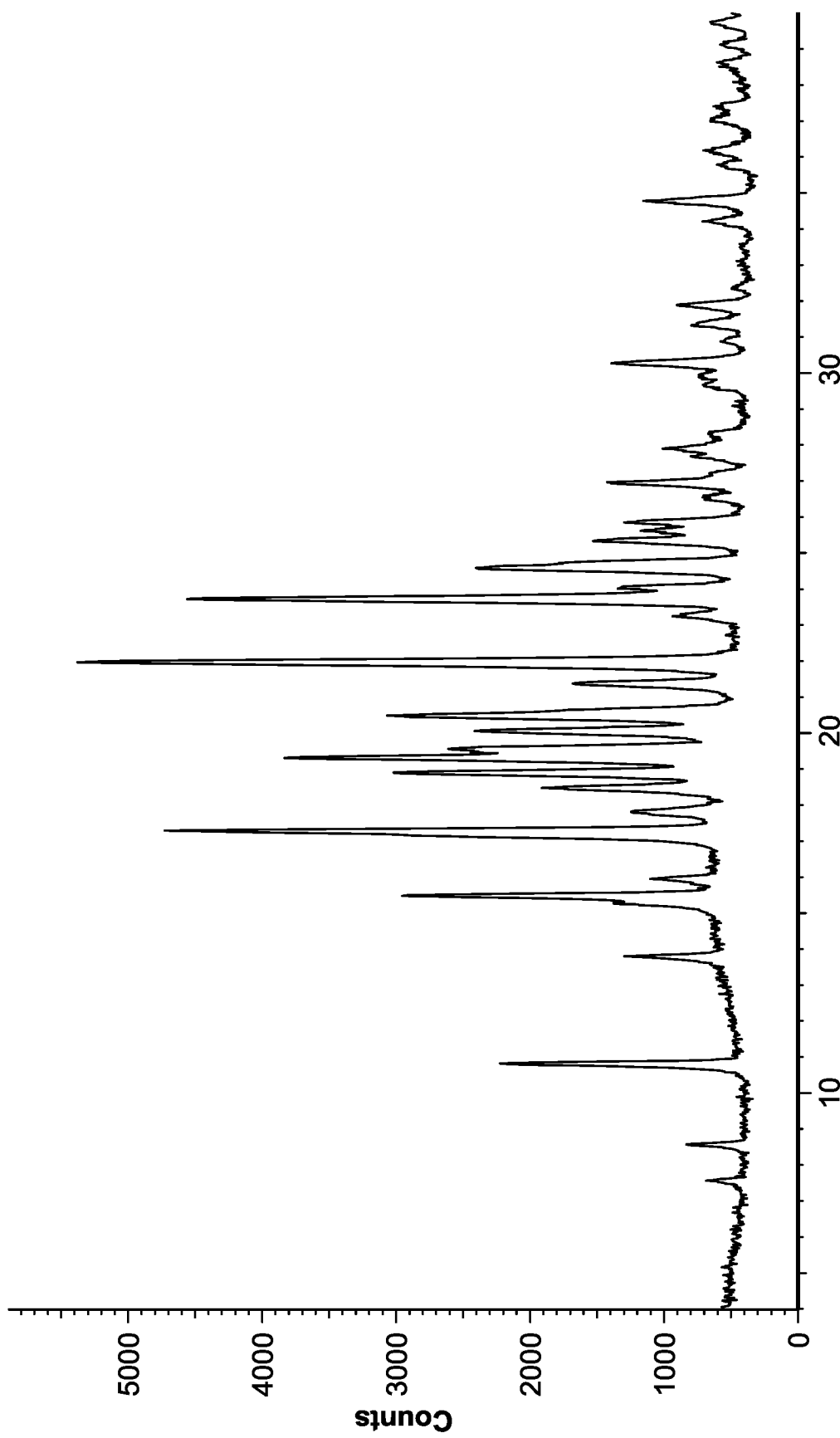
FIG. 2 depicts a powder X-ray diffractogram of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide (I-130.1) free base.

Further provided is a crystalline form of the free base of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide (I-130.1). See Example 3 below. In one aspect, the crystalline form of the free base of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by at least three X-ray powder diffraction peaks at 2Θ angles selected from 17.25°, 18.89°, 19.33°, 20.49°, 21.97°, and 23.73°. Alternatively, the crystalline form of the free base of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by at least four X-ray powder diffraction peaks at 2Θ angles selected from 17.25°, 18.89°, 19.33°, 20.49°, 21.97°, and 23.73°. In another alternative, the crystalline form of the free base of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by at least five X-ray powder diffraction peaks at 2Θ angles selected from 17.25°, 18.89°, 19.33°, 20.49°, 21.97°, and 23.73°. In yet another alternative, the crystalline form of the free base of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by X-ray powder diffraction peaks at 2Θ angles 17.25°, 18.89°, 19.33°, 20.49°, 21.97°, and 23.73°. In yet another embodiment, the crystalline form of the free base of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by X-ray powder diffraction peaks at 2Θ angles selected from Table 2a. In yet another embodiment, the crystalline form of the free base of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is characterized by an X-ray powder diffraction pattern substantially similar to FIG. 2.

TABLE 2a

| 2-Theta | d Value | Intensity | Rel. Intensity (%) |
|---|---|---|---|
| 7.55 | 11.70 | 197 | 4.1 |
| 8.56 | 10.33 | 408 | 8.4 |
| 10.81 | 8.18 | 1733 | 35.7 |
| 13.78 | 6.42 | 599 | 12.3 |
| 15.47 | 5.72 | 2115 | 43.6 |
| 15.94 | 5.56 | 398 | 8.2 |
| 17.25 | 5.14 | 3538 | 72.9 |
| 17.81 | 4.98 | 621 | 12.8 |
| 18.48 | 4.80 | 1280 | 26.4 |
| 18.89 | 4.69 | 2407 | 49.6 |
| 19.33 | 4.59 | 3149 | 64.9 |
| 19.51 | 4.55 | 1838 | 37.9 |
| 20.06 | 4.42 | 1841 | 37.9 |
| 20.49 | 4.33 | 2492 | 51.3 |
| 21.37 | 4.15 | 1160 | 23.9 |
| 21.97 | 4.04 | 4853 | 100 |
| 23.27 | 3.82 | 358 | 7.4 |
| 23.73 | 3.75 | 4074 | 83.9 |
| 24.00 | 3.70 | 714 | 14.7 |
| 24.61 | 3.61 | 1852 | 38.2 |
| 25.35 | 3.51 | 1043 | 21.5 |
| 25.64 | 3.47 | 667 | 13.7 |
| 25.84 | 3.45 | 772 | 15.9 |
| 26.54 | 3.36 | 277 | 5.7 |
| 26.95 | 3.31 | 943 | 19.4 |
| 27.10 | 3.29 | 264 | 5.4 |
| 27.74 | 3.21 | 306 | 6.3 |
| 27.90 | 3.20 | 570 | 11.7 |
| 28.28 | 3.15 | 238 | 4.9 |
| 29.69 | 3.01 | 294 | 6.1 |
| 29.93 | 2.98 | 305 | 6.3 |
| 30.28 | 2.95 | 976 | 20.1 |
| 30.90 | 2.89 | 146 | 3 |
| 31.37 | 2.85 | 360 | 7.4 |
| 31.88 | 2.80 | 516 | 10.6 |
| 32.39 | 2.76 | 114 | 2.3 |
| 33.51 | 2.67 | 61.4 | 1.3 |
| 34.22 | 2.62 | 356 | 7.3 |
| 34.78 | 2.58 | 783 | 16.1 |
| 35.79 | 2.51 | 247 | 5.1 |
| 36.17 | 2.48 | 299 | 6.2 |
| 37.05 | 2.42 | 260 | 5.4 |
| 37.39 | 2.40 | 187 | 3.8 |
| 37.85 | 2.38 | 61.6 | 1.3 |
| 38.60 | 2.33 | 181 | 3.7 |
| 39.13 | 2.30 | 173 | 3.6 |
| 39.73 | 2.27 | 205 | 4.2 |

In one aspect, the crystalline form of the free base of (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide is at least 50% pure by weight, at least 75% pure by weight, at least 80% pure by weight, at least 90% pure by weight, at least 95% pure by weight, or at least 98% pure by weight.

Further provided is a crystalline Form I of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide (I-11.1) See Example 2 below.

Figure 3:
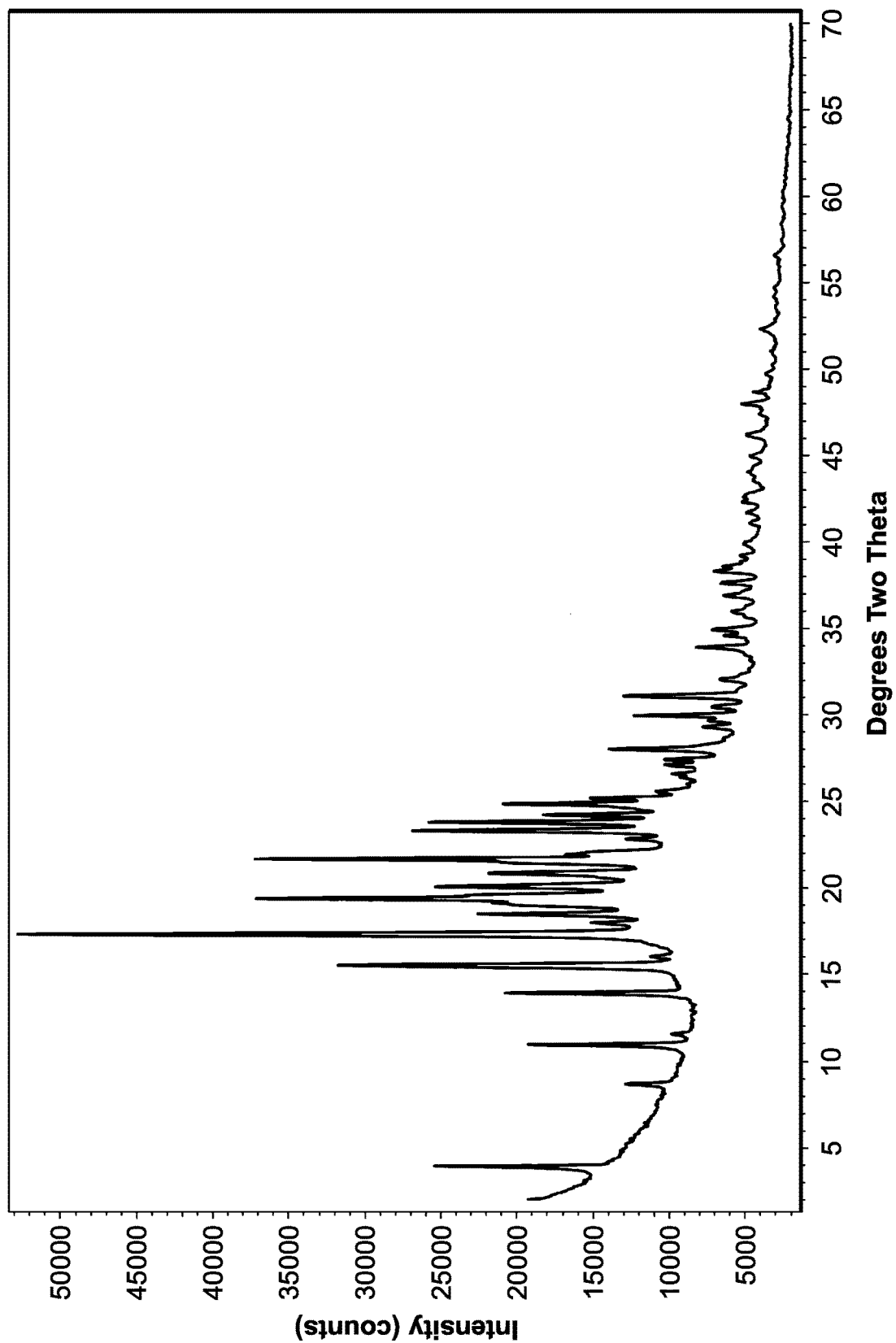
FIG. 3 depicts a powder X-ray diffractogram of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide (I-11.1) Form I.

In one aspect, crystalline Form I of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by at least three X-ray powder diffraction peaks at 2Θ angles selected from 15.52°, 17.30°, 19.39°, 21.68°, 23.32°, and 23.82°. Alternatively, crystalline Form I of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by at least four X-ray powder diffraction peaks at 2Θ angles selected from 15.52°, 17.30°, 19.39°, 21.68°, 23.32°, and 23.82°. In another alternative, crystalline Form I of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by at least five X-ray powder diffraction peaks at 2Θ angles selected from 15.52°, 17.30°, 19.39°, 21.68°, 23.32°, and 23.82°. In yet another alternative, crystalline Form I of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by X-ray powder diffraction peaks at 2Θ angles 15.52°, 17.30°, 19.39°, 21.68°, 23.32°, and 23.82°. In yet another embodiment, crystalline Form I of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by X-ray powder diffraction peaks at 2Θ angles selected from Table 2b. In yet another embodiment, crystalline Form I of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by an X-ray powder diffraction pattern substantially similar to FIG. 3.

TABLE 2b

| 2-Theta | Rel. Intensity (%) |
|---|---|
| 3.92 | 26.88 |
| 8.69 | 7.61 |
| 10.94 | 27.24 |
| 11.54 | 3.51 |
| 13.94 | 29.53 |
| 15.52 | 50.94 |
| 16.04 | 2.49 |
| 17.30 | 100.00 |
| 18.01 | 7.41 |
| 18.49 | 24.12 |
| 18.99 | 7.41 |
| 19.11 | 19.74 |
| 19.39 | 46.72 |
| 19.59 | 17.66 |
| 20.07 | 29.29 |
| 20.85 | 23.01 |
| 21.45 | 19.91 |
| 21.68 | 60.81 |
| 21.88 | 10.16 |
| 22.09 | 8.61 |
| 22.82 | 6.22 |
| 23.32 | 39.18 |

TABLE 2b-continued

| 2-Theta | Rel. Intensity (%) |
|---------|--------------------|
| 23.82 | 37.88 |
| 24.22 | 20.39 |
| 24.86 | 29.02 |
| 25.17 | 16.01 |
| 25.55 | 5.45 |
| 26.59 | 4.17 |
| 27.10 | 7.44 |
| 27.41 | 9.68 |
| 28.02 | 18.93 |
| 29.29 | 4.98 |
| 29.63 | 3.95 |
| 29.95 | 18.31 |
| 30.44 | 4.74 |
| 31.07 | 20.50 |
| 32.00 | 4.22 |
| 33.93 | 10.91 |
| 34.57 | 4.98 |
| 34.92 | 7.18 |
| 35.93 | 2.79 |
| 36.85 | 4.56 |
| 37.60 | 6.58 |
| 38.26 | 6.78 |
| 38.59 | 5.34 |
| 38.85 | 2.44 |
| 39.21 | 2.45 |
| 39.88 | 1.63 |
| 41.67 | 2.22 |
| 42.29 | 3.29 |
| 42.58 | 2.65 |
| 43.97 | 1.59 |
| 44.95 | 2.20 |
| 46.16 | 3.31 |
| 47.35 | 1.26 |
| 47.99 | 5.28 |
| 48.68 | 3.52 |
| 49.67 | 1.37 |
| 52.34 | 2.43 |
| 54.12 | 0.61 |
| 56.58 | 1.12 |

In one aspect, crystalline Form I of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is at least 50% pure by weight, at least 75% pure by weight, at least 80% pure by weight, at least 90% pure by weight, at least 95% pure by weight, or at least 98% pure by weight.

Further provided is a crystalline Form II of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide (I-11.1) See Example 2 below.

Figure 4:
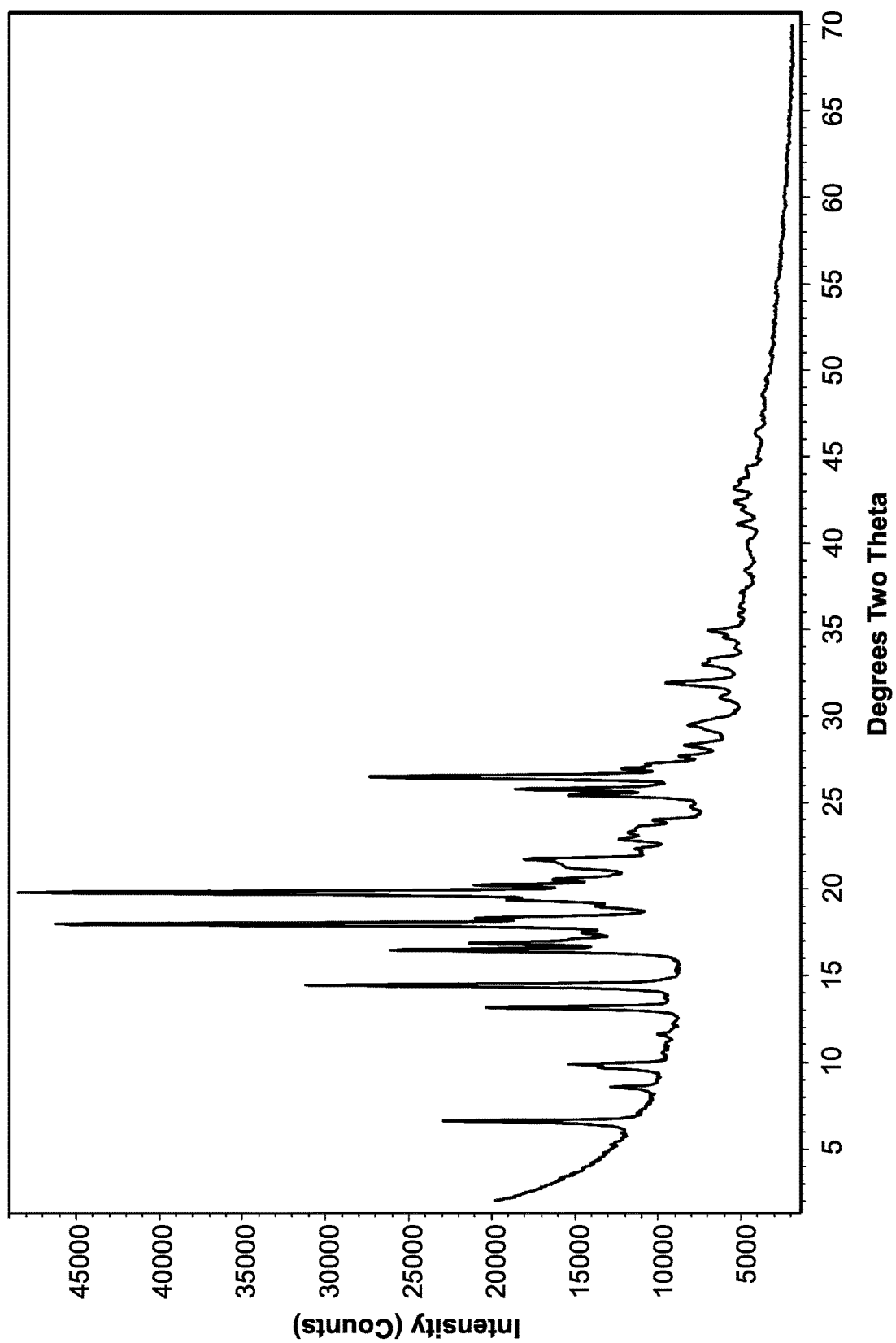
FIG. 4 depicts a powder X-ray diffractogram of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide (I-11.1) Form II.

In one aspect, crystalline Form II of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by at least three X-ray powder diffraction peaks at 2Θ angles selected from 13.18°, 14.46°, 16.47°, 17.97°, 19.80°, and 26.52°. Alternatively, crystalline Form II of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by at least four X-ray powder diffraction peaks at 2Θ angles selected from 13.18°, 14.46°, 16.47°, 17.97°, 19.80°, and 26.52°. In another alternative, crystalline Form II of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by at least five X-ray powder diffraction peaks at 2Θ angles selected from 13.18°, 14.46°, 16.47°, 17.97°, 19.80°, and 26.52°. In yet another alternative, crystalline Form II of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by X-ray powder diffraction peaks at 2Θ angles 13.18°, 14.46°, 16.47°, 17.97°, 19.80°, and 26.52°. In yet another embodiment, crystalline Form II of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by X-ray powder diffraction peaks at 2Θ angles selected from Table 2c. In yet another embodiment, crystalline Form II of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by an X-ray powder diffraction pattern substantially similar to FIG. 4.

TABLE 2c

| 2-Theta | Rel. Intensity (%) |
|---------|--------------------|
| 6.61 | 34.38 |
| 8.58 | 7.82 |
| 9.69 | 10.60 |
| 9.88 | 12.74 |
| 11.64 | 2.61 |
| 13.18 | 34.62 |
| 14.46 | 69.36 |
| 16.47 | 48.21 |
| 16.84 | 29.84 |
| 17.45 | 8.77 |
| 17.97 | 100.00 |
| 18.32 | 28.19 |
| 18.97 | 6.41 |
| 19.36 | 19.02 |
| 19.80 | 98.44 |
| 20.24 | 22.84 |
| 20.56 | 10.60 |
| 21.21 | 7.35 |
| 21.74 | 15.98 |
| 22.84 | 5.81 |
| 23.21 | 5.27 |
| 23.57 | 5.57 |
| 23.96 | 5.24 |
| 24.89 | 0.99 |
| 25.47 | 24.01 |
| 25.78 | 32.32 |
| 26.52 | 61.94 |
| 26.96 | 12.84 |
| 27.29 | 9.18 |
| 27.70 | 6.09 |
| 28.31 | 5.59 |
| 29.49 | 5.66 |
| 31.00 | 2.23 |
| 31.92 | 12.31 |
| 32.97 | 3.25 |
| 33.29 | 5.23 |
| 33.91 | 0.92 |
| 34.45 | 2.32 |
| 34.92 | 6.63 |
| 35.86 | 1.37 |
| 36.30 | 0.99 |
| 38.44 | 0.31 |
| 39.91 | 0.50 |
| 41.11 | 3.30 |
| 41.90 | 2.17 |
| 42.31 | 3.38 |
| 43.11 | 3.55 |
| 43.61 | 0.98 |
| 44.37 | 1.88 |
| 46.39 | 1.44 |
| 48.54 | 0.71 |

In one aspect, crystalline Form II of (R)-1-((2,2-difluorobenzo[d][1,3]dioxol-4-yl)methyl)-N-(1-(4-(ethylsulfonyl)phenyl)-2-(trifluoromethyl)-1H-benzo[d]imidazole-5-carboxamide is at least 50% pure by weight, at least 75% pure by weight, at least 80% pure by weight, at least 90% pure by weight, at least 95% pure by weight, or at least 98% pure by weight.

Further provided is a crystalline Form III of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide (I-11.1) See Example 2 below.

Figure 5:
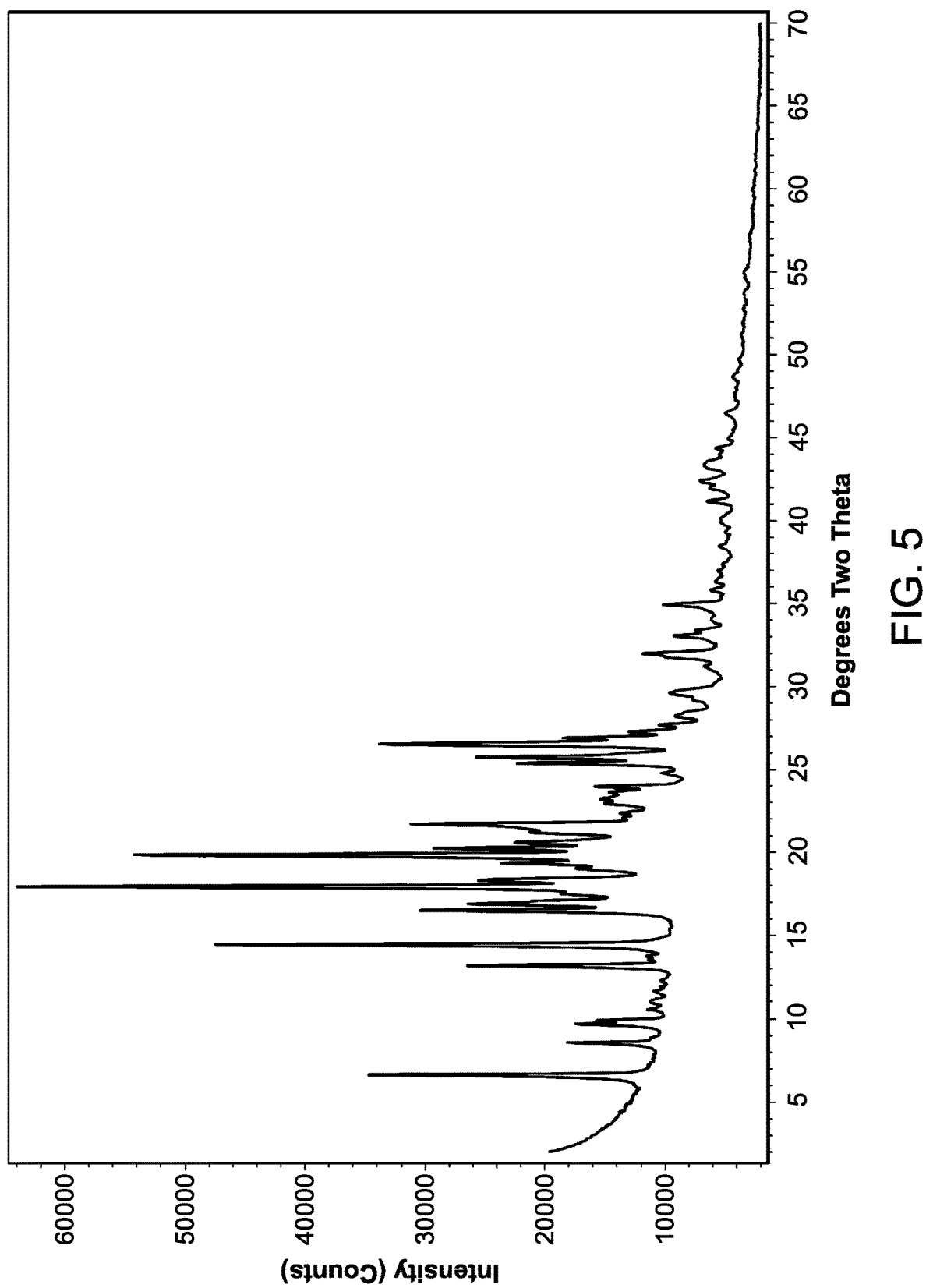
FIG. 5 depicts a powder X-ray diffractogram of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide (I-11.1) Form III.

In one aspect, crystalline Form III of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by at least three X-ray powder diffraction peaks at 2Θ angles selected from 6.62°, 14.48°, 16.53°, 17.96°, 19.89°, and 26.53°. Alternatively, crystalline Form III of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by at least four X-ray powder diffraction peaks at 2Θ angles selected from 6.62°, 14.48°, 16.53°, 17.96°, 19.89°, and 26.53°. In another alternative, crystalline Form III of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by at least five X-ray powder diffraction peaks at 2Θ angles selected from 6.62°, 14.48°, 16.53°, 17.96°, 19.89°, and 26.53°. In yet another alternative, crystalline Form III of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by X-ray powder diffraction peaks at 2Θ angles 6.62°, 14.48°, 16.53°, 17.96°, 19.89°, and 26.53°. In yet another embodiment, crystalline Form III of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by X-ray powder diffraction peaks at 2Θ angles selected from Table 2d. In yet another embodiment, crystalline Form III of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is characterized by an X-ray powder diffraction pattern substantially similar to FIG. 5.

TABLE 2d

| 2-Theta | Rel. Intensity (%) |
|---|---|
| 5.44 | 1.17 |
| 6.62 | 52.21 |
| 8.54 | 16.72 |
| 9.68 | 11.14 |
| 9.90 | 10.29 |
| 10.52 | 2.38 |
| 11.01 | 2.30 |
| 11.58 | 1.62 |
| 12.33 | 1.67 |
| 13.23 | 34.69 |
| 13.56 | 1.54 |
| 13.78 | 1.82 |
| 14.48 | 74.59 |
| 14.57 | 4.82 |
| 16.53 | 39.88 |
| 16.93 | 30.23 |
| 17.07 | 14.59 |
| 17.53 | 12.30 |
| 17.96 | 100.00 |
| 18.36 | 25.05 |
| 19.02 | 7.37 |
| 19.36 | 18.85 |
| 19.89 | 84.77 |
| 20.27 | 33.31 |
| 20.61 | 17.14 |
| 21.19 | 14.50 |
| 21.74 | 31.45 |
| 22.35 | 2.94 |
| 22.91 | 5.82 |
| 23.26 | 7.72 |
| 23.61 | 7.76 |
| 23.96 | 12.80 |
| 24.79 | 2.30 |
| 25.42 | 29.67 |
| 25.76 | 35.78 |
| 26.53 | 55.30 |
| 26.92 | 22.87 |
| 27.28 | 12.20 |
| 27.68 | 7.61 |
| 28.23 | 5.41 |
| 29.68 | 6.84 |
| 31.18 | 1.92 |
| 31.73 | 4.74 |
| 32.02 | 12.59 |
| 33.03 | 7.60 |
| 33.37 | 4.33 |
| 33.97 | 1.63 |
| 34.94 | 11.41 |
| 35.76 | 2.60 |
| 36.28 | 1.64 |
| 36.90 | 1.08 |
| 38.40 | 1.53 |
| 40.18 | 1.64 |
| 41.14 | 4.85 |
| 41.94 | 3.51 |
| 42.33 | 3.68 |
| 43.31 | 5.00 |
| 43.96 | 1.80 |
| 44.38 | 3.09 |
| 44.91 | 1.28 |
| 46.46 | 1.94 |
| 47.38 | 0.58 |
| 48.55 | 1.12 |
| 54.94 | 0.73 |

In one aspect, crystalline Form III of (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide is at least 50% pure by weight, at least 75% pure by weight, at least 80% pure by weight, at least 90% pure by weight, at least 95% pure by weight, or at least 98% pure by weight.

Further provided is a crystalline form of the HCl salt of (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide (I-131.1). See Example 4 below.

Figure 6:
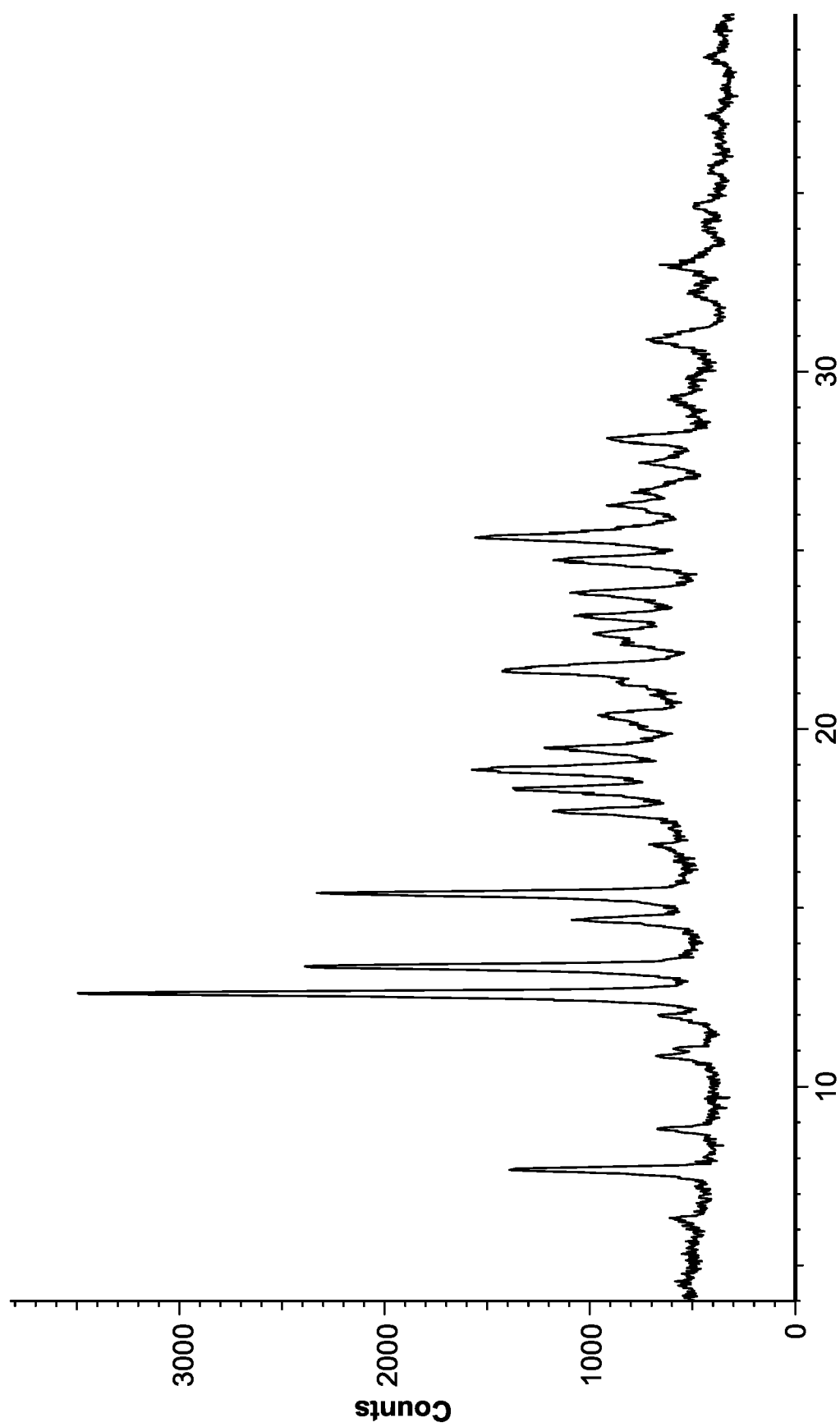
FIG. 6 depicts a powder X-ray diffractogram of (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide (I-131.1) HCl salt.

In one aspect, the crystalline form of the HCl salt of (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide is characterized by at least three X-ray powder diffraction peaks at 2Θ angles selected from 7.67°, 12.60°, 13.35°, 15.39°, 18.86°, and 25.380. Alternatively, the crystalline form of the HCl salt of (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide is characterized by at least four X-ray powder diffraction peaks at 2Θ angles selected from 7.67°, 12.60°, 13.35°, 15.39°, 18.86°, and 25.380. In another alternative, the crystalline form of the HCl salt of (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide is characterized by at least five X-ray powder diffraction peaks at 2Θ angles selected from 7.67°, 12.60°, 13.35°, 15.39°, 18.86°, and 25.38°. In yet another alternative, the crystalline form of the HCl salt of (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide is characterized by X-ray powder diffraction peaks at 2Θ angles 7.67°, 12.60°, 13.35°, 15.39°, 18.86°, and 25.38°. In yet another embodiment, the crystalline form of the HCl salt of (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide is characterized by X-ray powder diffraction peaks at 2θ angles selected from Table 2e. In yet another embodiment, the crystalline form of the HCl salt (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide is characterized by an X-ray powder diffraction pattern substantially similar to FIG. 6.

TABLE 2e

| 2-Theta | d Value | Intensity | Rel. Intensity (%) |
|---|---|---|---|
| 6.28 | 14.06 | 121 | 4.1 |
| 7.67 | 11.52 | 962 | 32.2 |
| 8.81 | 10.03 | 265 | 8.8 |
| 10.86 | 8.14 | 269 | 9 |
| 11.01 | 8.03 | 135 | 4.5 |
| 11.98 | 7.38 | 216 | 7.2 |
| 12.60 | 7.02 | 2992 | 100 |
| 13.35 | 6.63 | 1883 | 62.9 |
| 14.67 | 6.03 | 581 | 19.4 |
| 15.39 | 5.75 | 1714 | 57.3 |
| 16.73 | 5.29 | 132 | 4.4 |
| 17.70 | 5.01 | 583 | 19.5 |
| 18.32 | 4.84 | 738 | 24.7 |
| 18.86 | 4.70 | 962 | 32.2 |
| 19.45 | 4.56 | 552 | 18.4 |
| 20.37 | 4.36 | 326 | 10.9 |
| 21.33 | 4.16 | 276 | 9.2 |
| 21.66 | 4.10 | 821 | 27.4 |
| 22.45 | 3.96 | 268 | 8.9 |
| 22.66 | 3.92 | 423 | 14.1 |
| 23.15 | 3.84 | 451 | 15.1 |
| 23.81 | 3.73 | 509 | 17 |
| 24.73 | 3.60 | 641 | 21.4 |
| 25.38 | 3.51 | 1014 | 33.9 |
| 26.27 | 3.39 | 406 | 13.6 |
| 26.65 | 3.34 | 262 | 8.7 |
| 27.46 | 3.25 | 274 | 9.2 |
| 28.11 | 3.17 | 429 | 14.3 |
| 29.24 | 3.05 | 114 | 3.8 |
| 30.90 | 2.89 | 324 | 10.8 |
| 32.21 | 2.78 | 106 | 3.5 |
| 32.95 | 2.72 | 211 | 7.1 |
| 34.10 | 2.63 | 77.6 | 2.6 |
| 34.63 | 2.59 | 138 | 4.6 |
| 35.67 | 2.51 | 70.1 | 2.3 |
| 38.81 | 2.32 | 90.9 | 3 |
| 39.69 | 2.27 | 48.9 | 1.6 |

In one aspect, the crystalline form of the HCl salt (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide is at least 50% pure by weight, at least 75% pure by weight, at least 80% pure by weight, at least 90% pure by weight, at least 95% pure by weight, or at least 98% pure by weight.

Further provided is a crystalline form of (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide (I-132.1). See Example 5 below.

Figure 7:
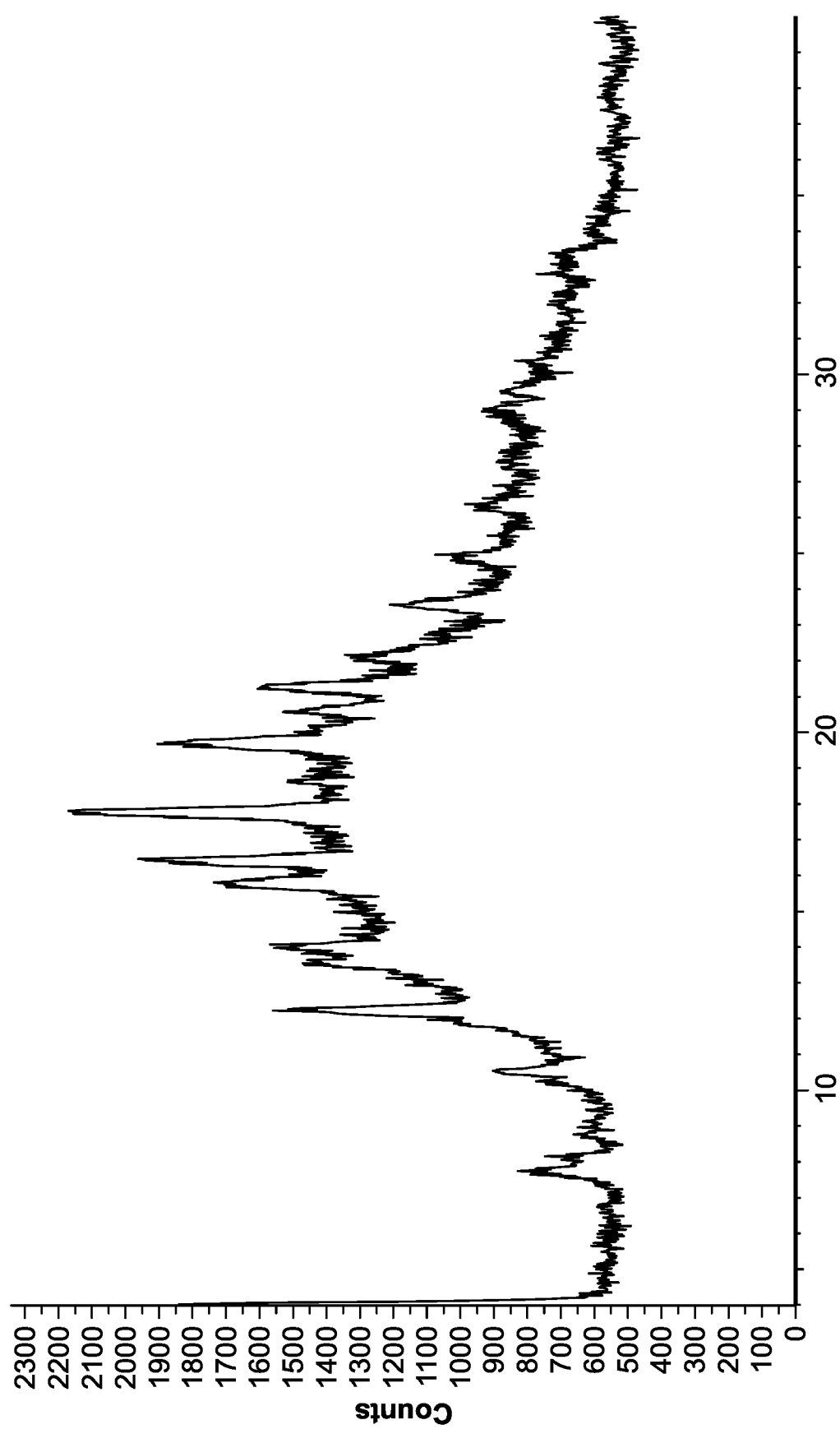
FIG. 7 depicts a powder X-ray diffractogram of (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide (I-132.1) free base.

In one aspect, the crystalline form of (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide is characterized by at least three X-ray powder diffraction peaks at 2Θ angles selected from 12.23°, 14.00°, 15.78°, 16.41°, 17.77°, and 19.70°. Alternatively, the crystalline form of (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide is characterized by at least four X-ray powder diffraction peaks at 2Θ angles selected from 12.23°, 14.00°, 15.78°, 16.41°, 17.77°, and 19.70°. In another alternative, the crystalline form of (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide is characterized by at least five X-ray powder diffraction peaks at 2Θ angles selected from 12.23°, 14.00°, 15.78°, 16.41°, 17.77°, and 19.70°. In yet another alternative, the crystalline form of (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide is characterized by X-ray powder diffraction peaks at 2Θ angles 12.23°, 14.00°, 15.78°, 16.41°, 17.77°, and 19.70°. In yet another embodiment, the crystalline form of (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide is characterized by X-ray powder diffraction peaks at 2Θ angles selected from Table 2f. In yet another embodiment, the crystalline form of (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide is characterized by an X-ray powder diffraction pattern substantially similar to FIG. 7.

TABLE 2f

| 2-Theta | d Value | Intensity | Rel. Intensity (%) |
|---|---|---|---|
| 7.74 | 11.41 | 260 | 22.5 |
| 8.11 | 10.90 | 137 | 11.8 |
| 8.75 | 10.09 | 74 | 6.4 |
| 10.25 | 8.62 | 145 | 12.5 |
| 10.53 | 8.40 | 234 | 20.2 |
| 11.95 | 7.40 | 240 | 20.8 |
| 12.23 | 7.23 | 735 | 63.6 |
| 13.57 | 6.52 | 558 | 48.3 |
| 14.00 | 6.32 | 635 | 54.9 |
| 15.78 | 5.61 | 738 | 63.8 |
| 16.41 | 5.40 | 924 | 79.9 |
| 17.77 | 4.99 | 1156 | 100 |
| 18.64 | 4.76 | 472 | 40.8 |
| 19.70 | 4.50 | 853 | 73.8 |
| 20.59 | 4.31 | 511 | 44.2 |
| 21.27 | 4.17 | 602 | 52.1 |
| 22.08 | 4.02 | 352 | 30.5 |
| 23.56 | 3.77 | 284 | 24.6 |
| 24.90 | 3.57 | 156 | 13.5 |
| 26.32 | 3.38 | 113 | 9.8 |
| 29.02 | 3.07 | 142 | 12.2 |
| 29.54 | 3.02 | 129 | 11.1 |

In one aspect, the crystalline form of (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide is at least 50% pure by weight, at least 75% pure by weight, at least 80% pure by weight, at least 90% pure by weight, at least 95% pure by weight, or at least 98% pure by weight.

Unless otherwise indicated, the XRPD patterns/assignments for the crystalline forms defined herein are not to be construed as absolute and can vary ±0.2 degrees.

Specific examples of compounds are provided in the EXEMPLIFICATION. Pharmaceutically acceptable salts as well as the neutral forms of these compounds are included herein.

In certain embodiments, the present disclosure provides a method of treating a patient (e.g., a human) with a disorder mediated by RORγ comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present disclosure provides a method of treating a subject (e.g., a human) with a disorder mediated by RORγ using a composition comprising a compound of Formula I and a pharmaceutically acceptable carrier, adjuvant, or vehicle.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, organic or inorganic carriers, excipients or diluents suitable for pharmaceutical applications.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable prepartions, solid dispersion forms, and dosage forms for topical or transdermal administration of a compound are included herein.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for modulating RORγ. Thus, in some embodiments, the present disclosure provides a method of treating inflammatory, metabolic and autoimmune diseases or disorders mediated by RORγ, comprising administering a provided compound or composition. More particularly, the compounds and compositions described herein act as inverse agonists or antagonists of RORγ.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

Modulation of RORγ (or to modulate RORγ), means that a change or alteration in the activity of RORγ has occurred from the administration of one or more of the compounds described herein. Modulation may be an upregulation (increase) or a downregulation (decrease) in the magnitude of the activity or function of RORγ. Exemplary activities and functions include e.g., binding characteristics, enzymatic activity, cell receptor activation, transcriptional activity, and signal transduction. In one aspect, the compounds described herein inhibit RORγ. In further aspects, the compounds described herein act as agonists, antagonists, or inverse agonists of RORγ.

In another aspect, compounds and compositions described herein are useful for reducing the amount of IL-17 in a subject. Thus, in some embodiments, provided herein are methods of reducing the amount of IL-17 in a subject comprising administering an effective amount of a provided compound or composition. RORγ modulators disclosed in WO 2014/179564, WO 2015/116904, WO 2016/061160, PCT/US2016/045318, PCT/US2016/062422, and U.S. patent publication Nos. US 2016-0122318 and US 2016-0122345 can also be used in such methods.

In another aspect, compounds and compositions described herein are useful for inhibiting the synthesis of IL-17 in a subject. Thus, in some embodiments, provided herein are methods of inhibiting the synthesis of IL-17 in a subject comprising administering an effective amount of a provided compound or composition. RORγ modulators disclosed in WO 2014/179564, WO 2015/116904, WO 2016/061160, PCT/US2016/045318, PCT/US2016/062422, and U.S. patent publication Nos. US 2016-0122318 and US 2016-0122345 can also be used in such methods.

Diseases and conditions treatable according to the methods herein include, but are not limited to, inflammatory, metabolic and autoimmune diseases or disorders mediated by RORγ. These diseases and conditions include, for example, asthma, chronic obstructive pulmonary disease (COPD), bronchitis, allergic rhinitis, atopic dermatitis, contact dermatitis, acne, urticaria, hives, angioedema, cystic fibrosis, allograft rejection, multiple sclerosis, Balo's concentric (circular) sclerosis, Balo disease, leukoencephalitis periaxialis concentrica, encephalitis periaxialis concentrica, scleroderma, limited scleroderma, CREST syndrome, arthritis, rheumatoid arthritis, juvenile rheumatoid arthritis, reactive arthritis, Reiter's syndrome, osteoarthritis, ankylosing spondylitis, systemic lupus erythematosus (SLE), Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, plaque psoriasis, guttate psoriasis, inverse psoriasis, pustular psoriasis, erythrodermic psoriasis, psoriatic epidermal hyperplasia, epidermal hyperplasia, psoriatic arthritis (PsA), steroid resistant asthma, Graves' disease, scleritis, endometriosis, obstructive sleep apnea syndrome (OSAS), Behcet's disease, dermatomyositis, polymyocitis, graft versus host disease, chronic graft versus host disease, acute graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, celiac sprue, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to lung cancer, gastric cancer, breast cancer and colon cancer. In one aspect, an exemplified form of cancer treatable according to the methods herein also includes prostate cancer e.g., (metastatic castration-resistant prostate cancer tumors). In another aspect, an exemplified form of cancer treatable according to the methods herein includes e.g., malignant tumor, angiogenesis glaucoma, infantile hemangioma, multiple myeloma, acute myeloblastic leukemia, chronic sarcoma, chronic myelogenous leukemia, metastasis melanoma, Kaposi's sacroma, vascular proliferation, cachexia, colorectal cancer (e.g., familial colorectal cancer, hereditary nonpolyposis colorectal cancer, and gastrointestinal stromal tumor), lung cancer (e.g., non-small cell lung cancer, small cell lung cancer and malignant mesothelioma), mesothelioma, pancreatic cancer (e.g., pancreatic duct cancer), gastric cancer (e.g., papillary adenocarcinoma, mucinous adenocarcinoma and adenosquamous carcinoma), breast cancer (e.g., invasive ductal carcinoma, ductal carcinoma in situ, inflammatory breast cancer and metastatic breast cancer), ovarian cancer (e.g., ovarian epithelial carcinoma, extragonadal germ cell tumor, ovarian germ cell tumor, and ovarian low malignant potential tumor), hormone-dependent prostate cancer, non-hormone dependent prostate cancer, liver cancer (e.g., primary liver cancer and extrahepatic bile duct cancer), thyroid cancer (e.g., medullary thyroid carcinoma), kidney cancer (e.g., renal cell carcinoma, and transitional cell carcinoma in kidney and urinary duct), uterine cancer, endometrial cancer, brain tumor (e.g., pineal astrocytoma, pilocytic astrocytoma, diffuse astrocytoma and anaplastic astrocytoma), melanoma, sarcoma, urinary bladder cancer, hematologic cancer, hypophyseal adenoma, glioma, acoustic neurinoma, retinoblastoma, head and neck cancer, head and neck squamous cell carcinoma, pharyngeal cancer, laryngeal cancer, cancer of the tongue, thymoma, esophagus cancer, duodenal cancer, colorectal cancer, rectal cancer, hepatoma, pancreatic endocrine tumor, cancer of the bile duct, gallbladder cancer, penile cancer, urinary duct cancer, testis tumor, vulvar cancer, cervical cancer, endometrial cancer, uterus sarcoma, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, chronic myelocytic leukemia, malignant myeloma, adult T cell leukemia, chronic bone marrow proliferative disease, pancreatic endocrine tumor, fibrous histiocytoma, leiomyosarcoma, rhabdomyosarcoma, cancer of unknown primary, cancer-driven myelopoiesis, tumor growth, and metastasis.

Diseases and disorders mediated by IL-17 expression, and which are treatable using the compounds described herein also include, e.g., emphysema, lung fibrosis, idiopathic pulmonary fibrosis, retroperitoneal fibrosis, giant cell arteritis, giant cell myocarditis, arteriosclerosis, hepatitis, chronic active hepatitis, alcoholic hepatitis, alcoholic liver fibrosis, alcoholic cirrhosis, viral hepatitis, hepatitis B viral liver disorder, autoimmune hepatitis, cartilage inflammation, bone degradation, juvenile arthritis, pauciarticular juvenile rheumatoid arthritis, polyarticular juvenile rheumatoid arthritis, systemic onset juvenile rheumatoid arthritis, spondyloarthritis, juvenile ankylosing spondylitis, juvenile enteropathic arthritis, juvenile reactive arthritis, juvenile Reiter's syndrome, seronegative enthesopathy and arthropathy (SEA) syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, vasculitis, leukocytoclastic vasculitis, myositis, juvenile myositis, polymyositis, autoimmune myositis, osteoarthritis, polyarteritis nodosa, arteritis, Takayasu's arteritis, temporal arteritis, giant cell arteritistesticular autoimmunity, polymyalgia rheumatica, rheumatic fever, sclerosis, primary biliary sclerosis, primary biliary cirrhosis, sclerosing cholangitis, primary sclerosing cholangitis, enthesitis, enthesopathy, dermatitis, dermatitis herpetiformis, progesterone dermatitis, atopic eczema, contact eczema, eczema, atherosclerosis, Still's disease, Addison's disease, Raynaud's phenomenon, erythrodermic psoriasis, noninfectious uveitis, peripheral uveitis, Dressler's syndrome, eosinophilic esophagitis, eosinophilic fasciitis, erythema nodosum, experimental allergic encephalomyelitis, Evans syndrome, fibrosing alveolitis, Vogt-Koyanagi-Harada syndrome, mucosal leishmaniasis, Kawasaki disease or syndrome, Hashimoto's encephalitis, Hashimoto's thyroiditis, thrombocytopenic purpura, immune thrombocytopenic purpura (also known as immune thrombocytopenia, idiopathic immune thrombocytopenia, idiopathic thrombocytopenic thrombotic purpura, primary immune thrombocytopenia, idiopathic thrombocytopenic purpura (ITP), primary immune thrombocytopenic purpura, or autoimmune thrombocytopenic purpura), agammaglobulinemia, kidney inflammation, interstitial kidney inflammation, kidney disease, chronic kidney disease, renal failure, acute renal failure, end stage kidney disease, acute kidney injury, cisplatin induced acute renal failure, sepsis induced acute renal failure, anti-glomerular basement membrane (GBM) nephritis, anti-tubular basement membrane (TBM) nephritis, antiphospholipid syndrome (APS), nephritis, nephrotoxic nephritis, glomerulonephritis, acute glomerulonephritis, antineutrophil cytoplasmic autoantibody (ANCA) associated vasculitis, microscopic polyangiitis, granulomatosis with polyangiitis (GPA), Wegener's granulomatosis, amyotrophic lateral sclerosis, lupus nephritis, allergic eczema, transplant rejection, non-radiographic spondyloarthropathy, ophthalmic disorders, organ allograft rejection, fibroid lung, renal insufficiency, diabetic complications, diabetic nephropathy, diabetic retinopathy, diabetic retinitis, diabetic microangiopathy, insulitis, tuberculosis, invasive staphylococcia, invasive *Staphylococcus aureus* infection, inflammation after cataract surgery, allergic conjunctivitis, alopecia, alopecia areata, chronic urticaria, allergic asthma, neutrophilic asthma, periodontal diseases, periodonitis, gingivitis, gum disease, cardiomyopathy, diastolic cardiomyopathies, cardiac infarction, myocarditis, chronic heart failure, congenital heart block, coxsackie myocarditis, postmyocardial infarction syndrome, postpericardiotomy syndrome, endocarditis, subacute bacterial endocarditis (SBE), angiostenosis, restenosis, reperfusion disorders, autoimmune pancreatitis, acute pancreatitis, chronic pancreatitis, asthma, bronchial asthma, acute respiratory distress syndrome, adult respiratory distress syndrome, inflammatory bone disease, inflammatory pulmonary disease, ischemic attack, transient ischemic attack, systemic inflammatory response syndrome, glaucoma, orbital cellulitis, sudden orbital inflammation, postoperative inflammation, posttraumatic inflammation, allergic inflammation, intestinal inflammation, mucosal inflammation, prostate inflammation, prostatitis, chronic pelvic pain syndrome, testicular inflammation, chronic testicular inflammation, orchitis, orchitis mediated infertility, liver disorder, liver injury, hepatoxicity, pneumonia, meningitis, cystitis, interstitial cystitis, pharyngolaryngitis, gastric mucosal injury, chronic pneumonia, pulmonary infarction, silicosis, sarcoidosis, pulmonary sarcoidosis, autoimmune angioedema, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune aplastic anemia, autoimmune anemia, autoimmune hemolytic anemia, hemolytic anemia, autoimmune retinopathy, autoimmune thrombocytopenic purpura (ATP), autoimmune thyroid disease, autoimmune urticaria, Goodpasture's syndrome, sinusitis, chronic hypertrophic rhinitis, chronic inflammatory demyelinating polyneuropathy, mixed connective tissue disease, undifferentiated connective tissue disease (UCTD), cognitive impairment, cognitive impairment in Alzheimer's disease, Parkinson's disease, spinal muscular atrophy, spinal cerebellar atrophy, progressive supranuclear palsy, Fisher syndrome, dicoid lupus, central nervous system lupus, neuromyelitis optica (NMO; also known as Devic's disease or Devic's syndrome), encephalomyelitis, acute disseminated encephalomyelitis (ADEM), transverse myelitis, acute necrotizing hemorrhagic leukoencephalitis, multiple system atrophy, Huntington's disease, cerebrovascular dementia, diffuse Lewy body disease, amyloidosis, cerebrovascular disorder, cerebral infarction, transient ischemic attack, intracerebral hemorrhage, vascular disease of the spinal cord, spinal cord infarction, Lambert-Eaton syndrome, muscular dystrophy, metabolic myopathy, inflammatory myopathy, Chagas disease, chronic inflammatory demyelinating polyneuropathy (CIDP), chronic recurrent multifocal osteomyelitis (CRMO), Churg-Strauss syndrome, Cogan's syndrome, cold agglutinin disease, essential mixed cryoglobulinemia, demyelinating neuropathies, inclusion body myositis, encephalitis, pemphigoid, bullous pemphigoid, pemphigus, pemphigus vulgaris, pemphigus foliaceus, cicatricial pemphigoid, ocular cicatricial pemphigoid, benign mucosal pemphigoid, Castleman disease (also known as giant or angiofollicular lymph node hyperplasia, lymphoid hamartoma, and angiofollicular lymph node hyperplasia), profundus lupus erythematosus, chronic thyroiditis, autoimmune gastritis, sepsis, burn injury, axonal and neuronal neuropathies, pain, neuropathy, peripheral neuropathy, chronic pain, optic neuritis, optic neuropathy, traumatic optic neuropathy, ischemic brain injury, deep venous thrombosis, neutropenia, autoimmune neutropenia, thrombocytopenia, abnormal immunoresponse, radiodermatitis, osteoporosis, parasitic infection, clonorchiasis, *Cryptosporidium* infection, *Streptococcus pneumoniae* carriage, chronic pneumococcal carriage, an immune disorder associated with or arising from activity of pathogenic lymphocytes, Henoch-Schonlein purpura, herpes gestationis, hypogammaglobulinemia, IgA nephropathy, IgG4-related sclerosing disease, immunoregulatory lipoproteins, Lambert-Eaton syndrome, lichen planus, lichen sclerosus, ligneous conjunctivitis, linear IgA disease (LAD), chronic Lyme disease, Meniere's disease, microscopic polyangiitis, mixed connective tissue disease (MCTD), Mooren's ulcer, Mucha-Habermann disease, narcolepsy, palindromic rheumatism, pediatric autoimmune neuropsychiatric disorders associated with *streptococcus* (PANDAS), paraneoplastic cerebellar degeneration, paroxysmal nocturnal hemoglobinuria (PNH), Parry-Romberg syndrome, Parsonnage-Turner syndrome, pars planitis, perivenous encephalomyelitis, pernicious anemia, POEMS syndrome, type I autoimmune polyglandular syndrome, type II autoimmune polyglandular syndrome, type III autoimmune polyglandular syndrome, pyoderma gangrenosum, pure red cell aplasia, reflex sympathetic dystrophy, relapsing polychondritis, restless legs syndrome, Schmidt syndrome, sperm autoimmunity, stiff person syndrome, Susac's syndrome, sympathetic ophthalmia, Tolosa-Hunt syndrome, vesiculobullous dermatosis, and vitiligo.

Also included are diseases or disorders which are implicated by the regulation of the circadian rhythm of individuals and include, e.g., major depression, seasonal affective disorder, post-traumatic stress disorder (PTSD), bipolar disorder, autism, epilepsy, Alzheimer's disease and other central nervous system (CNS) disorders associated with altered sleep and/or circadian rhythms.

Further included are diseases and disorders mediated by IL-17 expression, including STAT3-mediated IL-17 expression, in neutrophils, and include, e.g., corneal fungal infection; risk of corneal fungal infection; corneal ulcer; corneal ulcer resulting from fungal keratitis; corneal ulcer resulting from fungal infection; corneal fungal infection and related inflammation; keratitis; fungal keratitis; corneal inflammation; corneal disease; ocular disease; fungal-mediated corneal infection, corneal ulcer, corneal inflammation, or ocular ulcer, inflammation or infection; bacterial-mediated corneal infection, corneal ulcer, corneal inflammation, or ocular ulcer, inflammation or infection; microbial disease; bacterial infections; fungal infections; *Aspergillus* keratitis; *Fusarium* keratitis; cutaneous T cell lymphoma; lung inflammation; acute kidney ischemia-reperfusion injury; anthrax, including, cutaneous anthrax, inhalation anthrax, gastrointestinal anthrax and injection anthrax; aspergillosis, including, pulmonary aspergillosis, chronic pulmonary aspergillosis (CPA), chronic aspergillosis, chronic cavitary pulmonary aspergillosis (CCPA), allergic bronchopulmonary aspergillosis (ABPA), allergic *Aspergillus* sinusitis, aspergilloma, invasive aspergillosis, chronic necrotizing aspergillosis and cutaneous (skin) aspergillosis; and histoplasmosis, including, systemic histoplasmosis. In particular embodiments, the fungus or fungal infection meditating the disease or disorder described above includes one or more of *Aspergillus, Fusarium, Alternaria, Candida, Curvularia* or *Histoplasma*.

Compounds described herein can also be used to treat or reduce the risk of abnormal cortical development or psychiatric disorder, e.g., autism spectrum disorder (ASD), schizophrenia, and/or depression, in a fetus. Compounds described herein can also be used to treat a pregnant female having a hyper-inflammatory condition associated with an infection, such as a viral or bacterial infection, or associated with exposure to an inflammatory or environmental toxin during pregnancy. In particular embodiments, a fetus is treated in utero in a pregnant female with a compound disclosed herein to decrease the risk of the fetus developing a psychiatric disorder, to reduce inflammation in the pregnant female, to reduce the risk of abnormal cortical development in the fetus, and/or to decrease symptoms of a psychiatric disorder in offspring of a pregnant female.

In one embodiment, a human patient is treated with a compound of Formula I and a pharmaceutically acceptable carrier, adjuvant, or vehicle, wherein said compound is present in an amount to treat or ameliorate one or more of the diseases and conditions recited above. In an alternative embodiment, the diseases and conditions treated or ameliorated by a compound of Formula I include, e.g., asthma, atopic dermatitis, acne, Crohn's disease, regional enteritis, ulcerative colitis, Sjigren's syndrome, uveitis, Behcet's disease, dermatomyositis, multiple sclerosis, ankylosing spondylitis, systemic lupus erythematosus (SLE), scleroderma, psoriasis, psoriatic arthritis (PsA), steroid resistant asthma and rheumatoid arthritis in the patient. In an alternative embodiment, the diseases and conditions treated or ameliorated by a compound of Formula I include e.g., atopic dermatitis, acne, dermatomyositis, scleroderma, psoriasis, psoriatic arthritis (PsA), and rheumatoid arthritis.

The present disclosure further relates to a combination therapy for treating or ameliorating a disease or a disorder described herein. In some embodiments, the combination therapy comprises administering at least one compound represented by Structural Formula I in combination with one or more agents for treating or ameliorating inflammatory, metabolic and autoimmune diseases or disorders mediated by RORγ. In some embodiments, the combination therapy comprises administering at least one compound represented by Structural Formula I in combination with one or more agents for the treatment of diseases including asthma, chronic obstructive pulmonary disease (COPD), bronchitis, allergic rhinitis, atopic dermatitis, contact dermatitis, acne, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjigren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, major depression, seasonal affective disorder, PTSD, bipolar disorder, autism, epilepsy, Alzheimer's, CNS disorders associated with altered sleep and/or circadian rhythms, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to, lung cancer, gastric cancer, breast cancer and colon cancer.

The compounds herein may also be used alone or in combination with immunotherapies for the treatment of a disease or disorder disclosed herein.

Combination therapy includes, e.g., co-administration of a compound described herein and one or more other agents, sequential administration of a compound described herein and one or more other agents, administration of a composition containing a compound described herein and one or more other agents, or simultaneous administration of separate compositions containing a compound described herein and one or more other agents.

The present disclosure further provides a method of treating a subject, such as a human, suffering from one of the abovementioned disorders or diseases.

In one aspect, RORγ modulators disclosed in WO 2014/179564, WO 2015/116904, WO 2016/061160, PCT/US2016/045318, PCT/US2016/062422, and U.S. patent publication Nos. US 2016-0122318 and US 2016-0122345 can also be used in the methods disclosed herein to treat or ameliorate, in a subject, one or more of the diseases and/or disorders and/or conditions recited herein. In one embodiment, a subject is treated with one or more RORγ modulators disclosed in WO 2014/179564, WO 2015/116904, WO 2016/061160 PCT/US2016/045318, PCT/US2016/062422, and U.S. patent publication Nos. US 2016-0122318 or US 2016-0122345 and a pharmaceutically acceptable carrier, adjuvant, or vehicle, wherein said RORγ modulator is present in an amount to treat or ameliorate a disease or disorder selected from corneal fungal infection; risk of corneal fungal infection; corneal ulcer; corneal ulcer resulting from fungal keratitis; corneal ulcer resulting from fungal infection; corneal fungal infection and related inflammation; keratitis; fungal keratitis; corneal inflammation; corneal disease; ocular disease; fungal-mediated corneal infection, corneal ulcer, corneal inflammation, or ocular ulcer, inflammation or infection; bacterial-mediated corneal infection, corneal ulcer, corneal inflammation, or ocular ulcer, inflammation or infection; microbial disease; bacterial infections; fungal infections; *Aspergillus* keratitis; *Fusarium* keratitis; cutaneous T cell lymphoma; lung inflammation; acute kidney ischemia-reperfusion injury; anthrax, including, cutaneous anthrax, inhalation anthrax, gastrointestinal anthrax and injection anthrax; aspergillosis, including, pulmonary aspergillosis, chronic pulmonary aspergillosis (CPA), chronic aspergillosis, chronic cavitary pulmonary aspergillosis (CCPA), allergic bronchopulmonary aspergillosis (ABPA), allergic *Aspergillus* sinusitis, aspergilloma, invasive aspergillosis, chronic necrotizing aspergillosis and cutaneous (skin) aspergillosis; histoplasmosis, including, systemic histoplasmosis; and prostate cancer. In some embodiments, the one or more RORγ modulator disclosed in WO 2014/179564, WO 2015/116904, WO 2016/061160 PCT/US2016/045318, PCT/US2016/062422, and U.S. patent publication Nos. US 2016-0122318 and US 2016-0122345 is administered in combination with one or more additional agent for treating the disease or disorder.

The present disclosure further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the diseases and conditions described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed;

the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, creams, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In other embodiments, provided compounds are administered topically.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

EXEMPLIFICATION

As depicted in the Examples below, in certain exemplary embodiments, compounds are prepared according to the following general procedures. It will be appreciated that, although the general methods depict the synthesis of certain compounds herein, the following general methods, and other methods known to one of ordinary skill in the art, can be applied to all compounds and subclasses and species of each of these compounds, as described herein.

GENERAL DESCRIPTION OF SYNTHESIS

The compounds described herein can be readily prepared according to the following reaction schemes and examples, or modifications thereof, using readily available starting materials, reagents and conventional synthesis procedures. Many of the reactions can also be carried out under microwave (MW) conditions or using conventional heating or utilizing other technologies such as solid phase reagents/scavengers or flow chemistry. In these reactions, it is also possible to make use of variants which are themselves known to those of ordinary skill in the art, but are not mentioned in greater detail. Furthermore, other methods for preparing compounds described herein will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below variables have the meanings indicated above unless otherwise indicated. The abbreviations used in these experimental details are listed below and additional ones should be known to a person skilled in the art of synthesis. In addition, one can refer to the following references for suitable methods of synthesis as described in March, Advanced Organic Chemistry, 3rd edition, John Wiley & Sons, 1985, Greene and Wuts, Protective Groups in Organic Synthesis, $2^{nd}$ edition, John Wiley & Sons, 1991, and Richard Larock, Comprehensive Organic Transformations, $4^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

The invention is illustrated by way of the following examples, in which the following abbreviations may be employed.

| Abbreviation | Meaning |
| --- | --- |
| ACN, MeCN, $CH_3CN$ | acetonitrile |
| AIBN | azobisisobutyronitrile |
| aq | aqueous |
| Boc | tert-butoxycarbonyl or t-butoxycarbonyl |
| brine | saturated aqueous NaCl |
| c-Bu | cyclobutyl |
| Cbz | benzyloxy carbonyl |
| $CeCl_3$ | ceric chloride |
| $Cs_2CO_3$ | cesium carbonate |
| CuI | cuprous iodide |
| c-Pr | cyclopropyl |
| DCM or $CH_2Cl_2$ | methylene chloride |
| DIEA, i-$Pr_2NEt$ | diisopropyl ethyl amine |
| DMF | dimethyl formamide |
| DMS/$Me_2S$ | dimethyl sulfide |
| DMSO | dimethyl sulfoxide |
| EDCI, EDC | 1-(3-dimethylaminopropyl)-3-ethylcarbodiimide hydrochloride |
| EtI | ethyl iodide |
| Et | ethyl |
| $Et_2O$ | ethyl ether |
| $Et_3SiH$ | triethylsilane |
| $Et_3N$ | triethylamine |
| EtOAc, EA, AcOEt | ethyl acetate |
| EtOH | ethanol |
| $FeCl_3$ | ferric chloride |
| h, hr | hour(s) |
| HATU | O-(7-azabenzotriazol-1-yl)-N,N,N',N'-tetramethyluronium-hexafluorophosphate |
| HBTU | O-benzotriazole-1-yl-N,N,N',N'-tetramethyluronium-hexafluorophosphate |
| HCl | hydrochloric acid |
| $H_2O$ | water |
| $H_2O_2$ | hydrogen peroxide |
| HOAc | acetic acid |
| HOBt | N-hydroxybenzotriazole |
| HPLC | high performance liquid chromatography |
| i-BuOCOCl | iso-butoxycarbonyl chloride |
| ICl | iodochloride |
| $K_2CO_3$ | potassium carbonate |
| $K_3PO_4$ | tripotassium phosphate |
| LC-MS | liquid chromatography-mass spectrometry |
| LDA | lithium diiisopropylamide |

| Abbreviation | Meaning |
|---|---|
| LiCl | lithium chloride |
| LiOH | lithium hydroxide |
| MCPBA, m-CPBA | meta-chloroperoxybenzoic acid |
| MeOH | methanol |
| MeI | methyl iodide |
| Me | methyl |
| mg | milligram |
| $MgSO_4$ | magnesium sulfate (anhydrous) |
| min | minute(s) |
| mL | milliliters |
| mmol | millimoles |
| mp, m.p. | melting point |
| MS | mass spectrometry |
| MW, uwave | microwave |
| $NaBH_4$ | sodium borohydride |
| $NaBH_3CN$ | sodium cyanoborohydride |
| NaH | sodium hydride |
| $NaHCO_3$ | sodium bicarbonate |
| NaOH | sodium hydroxide |
| NaOMe | sodium methoxide |
| $Na_2S_2O_3$ | sodium thiosulfate |
| $Na_2S_2O_5$ | sodium dithionate |
| $Na_2SO_4$ | sodium sulfate |
| $NH_4OH$ | ammonium hydroxide |
| $(NH_4)_2CO_3$ | ammonium carbonate |
| $NH_4Cl$ | ammonium chloride |
| $Na_2CO_3$ | sodium carbonate |
| NaH | sodium hydride |
| NBS | N-bromosuccinimide |
| n-BuLi | n-butyllithium |
| NMM | N-methyl-morpholine |
| NMP | N-methyl-pyrrolidin-2-one |
| OTf | trifluoromethanesulfonate |
| OTs | tosylate |
| oxone | potassium peroxymonosulfate |
| $PdCl_2dppf$ | [1,1-bis(diphenylphosphino)ferrocene] dichloropalladium(ii) |
| $Pd_2(dba)_3$ | tris(dibenzylideneacetone)dipalladium(0) |
| PE | petroleum ether |
| rt | room temperature |
| sat., satd | saturated |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| $Ti(OEt)_4$ | titanium tetra ethoxide |
| μmol | micromoles |
| Zn | zinc |
| $Zn(CN)_2$ | zinc cyanide |

PREPARATION OF COMPOUNDS OF FORMULA I

Compounds of Formula I were prepared according to the general procedures outlined below.

In a first process, a compound of Formula I, wherein X=CONH, is prepared from a benzimidazole carboxylic acid of Formula 100 and an amine of Formula 105, using peptide bond formation reagents such as EDC with HOBt, PyBOP or HATU. Alternatively, the acid chloride of 100 is used.

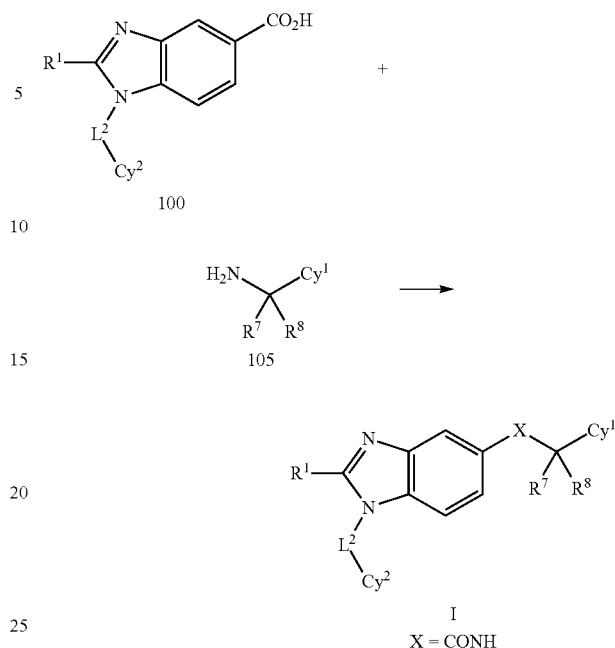

In a second process, a compound of Formula I, wherein X=NHCO, is prepared from an aminobenzimidazole of Formula 110 and a carboxylic acid of Formula 115, using peptide bond formation reagents such as EDC with HOBt, PyBOP or HATU. Alternatively, the acid chloride of 115 is used.

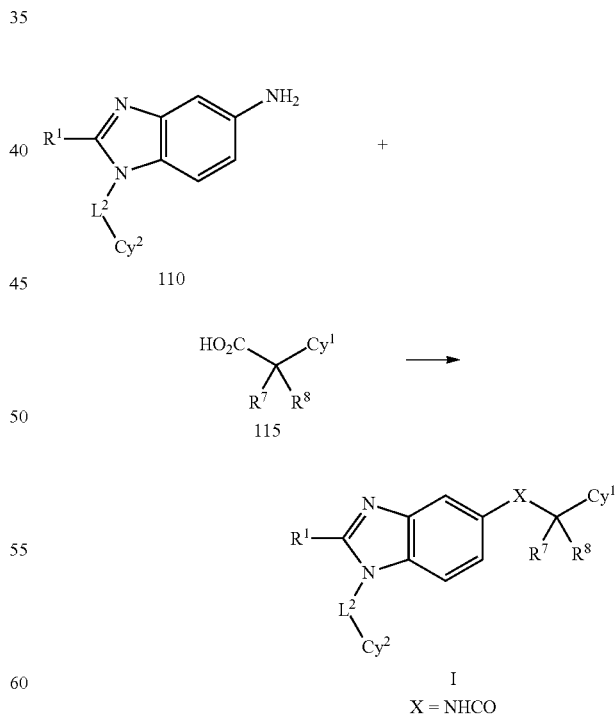

In a third process, a compound of Formula I is prepared by heating a diamine of Formula 125 with a carboxylic acid of Formula 120. Carboxylic acids of Formula 125 can be purchased or prepared by literature methods.

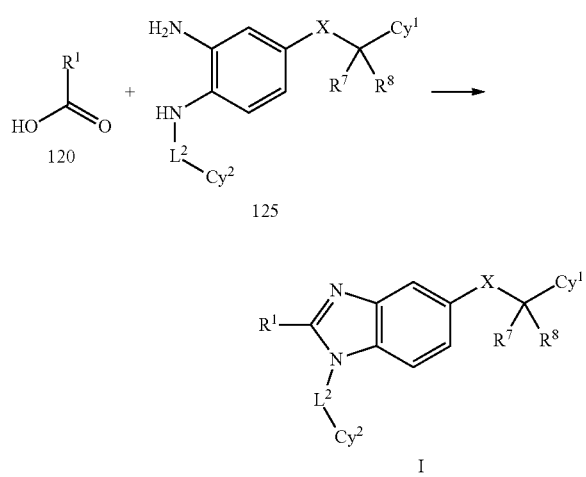

In an alternative to the third process, a compound of Formula I is prepared in two steps from a diamine of Formula 125. In the first step, a carboxylic acid of Formula 120 is reacted with a diamine of Formula 125 using peptide bond formation reagents such as EDC, HOBt or HATU to give a monoamide of Formula 130. Alternatively, the acid chloride of 120 is used. In the second step, a monoamide of Formula 130 is heated with an acid such as HOAc or TFA to give a compound of Formula I.

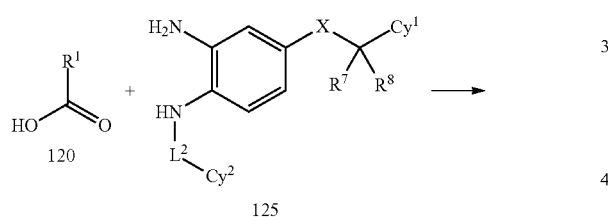

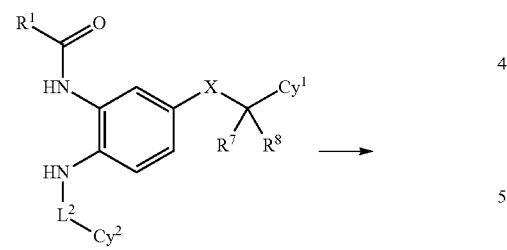

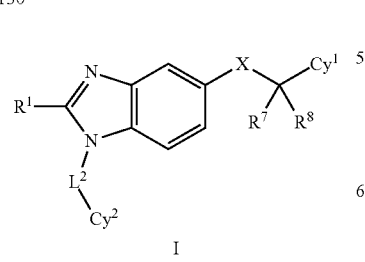

In a fourth process, a diamine of Formula 125 is reacted with an α,α-dichloro ester of Formula 135 to give a compound of Formula I in which $R^1$ is —C(=O)$OR^c$.

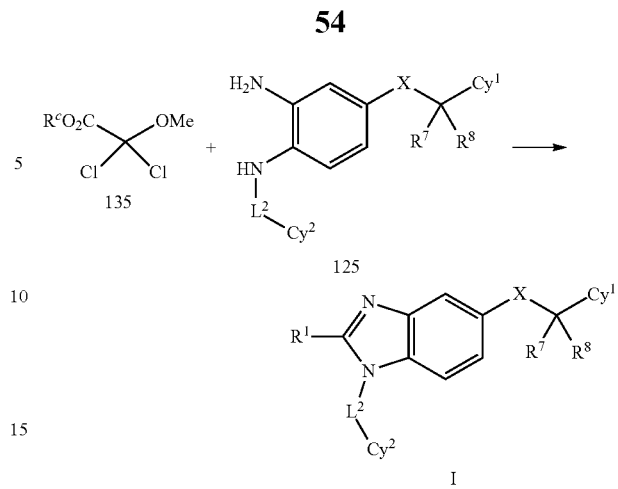

In a fifth process, a diamine of Formula 125 is reacted with a dichloroiminium salt of Formula 140 to give a compound of Formula I, wherein $R^1$ is $NR^dR^e$.

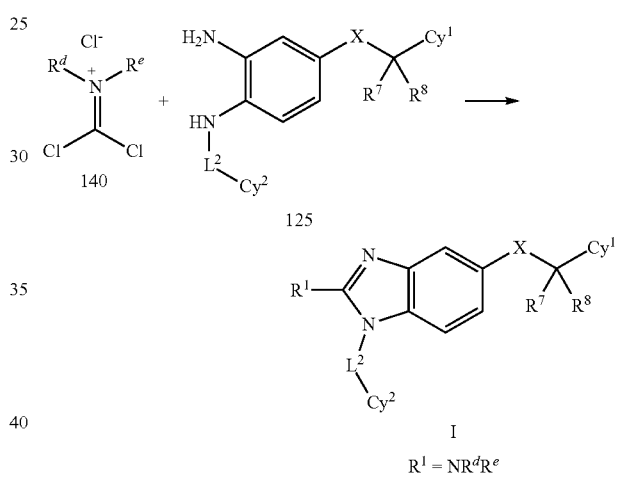

In a sixth process, a compound of Formula I is prepared by reaction of a benzimidazole of Formula 145 with a compound of Formula 150, wherein $R^{100}$ is a leaving group such as iodide, bromide, chloride, methanesulfonate, tosylate or triflate, in the presence of an organic or inorganic base.

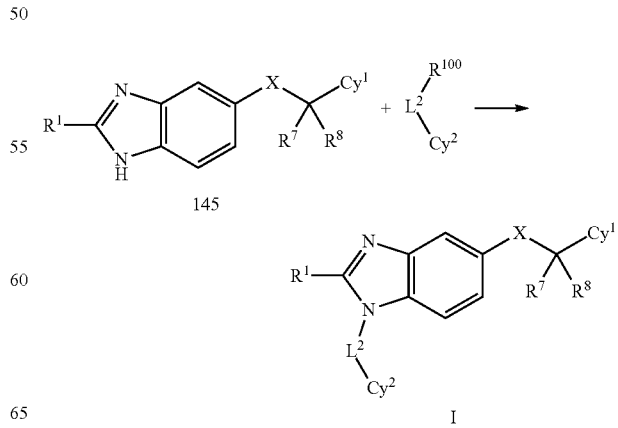

In a seventh process, a compound of Formula I is prepared from another compound of Formula I. Non-limiting examples of this process include: (1) Treatment of a compound of Formula I wherein $R^5$ or $R^6$ is OMe with $BBr_3$ or $Me_3SiI$ to give a compound of Formula I wherein $R^5$ or $R^6$ is OH; (2) Reaction of a compound of Formula I wherein $Cy^1$ or $Cy^2$ is azetidinyl, pyrrolidinyl or piperidinyl bearing a free NH with an alkylating agent such as an $(C_1-C_6)$alkyl halide or halo$(C_1-C_6)$alkyl triflate to give a compound of Formula I, wherein $R^5$ or $R^6$ is $(C_1-C_6)$alkyl or halo$(C_1-C_6)$ alkyl attached to the N of the azetidine, pyrrolidine or piperidine ring; (3) Reaction of a compound of Formula I wherein $Cy^1$ or $Cy^2$ is azetidinyl, pyrrolidinyl or piperidinyl bearing a free NH with an heteroaryl halide such as an optionally substituted 2-chloropyridine, 2-chloropyrimidine or 4-chloropyrimidine to give a compound of Formula I, wherein $R^5$ or $R^6$ is a heteroaryl group such as an optionally substituted pyridinyl or pyrimidinyl group attached to the N of the azetidine, pyrrolidine or piperidine ring; (4) Oxidation of compound of Formula I in which $Cy^1$ or $Cy^2$ is a pyridine ring with a peracid, such as m-CPBA, to the corresponding pyridine N-oxide of Formula I; (5) Reduction of a compound of Formula I, wherein $R^5$, $R^6$, $R^7$ or $R^8$ is —C(=O)$OR^c$, or $(C_1-C_2)$alkyl substituted by —C(=O)$OR^c$, with a hydride reducing agent such as $NaBH_4$, $NaBH_4/CaCl_2$ or $LiBH_4$ to give a compound of Formula I in which $R^5$, $R^6$, $R^7$ or $R^8$ is $(C_1-C_3)$alkyl substituted by OH; (6) Hydrolysis of a compound of Formula I, wherein $R^5$, $R^6$, $R^7$ or $R^8$ is —C(=O)$OR^c$, or $(C_1-C_3)$alkyl substituted —C(=O)$OR^c$ and $R^c$ is $(C_1-C_3)$alkyl with an alkali metal hydroxide to provide a compound of Formula I, wherein $R^5$, $R^6$, $R^7$ or $R^8$ is —C(=O)OH, or $(C_1-C_3)$alkyl substituted —C(=O)OH; (7) Reaction of a compound of Formula I, wherein $R^5$, $R^6$, $R^7$ or $R^8$ is —C(=O)OH, or $(C_1-C_3)$alkyl substituted —C(=O)OH with an amine $R^dR^eNH$ under peptide coupling conditions to give a compound of Formula I, wherein $R^5$, $R^6$, $R^7$ or $R^8$ is —C(=O)$NR^dR^e$, or $(C_1-C_3)$alkyl substituted —C(=O)$NR^dR^e$; (8) Oxidation of a compound of Formula I, in which $Cy^1$ and/or $Cy^2$ is substituted with $R^5$ or $R^6$ which is —$SR^b$, with a peracid, such as m-CPBA, to give a compound of Formula I wherein $R^5$ and/or $R^6$ is —$S(O)_k$ $R^b$ in which k is 1 or 2.

In an eighth process, benzimidazole carboxylic acids of Formula 100, which are precursors to compounds of Formula I, are prepared in four steps. An amine of Formula 155 and a halonitroester of Formula 160, wherein $R^{110}$ is F or Cl, are reacted in the presence of an organic base, such as i-$Pr_2NEt$, to give a nitroaniline of Formula 165. The nitro group of 165 is reduced using, for example, zinc dust in the presence of $NH_4Cl$, iron powder in HOAc, $SnCl_2$, or $H_2$ in the presence of Pd on C, to give a diaminoester of Formula 170. Diaminoester 170 is converted to benzimidazole ester 175 using procedures described in the third process. Finally, the ester in 175 is hydrolyzed using an alkali metal hydroxide to give 100.

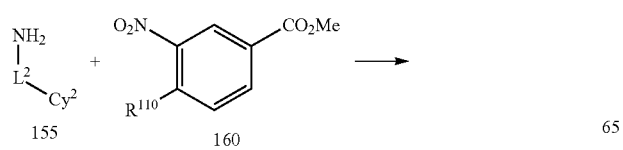

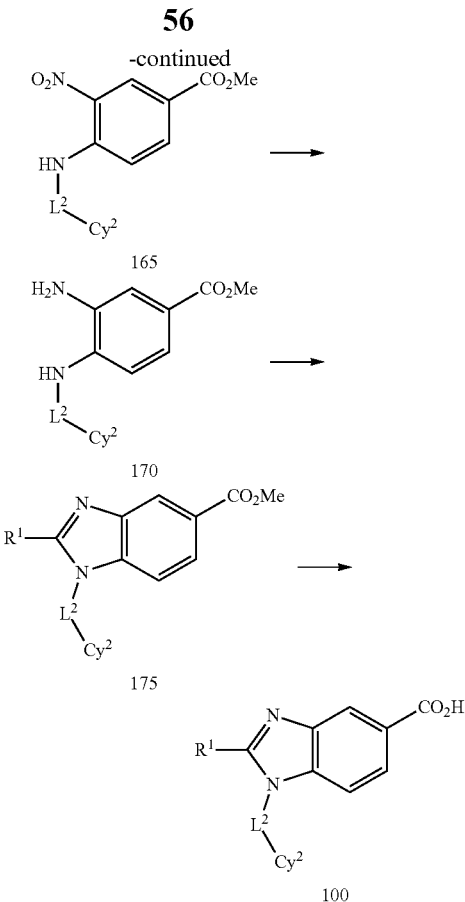

In a ninth process, aminobenzimidazoles of Formula 110, which are precursors to compounds of Formula I, are prepared in four steps. An amine 155 is reacted with a nitrobenzene 180, wherein $R^{110}$ is F or Cl to given a nitroaniline 185. Reduction of 185 using, for example, $SnCl_2$ gives diamine 190. Diamine 190 is converted to bromobenzimidazole 195 using procedures described in the third process. Bromobenzimidazole 195 is converted to aminobenzimidazole 110 using for example $NaN_3$, CuI.

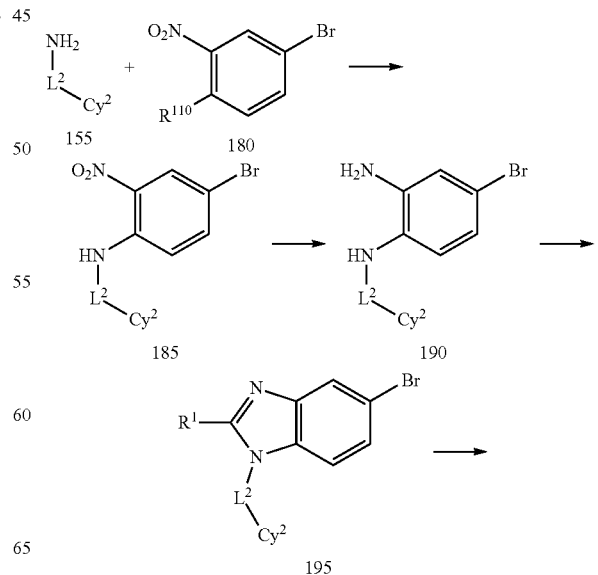

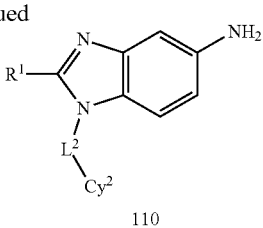

110

In a tenth process, diamines of Formula 125, which are precursors to compounds of Formula I, are prepared in three steps. Reaction of benzoic acids of Formula 200 with amines of Formula 105 under peptide coupling conditions, mediated by for example HATU, HBTU or EDC, gives amides of Formula 205. Reaction of 205 with amine of Formula 155 gives nitroanilines of Formula 210 which are reduced using, for example, $SnCl_2$ to give diamines 125.

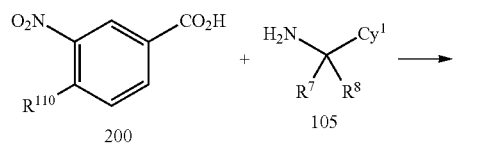

200

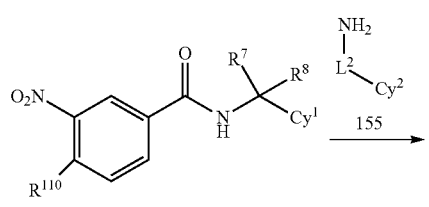

205

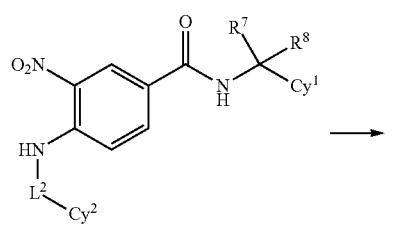

210

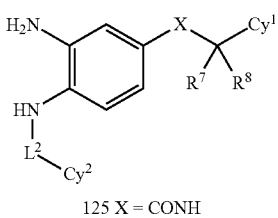

125 X = CONH

In an eleventh process, benzimidazoles of Formula 145, which are precursors of compounds of Formula I, are prepared in three steps. Diaminoester 215 is reacted with carboxylic acids of Formula 120, as described in the third process, to give benzimidazole esters of Formula 220. Treatment of esters 220 with alkali metal hydroxides gives acids of Formula 225 which are reacted with amines of Formula 105 under peptide coupling conditions, mediated by for example HATU, HBTU or EDC, to afford amides of Formula 145.

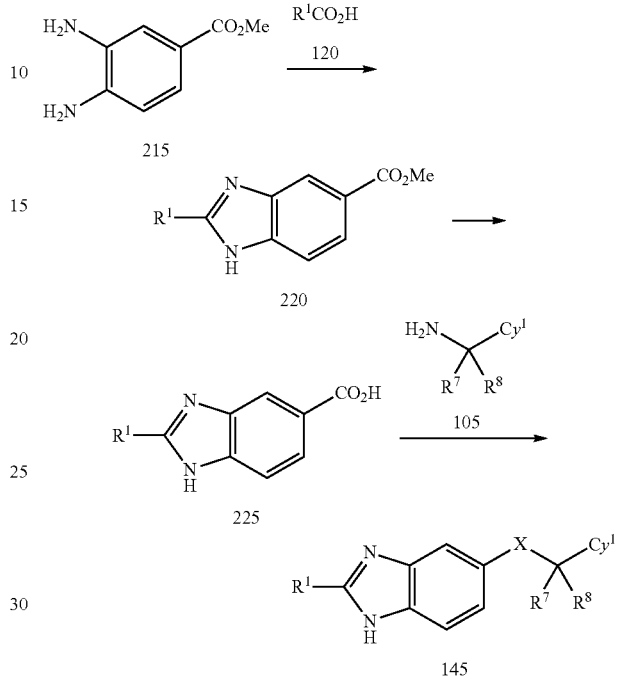

X = CONH

Exemplary LC-MS Methods Include:
Method 1
HPLC System: Waters ACQUITY
Column: Waters ACQUITY CSH™ C18 1.7 uM
Guard column: Waters Assy. Frit, 0.2 uM, 2.1 mm.
Column temp: 40° C.
Mobile Phase: A: TFA:Water (1:1000, v:v)
 B: TFA:ACN (1:1000, v:v)
Gradient Program:

| Time (min) | B % |
| --- | --- |
| 0 | 5 |
| 1.9 | 95 |
| 2.20 | 95 |
| 2.21 | 5 |

Flow Rate: 0.65 mL/min
Mass Spectrometer Parameters
Mass Spectrometer Waters SQD
Ionization Positive Electrospray Ionization (ESI)
Mode Scan (100-1400 m/z in every 0.2 second)
ES Capilary Voltage: 3.5 kv
ES Cone Voltage: 25 v
Source Temperature 120° C.
Disolvation Temperature: 500° C.

| Desolvation Gas Flow: | Nitrogen | Setting 650 (L/hr) |
| --- | --- | --- |
| Cone Gas Flow: | Nitrogen | Setting 50 (L/hr) |

Method 2

| 10-80AB_2 MIN | |
| --- | --- |
| Column | Xtimate C18 2.1*30 mm, 3 um |
| Mobile Phase | A: water(4 L) + TFA(1.5 mL) |
| | B: acetonitrile(4 L) + TFA(0.75 mL) |

| TIME(min) | B % |
| --- | --- |
| 0 | 10 |
| 0.9 | 80 |
| 1.5 | 80 |
| 1.51 | 10 |
| 2 | 10 |

| Flow Rate | 1.2 mL/min |
| --- | --- |
| wavelength | UV 220 nm |
| Oven Temp | 50° C. |

Method 3

| 5-95AB_1.5 MIN | |
| --- | --- |
| Column | MERCK, RP-18e 25-2 mm |
| Mobile Phase | A: water(4 L) + TFA(1.5 mL) |
| | B: acetonitrile(4 L) + TFA(0.75 mL) |

| TIME(min) | B % |
| --- | --- |
| 0 | 5 |
| 0.7 | 95 |
| 1.1 | 95 |
| 1.11 | 5 |
| 1.5 | 5 |

| Flow Rate | 1.5 mL/min |
| --- | --- |
| wavelength | UV 220 nm |
| Oven Temp | 50° C. |
| MS ionization | ESI |

PREPARATIONS OF PRECURSORS TO COMPOUNDS OF FORMULA I

Carboxylic acids AC1-AC6 were purchased:

AC1

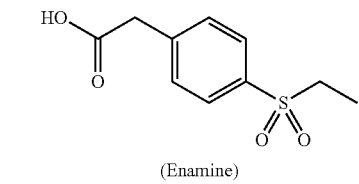

(Enamine)

AC2

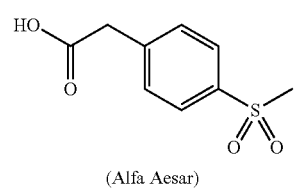

(Alfa Aesar)

AC3

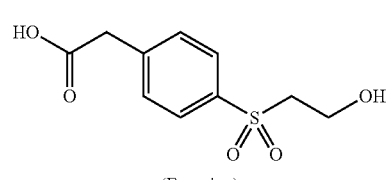

(Enamine)

AC4

(Enamine)

AC5

(UORSY)

AC6

(CombiBlocks)

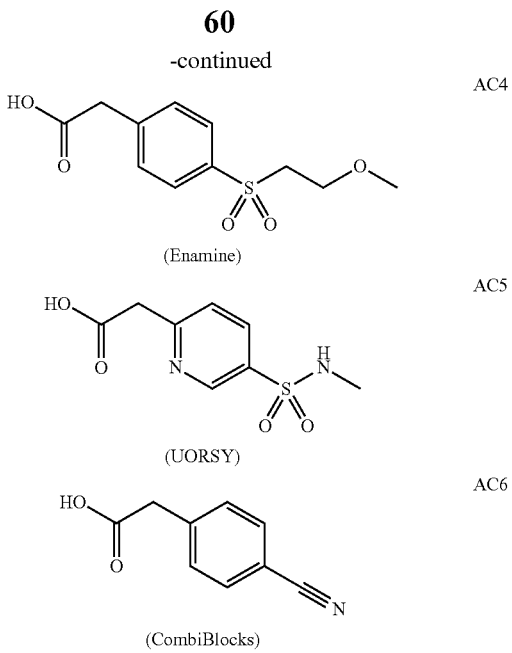

Preparation 1

2-(1-(methylsulfonyl)piperidin-4-yl)acetic acid (AC7)

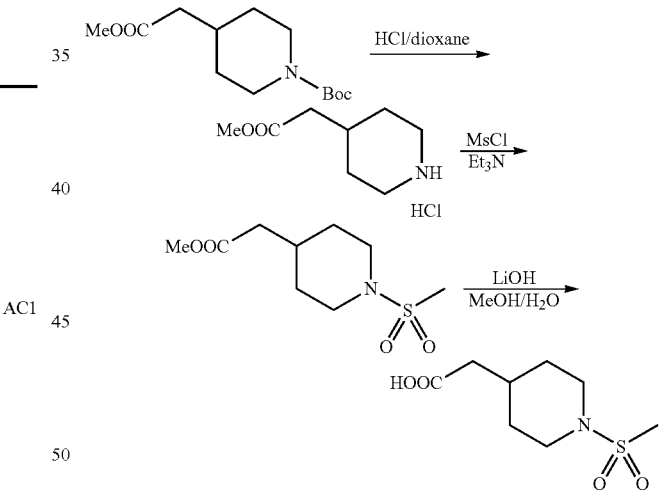

Step 1

To a mixture of tert-butyl 4-(2-methoxy-2-oxoethyl)piperidine-1-carboxylate (100 mg, 0.39 mmol) in anhydrous $CH_2Cl_2$ (3 mL), HCl/dioxane (1 mL, 4 N) was added dropwise. The mixture was stirred at 10° C. for 2 h. TLC showed the starting material was consumed. The mixture was concentrated under reduced pressure to afford crude methyl 2-(piperidin-4-yl)acetate HCl salt (75 mg, 99%) as a white solid, which was used for the next step directly without further purification.

Step 2

To a mixture of crude methyl 2-(piperidin-4-yl)acetate HCl salt (34 mg, 0.18 mmol) in anhydrous $CH_2Cl_2$ (2 mL) was added $Et_3N$ (88 mg, 0.88 mmol). The mixture was stirred at 0° C. under N₂ for 10 min. MsCl (30 mg, 0.26 mmol) was added. The mixture was stirred at 0° C. for 2 h. TLC (petroleum ether/EtOAc=1/2) showed a new spot was observed. The mixture was quenched with H₂O (10 mL) and extracted with CH₂Cl₂ (3×10 mL). The combined organic layers were washed with H₂O (10 mL) and brine (10 mL), dried over anhydrous Na₂SO₄, filtered and concentrated under reduced pressure to afford crude methyl 2-(1-(methylsulfonyl)piperidin-4-yl)acetate (41 mg, 99%) as a white solid, which was used for the next step directly without further purification. ¹H NMR (CDCl₃ 400 MHz): δ 3.80 (d, J=12.4 Hz, 2H), 3.69 (s, 3H), 2.78 (s, 3H), 2.71-2.65 (m, 2H), 2.30 (d, J=7.2 Hz, 2H), 1.92-1.90 (m, 1H), 1.85 (d, J=14.0 Hz, 2H), 1.42-1.33 (m, 2H)

Step 3

To a mixture of crude methyl 2-(1-(methylsulfonyl)piperidin-4-yl)acetate (20 mg, 0.085 mmol) in MeOH/H₂O/CH₂Cl₂ (2 mL, v/v/v=1/1/1) was added LiOH.H₂O (18 mg, 0.43 mmol). The mixture was stirred at rt for 4 h. TLC (petroleum ether/EtOAc=1/5) showed the starting material was consumed. The mixture was concentrated under reduced pressure. The residue was neutralized with 2 N HCl solution (5 mL) and extracted with CH₂Cl₂ (3×5 mL). The combined organic layers were washed with H₂O (5 mL) and brine (5 mL), dried over anhydrous Na₂SO₄, filtered and concentrated under reduced pressure to afford crude 2-(1-(methylsulfonyl)piperidin-4-yl)acetic acid (15 mg, 80%) as a white solid, which was used for next step directly without further purification. ¹H NMR (CDCl₃ 400 MHz): δ 3.81 (d, J=12.0 Hz, 2H), 3.78 (s, 3H), 2.72-2.66 (m, 2H), 2.34 (d, J=6.4 Hz, 2H), 1.98-1.85 (m, 3H), 1.42-1.30 (m, 2H).

Preparation 2

2-(4-(2-ethoxy-2-oxoethyl)phenyl)acetic acid (AC8) and 2,2'-(1,4-phenylene)diacetic acid (AC9)

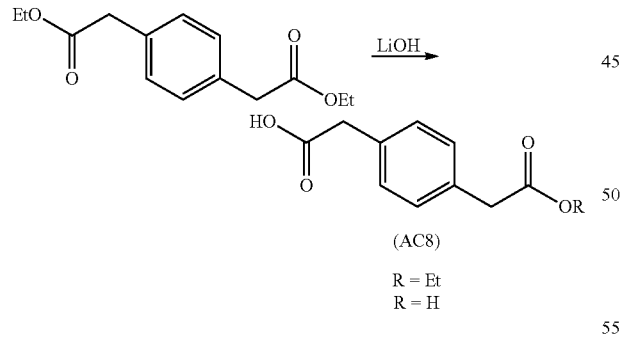

(AC8)
R = Et
R = H

To a stirred solution of diethyl 2,2'-(1,4-phenylene)diacetate (950 mg, 3.8 mmol) in 3:1:1 EtOH/THF/H₂O (50 mL) was added LiOH.H₂O (200 mg, 4.7 mmol). The mixture was stirred overnight and concentrated. The aq residue was diluted with water (10 mL), washed with ether (60 mL) and acidified with conc HCl. The acidic solution was extracted with ether (2×50 mL). These ether extracts were combined, washed with brine (10 mL), dried over Na₂SO₄ and concentrated to leave a white solid. 1H NMR indicated a ~2:1 mixture of the desired monoester (AC8, R=Et) and diacid (AC9, R=H) which was used without further purification.

Preparation 3

2-(4-(ethylthio)phenyl)-2-oxoacetic acid (AC10)

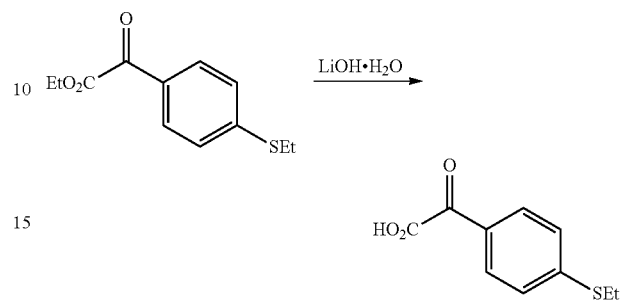

The title compound is prepared from ethyl 2-(4-(ethylthio)phenyl)-2-oxoacetate (Matrix Scientific) following a procedure similar to that described for AC8.

The following amines were purchased.

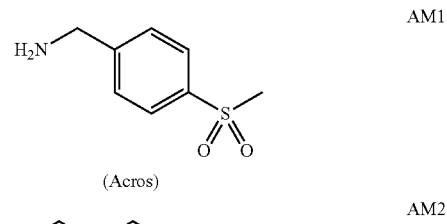

(Acros)    AM1

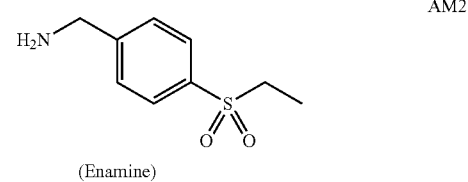

(Enamine)    AM2

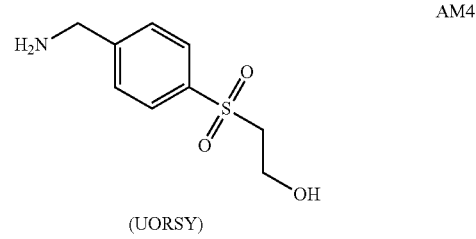

(UORSY)    AM4

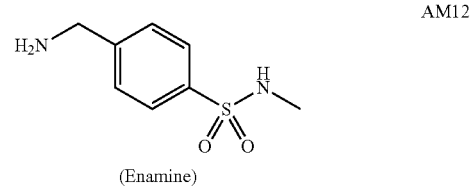

(Enamine)    AM12

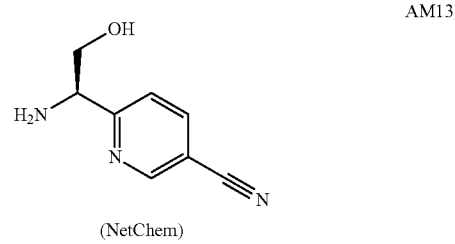

(NetChem)    AM13

AM13

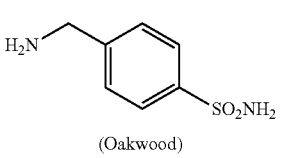

(Oakwood)

AM23

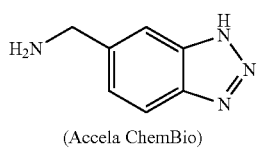

(Accela ChemBio)

AM24

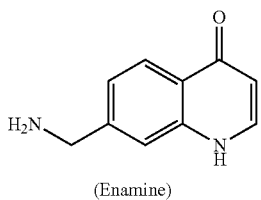

(Enamine)

AM30

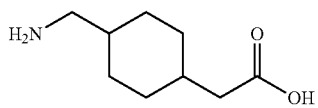

Preparation 4

(4-(propylsulfonyl)phenyl)methanamine (AM3)

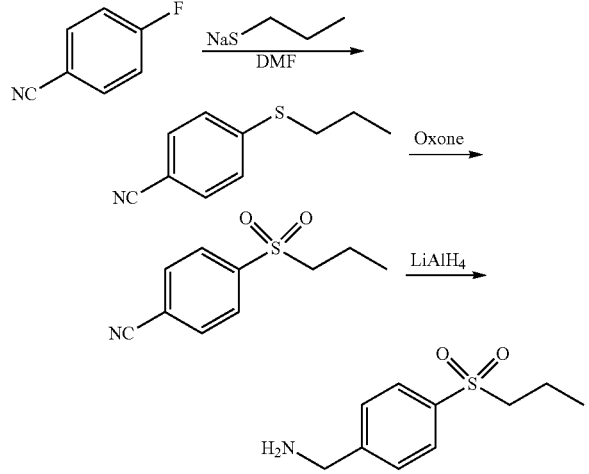

Step 1

To a mixture of 4-fluorobenzonitrile (1.1 g, 9 mmol) in anhydrous DMF (20 mL) was added sodium propane-1-thiolate (1 g, 10 mmol). The mixture was stirred at 0° C. for 2 h. The mixture was diluted with water (20 mL) and extracted with EtOAc (3×20 mL). The combined organic layers were washed with water (3×20 mL), dried over anhydrous $Na_2SO_4$, filtered and concentrated under reduced pressure to afford crude 4-(propylthio)benzonitrile (1.6 g, 100%) as a colorless oil, which was used for next step directly without further purification. $^1$H NMR (CDCl$_3$ 400 MHz): δ 7.51 (d, J=4.8 Hz, 2H), 7.28 (d, J=4.8 Hz, 2H), 2.95 (t, J=7.6 Hz, 2H), 1.76-1.69 (m, 2H), 1.06 (t, J=4.0 Hz, 3H).

Step 2

To a mixture of crude 4-(propylthio)benzonitrile (1 g, 5.6 mmol) in MeOH (10 mL) and $H_2O$ (2 mL) was added oxone (6.9 g, 11.2 mmol). The mixture was stirred at 16° C. for 2 h. TLC (petroleum ether/EtOAc=1/1) showed that the reaction was completed. The mixture was lyophilized directly. Then the mixture was dissolved in $CH_2Cl_2$ (30 mL) and filtered. The filtrate was concentrated under reduced pressure to afford crude 4-(propylsulfonyl)benzonitrile (500 mg, 42%) as a white solid, which was used for next step directly without further purification. $^1$H NMR (CDCl$_3$ 400 MHz): δ 8.04 (d, J=6.8 Hz, 2H), 7.88 (d, J=5.2 Hz, 2H), 3.11 (t, J=5.4 Hz, 2H), 1.78-1.72 (m, 2H), 1.02 (t, J=7.2 Hz, 3H).

Step 3

To a mixture of crude 4-(propylsulfonyl)benzonitrile (100 mg, 0.48 mmol) in anhydrous THF (5 mL) was added LiAlH$_4$ (0.95 mL, 0.95 mmol, 1 M in THF) at 0° C. under $N_2$. The mixture was stirred at rt for 2 h. TLC (EtOAc) showed that the reaction was completed. The mixture was quenched with water (0.04 mL) and aq. NaOH solution (0.04 mL, 10%) at 0° C. The mixture was filtered and the filtrate was concentrated under reduced pressure. The residue was purified by preparative TLC (EtOAc) to afford (4-(propylsulfonyl)phenyl)methanamine (25 mg, 24%) as a yellow oil.

Preparation 5

(5-(methylsulfonyl)pyridin-2-yl)methanamine (AM4)

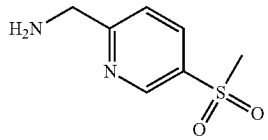

This compound is prepared following a procedure analogous to that described for AM5.

Preparation 6

(5-(ethylsulfonyl)pyridin-2-yl)methanamine (AM5)

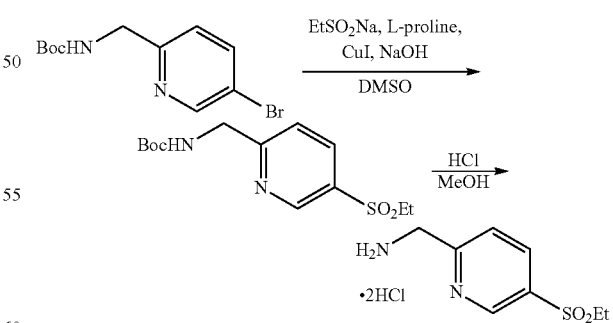

Step 1

To a flame dried flask equipped with a stir bar were added tert-butyl ((5-bromopyridin-2-yl)methyl)carbamate (2.92 g, 10.2 mmol), ethane sulfinic acid sodium salt (2.36 g, 20.3 mmol), L-proline (234 mg, 2.03 mmol), copper (I) iodide (194 mg, 1.02 mmol) and sodium hydroxide (81.3 mg, 2.03 mmol). The flask was purged with N₂, then DMSO (35 mL) was added. The reaction mixture was heated to 110° C. and stirred for 15 h. The flask was then cooled to rt and the mixture was partitioned between EtOAc (150 mL) and satd aq NH₄Cl (150 mL). The organic phase was separated, washed with brine (50 mL), dried over anhydrous MgSO₄, filtered and concentrated under reduced pressure. The residue was purified by silica gel chromatography (eluting with 35% EtOAc in hexanes, gradient to 60%) to afford 1.81 g tert-butyl ((5-bromopyridin-2-yl)methyl)carbamate (59%). LC-MS $t_R$=0.74 min in 1 min chromatography, MS (ESI) m/z 301.4 [M+H]+ ¹H NMR (CDCl₃, 400 MHz): δ 9.02 (dd, J=0.8 Hz, 2.0 Hz, 1H), 8.15 (dd, J=2.4 Hz, 8.4 Hz, 1H), 7.49 (dd, J=0.8 Hz, 8.4 Hz, 1H), 5.49 (broad s, 1H), 4.55 (d, J=7.0 Hz, 2H), 3.15 (q, J=7.2 Hz, 2H), 1.47 (s, 9H), 1.31 (t, J=7.2 Hz, 3H).

Step 2

To a solution of tert-butyl ((5-bromopyridin-2-yl)methyl)carbamate (1.81 g, 6.03 mmol) in MeOH (40 mL) at 0° C. was added acetyl chloride (4.30 mL, 60.3 mmol) dropwise over 5 min. The solution was allowed to warm to rt and was stirred for 3 h. The mixture was concentrated under reduced pressure to yield 1.64 g (5-(ethylsulfonyl)pyridin-2-yl)methanamine bishydrochloride (~100%). LC-MS $t_R$=0.25 min in 1 min chromatography, MS (ESI) m/z 201.2 [M+H]⁺. ¹H NMR (CD₃OD, 400 MHz): δ 9.09 (d, J=1.2 Hz, 1H), 8.35 (dd, J=2.4 Hz, 8.4 Hz, 1H), 7.49 (d, J=8.4 Hz, 1H), 4.45 (s, 2H), 3.31 (q, J=7.2 Hz, 2H), 1.26 (t, J=7.2 Hz, 3H).

Preparation 7

(R)-2-amino-2-(4-(methylsulfonyl)phenyl)ethanol (AM7.1)

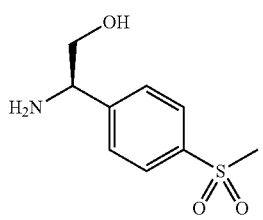

This compound is prepared using procedures analogous to those described for AM8.1, substituting MeI for EtBr in Step 1.

Preparation 8

(S)-2-amino-2-(4-(methylsulfonyl)phenyl)ethanol (AM7.2)

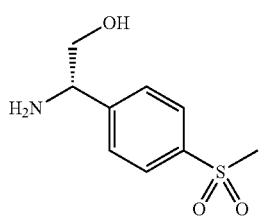

This compound is prepared following procedures analogous to those described for AM8.1 using methyl iodide in place of EtBr in Step 1 and (S)-2-methylpropane-2-sulfinamide in Step 4.

Preparation 9

(R)-2-amino-2-(4-(ethylsulfonyl)phenyl)ethanol (AM8.1)

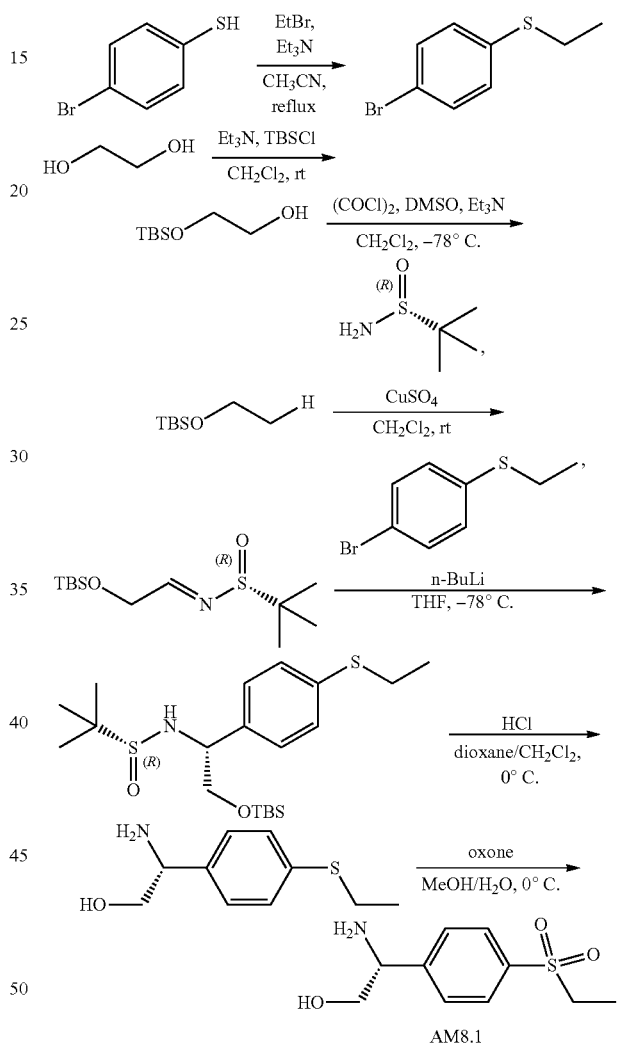

Step 1: (4-bromophenyl)(ethyl)sulfane

A mixture of 4-bromobenzenethiol (50 g, 0.26 mol), bromoethane (58 g, 0.53 mol) and triethylamine (78 g, 0.78 mol) in acetonitrile (1 L) was stirred at reflux for 17 h. The mixture was cooled to rt and filtered. The filtrate was concentrated under vacuum. The residue was purified by silica gel chromatography (eluting with petroleum ether) to give (4-bromophenyl)(ethyl)sulfane (55 g, 96%) as an oil. ¹H NMR (CDCl₃, 400 MHz): δ 7.40-7.42 (dd, J=6.4, 2.0 Hz, 2H), 7.18-7.20 (dd, J=6.4, 2.0 Hz, 2H), 2.91-2.96 (q, J=7.2 Hz, 2H), 1.30-1.33 (t, J=7.2 Hz, 3H).

Step 2: 2-((tert-butyldimethylsilyl)oxy)ethanol

To a solution of ethane-1,2-diol (110 g, 1.77 mol) in anhydrous $CH_2Cl_2$ (1.1 L) was added triethylamine (215.2 g, 296 mL, 2.13 mol) at rt. The mixture was cooled to 0° C., then tert-butylchlorodimethylsilane (267.1 g, 1.77 mol) dissolved in $CH_2Cl_2$ (300 mL) was added dropwise over 1 h. The mixture was stirred at rt overnight. The reaction mixture was quenched with satd aq $NH_4Cl$ solution (400 mL) and separated. The aqueous phase was extracted with MTBE (2×400 mL). The combined organic layers were concentrated under vacuum and the residue was redissolved in MTBE (400 mL). The MTBE layer was washed with water (2×500 mL) and brine (500 mL), dried over anhydrous $Na_2SO_4$, filtered and concentrated under vacuum to give 2-((tert-butyldimethylsilyl)oxy)ethanol (280 g, 90%) as a slight oil, which was used for the next step directly without further purification. $^1H$ NMR ($CDCl_3$, 400 MHz): δ 3.64-3.66 (m, 2H), 3.57-3.60 (m, 2H), 0.85 (s, 9H), 0.02 (s, 6H).

Step 3: 2-((tert-butyldimethylsilyl)oxy)acetaldehyde

To a solution of $CH_2Cl_2$ (1.8 L) cooled to −30° C. was added oxalyl chloride (79.2 g, 52.8 mL, 624 mmol) dropwise. The mixture was cooled to −78° C., then DMSO (62.5 g, 88.5 mL, 1.25 mmol) was added dropwise. After addition, the mixture was stirred at −78° C. for 30 min. A solution of 2-((tert-butyldimethylsilyl)oxy)ethanol (100 g, 567 mmol) dissolved in $CH_2Cl_2$ (200 mL) was added slowly at −78° C. The reaction mixture was stirred at −78° C. for 1 h. Triethylamine (287 g, 395 mL, 2.84 mmol) was added dropwise at −78° C. The mixture was stirred at −78° C. for 30 min and then rt overnight. The reaction mixture was washed with water (1 L), 1 N HCl (2×1 L), satd aq $NaHCO_3$ solution (1 L) and brine (1 L). The organic layer was dried over anhydrous $Na_2SO_4$, filtered and concentrated under vacuum to give 2-((tert-butyldimethylsilyl)oxy)acetaldehyde (98.5 g, 99.8%) as a brown oil, which was used for the next step directly without further purification. $^1H$ NMR ($CDCl_3$, 400 MHz): δ 9.70 (s, 1H), 4.22 (s, 2H), 0.93 (s, 9H), 0.11 (s, 6H).

Step 4: (R,E)-N-(2-((tert-butyldimethylsilyl)oxy)ethylidene)-2-methylpropane-2-sulfinamide A mixture of 2-((tert-butyldimethylsilyl)oxy)acetaldehyde (93.5 g, 0.54 mol), (R)-2-methylpropane-2-sulfinamide (78.8 g, 0.65 mol) and copper (II) sulfate (215 g, 1.35 mol) in anhydrous $CH_2Cl_2$ (1.5 L) was stirred at rt for 16 h. The mixture was quenched with $H_2O$ (800 mL) and separated. The aqueous phase was extracted with $CH_2Cl_2$ (2×1 L). The combined organic layers were washed with water (1 L) and brine (1 L), dried over anhydrous Na2SO4, filtered and concentrated under vacuum. The residue was purified by silica gel chromatography (eluting with petroleum ether:EtOAc=8:1) to give (R,E)-N-(2-((tert-butyldimethylsilyl)oxy)ethylidene)-2-methylpropane-2-sulfinamide (38.5 g, 26%) as a yellow oil. $^1H$ NMR ($CDCl_3$, 400 MHz): δ 7.96-7.97 (t, J=3.2 Hz, 1H), 4.44-4.45 (d, J=2.8 Hz, 2H), 1.11 (s, 9H), 0.00 (s, 6H).

Step 5: (R)—N—((R)-2-((tert-butyldimethylsilyl)oxy)-1-(4-(ethylthio)phenyl)ethyl)-2-methylpropane-2-sulfinamide To a solution of (4-bromophenyl)(ethyl)sulfane (28.9 g, 133.1 mmol) in anhydrous THF (500 mL) was added dropwise n-butyllithium (73 mL, 181.5 mmol, 2.5 M in hexanes) at −78° C. The mixture was stirred at −78° C. for 30 min. A solution of (R,E)-N-(2-((tert-butyldimethylsilyl)oxy)ethylidene)-2-methylpropane-2-sulfinamide (33.5 g, 121 mmol) in anhydrous THF (100 mL) was added to the mixture at −78° C. The mixture was stirred at −78° C. for 2 h, then allowed to warm to rt and stirred for 2 h. The mixture was quenched with satd aq $NH_4Cl$ solution (200 mL) and extracted with EtOAc (3×300 mL). The combined organic layer was washed with water (200 mL) and brine (200 mL), dried over anhydrous $Na_2SO_4$, filtered and concentrated under vacuum. The residue was purified by silica gel chromatography (eluting with petroleum ether:EtOAc=15:1) three times to afford (R)—N—((R)-2-((tert-butyldimethylsilyl)oxy)-1-(4-(ethylthio)phenyl)ethyl)-2-methylpropane-2-sulfinamide (22 g, 44%) as a yellow oil. $^1H$ NMR ($CDCl_3$, 400 MHz): δ 7.21-7.24 (d, J=7.2 Hz, 2H), 7.18-7.21 (d, J=8.4 Hz, 2H), 4.42-4.45 (dd, J=8.8, 2.4 Hz, 1H), 4.21 (brs, 1H), 3.69-3.73 (dd, J=10.4, 4.4 Hz, 1H), 3.51-3.56 (t, J=9.6 Hz, 1H), 2.87-2.92 (q, J=7.6 Hz, 2H), 1.25-1.29 (t, J=7.2 Hz, 3H), 1.18 (s, 9H), 0.88 (s, 9H), 0.02 (s, 6H). LC-MS Method 3 $t_R$=1.010 min MS (ESI) m/z 437.9 [M+Na]$^+$. Isomer SFC $t_R$=3.607 and 4.014 min in 12 min chromatography (AD-H_5_5_40_2.3 5 ML), ee=90.85%.

Step 6: (R)-2-amino-2-(4-(ethylthio)phenyl)ethanol

To a solution of (R)—N—((R)-2-((tert-butyldimethylsilyl)oxy)-1-(4-(ethylthio)phenyl)ethyl)-2-methylpropane-2-sulfinamide (22 g, 52.9 mmol) in $CH_2Cl_2$ (250 mL) was added HCl (26.5 mL, 4 N in dioxane) at 0° C. The mixture was stirred at rt for 2 h. LC-MS showed no starting material remaining. The mixture was concentrated under reduced pressure to afford crude (R)-2-amino-2-(4-(ethylthio)phenyl)ethanol HCl salt (12.3 g, 100%) as a brown solid, which was used for the next step directly without further purification. LC-MS $t_R$=1.226 min in 0-30AB_2 min chromatography (Xtimate 3 um, C18, 2.1*30 mm), MS (ESI) m/z 180.9 [M-OH]$^+$.

Step 7: (R)-2-amino-2-(4-(ethylsulfonyl)phenyl)ethanol

To a mixture of (R)-2-amino-2-(4-(ethylthio)phenyl)ethanol (15.2 g, 65.0 mmol) in methanol (200 mL) was added dropwise a solution of oxone reagent (80.0 g, 130.0 mmol) in water (200 mL) at 0° C. The mixture was stirred at rt for 1.5 h; LC-MS showed no starting material remaining. The mixture was filtered and methanol was removed under reduced pressure. The aqueous phase was extracted with EtOAc (2×80 mL), then the aqueous layer was basified to pH=8-9 with solid sodium carbonate portionwise at 0° C., then this solution was lyophilized (contained the $Na_2CO_3$). The solid was dissolved in $CH_2Cl_2$:MeOH (3:1, 600 mL) and stirred for 30 min, filtered, then concentrated under reduced pressure. The residue was purified by silica gel chromatography (eluting with $CH_2Cl_2$:MeOH=1:0 to 4:1) to give (R)-2-amino-2-(4-(ethylsulfonyl)phenyl)ethanol (11.5 g, 77%) as a white solid. LC-MS $t_R$=0.738 min in 0-30CD_POS chromatography (Xtimate ODS 2.1*30 mm, 3 um), MS (ESI) m/z 230.1 [M+H]$^+$. Isomer SFC $t_R$=6.99 min in 30 min chromatography (CD-PH_10-80_B_08 ML), ee=97.42%. $^1H$ NMR ($D_2O$, 400 MHz): δ 7.82-7.84 (d, J=8.0 Hz, 2H), 7.54-7.56 (d, J=8.4 Hz, 2H), 4.33-4.35 (t, J=6.4 Hz, 1H), 3.72-3.78 (m, 2H), 3.19-3.25 (q, J=7.6 Hz, 2H), 1.03-1.07 (t, J=7.6 Hz, 3H).

Preparation 10

Alternate Preparation of AM8.1

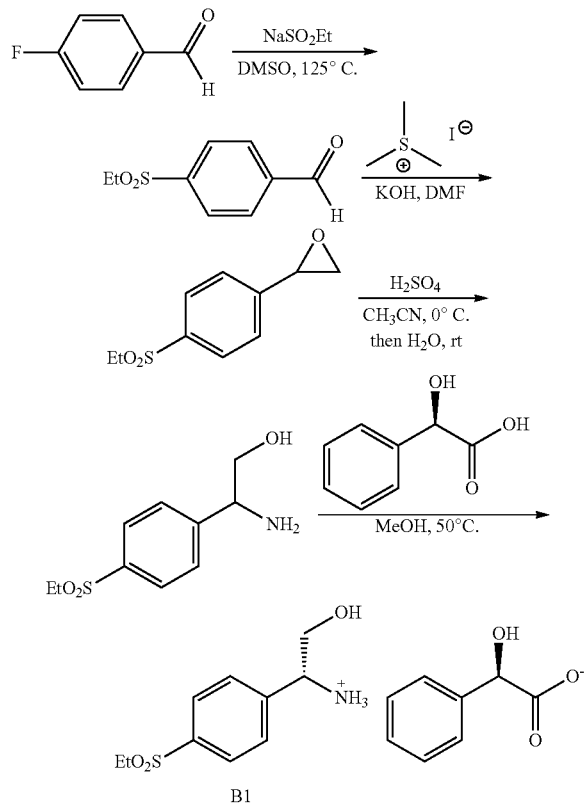

Step 1: 4-(ethylsulfonyl)benzaldehyde

To a solution of 4-fluorobenzaldehyde (24.6 g, 198 mmol) in dimethylsulfoxide (60 mL) was added sodium ethanesulfinate (46 g, 396 mmol). The resulting mixture was stirred at 125° C. for 20 h. After cooling to rt, the reaction mixture was triturated with 350 mL of $H_2O$. The product was filtered, washed with two 10-mL portions of EtOH and dried under vacuum to afford 4-(ethylsulfonyl)benzaldehyde as a light yellow solid (31.2 g, 80% yield). LC-MS $t_R$=1.19 min in 2 min chromatography, MS (ESI) m/z 199.1 [M+H]+ $^1$H NMR ($CDCl_3$) δ 10.14 (s, 1H), 8.09 (s, 4H), 3.16 (q, J=7.2 Hz, 2H), 1.30 (t, J=7.2 Hz, 3H).

Step 2: 2-(4-(ethylsulfonyl)phenyl)oxirane

To a solution of 4-(ethylsulfonyl)benzaldehyde (10 g, 50.5 mmol) in DMF (85 mL) at rt was added trimethylsulfonium iodide (11.9 g, 58.1 mmol) followed by potassium hydroxide powder (5.66 g, 101 mmol). The reaction mixture was stirred at rt for 20 min before quenching with $H_2O$ (50 mL). The mixture was carefully neutralized with 1 N HCl solution (55 mL) and extracted with EtOAc (3×100 mL). The combined organic phase was washed with brine, dried over anhydrous $Na_2SO_4$, and passed through a pad of silica gel (eluting with EtOAc). It was concentrated under reduced pressure to afford crude 2-(4-(ethylsulfonyl)phenyl)oxirane as yellow oil, which was used directly for the next step without further purification. LC-MS $t_R$=1.13 min in 2 min chromatography, MS (ESI) m/z 213.2 [M+H]+.

Step 3: 2-amino-2-(4-(ethylsulfonyl)phenyl)ethan-1-ol

To a solution of crude 2-(4-(ethylsulfonyl)phenyl)oxirane (50.5 mmol) in $CH_3CN$ (200 mL) at 0° C. was slowly added concentrated sulfuric acid (5.4 mL, 101 mmol). The mixture was allowed to stir at rt for 1.5 h. LC-MS showed the starting material was consumed. $H_2O$ (15 mL) was added to the reaction mixture. Stirring continued at rt for 8 h, then at 45° C. for 10 h. After cooling to rt, the pH of the reaction mixture was adjusted to 3-4 by addition of 1 N NaOH solution (90 mL). The mixture was extracted with EtOAc (100 mL). The organic phase was then extracted with $H_2O$ (2×30 mL). The combined aqueous layers were then basified with 1 N NaOH solution (110 mL) to pH=9 and extracted with 1-butanol (5×60 mL). The combined organic layer (consisting of 1-butanol extracts) was dried over anhydrous $Na_2SO_4$, filtered and concentrated under reduced pressure. It was dried under high vacuum to afford crude 2-amino-2-(4-(ethylsulfonyl)phenyl)ethan-1-ol as an off-white solid. 4 g, 35% yield over 3 steps. Intermediate 4-(4-(ethylsulfonyl)phenyl)-2-methyl-4,5-dihydrooxazole: LC-MS $t_R$=0.77, 0.81 min in 2 min chromatography, MS (ESI) m/z 254.26 [M+H]+. 2-amino-2-(4-(ethylsulfonyl)phenyl)ethan-1-ol: LC-MS $t_R$=0.61 min in 2 min chromatography, MS (ESI) m/z 230.21 [M+H]+. $^1$H NMR ($CD_3OD$): δ 7.88 (d, J=8.4 Hz, 2H), 7.64 (d, J=8.4 Hz, 2H), 4.16-4.12 (m, 1H), 3.76-3.72 (m, 1H), 3.66-3.61 (m, 1H), 3.17 (q, J=7.2 Hz, 2H), 1.19 (t, J=7.2 Hz, 3H).

Step 4: 2-amino-2-(4-(ethylsulfonyl)phenyl)ethan-1-ol mono-mandelate salt

To a solution of 2-amino-2-(4-(ethylsulfonyl)phenyl)ethan-1-ol (238 mg, 1.0 mmol) in MeOH (3 mL) at 50° C. was added a solution of (R)-Mandelic acid (76 mg, 0.5 mmol) in MeOH (1 mL). The resulting solution was allowed to cool down to ambient temperature slowly. After stirring for 1 day, the resulting crystals were collected by vacuum filtration and dried under high vacuum, providing the mono-mandelate salt as a white crystal, 107 mg (28% yield), 92.5% ee. $^1$H NMR ($CD_3OD$): δ 7.97 (d, J=8.0 Hz, 2H), 7.71 (d, J=8.4 Hz, 2H), 7.46 (d, J=8.0 Hz, 2H), 7.46 (d, J=8.0 Hz, 2H), 7.31-7.27 (m, 2H), 7.25-7.22 (m, 1H), 4.42-4.42 (m, 1H), 3.92-3.89 (m, 1H), 3.81-3.77 (m, 1H), 3.21 (q, J=7.2 Hz, 2H), 1.21 (t, J=7.2 Hz, 3H).

Preparation 11

(S)-2-amino-2-(4-(ethylsulfonyl)phenyl)ethanol (AM8.2)

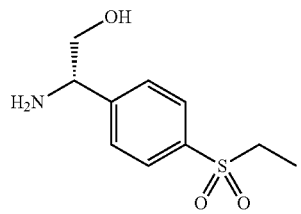

This compound is prepared following procedures analogous to those described for AM8.1 using (S)-2-methylpropane-2-sulfinamide in Step 4

Preparation 12

(R)-2-amino-2-(4-(ethylsulfonyl)-2-fluorophenyl)ethan-1-ol (AM9.1)

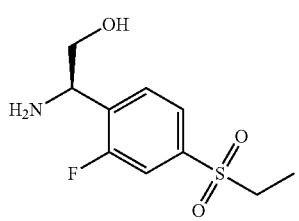 [SMILES: CCS(=O)(=O)c1ccc([C@@H](N)CO)c(F)c1]

This compound is prepared following procedures analogous to those described for AM8.1 using (4-bromo-3-fluorophenyl)(ethyl)sulfane in Step 5.

Preparation 13

(R)-2-amino-2-(5-(methylsulfonyl)pyridin-2-yl)ethanol (AM10.1)

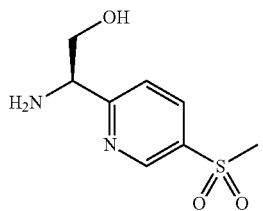

This compound is prepared using procedures analogous to those described for AM11.1 using NaSMe in Step 1.

Preparation 14

(S)-2-amino-2-(5-(methylsulfonyl)pyridin-2-yl)ethanol (AM10.2)

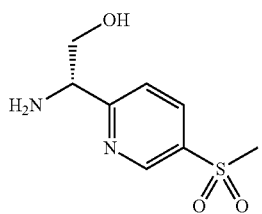

This compound is prepared following procedures analogous to those described for AM11.1 using NaSMe in Step 1 and (S,E)-N-(2-((tert-butyldimethylsilyl)oxy)ethylidene)-2-methylpropane-2-sulfinamide in Step 2.

Preparation 15

(R)-2-amino-2-(5-(ethylsulfonyl)pyridin-2-yl)ethanol (AM11.1)

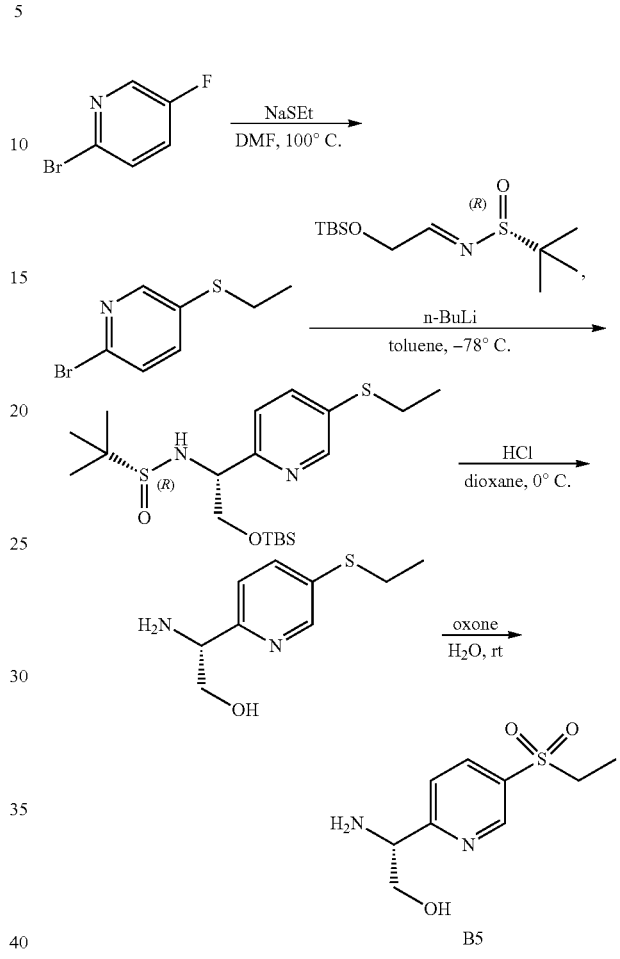

Step 1: 2-bromo-5-(ethylthio)pyridine

To a mixture of 2-bromo-5-fluoropyridine (6.28 g, 35.66 mmol) in anhydrous DMF (60 mL) was added sodium ethanethiolate (3 g, 35.66 mmol). The mixture was stirred at 100° C. for 3 h. TLC (petroleum ether/EtOAc 10/1) showed that the starting material was not consumed completely. Additional sodium ethanethiolate (0.9 g, 9.56 mmol) was added to the mixture. The mixture was stirred at 100° C. for 12 h. The mixture was quenched with $H_2O$ (150 mL) and extracted with EtOAc (3×150 mL). The combined organic layers were washed with brine (400 mL), dried over anhydrous $Na_2SO_4$, filtered and concentrated under reduced pressure. The residue was purified by silica gel chromatography (eluting with petroleum ether/EtOAc 80/1) to afford 2-bromo-5-(ethylthio)pyridine (7.0 g, 90%) as a colorless oil. LC-MS Method 3 $t_R$=0.717 min, MS (ESI) m/z 217.6 $[M+H]^+$.

Step 2: (R)—N—((R)-2-((tert-butyldimethylsilyl)oxy)-1-(5-(ethylthio)pyridin-2-yl)ethyl)-2-methylpropane-2-sulfinamide To a solution of toluene (60 mL) was added n-BuLi (10.6 mL, 26.48 mmol, 2.5 M in hexanes) dropwise at −78° C.; the internal temperature did not exceed −50° C. A solution of 2-bromo-5-(ethylthio)pyridine (3.85 g, 17.65 mmol) in toluene (10 mL) was then added to the reaction mixture at −78° C.; the internal temperature did not exceed −65° C. The mixture was stirred at −78° C. for 1 h. A solution of (R,E)-N-(2-((tert-butyldimethylsilyl)oxy)ethylidene)-2-methylpropane-2-sulfinamide (4.90 g, 17.65 mmol) in toluene (10 mL) was added to the reaction mixture at −78° C.; the internal temperature did not exceed −60° C. The mixture was stirred at −78° C. for another 2 h. The mixture was quenched with brine (150 mL) at −78° C. and extracted with EtOAc (3×150 mL). The combined organic layers were washed with brine (400 mL), dried over anhydrous $Na_2SO_4$, filtered and concentrated under reduced pressure. The residue was purified by silica gel chromatography (eluting with petroleum ether/EtOAc 10/1 to 3/1) to afford (R)—N—((R)-2-((tert-butyldimethylsilyl)oxy)-1-(5-(ethylthio)pyridin-2-yl)ethyl)-2-methylpropane-2-sulfinamide (3.0 g, 41%) as a pale yellow oil. LC-MS Method 3 $t_R$=1.014 min, MS (ESI) m/z 417.2 [M+H]+.

Step 3: (R)-2-amino-2-(5-(ethylthio)pyridin-2-yl)ethanol

A procedure analogous to that in Preparation 9 Step 6 is employed.

Step 4: (R)-2-amino-2-(5-(ethylsulfonyl)pyridin-2-yl)ethanol

A procedure analogous to that in Preparation 9 Step 7 is employed. 1H NMR (CD3OD, 400 MHz): δ 9.08 (s, 1H), 8.35 (dd, J=2.0, 8.4 Hz, 1H), 7.79 (d, J=8.4 Hz, 1H), 4.70 (t, J=5.6 Hz, 1H), 4.03 (dd, J=4.8, 12.0 Hz, 1H), 3.91 (dd, J=4.8, 11.6 Hz, 1H), 3.29 (q, J=7.2 Hz, 2H), 1.25 (t, J=7.2 Hz, 3H).

Preparation 16

(S)-2-amino-2-(5-(ethylsulfonyl)pyridin-2-yl)ethanol (AM11.2)

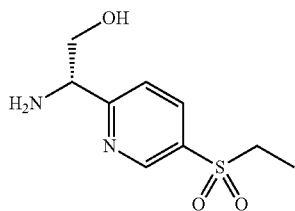

This compound was prepared using procedures analogous to those described for AM11.1 using (S,E)-N-(2-((tert-butyldimethylsilyl)oxy)ethylidene)-2-methylpropane-2-sulfinamide in Step 2.

Preparation 17

Methyl 2-((4-(aminomethyl)piperidin-1-yl)sulfonyl)acetate (AM13)

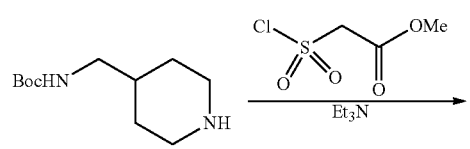

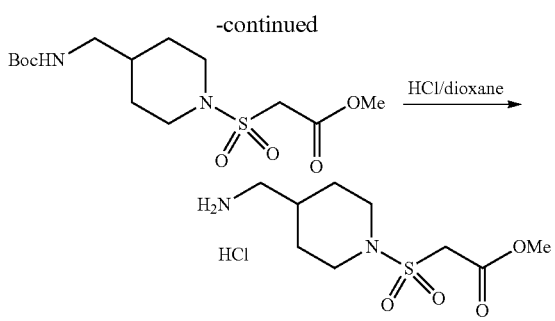

Step 1

To a mixture of tert-butyl (piperidin-4-ylmethyl)carbamate (100 mg, 0.469 mmol) in $CH_2Cl_2$ (2 mL) was added methyl 2-(chlorosulfonyl)acetate (89 mg, 0.516 mmol) and $Et_3N$ (95 mg, 0.938 mmol). The mixture was stirred at rt for 16 h. TLC (petroleum ether/EtOAc=1/1) showed that a new spot was observed and TLC ($CH_2Cl_2$/MeOH=10/1) showed that the starting material was consumed completely. The mixture was quenched with $H_2O$ (20 mL) and extracted with $CH_2Cl_2$ (3×20 mL). The combined organic layers were dried over anhydrous $Na_2SO_4$, filtered and concentrated under reduced pressure. The residue was purified by preparative TLC with petroleum ether/EtOAc=1/1 to afford methyl 2-((4-(((tert-butoxycarbonyl)amino)methyl)piperidin-1-yl)sulfonyl)acetate (100 mg, 61%) as a white solid. 1H NMR (CDCl3 400 MHz): δ 4.70-4.59 (m, 1H), 3.93 (s, 2H), 3.85 (d, J=12.4 Hz, 2H), 3.80 (s, 3H), 3.04 (t, J=6.0 Hz, 2H), 2.86 (dt, J=2.0, 12.0 Hz, 2H), 1.78 (d, J=10.4 Hz, 2H), 1.70-1.53 (m, 1H), 1.44 (s, 9H), 1.38-1.24 (m, 2H).

Step 2

A solution of methyl 2-((4-(((tert-butoxycarbonyl)amino)methyl)piperidin-1-yl)sulfonyl)acetate (60 mg, 0.33 mmol) in dioxane (1 mL) was added HCl/dioxane (3 mL, 4 M) and then stirred at rt for 2 h. TLC (petroleum ether/EtOAc=1/1) showed that the reaction was completed. The mixture was concentrated under reduced pressure to afford crude methyl 2-((4-(aminomethyl)piperidin-1-yl)sulfonyl)acetate HCl salt (36 mg, 73%) as a yellow oil, which was used for the next step directly without further purification.

Preparation 18

(R)-1-(4-(ethylsulfonyl)phenyl)-2-methoxyethan-1-amine (AM16)

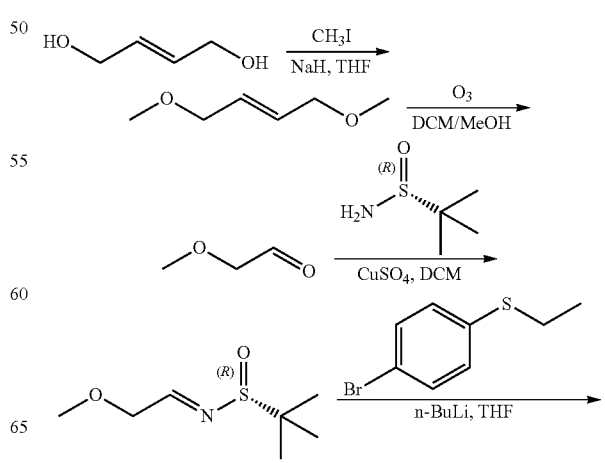

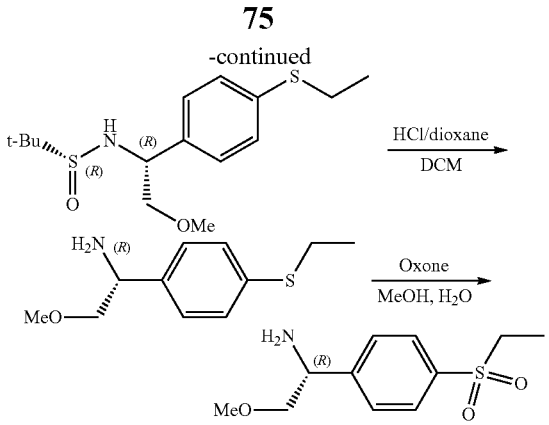

Step 1

NaH (87 g, 2179.08 mmol, 60% in mineral oil) in anhydrous THF (600 mL) was added (E)-but-2-ene-1,4-diol (80 g, 907.95 mmol) in anhydrous THF (200 mL) dropwise via dropping funnel over 20 min under $N_2$ with an ice-water bath. The reaction mixture was stirred at 0-5° C. for 1 h. Then $CH_3I$ (758 g, 5340.28 mmol) was added dropwise over 30 min. The resulting mixture was stirred at 16-19° C. for 16 h. TLC (petroleum ether:EtOAc=5:1) showed the starting material was consumed. The reaction was cooled with an ice-water bath, quenched with water (100 mL), diluted with EtOAc (1.5 L). The mixture was washed with brine (3×500 mL), dried over anhydrous $Na_2SO_4$, filtered and the filtrate was concentrated under reduced pressure to afford (E)-1,4-dimethoxybut-2-ene (94.9 g crude, 90% purity, 90%) as a colorless oil which was used for the next step directly without further purification. $^1$H NMR ($CDCl_3$, 400 MHz): δ 5.71 (t, J=3.6 Hz, 2H), 4.00 (d, J=4.4 Hz, 4H), 3.33 (s, 6H).

Step 2

A solution of (E)-1,4-dimethoxybut-2-ene (86.9 g, 748.28 mmol) in anhydrous $CH_2Cl_2$ (1 L) and anhydrous MeOH (0.5 L) was bubbled with Ozone at −78° C. After the reaction mixture was stirred at −78° C. for 1 h and the reaction mixture turn blue. Excess Ozone was removed by bubbling argon through the reaction mixture. TLC (petroleum ether:EtOAc=5:1) showed the starting material was consumed. The 2-methoxyacetaldehyde (crude in $CH_2Cl_2$ and MeOH, 100%) was used for the next step directly without further purification.

Step 3

To a solution of above 2-methoxyacetaldehyde (crude in $CH_2Cl_2$ and MeOH, 748.28 mmol) was add a solution of (R)-2-methylpropane-2-sulfinamide (109 g, 897.93 mmol) in anhydrous $CH_2Cl_2$ (500 mL) and $CuSO_4$ (179 g, 1127.42 mmol) in anhydrous $CH_2Cl_2$ (1.5 L) under $N_2$. The reaction mixture was stirred at 18-20° C. for 20 h. TLC (petroleum ether:EtOAc=5:1) showed the reaction was completed. The reaction mixture was filtered and the filter cake was washed with $CH_2Cl_2$ (3×1.5 L). The combined organic layers were concentrated under reduced pressure, purified by column chromatograph on silica gel (eluting with petroleum ether:EtOAc=20:1-3:1) to give (R,E)-N-(2-methoxyethylidene)-2-methylpropane-2-sulfinamide (47 g, 92% purity, 35%) as a brown oil. $^1$H NMR ($CDCl_3$ 400 MHz): δ 8.08 (t, J=2.8 Hz, 1H), 4.32 (t, J=3.6 Hz, 2H), 3.45 (s, 3H), 1.20 (s, 9H).

Step 4

To a solution of (4-bromophenyl)(ethyl)sulfane (51.2 g, 235.8 mmol) in anhydrous THF (1 L) was added n-BuLi (128.6 mL, 321.55 mmol, 2.5 M in hexane) dropwise via dropping funnel over 30 min at −78° C. under $N_2$. After addition, the reaction mixture was stirred at −78° C. for 30 min. Then a solution of (R,E)-N-(2-methoxyethylidene)-2-methylpropane-2-sulfinamide (38 g, 214.37 mmol) in anhydrous THF (300 mL) was added dropwire via dropping funnel over 30 min. The reaction mixture was stirred at −78° C. for 1 h. TLC (petroleum ether:EtOAc=2:1) showed the starting material was consumed. The mixture was quenched with satd aq $NH_4Cl$ solution (100 mL). The mixture was added with EtOAc (1.2 L), washed with brine (3×500 mL), dried over anhydrous $Na_2SO_4$, filtered and concentrated under reduced pressure, purified by column chromatograph on silica gel (eluting with petroleum ether:EtOAc=10:1-2:3) to afford (R)—N—((R)-1-(4-(ethylthio)phenyl)-2-methoxyethyl)-2-methylpropane-2-sulfinamide (9 g, 93% purity), and the mixture of racemic (R)—N—((R)-1-(4-(ethylthio)phenyl)-2-methoxyethyl)-2-methylpropane-2-sulfinamide and (R)—N—((S)-1-(4-(ethylthio)phenyl)-2-methoxyethyl)-2-methylpropane-2-sulfinamide (35 g). The racemic was further purified by preparative HPLC (neutral) to give (R)—N—((R)-1-(4-(ethylthio)phenyl)-2-methoxyethyl)-2-methylpropane-2-sulfinamide (18 g, 99% purity, 40%) and (R)—N—((S)-1-(4-(ethylthio)phenyl)-2-methoxyethyl)-2-methylpropane-2-sulfinamide (7.0 g, 99% purity, 10%) as colorless oil. LC-MS Method 2 $t_R$=1.306 min, MS (ESI) m/z 316.2 [M+H]$^+$.

Neutral preparative HPLC method
Mobile phase A: water with 10 mM $NH_4HCO_3$
Mobile phase B: $CH_3CN$
Flow rate: 150 mL/min.
Detection: UV 220 nm/254 nm
Column: Phenomenex luna C18 250*77 mm*10 um
Column temperature: 30° C.

| Time in min | % A | % B |
|---|---|---|
| 0.00 | 80 | 20 |
| 30.00 | 36 | 64 |
| 31.00 | 0 | 100 |
| 40.00 | 0 | 100 |

Step 5

To a solution of (R)—N—((R)-1-(4-(ethylthio)phenyl)-2-methoxyethyl)-2-methylpropane-2-sulfinamide (18.0 g, 57.05 mmol) in anhydrous $CH_2Cl_2$ (400 mL) was added HCl/dioxane (28.5 mL, 114.10 mmol, 4.0 M in 1,4-dioxane) dropwise via dropping funnel over 10 min under $N_2$. Then the reaction was stirred at rt for 16 h. TLC (petroleum ether:EtOAc=1:3) showed the starting material was consumed. The solvent was removed under reduced pressure to afford crude (R)-1-(4-(ethylthio)phenyl)-2-methoxyethanamine HCl salt (20 g crude, 89.48% purity, 100%) as a brown solid, which was used for the next step directly without further purification. LC-MS: $t_R$=1.225 min in 0-60AB_2.0 min chromatography (A: Xtimate ODS 2.1*30 mm, B: XBrige Shield RP18 2.1*50 mm), MS (ESI) m/z 195.2 [M-NH$_3$]$^+$.

Step 6

To a solution of (R)-1-(4-(ethylthio)phenyl)-2-methoxyethanamine (20 g crude, 57.05 mmol) in MeOH (300 mL) was added a solution of oxone (63 g, 102.69 mmol) in $H_2O$ (500 mL) dropwise via dropping funnel over 30 min at 0-5° C. with an ice-water bath. Then the reaction mixture was stirred at rt for 2 h. LC-MS showed the starting material was consumed. The mixture was cooled down to 0-5° C. with an ice-water bath for 10 min, quenched with sat. $Na_2SO_3$ solution (300 mL), basified to pH=12-14 with 10% w/w NaOH solution, extracted with EtOAc (3×1 L). The combined organic layers were washed with brine (3×1.2 L), dried over anhydrous Na₂SO₄, filtered and concentrated under reduced pressure. The residue was purified by column chromatograph on silica gel (eluting with CH₂Cl₂: MeOH=50:1 to 10:1) to give (R)-1-(4-(ethylsulfonyl)phenyl)-2-methoxyethanamine (12.5 g, 97% purity, 90%) as a brown oil. LC-MS: t$_R$=1.428 min in 0-60CD_POS_3.0 min chromatography (A: Xtimate ODS 2.1*30 mm, B: XBrige Shield RP18 2.1*50 mm), MS (ESI) m/z 244.1 [M+H]⁺.

Preparation 19

(R)-1-(5-(ethylsulfonyl)pyridin-2-yl)-2-methoxyethan-1-amine (AM17)

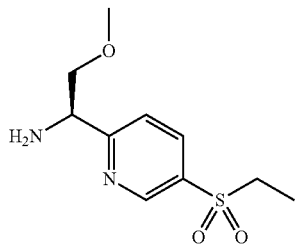 [SMILES: CCS(=O)(=O)c1ccc([C@@H](N)COC)nc1]

This compound was prepared using procedures analogous to those described for AM17

Preparation 20

4-(aminomethyl)-N-methylpiperidine-1-sulfonamide (AM18)

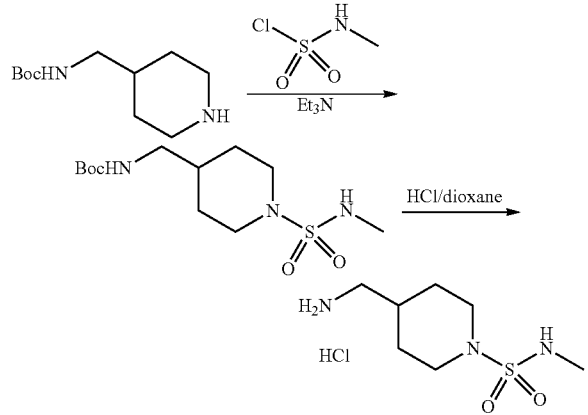

Step 1

To a mixture of tert-butyl (piperidin-4-ylmethyl)carbamate (30 mg, 0.141 mmol) in CH₂Cl₂ (1 mL) was added methylsulfamoyl chloride (21 mg, 0.155 mmol) and Et₃N (43 mg, 0.423 mmol). The mixture was stirred at rt for 16 h under N₂. TLC (petroleum ether/EtOAc=1/2) showed that a new major spot was observed. The mixture was diluted with CH₂Cl₂ (20 mL) and washed with brine (20 mL). The organic layer was dried over anhydrous Na₂SO₄, filtered and concentrated under reduced pressure. The residue was purified by preparative TLC with petroleum ether/EtOAc=1/2 to afford tert-butyl ((1-(N-methylsulfamoyl)piperidin-4-yl)methyl)carbamate (35 mg, 81%) as a yellow oil. ¹H NMR (CDCl₃ 400 MHz): δ 4.66-4.55 (m, 1H), 4.00-3.92 (m, 1H), 3.96 (d, J=4.8 Hz, 2H), 3.03 (t, J=6.4 Hz, 2H), 2.80-2.69 (m, 5H), 1.76 (d, J=13.2 Hz, 2H), 1.62-1.55 (m, 1H), 1.43 (s, 9H), 1.33-1.20 (m, 2H).

Step 2

To a solution of tert-butyl ((1-(N-methylsulfamoyl)piperidin-4-yl)methyl)carbamate (35 mg, 0.114 mmol) in dioxane (1 mL) was added HCl/dioxane (3 mL, 4 M). The mixture was stirred at rt for 2 h. TLC (petroleum ether/EtOAc=1/2) showed that the starting material was consumed completely. The mixture was concentrated under reduced pressure to afford crude 4-(aminomethyl)-N-methylpiperidine-1-sulfonamide HCl salt (28 mg, 100%) as a pale yellow oil, which was used for the next step directly without further purification.

Preparation 21

2-((4-(aminomethyl)piperidin-1-yl)sulfonyl)-N-methylacetamide (AM19)

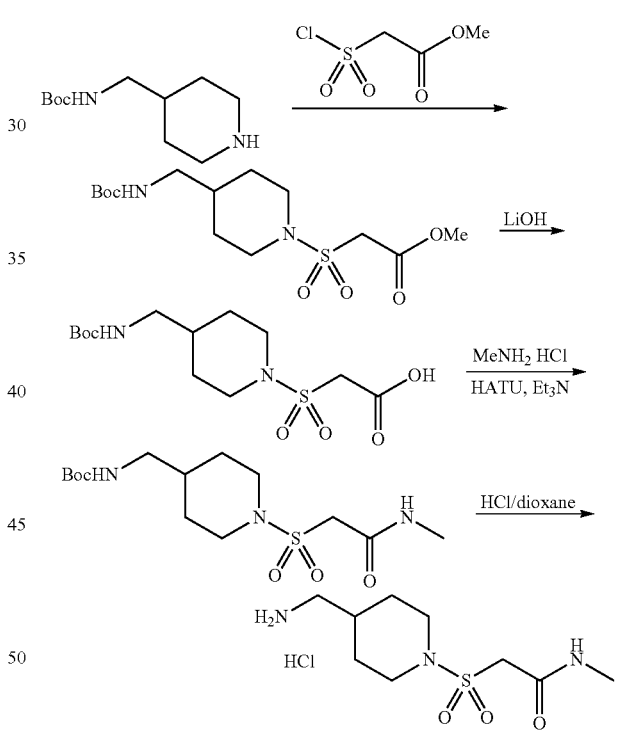

Step 1

To a mixture of tert-butyl (piperidin-4-ylmethyl)carbamate (100 mg, 0.469 mmol) in CH₂Cl₂ (2 mL) was added methyl 2-(chlorosulfonyl)acetate (89 mg, 0.516 mmol) and Et₃N (95 mg, 0.938 mmol). The mixture was stirred at rt for 16 h. TLC (petroleum ether/EtOAc=1/1) showed that the desired spot was observed and TLC (CH₂Cl₂/MeOH=10/1) showed that the starting material was consumed completely. The mixture was quenched with H₂O (20 mL) and extracted with CH₂Cl₂ (3×20 mL). The combined organic layers were dried over anhydrous Na₂SO₄, filtered and concentrated under reduced pressure. The residue was purified by preparative TLC with petroleum ether/EtOAc=1/1 to afford methyl 2-((4-(((tert-butoxycarbonyl)amino)methyl)piperidin-1-yl)sulfonyl)acetate (100 mg, 61%) as a white solid. ¹H NMR (CDCl₃ 400 MHz): δ 4.70-4.59 (m, 1H), 3.93 (s, 2H), 3.85 (d, J=12.4 Hz, 2H), 3.80 (s, 3H), 3.04 (t, J=6.0 Hz, 2H), 2.86 (dt, J=2.0, 12.0 Hz, 2H), 1.78 (d, J=10.4 Hz, 2H), 1.70-1.53 (m, 1H), 1.44 (s, 9H), 1.38-1.24 (m, 2H).

Step 2

To a mixture of methyl 2-((4-(((tert-butoxycarbonyl)amino)methyl)piperidin-1-yl)sulfonyl)acetate (100 mg, 0.286 mmol) in MeOH (5 mL) was added LiOH.H₂O (120 mg, 2.86 mmol) and H₂O (1 mL). The mixture was stirred at rt for 5 h. TLC (EtOAc) showed that the reaction was completed. The mixture was concentrated under reduced pressure. The residue was diluted with H₂O (10 mL) and adjusted to pH=4-5 with 1 N HCl solution. The aqueous layer was extracted with EtOAc (3×15 mL). The combined organic layers were dried over anhydrous Na₂SO₄, filtered and concentrated under reduced pressure to afford crude 2-((4-(((tert-butoxycarbonyl)amino)methyl)piperidin-1-yl)sulfonyl)acetic acid (96 mg, 100%) as a pale yellow solid, which was used for the next step directly without further purification.

Step 3

To a mixture of crude 2-((4-(((tert-butoxycarbonyl)amino)methyl)piperidin-1-yl)sulfonyl)acetic acid (96 mg, 0.286 mmol) in DMF (5 mL) was added MeNH₂.HCl (38 mg, 0.572 mmol), HATU (217 mg, 0.572 mmol) and Et₃N (58 mg, 0.572 mmol). The mixture was stirred at rt for 16 h under N₂. TLC (EtOAc) showed that a new spot was observed. The mixture was diluted with EtOAc (30 mL) and washed with brine (3×30 mL). The organic layer was dried over anhydrous Na₂SO₄, filtered and concentrated under reduced pressure. The residue was purified by preparative TLC with EtOAc to afford tert-butyl ((1-((2-(methylamino)-2-oxoethyl)sulfonyl)piperidin-4-yl)methyl)carbamate (65 mg, 65%) as a pale yellow solid. ¹H NMR (CDCl₃ 400 MHz): δ 6.47-6.39 (m, 1H), 4.60-4.50 (m, 1H), 3.80-3.70 (m, 4H), 3.03-2.94 (m, 2H), 2.82-2.70 (m, 5H), 1.75-1.68 (m, 2H), 1.61-1.57 (m, 1H), 1.37 (s, 9H), 1.30-1.16 (m, 2H).

Step 4

To a mixture of tert-butyl ((1-((2-(methylamino)-2-oxoethyl)sulfonyl)piperidin-4-yl)methyl)carbamate (35 mg, 0.1 mmol) in dioxane (0.5 mL) was added HCl/dioxane (2 mL, 4 M). The mixture was stirred at rt for 2 h. TLC (EtOAc) showed that the reaction was completed. The mixture was concentrated under reduced pressure to afford crude 2-((4-(aminomethyl)piperidin-1-yl)sulfonyl)-N-methylacetamide HCl salt (28 mg, 100%) as a yellow oil, which was used for the next step directly without further purification.

Preparation 22

Methyl 2-amino-2-(1-(methylsulfonyl)piperidin-4-yl)acetate (AM21)

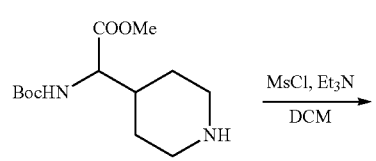

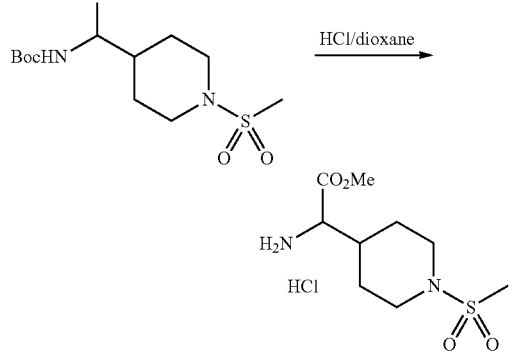

Step 1

To a solution of methyl 2-((tert-butoxycarbonyl)amino)-2-(piperidin-4-yl)acetate (0.3 g, 1.1 mmol) in anhydrous CH₂Cl₂ (6 mL) was added Et₃N (0.33 g, 3.3 mmol) at 0° C. under N₂. Then MsCl (0.13 mL, 1.7 mmol) was added dropwise at 0° C. under N₂. Then the mixture was stirred at 0° C. for 1.5 h. TLC (CH₂Cl₂/MeOH=15/1) showed the reaction was completed. The mixture was added with ice-water (10 mL) at 0° C. The mixture was extracted with CH₂Cl₂ (3×10 mL). The combined organic layers were dried over anhydrous Na₂SO₄, filtered and concentrated under reduced pressure to afford crude methyl 2-((tert-butoxycarbonyl)amino)-2-(1-(methylsulfonyl)piperidin-4-yl)acetate (360 mg, 93%) as a white solid, which was used for the next step directly without further purification.

Step 2

A procedure analogous to that used in Step 2 of the preparation of AM26 is employed.

Preparation 23

2-((4-(aminomethyl)piperidin-1-yl)sulfonyl)acetamide (AM22)

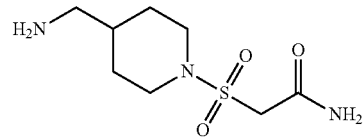 [SMILES: NCC1CCN(S(=O)(=O)CC(N)=O)CC1]

The title compound is prepared following procedures analogous to those used for AM19, substituting NH₄Cl for MeNH₂.HCl in Step 3.

Preparation 24

Methyl (S)-3-amino-3-(4-(ethylsulfonyl)phenyl)propanoate (AM25)

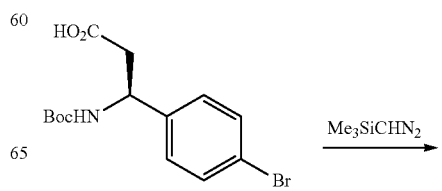

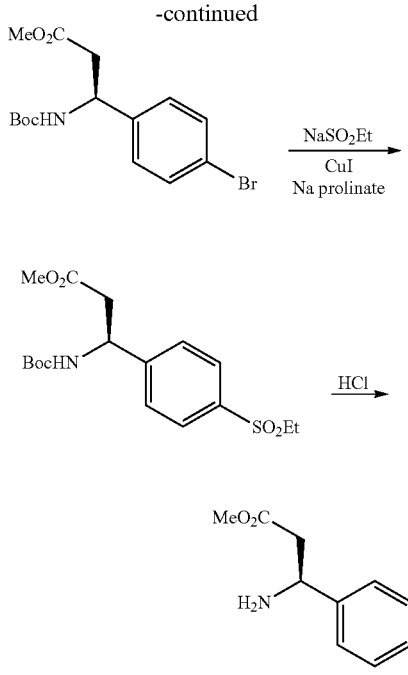

Step 1

To a stirred solution of (S)-3-(4-bromophenyl)-3-((tert-butoxycarbonyl)amino)propanoic acid (AstaTech, 990 mg, 2.88 mmol) in MeOH (5 mL) and ether (5 mL) was added 2 M Me$_3$SiCHN$_2$ in hexanes (5 mL in 1 mL aliquots at 2 minute intervals, 10 mmol) until a persistent yellow solution was obtained. The solution was stirred for 15 min and glacial HOAc was added dropwise until the yellow color was quenched and gas evolution ceased. The solution was concentrated and the residue was purified by chromatography on a 12-g silica cartridge eluted with a 0-50% EtOAc in hexanes gradient to afford methyl (S)-3-(4-bromophenyl)-3-((tert-butoxycarbonyl)amino)propanoate (890 mg, 86%) as a waxy solid. LC-MS 1.5 minute method $t_R$=0.97 min, m/z=360, 358, 304, 302.

Step 2

A flask was charged with methyl (S)-3-(4-bromophenyl)-3-((tert-butoxycarbonyl)amino)propanoate (890 mg, 2.5 mmol), NaSO$_2$Et (1.16 g, 10.0 mmol), CuI (95 mg, 0.5 mmol) and L-proline sodium salt (137 mg, 1.0 mmol). The flask was capped with a septum and flushed with dry N$_2$ for 10 min. Dry DMSO (6 mL) was introduced by syringe and the mixture was heated at 100° C. for 1 day. The mixture was cooled, diluted with EtOAc (100 mL), washed with water (3×10 mL) and brine (10 mL), and dried over Na$_2$SO$_4$. Removal of the solvent left an oil (909 mg). Chromatography on a 12-g silica cartridge eluted with a 0-80% EtOAc in hexanes gradient afforded methyl (S)-3-((tert-butoxycarbonyl)amino)-3-(4-(ethylsulfonyl)phenyl)propanoate (494 mg, 53%). LC-MS 1.5 minute method $t_R$=0.80 min, m/z=316. Unreacted starting material (147 mg, 16%) was also recovered.

Step 3

A procedure analogous to that used in Step 2 of the preparation of AM26 is employed.

Preparation 25

2-amino-2-(1-(methylsulfonyl)piperidin-4-yl)ethan-1-ol (AM26)

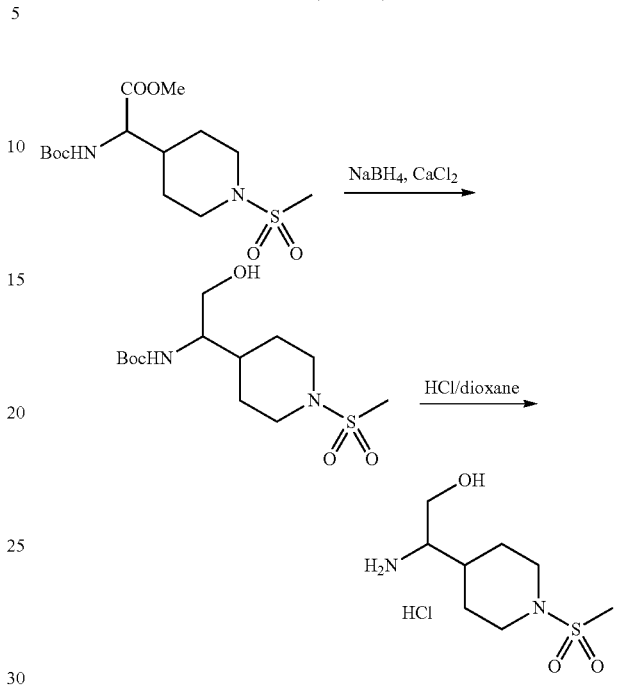

Step 1

To a solution of CaCl$_2$ (158 mg, 1.42 mmol) in THF/EtOH (1 mL, $V_{THF}/V_{EtOH}$=1/1) was added NaBH$_4$ (108 mg, 2.84 mmol) at 0° C. under N$_2$. The mixture was stirred at 0° C. for 1 h under N$_2$. Then a solution of crude methyl 2-((tert-butoxycarbonyl)amino)-2-(1-(methylsulfonyl)piperidin-4-yl)acetate (50 mg, 0.14 mmol) in THF/EtOH (1 mL, $V_{THF}/V_{EtOH}$=1/1) was added to the reaction mixture at 0° C. The mixture was allowed to warm to rt and stirred at rt overnight under N$_2$. The mixture was quenched with water (10 mL) slowly at 0° C. The mixture was lyophilized directly and then EtOAc (30 mL) was added. The mixture was stirred at 25° C. for 1 h and filtered. The filter cake was washed with EtOAc (2×10 mL). The combined organic layers were concentrated under reduced pressure to afford crude tert-butyl (2-hydroxy-1-(1-(methylsulfonyl)piperidin-4-yl)ethyl)carbamate (45 mg, 98%) as a white solid, which was used for the next step directly without further purification. $^1$H NMR (CDCl$_3$ 400 MHz): δ 4.92 (d, J=9.2 Hz, 1H), 3.90-3.75 (m, 2H), 3.73-3.60 (m, 2H), 3.55-3.40 (m, 1H), 2.83 (brs, 1H), 2.77 (s, 3H), 2.68-2.55 (m, 2H), 1.95-1.76 (m, 2H), 1.75-1.66 (m, 1H), 1.42 (s, 9H), 1.42-1.30 (m, 2H).

Step 2

To a solution of crude tert-butyl (2-hydroxy-1-(1-(methylsulfonyl)piperidin-4-yl)ethyl)carbamate (45 mg, 0.14 mmol) in dry CH$_2$Cl$_2$ (2 mL) was added HCl/dioxane (2 mL, 4 M) at rt. The mixture was stirred for 1 h. The solvent was removed under reduced pressure and water (5 mL) was added. The mixture was extracted with MTBE (3×5 mL). The aqueous layer was lyophilized directly to give crude 2-amino-2-(1-(methylsulfonyl)piperidin-4-yl)ethanol HCl salt (36 mg, 100%) as a colorless oil, which was used for the next step directly without further purification. $^1$H NMR (CD$_3$OD 400 MHz): δ 3.90-3.80 (m, 2H), 3.75-3.70 (m, 2H), 3.20-3.05 (m, 1H), 2.86 (s, 3H), 2.85-2.70 (m, 2H), 1.95-1.80 (m, 3H), 1.60-1.40 (m, 2H).

Preparation 26

Methyl 2-((4-(aminomethyl)phenyl)sulfonyl)acetate (AM27)

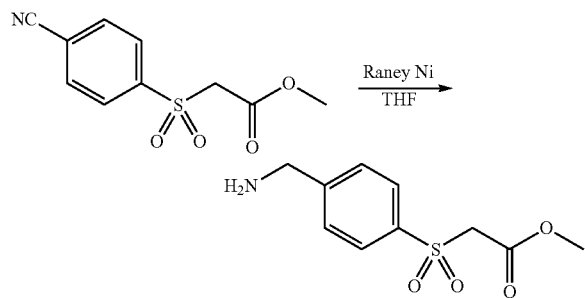

To a solution of methyl 2-((4-cyanophenyl)sulfonyl)acetate (10 mg, 0.042 mmol) in anhydrous THF (1 mL) was added Raney Ni (20 mg). The mixture was stirred at rt for 2 h under $H_2$ (30 psi). TLC (petroleum ether/EtOAc=3/1) showed the reaction was completed. The mixture was added with $CH_2Cl_2$ (10 mL) and filtered. The filtrate was dried over anhydrous $Na_2SO_4$, filtered and concentrated under reduced pressure to afford crude methyl 2-((4-(aminomethyl)phenyl) sulfonyl) acetate (10 mg, 100%) as a pale yellow oil, which was used for next step directly without further purification. LC-MS $t_R$=1.702 min in 0-30 CD_3.0 min chromatography (Xtimate ODS 2.1*30 mm, 3 um), MS (ESI) m/z 244.0 $[M+H]^+$

Preparation 27

Ethyl (R)-2-(2-amino-2-(4-(ethylsulfonyl)phenyl)ethoxy)acetate (AM28)

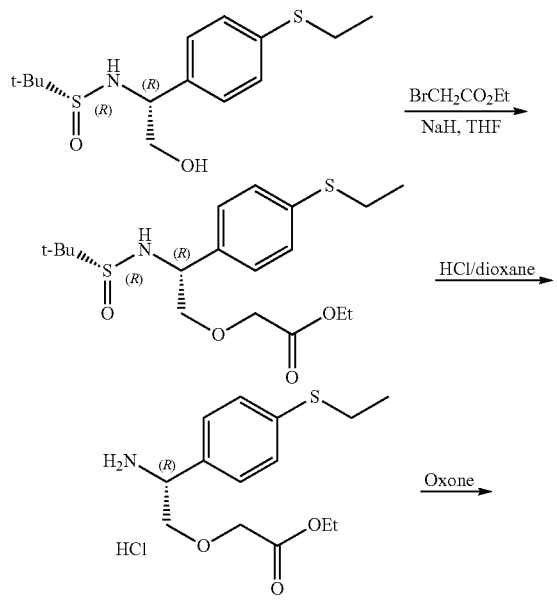

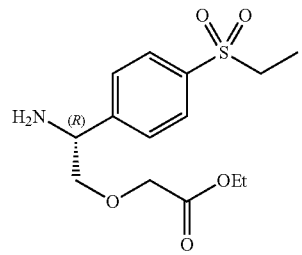

Step 1

To a solution of (R)—N—((R)-1-(4-(ethylthio)phenyl)-2-hydroxyethyl)-2-methylpropane-2-sulfinamide (500 mg, 1.65 mmol) and ethyl 2-bromoacetate (551 mg, 3.30 mmol) in anhydrous THF (10 mL) was added NaH (200 mg, 4.95 mmol, 60% in mineral oil) at 0° C. under $N_2$. After addition, the mixture was stirred at 70° C. for 4 h. LC-MS showed that the starting material was consumed completely and the ratio of product:byproduct (2-((R)-2-((R)-1,1-dimethylethylsulfinamido)-2-(4-(ethylthio)phenyl)ethoxy)acetic acid) was 3:5. The mixture was added with sat. $NH_4Cl$ solution (6 mL) and extracted with EtOAc (3×10 mL). The combined organic layers were washed with water (20 mL), dried over anhydrous $Na_2SO_4$, filtered and concentrated under reduced pressure. The residue was purified by column chromatography on silica gel eluting with petroleum ether/EtOAc=1/1 to afford ethyl 2-((R)-2-((R)-1,1-dimethylethylsulfinamido)-2-(4-(ethylthio)phenyl)ethoxy)acetate (150 mg, 23.5%) as a pale brown oil. LC-MS Method 3 $t_R$=0.780 min, MS (ESI) m/z 387.9 $[M+H]^+$ Step 2

To a solution of ethyl 2-((R)-2-((R)-1,1-dimethylethylsulfinamido)-2-(4-(ethylthio)phenyl)ethoxy)acetate (150 mg, 0.088 mmol) in anhydrous $CH_2Cl_2$ (1 mL) was added HCl/dioxane (1 mL, 4 M). The mixture was stirred at 14° C. for 2 h. TLC (petroleum ether/EtOAc=1/1) showed that the reaction was completed. The mixture was concentrated under reduced pressure to afford crude (R)-ethyl 2-(2-amino-2-(4-(ethylthio)phenyl)ethoxy)acetate HCl salt (150 mg, >100%) as a brown oil, which was used for next step directly without further purification.

Step 3

To a solution of crude (R)-ethyl 2-(2-amino-2-(4-(ethylthio)phenyl)ethoxy)acetate HCl salt (crude 150 mg, 0.088 mmol) in $H_2O$/MeOH (4 mL/2 mL) was added Oxone (475 mg, 0.773 mmol). The mixture was stirred at 13° C. for 2 h. LC-MS showed that most was the desired MS. The mixture was added with $H_2O$ (15 mL) and $Na_2SO_3$ (95 mg, 0.773 mmol), then dry-freezing directly to afford crude (R)-ethyl 2-(2-amino-2-(4-(ethylsulfonyl)phenyl)ethoxy)acetate (670 mg, >100%, containing a lot of salts) as a white solid, which was used for next step directly without further purification. LC-MS Method 3 $t_R$=0.471 min, MS (ESI) m/z 315.9 $[M+H]^+$

Preparation 28

4-benzyl 1-(tert-butyl) 5-(aminomethyl)-1,4-diazepane-1,4-dicarboxylate (AM29)

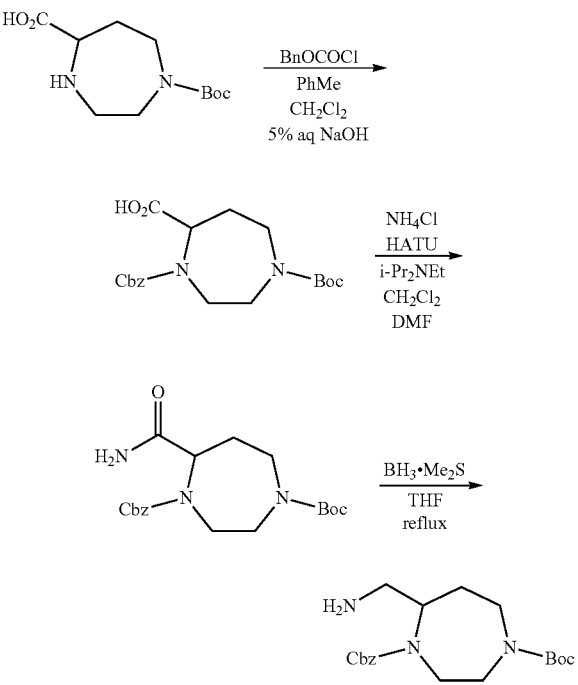

Preparation 29

2-(aminomethyl)-5-(ethylsulfonyl)phenol (AM30)

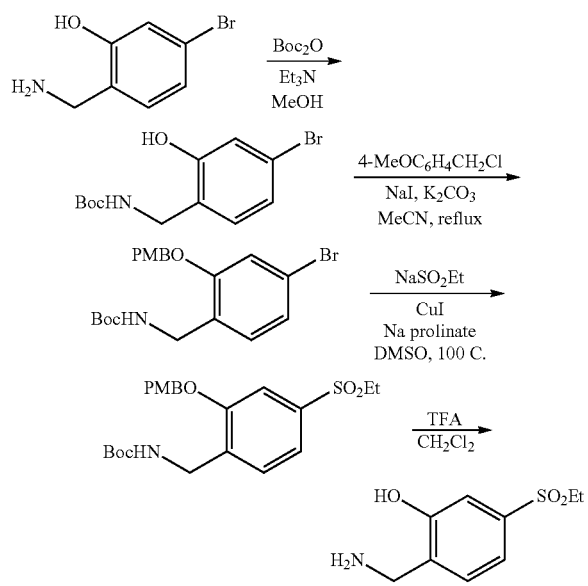

Diamine Preparations

Preparation 30

4-bromo-N1-((2,2-difluorobenzo[d][1,3]dioxol-4-yl)methyl)benzene-1,2-diamine

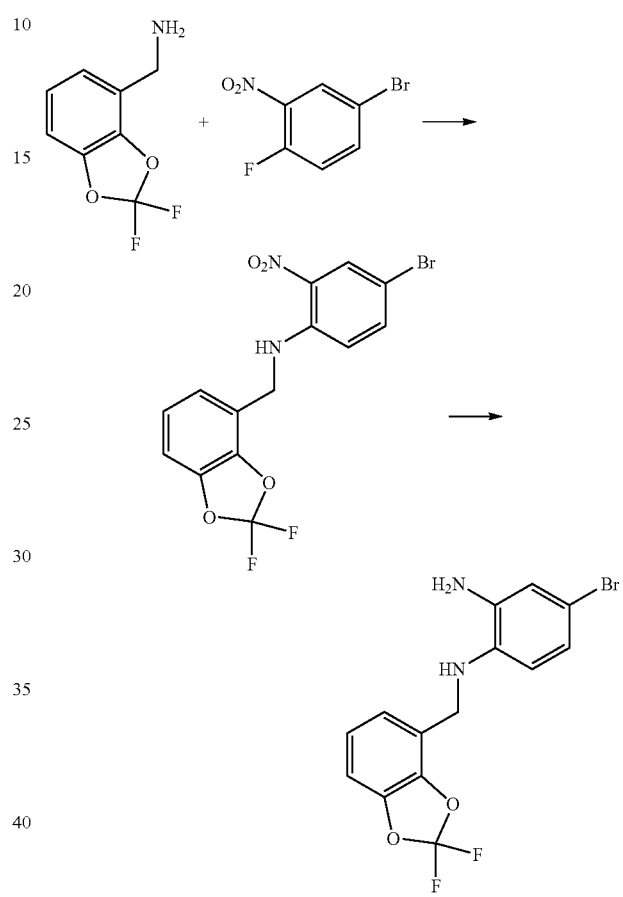

Step 1

A solution of (2,2-difluorobenzo[d][1,3]dioxol-4-yl)methanamine (265 mg, 1.4 mmol), 4-bromo-1-fluoro-2-nitrobenzene (0.17 mL, 1.4 mmol) and i-Pr$_2$NEt (0.53 mL, 2.9 mmol) in EtOH (7 mL) was stirred at rt for 2 h and at 50° C. for 17 h. The mixture was concentrated. The residue was taken up in EtOAc (90 mL), washed with 5% aq HCl (10 mL) and brine (10 mL), and dried over Na$_2$SO$_4$. Removal of the solvent left crude 4-bromo-N-((2,2-difluorobenzo[d][1,3]dioxol-4-yl)methyl)-2-nitroaniline (820 mg) as a yellow solid.

Step 2

A stirred mixture of crude 4-bromo-N-((2,2-difluorobenzo[d][1,3]dioxol-4-yl)methyl)-2-nitroaniline (820 mg, ≤1.4 mmol) and SnCl$_2$ (1.08 g, 5.7 mmol) in dry DMF (10 mL) was heated at 80° C. for 2 h. Additional SnCl$_2$ (1.08 g, 5.7 mmol) was added and heating was continued for 0.5 h. After cooling, satd aq NaHCO$_3$ (10 mL) was added, followed by Celite. The mixture was stirred for 15 min and filtered through additional Celite, washing with EtOAc. The filtrate was washed with brine, dried over Na$_2$SO$_4$ and rotovaped to leave a brown oil. Chromatography on 12 g silica cartridge, eluted with a 0-100% EtOAc in hexanes gradient, afforded 4-bromo-N1-((2,2-difluorobenzo[d][1,3]dioxol-4-yl)methyl)benzene-1,2-diamine (305 mg, 60% over two steps). LC-MS Method 1 $t_R$=1.89 min, m/z=359, 357.

Preparation 31

Methyl 3-amino-4-(((2,2-difluorobenzo[d][1,3]dioxol-4-yl) methyl) amino) benzoate

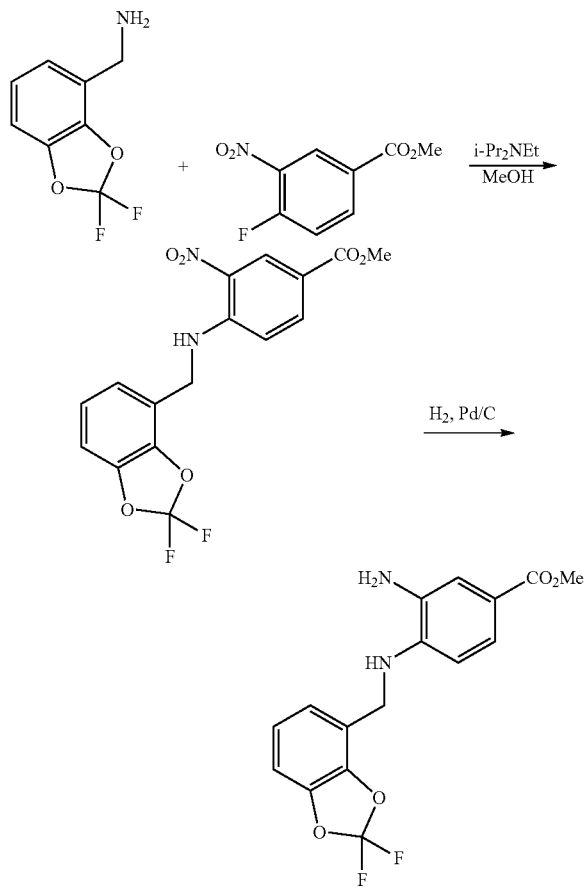

Step 1

To a stirred solution of (2,2-difluorobenzo[d][1,3]dioxol-4-yl)methanamine (PharmaBlock, 2.98 g, 15.9 mmol) and methyl 4-fluoro-3-nitrobenzoate (CombiBlocks, 3.33 g, 16.7 mmol) in MeOH (80 mL) was added i-Pr$_2$NEt (6 mL, 33.5 mmol). The mixture was stirred at rt for 2 days. A thick yellow ppt formed. The mixture was concentrated and the residue was taken up in 5% aq HCl (50 mL) and EtOAc (100 mL). The aqueous layer was separated and extracted with EtOAc (100 mL). The combined EtOAc layer was washed with brine (20 mL), dried over Na$_2$SO$_4$ and concentrated to leave crude methyl 4-(((2,2-difluorobenzo[d][1,3]dioxol-4-yl)methyl)amino)-3-nitrobenzoate (6.07 g, 104%) as a yellow solid. LC-MS 2.5 min method $t_R$=1.88 min, m/z=367.

Step 2

A solution of methyl 4-(((2,2-difluorobenzo[d][1,3]dioxol-4-yl)methyl)amino)-3-nitrobenzoate (5.88 g, 16.1 mmol) in 2:1 EtOAc/EtOH (150 mL) was stirred under H$_2$ (1 atm, balloon) in the presence of 10% Pd on C (250 mg) for 4 h. The mixture was filtered through Celite, washing with EtOAc. The filtrate was concentrated to leave a solid (6.69 g). Chromatography on an 80 g silica cartridge, eluted with a 0-60% EtOAc in hexanes gradient, gave methyl 3-amino-4-(((2,2-difluorobenzo[d][1,3]dioxol-4-yl)methyl)amino)benzoate (4.75 g, 87%) as an off-white solid. LC-MS 2.5 min method $t_R$=1.56 min, m/z=337.

Alternative Step 2

To a solution of methyl 4-(((2,2-difluorobenzo[d][1,3]dioxol-4-yl)methyl)amino)-3-nitrobenzoate (7.2 g, 19.7 mmol) in H$_2$O/MeOH/THF (120 mL, V/V/V=1:1:1) was added Zn (12.8 g, 197 mmol) and NH$_4$Cl (10.4 g, 197 mmol). The mixture was stirred at 22° C. for 45 min. TLC (petroleum ether/EtOAc=5/1) showed the reaction was completed. The mixture was added with CH$_2$Cl$_2$ (100 mL) and filtered. The filtrate was dried over anhydrous Na$_2$SO$_4$, filtered and concentrated under reduced pressure to afford methyl 3-amino-4-(((2,2-difluorobenzo[d][1,3]dioxol-4-yl)methyl) amino) benzoate (6.6 g, 99%) as a yellow solid, which was used for next step directly without further purification. LC-MS Method 3 $t_R$=0.708 min, MS (ESI) m/z 336.9 [M+H]$^+$ The diamines listed below are prepared following analogous procedures using the appropriate amine Cy$^2$-L$^2$-NH$_2$ in place of (2,2-difluorobenzo[d][1,3]dioxol-4-yl)methanamine in Step 1.

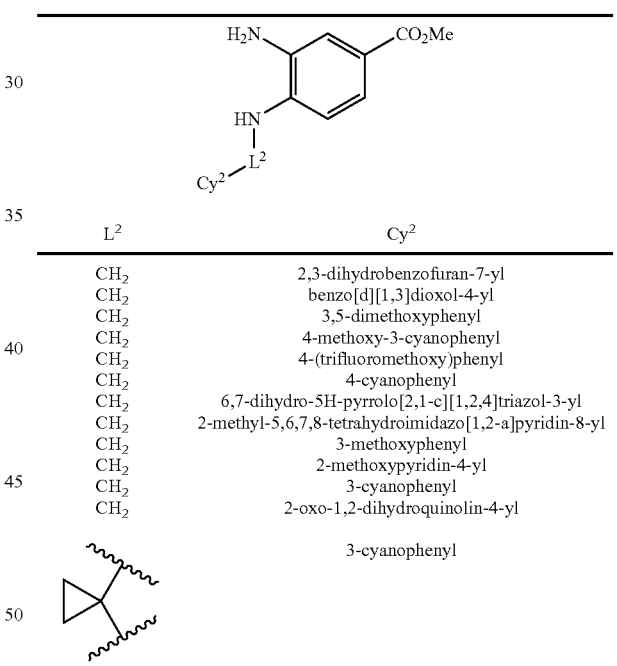

| L$^2$ | Cy$^2$ |
|---|---|
| CH$_2$ | 2,3-dihydrobenzofuran-7-yl |
| CH$_2$ | benzo[d][1,3]dioxol-4-yl |
| CH$_2$ | 3,5-dimethoxyphenyl |
| CH$_2$ | 4-methoxy-3-cyanophenyl |
| CH$_2$ | 4-(trifluoromethoxy)phenyl |
| CH$_2$ | 4-cyanophenyl |
| CH$_2$ | 6,7-dihydro-5H-pyrrolo[2,1-c][1,2,4]triazol-3-yl |
| CH$_2$ | 2-methyl-5,6,7,8-tetrahydroimidazo[1,2-a]pyridin-8-yl |
| CH$_2$ | 3-methoxyphenyl |
| CH$_2$ | 2-methoxypyridin-4-yl |
| CH$_2$ | 3-cyanophenyl |
| CH$_2$ | 2-oxo-1,2-dihydroquinolin-4-yl |
| cyclopropyl-1,1-diyl | 3-cyanophenyl |
| (S)-CHMe | 3-cyanophenyl |
| (R)-CHMe | 3-cyanophenyl |
| CH$_2$ | 2-fluoro-5-cyanophenyl |
| CH$_2$ | benzofuran-4-yl |
| CH$_2$ | 1H-indazol-4-yl |
| CH$_2$ | 3-(methoxycarbonyl)phenyl |
| CH$_2$ | 1H-pyrrolo[2,3-c]pyridin-4-yl |
| CH$_2$ | 2,2-dimethyl-2,3-dihydrobenzofuran-7-yl |
| CH$_2$ | 2,2-difluorobenzo[d][1,3]dioxol-5-yl |
| CH$_2$ | 2-(trifluoromethoxy)phenyl |
| CH$_2$ | (3R)-1-(t-butoxycarbonyl)pyrrolidin-3-yl |
| CH$_2$ | (2R)- 1-(t-butoxycarbonyl)pyrrolidin-3-yl |
| CH$_2$ | 3-(trifluoromethoxy)phenyl |
| CH$_2$ | 2-methoxy-3-(trifluoromethyl)phenyl |
| CH$_2$ | 1-(2,2,2-trifluoroethyl)-1H-pyrazol-4-yl |
| CH$_2$ | 3-cyanophenyl |
| CH$_2$ | 3-(difluoromethoxy)phenyl |

-continued

| L² | Cy² |
|---|---|
| CH₂ | 1-(2,2,2-trifluoroethyl)-1H-pyrazol-3-yl |
| CH₂ | 3-(trifluoromethoxy)-5-methoxyphenyl |
| (S)-CHMe | 2,2-difluorobenzo[d][1,3]dioxol-4-yl |
| CH₂ | 6-oxo-1-(2,2,2-trifluoroethyl)-1,6-dihydropyridin-3-yl |
| CH₂ | 2,3-dimethoxyphenyl |
| (R)-CHMe | 2,2-difluorobenzo[d][1,3]dioxol-4-yl |

Preparation 32

3-amino-N-(4-(ethylsulfonyl)benzyl)-4-((2-fluoro-3-methoxybenzyl)amino)benzamide

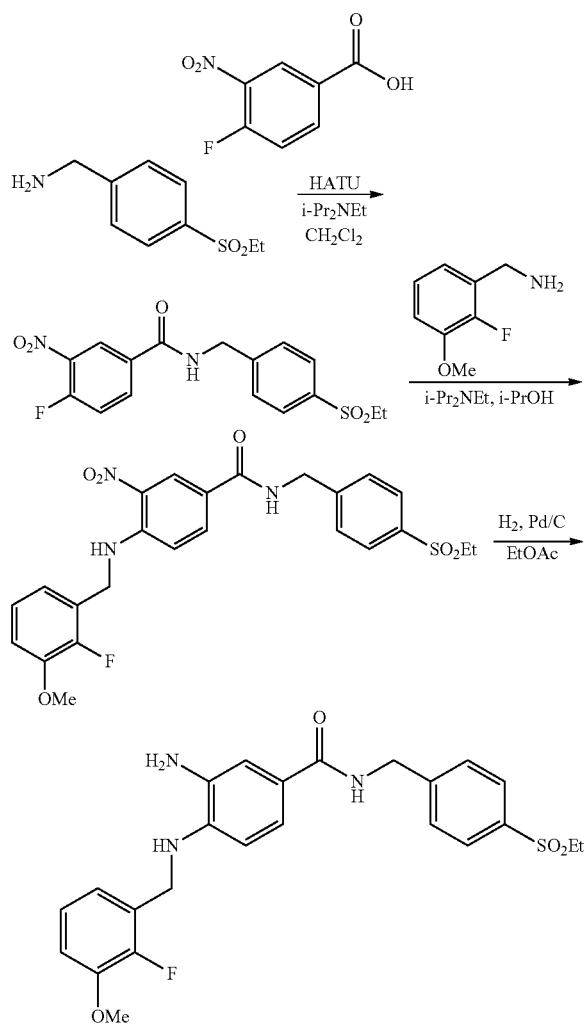

Step 1

To a stirred solution of 4-fluoro-3-nitrobenzoic acid (0.47 g, 2.5 mmol), AM2 (0.47 g, 2.4 mmol) and i-Pr₂NEt (1.4 mL, 7.8 mmol) in CH₂Cl₂ (20 mL) was added solid HATU (1.5 g, 3.9 mmol). The mixture was stirred at rt for 2 h and concentrated. The residue was taken up in EtOAc (90 mL), washed with 5% aq HCl (2×10 mL), satd aq NaHCO₃ (10 mL) and brine (10 mL), and dried over Na₂SO₄. Removal of the solvent left a yellow foam (1.72 g). Chromatography on a 40 g silica cartridge, eluted with a 20-100% EtOAc in hexanes gradient, afforded N-(4-(ethylsulfonyl)benzyl)-4-fluoro-3-nitrobenzamide (1.08 g, %) as a sticky solid. LC-MS Method 1 $t_R$=1.44 min, m/z=367.

Step 2

A mixture of N-(4-(ethylsulfonyl)benzyl)-4-fluoro-3-nitrobenzamide (99 mg, 0.27 mmol), 2-fluoro-3-methoxybenzylamine (52 mg, 0.34 mmol), i-Pr₂NEt (0.15 mL,). 82 mmol) and i-PrOH (1 mL) was heated in a 60° C. oil bath for 16 h. The mixture was diluted with EtOAc (90 mL), washed with 5% aq HCl (10 mL) and 1:1 satd aq NaHCO₃/brine (10 mL), and dried over Na₂SO₄. Concentration provided crude N-(4-(ethylsulfonyl)benzyl)-4-((2-fluoro-3-methoxybenzyl)amino)-3-nitrobenzamide (130 mg) as a yellow oil. LC-MS Method 1 $t_R$=1.67 min, m/z=502.

Step 3

A solution of crude N-(4-(ethylsulfonyl)benzyl)-4-((2-fluoro-3-methoxybenzyl)amino)-3-nitrobenzamide (26 mg, 52 mol) in EtOAc (10 mL) was stirred under H₂ (1 atm balloon) in the presence of 10% Pd on C (cat qty) for 45 min. The solution was filtered and concentrated to leave crude 3-amino-N-(4-(ethylsulfonyl)benzyl)-4-((2-fluoro-3-methoxybenzyl)amino)benzamide (16 mg) as a yellow oil. LC-MS Method 1 $t_R$=1.36 min, m/z=472.

The following compounds are prepared following analogous procedures using the appropriate amine Cy²-L²-NH₂ in place of 2-fluoro-3-methoxybenzylamine in Step 2.

| L² | Cy² |
|---|---|
| CH₂ | 1-methyl-1H-indazol-7-yl |
| CH₂ | 4-methyl-6-(trifluoromethyl)pyrimidin-2-yl |
| CH₂ | 2-methyl-2H-indazol-7-yl |
| CH₂ | 1,2-dimethyl-1H-benzo[d]imidazol-7-yl |
| CH₂ | 1-methyl-1H-indazol-4-yl |
| CH₂ | 1H-indazol-7-yl |
| CH₂ | 2-methyl-2H-indazol-4-yl |
| CH₂ | 6-oxo-1-(2,2,2-trifluoroethyl)-1,6-dihydropyridin-3-yl |
| CH₂ | 1-(t-butoxycarbonyl)piperidin-4-yl |
| CH₂ | 1-methyl-2-oxo-1,2-dihydropyridin-3-yl |
| CH₂ | benzo[d]oxazol-4-yl |
| CH₂ | 2,3-dihydrobenzo[b][1,4]dioxin-5-yl |
| (R)-CHMe | 2,2-difluorobenzo[d][1,3]dioxol-4-yl |
| CH₂ | phenyl |

Benzimidazole Preparations

Preparation 33

1-((2,2-difluorobenzo[d][1,3]dioxol-4-yl)methyl)-2-(trifluoromethyl)-1H-benzo[d]imidazol-5-amine

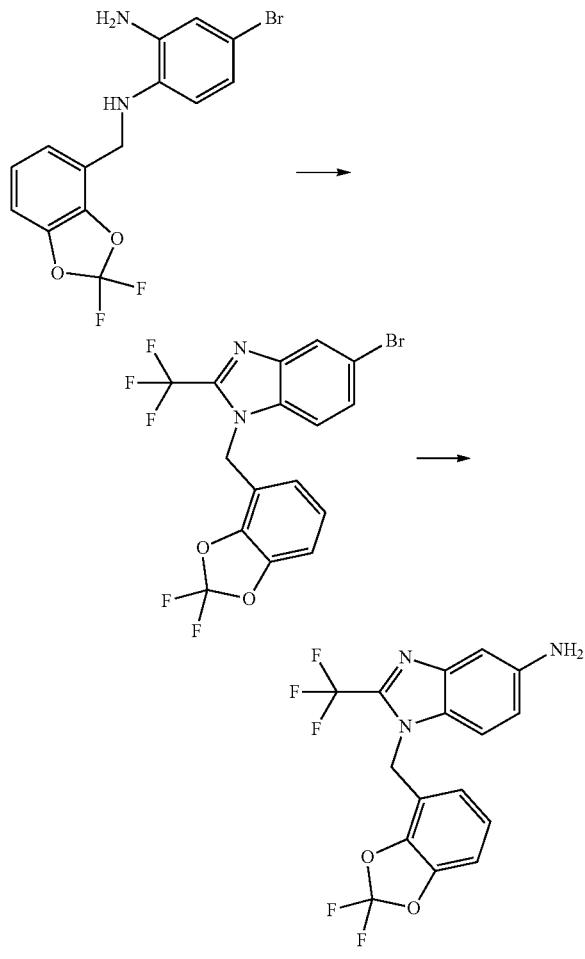

Step 1

A solution of 4-bromo-N1-((2,2-difluorobenzo[d][1,3]dioxol-4-yl)methyl)benzene-1,2-diamine (305 mg, 0.85 mmol) in TFA (5 mL) was heated at 70° C. for 2 h and concentrated. The residue was taken up in EtOAc (90 mL), washed with satd aq NaHCO$_3$ (10 mL) and brine (10 mL), dried over Na$_2$SO$_4$ and concentrated to leave an oil (283 mg). Chromatography on a 12 g silica cartridge, eluted with a 0-100% EtOAc in hexanes gradient, afforded 5-bromo-1-((2,2-difluorobenzo[d][1,3]dioxol-4-yl)methyl)-2-(trifluoromethyl)-1H-benzo[d]imidazole (138 mg, 37%) as an oil. LC-MS Method 1 t$_R$=2.03 min, m/z=437, 435.

Step 2

A flask was charge with 5-bromo-1-((2,2-difluorobenzo[d][1,3]dioxol-4-yl)methyl)-2-(trifluoromethyl)-1H-benzo[d]imidazole (40 mg, 0.09 mmol), CuI (22 mg, 0.12 mmol), Na$_2$CO$_3$ (15 mg, 0.14 mmol), NaN$_3$ (15 mg, 0.23 mmol) and DMEDA (17.5 µL, 0.16 mmol). The flask was sealed with a septum and flushed with N$_2$ for 5 min. Dry DMSO (1 mL) was introduced using a syringe and the mixture was heated at 110° C. for 1.5 h. After cooling, the mixture was diluted with EtOAc (80 mL), washed with water (10 mL) and brine (10 mL), and dried over Na$_2$SO$_4$. Removal of the solvent left an oil (37 mg) which was purified by chromatography on a 12 g silica cartridge, eluted with a 0-100% EtOAc in hexanes gradient, to afford 1-((2,2-difluorobenzo[d][1,3]dioxol-4-yl)methyl)-2-(trifluoromethyl)-1H-benzo[d]imidazol-5-amine (27 mg, 79%) as an oil. LC-MS Method 1 t$_R$=1.48 min, m/z=372.

Preparation 34

1-((2,2-difluorobenzo[d][1,3]dioxol-4-yl)methyl)-2-(trifluoromethyl)-1H-benzo[d]imidazole-5-carboxylic acid

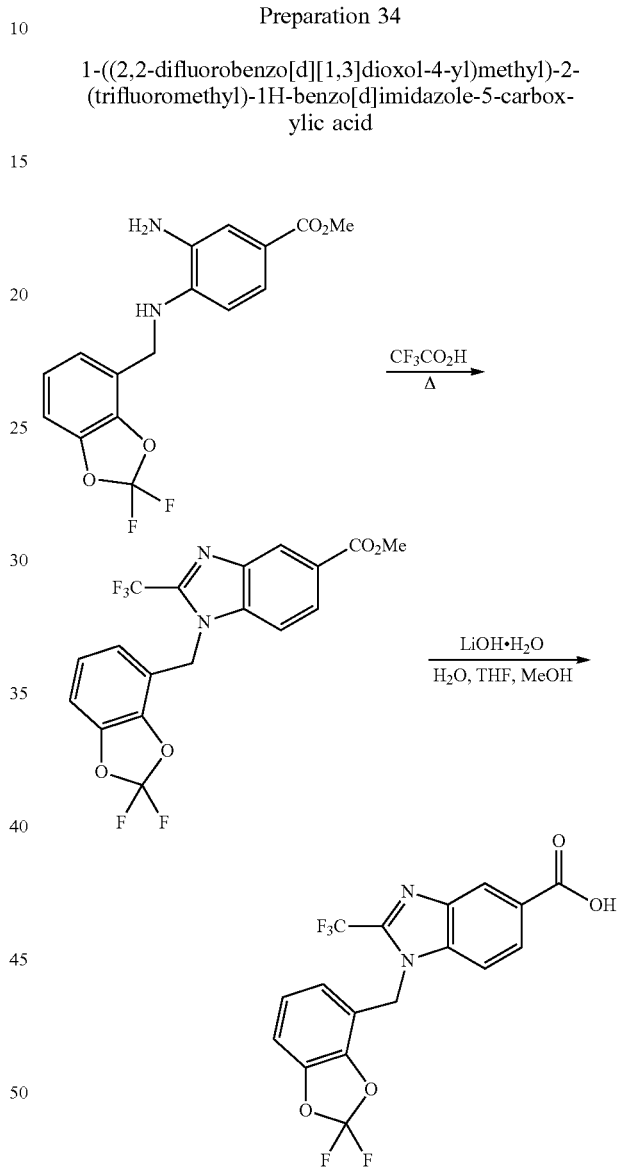

Step 1

A stirred solution of methyl 3-amino-4-(((2,2-difluorobenzo[d][1,3]dioxol-4-yl)methyl)amino)benzoate (290 mg, 0.86 mmol) in CF$_3$CO$_2$H (5 mL) at 70° C. for 2 h. The mixture was concentrated. The residue was taken up in CH$_2$Cl$_2$ (70 mL), washed with 9:1 brine/satd aq NaHCO$_3$ (10 mL) and dried over Na$_2$SO$_4$. Removal of the solvent left an oil (368 mg). Chromatography on a 12 g silica cartridge, eluted with a 0-100% EtOAc in hexanes gradient, afforded methyl 1-((2,2-difluorobenzo[d][1,3]dioxol-4-yl)methyl)-2-(trifluoromethyl)-1H-benzo[d]imidazole-5-carboxylate (292 mg, 82%) as a colorless oil. LC-MS Method 1 t$_R$=1.81 min, m/z=415.

Step 2

To a stirred solution of methyl 1-((2,2-difluorobenzo[d][1,3]dioxol-4-yl)methyl)-2-(trifluoromethyl)-1H-benzo[d]imidazole-5-carboxylate (292 mg, 0.70 mmol) in 2:1:1 MeOH/THF/H$_2$O (8 mL) was added LiOH.H$_2$O (93 mg, 2.2 mmol). After stirring overnight, the mixture was concentrated. The residue was partitioned between EtOAc (90 mL) and 5% aq HCl (10 mL). The organic layer was dried over Na$_2$SO$_4$ and concentrated to leave crude 1-((2,2-difluorobenzo[d][1,3]dioxol-4-yl)methyl)-2-(trifluoromethyl)-1H-benzo[d]imidazole-5-carboxylic acid (306 mg, 108%) as a solid, which was used without further purification. LC-MS Method 1 $t_R$=1.63 min, m/z=401.

The following benzimidazole carboxylic acids are prepared by analogous procedures.

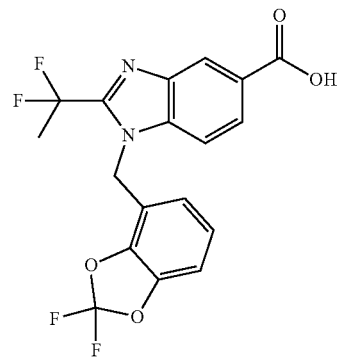 [SMILES: CC(F)(F)c1nc2cc(C(=O)O)ccc2n1Cc1cccc2c1OC(F)(F)O2]

| L$^2$ | Cy$^2$ |
|---|---|
| CH$_2$ | 2,3-dihydrobenzofuran-7-yl |
| CH$_2$ | benzo[d][1,3]dioxol-4-yl |
| CH$_2$ | 3,5-dimethoxyphenyl |
| CH$_2$ | 4-methoxy-3-cyanophenyl |
| CH$_2$ | 4-(trifluoromethoxy)phenyl |
| CH$_2$ | 4-cyanophenyl |
| CH$_2$ | 6,7-dihydro-5H-pyrrolo[2,1-c][1,2,4]triazol-3-yl |
| CH$_2$ | 2-methyl-5,6,7,8-tetrahydroimidazo[1,2-a]pyridin-8-yl |
| CH$_2$ | 3-methoxyphenyl |
| CH$_2$ | 2-methoxypyridin-4-yl |
| CH$_2$ | 3-cyanophenyl |
| CH$_2$ | 2-oxo-1,2-dihydroquinolin-4-yl |
| spiro-cyclopropyl-CH | 3-cyanophenyl |
| (S)-CHMe | 3-cyanophenyl |
| (R)-CHMe | 3-cyanophenyl |
| CH$_2$ | 2-fluoro-5-cyanophenyl |
| CH$_2$ | benzofuran-4-yl |
| CH$_2$ | 1H-indazol-4-yl |
| CH$_2$ | 3-(methoxycarbonyl)phenyl |
| CH$_2$ | 1H-pyrrolo[2,3-c]pyridin-4-yl |
| CH$_2$ | 2,2-dimethyl-2,3-dihydrobenzofuran-7-yl |

The following benzimidazole carboxylic acid was prepared by procedures analogous to those described above using MeCF$_2$CO$_2$H and heating to 80° C. in Step 1.

Preparation 35

2-cyclobutyl-1-((2,2-difluorobenzo[d][1,3]dioxol-4-yl)methyl)-1H-benzo[d]imidazole-5-carboxylic acid

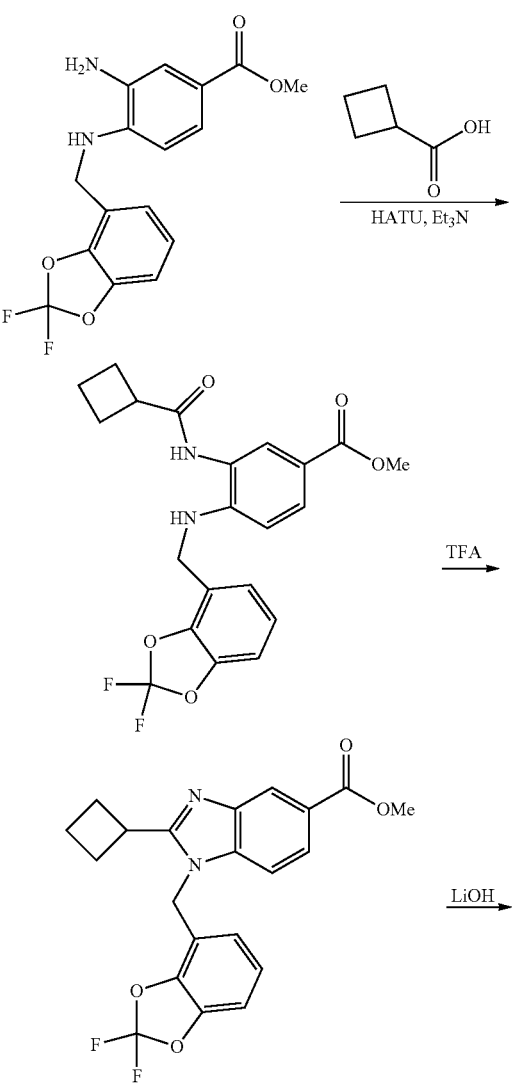

-continued

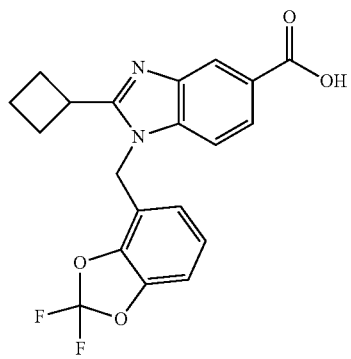

Step 1

A mixture of methyl 3-amino-4-(((2,2-difluorobenzo[d][1,3]dioxol-4-yl)methyl)amino)benzoate (6.6 g, 19.6 mmol), cyclobutanecarboxylic acid (3.94 g, 39.3 mmol), Et₃N (6.0 g, 58.9 mmol) and HATU (8.2 mg, 21.6 mmol) in anhydrous CH₂Cl₂ (150 mL) was stirred at 22° C. under N₂ for 2 h. LC-MS showed the reaction was completed. The mixture was added with CH₂Cl₂ (100 mL) and washed with water (200 mL×3), dried over anhydrous Na₂SO₄, filtered and concentrated under reduced pressure. The residue was purified by column chromatography on silica gel eluting with petroleum ether:EtOAc=10:1-5:1 to afford methyl 3-(cyclobutanecarboxamido)-4-(((2,2-difluorobenzo[d][1,3]dioxol-4-yl) methyl)amino)benzoate (8.2 g, 99%) as a pale yellow solid. LC-MS Method 3 $t_R$=0.789 min, MS (ESI) m/z 419.0 [M+H]⁺

Step 2

To a solution of methyl 3-(cyclobutanecarboxamido)-4-(((2,2-difluorobenzo[d][1,3]dioxol-4-yl) methyl) amino) benzoate (8.2 g, 19.6 mmol) in TFA (80 mL) was stirred at 70° C. for 8 h under N₂. LC-MS showed the reaction was completed. The mixture was concentrated under reduced pressure. The mixture was added with water (20 mL). The aqueous layer was adjusted to pH=6-7 with sat.NaHCO₃ solution and extracted with CH₂Cl₂ (3×50 mL). The combined organic layers were washed with brine (100 mL), dried over anhydrous Na₂SO₄, filtered and concentrated under reduced pressure. The residue was purified by column chromatography on silica gel eluting with petroleum ether: EtOAc=10:1-5:1 to afford methyl 2-cyclobutyl-1-((2,2-difluorobenzo[d][1,3]dioxol-4-yl)methyl)-1H-benzo[d]imidazole-5-carboxylate (6.7 g, 85%) as a pale yellow oil. LC-MS Method 3 $t_R$=0.701 min, MS (ESI) m/z 401.1 [M+H]⁺ ¹H NMR (CDCl₃ 400 MHz): δ 8.53 (s, 1H), 7.97 (d, J=8.4 Hz, 1H), 7.24 (d, J=8.4 Hz, 1H), 7.01 (d, J=8.0 Hz, 1H), 6.95 (t, J=8.0 Hz, 1H), 6.45 (d, J=8.0 Hz, 1H), 5.32 (s, 2H), 3.95 (s, 3H), 3.79-3.66 (m, 1H), 2.67-2.58 (m, 2H), 2.46-2.32 (m, 2H), 2.19-1.99 (m, 2H).

Step 3

To a solution of methyl 2-cyclobutyl-1-((2,2-difluorobenzo[d][1,3]dioxol-4-yl)methyl)-1H-benzo[d]imidazole-5-carboxylate (8.0 g, 20 mmol) in H₂O/MeOH (100 mL, V/V=1:5) was added LiOH.H₂O (4.2 g, 100 mmol). The mixture was stirred at 22° C. for 16 h and 40° C. for 3 h.

LC-MS showed the reaction was completed. The mixture was concentrated under reduced pressure. The residue was added with H₂O (50 mL) and adjusted to pH=3-4 with 1N HCl solution to give a precipitate. After filtered, the filter cake was dissolved in MeOH (500 mL), dried over anhydrous Na2SO4, filtered, and concentrated under reduced pressure to afford crude 2-cyclobutyl-1-((2,2-difluorobenzo[d][1,3]dioxol-4-yl)methyl)-1H-benzo[d]imidazole-5-carboxylic acid (7.68 g, 99%) as a yellow solid, which was used for next step directly without further purification. LC-MS Method 3 $t_R$=0.653 min, MS (ESI) m/z 387.0 [M+H]⁺

Preparation 36

1-((2,2-difluorobenzo[d][1,3]dioxol-4-yl)methyl)-2-(difluoromethyl)-1H-benzo[d]imidazole-5-carboxylic acid

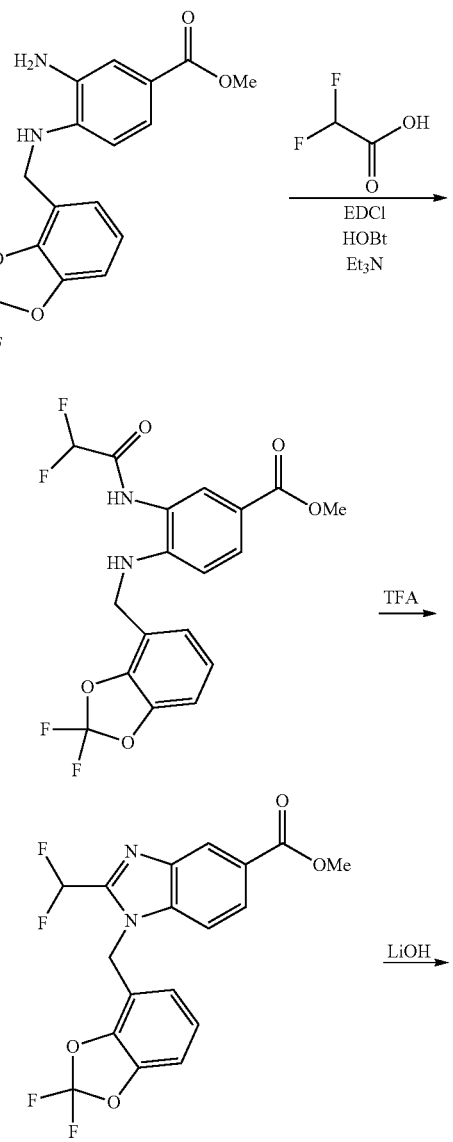

-continued

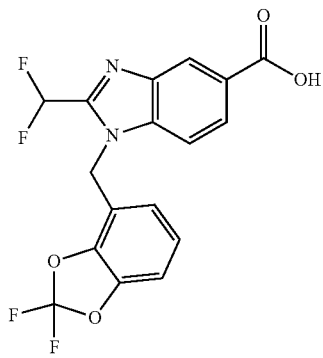

Preparation 37

2-cyclopropyl-1-((2,2-difluorobenzo[d][1,3]dioxol-4-yl)methyl)-1H-benzo[d]imidazole-5-carboxylic acid Step 1

A mixture of methyl 3-amino-4-(((2,2-difluorobenzo[d][1,3]dioxol-4-yl)methyl)amino)benzoate (16 g, 47.62 mmol), 2,2-difluoroacetic acid (9.1 g, 95.24 mmol), HOBt (12.9 g, 95.24 mmol) and EDCI (18.4 g, 95.24 mmol) in anhydrous $CH_2Cl_2$ (360 mL) was added $Et_3N$ (24 g, 0.24 mol) at 0° C. The mixture was stirred at 12-21° C. for 16 h under $N_2$. LC-MS showed that 10% of starting material was still remained. The mixture was added with water (600 mL) and a lot of precipitate was found. After filtered, the filtered cake was washed with petroleum ether (3×50 mL), then dissolved with $CH_2Cl_2$/MeOH (8:1, 400 mL), dried over anhydrous $Na_2SO_4$, filtered and concentrated under reduced pressure to afford crude methyl 3-(2,2-difluoroacetamido)-4-(((2,2-difluorobenzo[d][1,3]dioxol-4-yl)methyl)amino) benzoate (14.4 g, 73%) as a white solid, which was used for next step directly without further purification. LC-MS Method $3t_R$=0.888 min, MS (ESI) m/z 414.9 $[M+H]^+$.

Step 2

A mixture of methyl 3-(2,2-difluoroacetamido)-4-(((2,2-difluorobenzo[d][1,3]dioxol-4-yl)methyl)amino)benzoate (15 g, 36.23 mmol) in TFA (50 mL) was stirred at 70° C. for 3 h. TLC showed that the reaction was completed. The mixture was concentrated under reduced pressure. The residue was added with sat. $NaHCO_3$ solution to adjust pH=7-8 and extracted with EtOAc (2×100 mL). The combined organic layers were dried over anhydrous $Na_2SO_4$, filtered and concentrated under reduced pressure. The residue was purified by column chromatography on silica gel eluting with petroleum ether/EtOAc=7/3 to afford methyl 1-((2,2-difluorobenzo[d][1,3]dioxol-4-yl)methyl)-2-(difluoromethyl)-1H-benzo[d]imidazole-5-carboxylate (9.3 g, 65%) as a white solid. LC-MS Method 3 $t_R$=0.787 min, MS (ESI) m/z 396.9 $[M+H]^+$.

Step 3

To a mixture of methyl 1-((2,2-difluorobenzo[d][1,3]dioxol-4-yl)methyl)-2-(difluoromethyl)-1H-benzo[d]imidazole-5-carboxylate (15 g, 37.78 mmol) in MeOH/$H_2O$ (3/1, 180 mL) was added LiOH.$H_2O$ (7.9 g, 0.19 mol). The mixture was stirred at 15-19° C. for 16 h and 50° C. for 3 h. LC-MS showed that the reaction was completed. The mixture was concentrated under reduced pressure to remove MeOH. The residue was adjusted to pH=4-5 with 2N HCl solution. The aqueous layer was extracted with EtOAc (3×100 mL). The combined organic layers were dried over anhydrous $Na_2SO_4$, filtered and concentrated under reduced pressure to afford crude 1-((2,2-difluorobenzo[d][1,3]dioxol-4-yl)methyl)-2-(difluoromethyl)-1H-benzo[d]imidazole-5-carboxylic acid (14.5 g, 100%) as a white solid, which was used for the next step directly without further purification. LC-MS Method 3 $t_R$=0.717 min, MS (ESI) m/z 382.9 $[M+H]^+$.

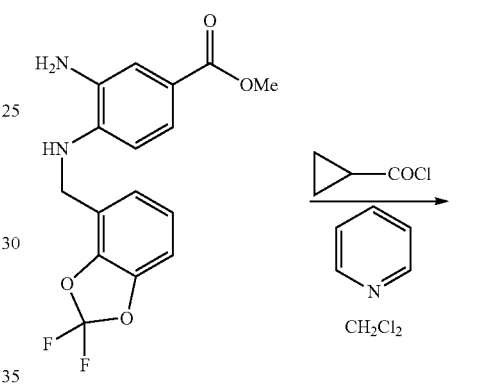

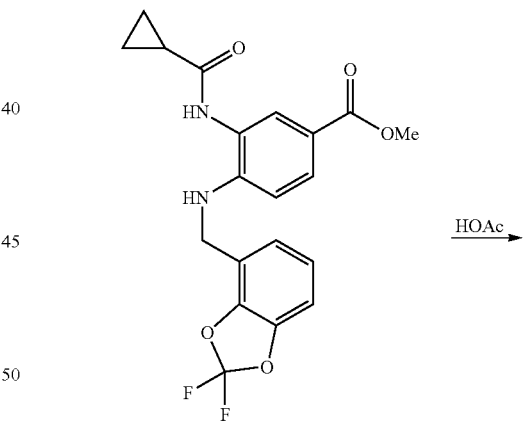

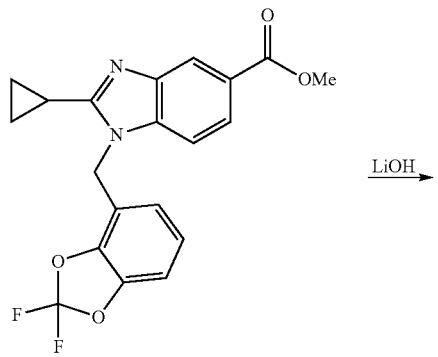

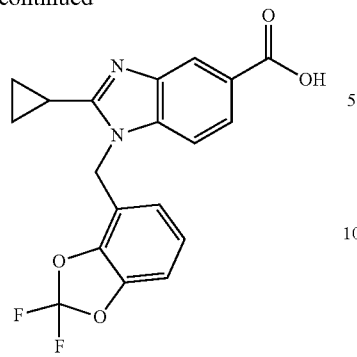

Step 1

A stirred solution of methyl 3-amino-4-(((2,2-difluorobenzo[d][1,3]dioxol-4-yl)methyl)amino)benzoate (252 mg, 0.75 mmol) and pyridine (0.13 mL, 1.5 mmol) in $CH_2Cl_2$ (10 mL) was cooled to −70° C. and cyclopropanecarbonyl chloride (65 μL, 0.71 mmol) was added. The dry ice bath was allowed to expire. After 2.5 h, the mixture had reached rt and water (5 mL) was added. The mixture was concentrated. The aqueous residue was diluted with EtOAc (90 mL), washed with water (5 mL), satd aq $NaHCO_3$ (10 mL) and brine (10 mL), and dried over $Na_2SO_4$. Removal of the solvent left crude methyl 3-(cyclopropanecarboxamido)-4-(((2,2-difluorobenzo[d][1,3]dioxol-4-yl)methyl)amino)benzoate (307 mg) as an oil which was used without further purification.

Step 2

Crude methyl 3-(cyclopropanecarboxamido)-4-(((2,2-difluorobenzo[d][1,3]dioxol-4-yl)methyl)amino)benzoate (307 mg) was dissolved in HOAc (2 mL) and heated at 100° C. for 2 h. The mixture was concentrated. The residue was taken up in $CH_2Cl_2$ (3 mL) and applied to a 10-mL ChemElut cartridge that had been prewetted with satd aq $NaHCO_3$ (5 mL). The cartridge was eluted with EtOAc (80 mL). The eluate was concentrated to leave a brown oil (261 mg). Chromatography on a 12-g silica cartridge eluted with a 0-100% EtOAc in hexanes gradient afforded methyl 2-cyclopropyl-1-((2,2-difluorobenzo[d][1,3]dioxol-4-yl)methyl)-1H-benzo[d]imidazole-5-carboxylate (63 mg, 22% over two steps) as an oil. LC-MS Method 1 $t_R$=1.29 min, m/z=387.

Step 3

A solution of methyl 2-cyclopropyl-1-((2,2-difluorobenzo[d][1,3]dioxol-4-yl)methyl)-1H-benzo[d]imidazole-5-carboxylate (63 mg, 0.16 mmol) and LiOH.H2O (75 mg, 1.8 mmol) in 2:1:1 MeOH/THF/H2O (2 mL) was stirred overnight at rt and concentrated to remove organic solvents. The aqueous residue was residue was acidified with 5% aq HCl (10 mL) and extracted with EtOAc (80 mL). The organic layer was separated, washed with brine (10 mL), dried over $Na_2SO_4$ and concentrated to provide the title compound (70 mg, quant). LC-MS Method 1 $t_R$=1.11 min, m/z=373.

The following benzimidazole carboxylic acids are prepared following procedures analogous to those described in Preparations 35, 36 and 37 using the acid $R^1CO_2H$ or the acid chloride $R^1COCl$ in Step 1.

| $R^1$ | $L^2$ | $Cy^2$ |
|---|---|---|
| (R)-tetrahydrofuran-2-yl | $CH_2$ | 2,2-difluorobenzo[d][1,3]dioxol-4-yl |
| Et | $CH_2$ | 2,2-difluorobenzo[d][1,3]dioxol-4-yl |
| 1-fluorocyclopropyl | $CH_2$ | 2,2-difluorobenzo[d][1,3]dioxol-4-yl |
| 1-fluorocyclobutyl | $CH_2$ | 2,2-difluorobenzo[d][1,3]dioxol-4-yl |
| t-Bu | $CH_2$ | 2,2-difluorobenzo[d][1,3]dioxol-4-yl |
| i-Pr | $CH_2$ | 2,2-difluorobenzo[d][1,3]dioxol-4-yl |
| Me | $CH_2$ | 2,2-difluorobenzo[d][1,3]dioxol-4-yl |
| i-Bu | $CH_2$ | 2,2-difluorobenzo[d][1,3]dioxol-4-yl |
| (S)-tetrahydrofuran-2-yl | $CH_2$ | 2,2-difluorobenzo[d][1,3]dioxol-4-yl |
| 1-methoxyethyl | $CH_2$ | 2,2-difluorobenzo[d][1,3]dioxol-4-yl |
| 2-methoxy-2-propyl | $CH_2$ | 2,2-difluorobenzo[d][1,3]dioxol-4-yl |
| cis-2-cyanocyclopropyl | $CH_2$ | 2,2-difluorobenzo[d][1,3]dioxol-4-yl |
| trans-2-cyancyclopropyl | $CH_2$ | 2,2-difluorobenzo[d][1,3]dioxol-4-yl |
| cis-2-(methoxycarbonyl)cyclopropyl | $CH_2$ | 2,2-difluorobenzo[d][1,3]dioxol-4-yl |
| cyclopropyl | $CH_2$ | 2,2-dimethyl-2,3-dihydrobenzofuran-7-yl |
| cyclopropyl | $CH_2$ | 2,3-dihydrobenzofuran-7-yl |
| cyclopropyl | $CH_2$ | 3,5-dimethoxyphenyl |
| cyclopropyl | $CH_2$ | 4-(trifluoromethoxy)phenyl |
| cyclopropyl | $CH_2$ | 2-(trifluoromethoxy)phenyl |
| cyclopropyl | $CH_2$ | (3R)-1-(t-butoxycarbonyl)pyrrolidin-3-yl |
| cyclopropyl | $CH_2$ | (2R)-1-(t-butoxycarbonyl)pyrrolidin-3-yl |
| cyclopropyl | $CH_2$ | 3-(trifluoromethoxy)phenyl |
| cyclopropyl | $CH_2$ | 2-methoxy-3-(trifluoromethyl)phenyl |
| cyclopropyl | $CH_2$ | 1-(2,2,2-trifluoroethyl)-1H-pyrazol-4-yl |
| cyclopropyl | $CH_2$ | 3-cyanophenyl |
| cyclopropyl | $CH_2$ | 3-(difluoromethoxy)phenyl |
| cyclopropyl | $CH_2$ | 1-(2,2,2-trifluoroethyl)-1H-pyrazol-3-yl |
| cyclopropyl | $CH_2$ | 3-(trifluoromethoxy)-5-methoxyphenyl |
| cyclopropyl | (S)-CHMe | 2,2-difluorobenzo[d][1,3]dioxol-4-yl |
| cyclopropyl | $CH_2$ | 6-oxo-1-(2,2,2-trifluoroethyl)-1,6-dihydropyridin-3-yl |
| cyclopropyl | $CH_2$ | 2,2-dimethyl-2,3-dihydrobenzofuran-7-yl |
| cyclopropyl | $CH_2$ | 2,3-dimethoxyphenyl |
| Et | (R)-CHMe | 2,2-difluorobenzo[d][1,3]dioxol-4-yl |
| Et | (S)-CHMe | 2,2-difluorobenzo[d][1,3]dioxol-4-yl |

Preparation 38

1-((2,2-difluorobenzo[d][1,3]dioxol-4-yl)methyl)-2-methoxy-1H-benzo[d]imidazole-5-carboxylic acid

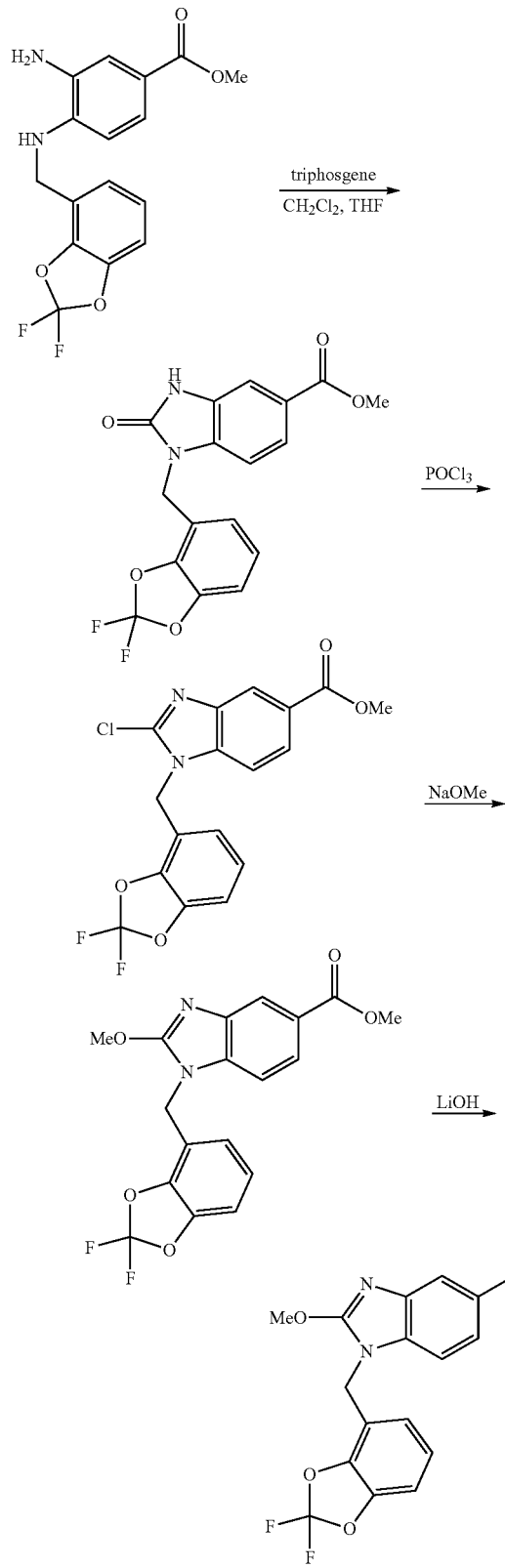

Step 1

To a stirred, ice cold solution of methyl 3-amino-4-(((2,2-difluorobenzo[d][1,3]dioxol-4-yl)methyl)amino)benzoate (66 mg, 0.2 mmol) in 2:1 THF/CH$_2$Cl$_2$ (6 mL) was added Et$_3$N (4 eq), followed by a solution of triphosgene (0.5 eq) in CH$_2$Cl$_2$ (3 mL) dropwise. After 15 min, the cooling bath was removed and the mixture was stirred at rt for 3 h. Aqueous work up afforded methyl 1-((2,2-difluorobenzo[d][1,3]dioxol-4-yl)methyl)-2-oxo-2,3-dihydro-1H-benzo[d]imidazole-5-carboxylate (66 mg, 93%). LC-MS Method 1 t$_R$=1.42 min, m/z=363.

Step 2

A solution of methyl 1-((2,2-difluorobenzo[d][1,3]dioxol-4-yl)methyl)-2-oxo-2,3-dihydro-1H-benzo[d]imidazole-5-carboxylate (66 mg, 0.18 mmol) in POCl$_3$ (4 mL) was heated at 120° C. for 2.5 h. The mixture was cooled and poured onto crushed ice. After the ice had melted, the aqueous mixture was extracted with EtOAc (3×). The combined organic layer was washed with water and brine, and dried over Na$_2$SO$_4$. Removal of the solvent left crude methyl 2-chloro-1-((2,2-difluorobenzo[d][1,3]dioxol-4-yl)methyl)-1H-benzo[d]imidazole-5-carboxylate (21 mg) which was used without further purification. LC-MS Method 1 t$_R$=1.73 min, m/z=381.

Step 3

A mixture of crude methyl 2-chloro-1-((2,2-difluorobenzo[d][1,3]dioxol-4-yl)methyl)-1H-benzo[d]imidazole-5-carboxylate (21 mg, 0.055 mmol), 25 wt % NaOMe in MeOH (0.5 mL) and MeOH (3 mL) was stirred at rt overnight. Satd aq NH$_4$Cl was added and the mixture concentrated to remove MeOH. The aq residue was diluted with EtOAc, washed with 1% aq HCl, water and brine, dried over Na$_2$SO$_4$ and concentrated. The residue was purified by chromatography on a 4-g silica cartridge, eluted with a 10-50% EtOAc in hexanes gradient, to afford methyl 1-((2,2-difluorobenzo[d][1,3]dioxol-4-yl)methyl)-2-methoxy-1H-benzo[d]imidazole-5-carboxylate (7.5 mg). LC-MS Method 1 t$_R$=1.69 min, m/z=377.

Step 4

Methyl 1-((2,2-difluorobenzo[d][1,3]dioxol-4-yl)methyl)-2-methoxy-1H-benzo[d]imidazole-5-carboxylate (7.5 mg) was reacted with LiOH using a procedure analogous to that described in Preparation 37, Step 3 to afford the title compound. LC-MS Method 1 t$_R$=1.36 min, m/z=363.

Preparation 39

N-(4-(ethylsulfonyl)benzyl)-2-(trifluoromethyl)-1H-benzo[d]imidazole-5-carboxamide

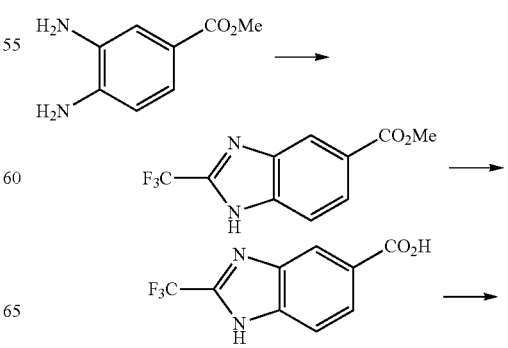

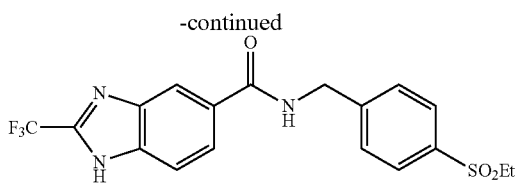

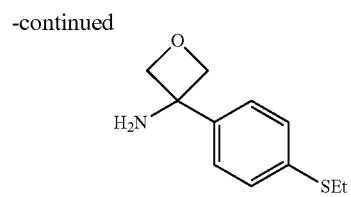

Step 1

A mixture of methyl 3,4-diaminobenzoate (2.93 g, 17.6 mmol) and TFA (10 mL) was heated at reflux for 2.5 h and concentrated. The residue was partitioned between EtOAc (175 mL) and satd aq NaHCO$_3$ (40 mL). The organic layer was separated, washed with satd aq NaHCO$_3$ (20 mL) and brine (20 mL), and dried over Na$_2$SO$_4$. Removal of the solvent left a dark solid (4.38 g). Chromatography on a 40-g silica cartridge, eluted with a 0-100% EtOAc in hexanes gradient, afforded methyl 2-(trifluoromethyl)-1H-benzo[d]imidazole-5-carboxylate (3.06 g, 71%). LC-MS Method 1 $t_R$=1.38 min, m/z=245.

Step 2

A stirred solution of methyl 2-(trifluoromethyl)-1H-benzo[d]imidazole-5-carboxylate (278 mg, 1.1 mmol), LiOH.H$_2$O (198 mg, 4.7 mmol) in 3:1 MeOH/H$_2$O (8 mL) was heated at 40° C. for 2 days and concentrated. The residue was taken up in 5% aq HCl (5 mL) and MeCN (5 mL) and concentrated again to leave crude 2-(trifluoromethyl)-1H-benzo[d]imidazole-5-carboxylic acid.

Step 3

Half of the crude 2-(trifluoromethyl)-1H-benzo[d]imidazole-5-carboxylic acid from Step 2 (≤0.55 mmol), AM2 (150 mg, 0.75 mmol) and i-Pr$_2$NEt (0.36 mL, 2.0 mmol) were stirred in 5:1 CH$_2$C$_{12}$/DMF (6 mL) and solid HATU (285 mg, 0.75 mmol) was added. After stirring for 2 h, the mixture was diluted with EtOAc (90 mL), washed with 5% aq HCl (10 mL), satd aq NaHCO$_3$ (10 mL) and brine (10 mL), and dried over Na$_2$SO$_4$. Removal of the solvent left an oil (348 mg). Chromatography on a 12 g silica cartridge, eluted with a 0-100% EtOAc in hexanes gradient, afforded N-(4-(ethylsulfonyl)benzyl)-2-(trifluoromethyl)-1H-benzo[d]imidazole-5-carboxamide (127 mg, 62%) as an oil. LC-MS Method 1 $t_R$=1.35 min, m/z=412.

Preparation 40

3-(4-(ethylthio)phenyl)oxetan-3-amine

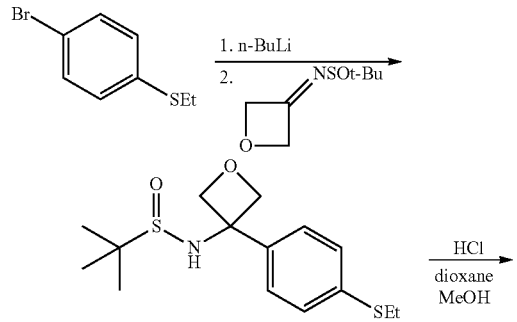

Step 1

A stirred solution of (4-bromophenyl)(ethyl)sulfane (1.05 g, 4.8 mmol) in dry THF (20 mL) was cooled to −70° C. and 2.2 M n-BuLI in cyclohexane (2.8 mL, 6.1 mmol) was added dropwise over 5 min. The mixture was stirred at −70° C. for 1 h. A solution of 2-methyl-N-(oxetan-3-ylidene)propane-2-sulfinamide (936 mg, 5.3 mmol) in dry THF (2 mL) was added dropwise over 2 min. The mixture was stirred at −70° C. for 0.5 h, removed from the cooling bath and quenched with satd aq NH$_4$Cl (20 mL) and water (10 mL). The mixture was extracted with EtOAc (2×40 mL). The combined organic layer was washed with brine (10 mL), dried over Na$_2$SO$_4$ and concentrated to leave a yellow oil (1.66 g). Chromatography on a 12 g silica cartridge, eluted with a 10-100% EtOAc in hexanes gradient, afforded N-(3-(4-(ethylthio)phenyl)oxetan-3-yl)-2-methylpropane-2-sulfinamide (1.07 g, 71%) as an oil. LC-MS Method 1 $t_R$=1.33 min, m/z=314.

Step 2

To a stirred, ice cold solution of N-(3-(4-(ethylthio)phenyl)oxetan-3-yl)-2-methylpropane-2-sulfinamide (1.07 g, 3.4 mmol) in MeOH (5 mL) was added 4 M HCl in dioxane (1.3 mL, 5.1 mmol). The mixture was stirred for 2 min and concentrated to leave the title compound as its HCl salt. LC-MS Method 1 $t_R$=0.65 min, m/z=193 [M-NH$_2$]+

Preparation of Compounds of Formula I

Example 1

N-(1-((2,2-difluoro-3a,7a-dihydrobenzo[d][1,3]dioxol-4-yl)methyl)-2-(trifluoromethyl)-1H-benzo[d]imidazol-5-yl)-2-(4-(ethylsulfonyl)phenyl)acetamide (I-1)

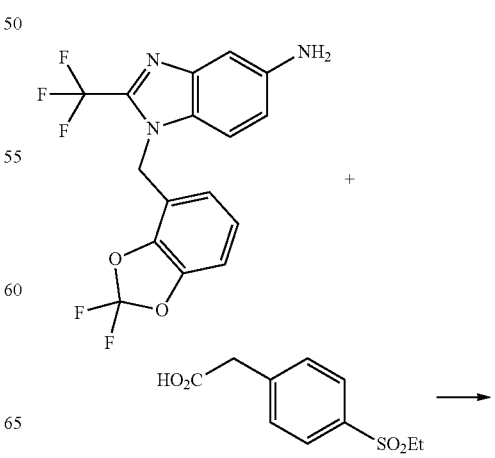

-continued

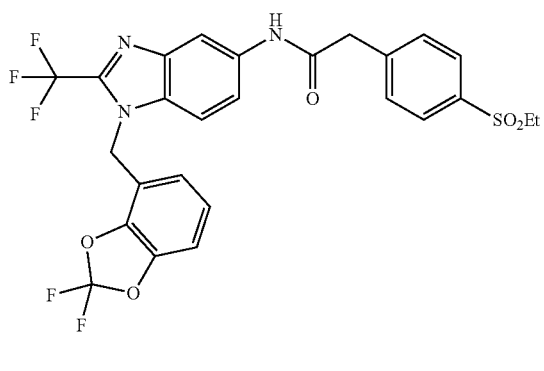

To a stirred solution of 1-((2,2-difluoro-3a,7a-dihydrobenzo[d][1,3]dioxol-4-yl)methyl)-2-(trifluoromethyl)-1H-benzo[d]imidazol-5-amine (13.5 mg, 36 μmol), AC1 (13 mg, 58 μmol) and i-Pr$_2$NEt (26 μL, 0.14 mmol) in CH$_2$Cl$_2$ (2 mL) was added solid HATU (40 mg, 0.11 mmol). The mixture was stirred at rt for 0.5 h and concentrated. The residue was purified by prep HPLC to afford N-(1-((2,2-difluoro-3a,7a-dihydrobenzo[d][1,3]dioxol-4-yl)methyl)-2-(trifluoromethyl)-1H-benzo[d]imidazol-5-yl)-2-(4-(ethylsulfonyl)phenyl)acetamide (16 mg, %). $^1$H NMR (d$_4$-MeOH) δ 1.20 (t, 3H), 3.18 (q, 2H), 3.84 (s, 2H), 5.72 (s, 2H), 6.77 (d, 1H), 7.04-7.18 (m, 2H), 7.47 (d, 1H), 7.59 (d, 1H), 7.62 (d, 2H), 7.86 (d, 2H), 8.19 (s, 1H). LC-MS Method 1 t$_R$=1.80 min, m/z=582.

The following compounds are prepared following a similar procedure using the appropriate acid p-R$^6$—C$_6$H$_4$CH$_2$CO$_2$H selected from AC1 to AC9:

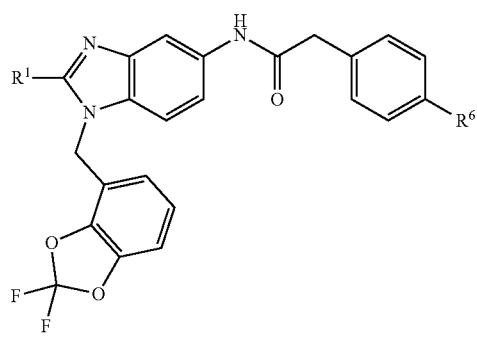

| Cpd. No. | R$^1$ | R$^5$ |
|---|---|---|
| I-2 | CF$_3$ | SO$_2$Me |
| I-3 | CF$_3$ | SO$_2$CH$_2$CH$_2$OH |
| I-4 | CF$_3$ | SO$_2$CH$_2$CH$_2$OMe |
| I-5 | CF$_3$ | SO$_2$NHMe |
| I-6 | CF$_3$ | CN |
| I-7 | CF$_3$ | CH$_2$CO$_2$Et |
| I-8 | CF$_3$ | CH$_2$CO$_2$H |
| I-9 | c-Pr | SO$_2$Et |

Compound I-10 was prepared by an analogous procedure:

I-10

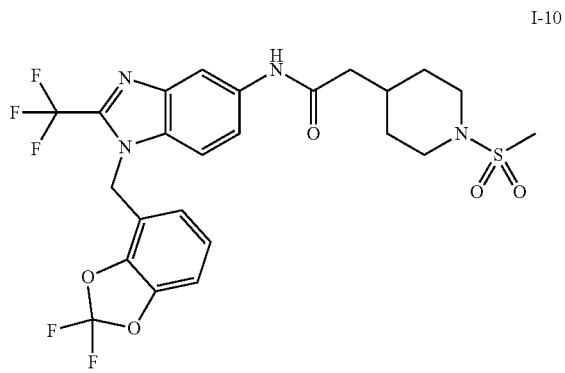 [SMILES: CS(=O)(=O)N1CCC(CC(=O)Nc2ccc3c(c2)nc(C(F)(F)F)n3Cc2cccc3c2OC(F)(F)O3)CC1]

Example 2

(R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide (I-11.1)

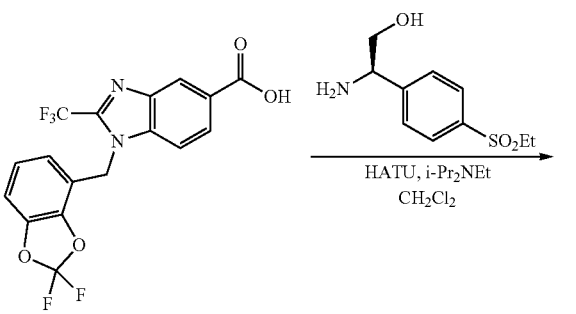

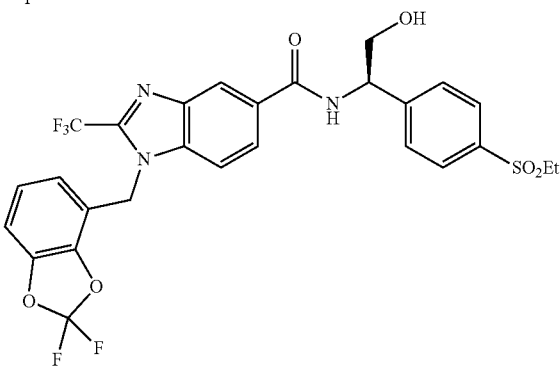

To a stirred solution of crude 1-((2,2-difluorobenzo[d][1,3]dioxol-4-yl)methyl)-2-(trifluoromethyl)-1H-benzo[d]imidazole-5-carboxylic acid (17 mg, 42 μmol), (R)-2-amino-2-(4-(ethylsulfonyl)phenyl)ethan-1-ol (AM8.1, 12.7 mg, 64 μmol) and i-Pr$_2$NEt (30 uL, 0.17 mmol) in CH$_2$Cl$_2$ (2 mL) was added solid HATU (25 mg, 65 μmol). The mixture was stirred overnight and concentrated. The residue was purified by prep HPLC to afford (R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide (22 mg, 84%) as an oil. 1H NMR (d$_4$-MeOH) δ 1.24 (t, 3H), 3.23 (q, 2H), 3.99 (d, 2H), 5.38 (t, 1H), 5.86 (s, 2H), 6.88 (d, 1H), 7.13-7.22 (m, 2H), 7.70 (d, 1H), 7.77 (d, 2H), 7.95 (d, 2H), 8.03 (d, 1H), 8.48 (s, 1H). LC-MS 2.5 min method t$_R$=1.47 min, m/z=612.

A solution of I-11.1 (100 mg) in CH₂Cl₂ (2 mL) was diluted with n-Pr₂O (4 mL). Additional CH₂Cl₂ (0.5 mL) was added to dissolve precipitate and a seed crystal of I-130.1 was added. The mixture was allowed to stand in a closed vial for 36 days, filtered and dried in vacuo to give I-11.1 (64 mg) with mp 134-136° C. This material gave the X-ray powder diffraction pattern shown in FIG. 3.

A solution of I-11.1 (150 mg) in i-PrOAc (2 mL) was diluted with CCl₄ (8 mL). The mixture was allowed to stand overnight and filtered. The white solid collected was dried in vacuo to give I-11.1 (106 mg) which softened at 97-102° C. and melted at 135-137° C. This material gave the X-ray powder diffraction pattern shown in FIG. 4.

A solution of I-11.1 (100 mg) in t-BuOAc (1 mL) was diluted with benzene (2 mL). The solution was seeded with solid prepared as described immediately above and allowed to stand overnight. The white solid was collected and dried in vacuo to give I-11.1 (77 mg) which softened at 97° C. and melted ~105° C. This material gave the X-ray powder diffraction pattern shown in FIG. 5.

Compound I-11.2, the enantiomer of I-11.1, is prepared using a similar procedure using AM8.2.

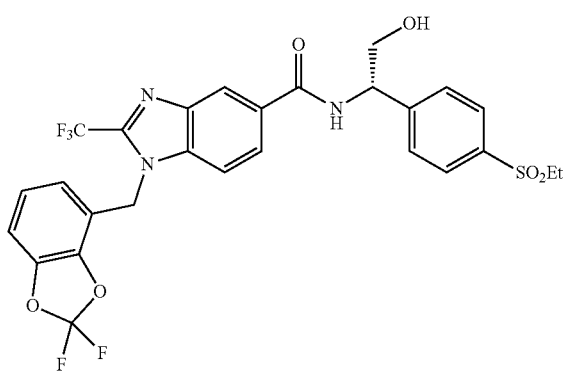

The compounds listed below are prepared following procedures analogous to those described for I-11.1 using the appropriate benzimidazole carboxylic acid in place of 1-((2,2-difluorobenzo[d][1,3]dioxol-4-yl)methyl)-2-(trifluoromethyl)-1H-benzo[d]imidazole-5-carboxylic acid.

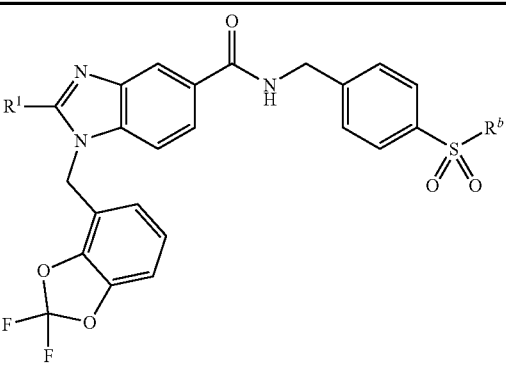

| Cpd. No. | R¹ |
|---|---|
| I-12 | c-Pr |
| I-13 | c-Bu |
| I-14 | CF₂Me |
| I-15 | 2-tetrahydrofuranyl |
| I-16 | Et |
| I-17 | CHF₂ |
| I-18 | 1-fluorocyclopropyl |
| I-19 | 1-fluorocyclobutyl |

The compounds listed below are prepared following similar procedures using amines AM7.1 and AM7.2.

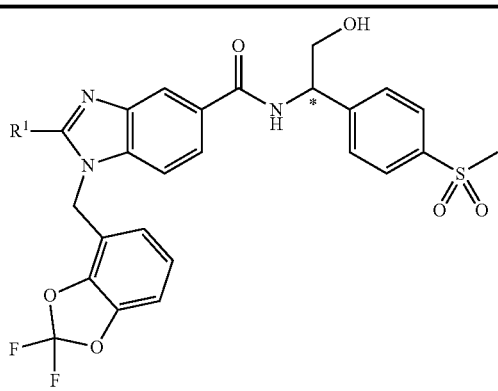

| Cpd. No. | * | R¹ |
|---|---|---|
| I-20.1 | R | CF₃ |
| I-20.2 | S | CF₃ |
| I-21 | R | c-Pr |
| I-22 | R | c-Bu |
| I-23.1 | R | CF₂H |
| I-23.2 | S | CF₂H |
| I-24 | R | 1-fluorocyclopropyl |

The following compounds are prepared following similar procedures.

| Cpd. No. | R¹ | $R^b$ |
|---|---|---|
| I-25 | CF₃ | Et |
| I-26 | c-Pr | Et |
| I-27 | 1-fluorocyclopropyl | Et |
| I-28 | MeOCH₂ | Et |
| I-29 | Et | Et |
| I-30 | t-Bu | Et |
| I-31 | i-Pr | Et |
| I-32 | Me | Et |
| I-33 | i-Bu | Et |
| I-34 | c-Pr | Me |
| I-35 | c-Pr | NHMe |
| I-36 | c-Bu | Et |
| I-37 | CF₂H | Et |
| I-38 | CF₂Me | Et |
| I-39.1[a] | (R)-2-tetrahydrofuranyl | Et |

-continued

| Cpd. No. | R¹ | (col3) |
|---|---|---|
| I-39.2[a] | (S)-2-tetrahydrofuranyl | Et |
| I-40 | 1-fluorocyclopropyl | Me |
| I-41 | 1-fluorocyclopropyl | CH₂CH₂OH |
| I-42 | 1-fluorocyclopropyl | NHMe |
| I-43 | 1-fluorocyclobutyl | Et |
| I-44 | CF₂H | CH₂CH₂OH |
| I-45 | CF₃ | CH₂CH₂OH |
| I-46 | CF₃ | NHMe |
| I-47 | c-Pr | CH₂CH₂OH |
| I-48 | CF₃ | Me |
| I-49.1[b] | MeOCHMe | Et |
| I-49.2[b] | MeOCHMe | Et |
| I-50 | CF₂H | Me |
| I-51 | CF₃ | NH₂ |
| I-52 | CF₃ | n-Pr |
| I-53 | CF₃ | CH₂CO₂Me |
| I-54 | MeOC(Me₂) | Et |
| I-55 | MeO | Et |
| I-56 | cis-2-cyanocyclopropyl | Et |
| I-57 | trans-2-cyanocyclopropyl | Et |
| I-58 | trans-2-(MeO₂C)cyclopropyl | Et |

[a]Prepared from the corresponding chiral tetrahydrofuran-2-carboxylic acids. The stereochemical integrity of the chiral center in the final products was not confirmed.
[b]The enantiomers were separated by chromatography on a chiral column.

The following compounds are prepared following similar procedures.

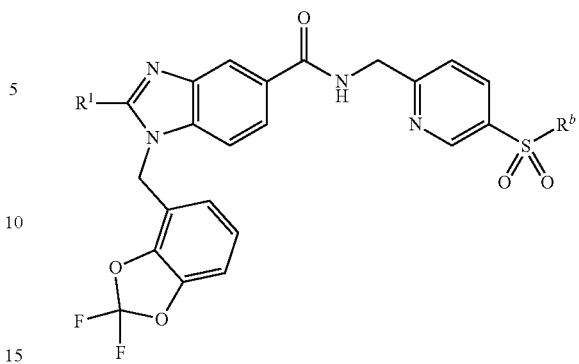

| Cpd. No. | R¹ | A |
|---|---|---|
| I-59 | CF₃ | CH |
| I-60 | c-Pr | CH |
| I-61 | 1-fluorocyclopropyl | CH |
| I-62 | CF₃ | N |

The following compounds are prepared following similar procedures.

| Cpd. No. | R¹ | R$^b$ |
|---|---|---|
| I-63 | CF₃ | Et |
| I-64 | c-Pr | Et |
| I-65 | c-Bu | Et |
| I-66 | CF₂Me | Et |
| I-67 | 1-fluorocyclopropyl | Et |
| I-68 | 1-fluorocyclopropyl | Me |
| I-69 | 1-fluorocyclobutyl | Et |
| I-70 | CF₃ | Me |

The following compounds are prepared following similar procedures.

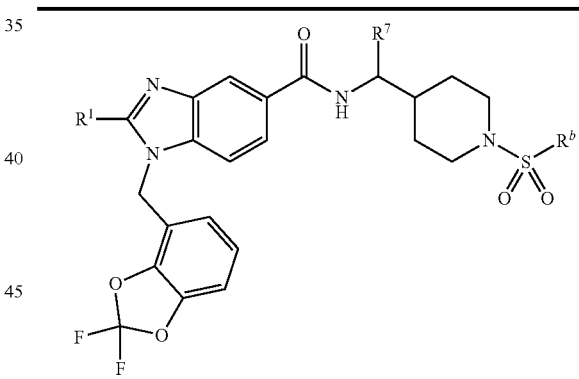

| Cpd. No. | R¹ | R7 | R$^b$ |
|---|---|---|---|
| I-71 | CF₃ | H | Me |
| I-72 | c-Pr | H | Me |
| I-73 | 1-fluorocyclopropyl | H | Me |
| I-74 | CF₃ | H | CH₂CO₂Me |
| I-75 | CF₃ | H | CH₂CONHMe |
| I-76 | CF₃ | CO₂Me | Me |
| I-77 | CF₃ | H | NHMe |
| I-78 | CF₃ | H | CH₂CONH₂ |
| I-79 | c-Pr | H | CH₂CONHMe |
| I-164.1[a] | CF₃ | CH₂OH | Me |
| I-164.2[a] | CF₃ | CH₂OH | Me |

[a]The isomers were separated by chromatography on a chiral column. The stereochemical configuration of the isomers was not established.

The following compounds are prepared following similar procedures.

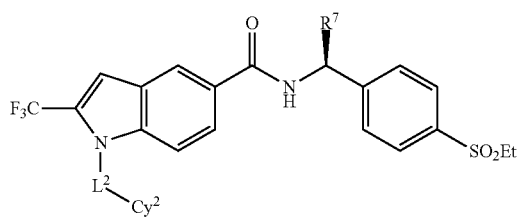

| Cpd. No. | L² | Cy² | R⁷ |
|---|---|---|---|
| I-80 | CH₂ | 2,3-dihydro7-benzofuranyl | CH₂OH |
| I-81 | CH₂ | benzo[d][1,3]dioxol-4-yl | CH₂OH |
| I-82 | CH₂ | 3,5-dimethoxyphenyl | H |
| I-83 | CH₂ | 4-methoxy-3-cyanophenyl | H |
| I-84 | CH₂ | 4-(trifluoromethoxy)phenyl | H |
| I-85 | CH₂ | 4-cyanophenyl | H |
| I-86 | CH₂ | 6,7-dihydro-5H-pyrrolo[2,1-c][1,2,4]triazol-3-yl | H |
| I-87 | CH₂ | 2-methyl-5,6,7,8-tetrahydroimidazo[1,2-a]pyridin-8-yl | H |
| I-88 | CH₂ | 3-methoxyphenyl | H |
| I-89 | CH₂ | 2-methoxy-4-pyridyl | H |
| I-90 | CH₂ | 3-cyanophenyl | H |
| I-91 | CH₂ | 2-oxo-1,2-dihydroquinolin-4-yl | H |
| I-92 | c-Pr | 3-cyanophenyl | H |
| I-93.1 | (S)-CHMe | 3-cyanophenyl | H |
| I-93.2 | (R)-CHMe | 3-cyanophenyl | H |
| I-94 | CH₂ | 2-fluoro-5-cyanophenyl | H |
| I-95 | CH₂ | 4-benzofuranyl | H |
| I-96 | CH₂ | 2,3-dihydro-4-benzofuranyl | H |
| I-97 | CH₂ | 4-indazolyl | H |
| I-98 | CH₂ | benzo[d][1,3]dioxo1-4-yl | H |
| I-99 | CH₂ | 3-(methoxycarbonyl)phenyl | H |
| I-100 | CH₂ | 1H-pyrrolo[2,3-c]pyridin-4-yl | H |

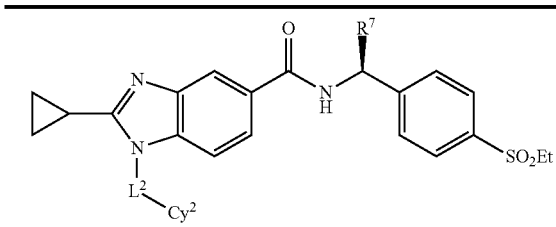

| Cpd. No. | L² | Cy² | R⁷ |
|---|---|---|---|
| I-101 | CH₂ | 2,2-dimethyl-2,3-dihydrobenzofuran-7-yl | CH₂OH |
| I-102 | CH₂ | 2,3-dihydrobenzofuran-7-yl | CH₂OH |
| I-103 | CH₂ | 3,5-dimethoxyphenyl | H |
| I-104 | CH₂ | 4-(trifluoromethoxy)phenyl | H |
| I-105 | CH₂ | 2,2-difluorobenzo[d][1,3]dioxo1-5-yl | H |
| I-106 | CH₂ | 2-(trifluoromethoxy)phenyl | H |
| I-107 | CH₂ | (3R)-1-(tert-butoxycarbonyl)pyrrolidin-3-yl | H |
| I-108 | CH₂ | (2R)-1-(tert-butoxycarbonyl)pyrrolidin-2-yl | H |
| I-109 | CH₂ | 3-(trifluoromethoxy)phenyl | H |
| I-110 | CH₂ | 2-methoxy-3-(trifluoromethyl)phenyl | H |
| I-111 | CH | 1-(2,2,2-trifluoroethyl)-1H-pyrazol-4-yl | H |
| I-112 | CH₂ | 3-cyanophenyl | H |
| I-113 | CH₂ | 3-(difluoromethoxy)phenyl | H |
| I-114 | CH₂ | 1-(2,2,2-trifluoroethyl)-1H-pyrazol-3-yl | H |
| I-115 | CH₂ | 3-(trifluoromethoxy)-5-methoxyphenyl | H |
| I-116 | (s)-CHMe | 2,2-difluorobenzo[d][1,3]dioxol-4-yl | H |
| I-117 | CH₂ | 6-oxo-1-(2,2,2-trifluoroethyl)-1,6-dihydropyridin-3-yl | H |
| I-118 | CH₂ | 2,2-dimethyl-2,3-dihydrobenzofuran-7-yl | H |
| I-119 | CH₂ | 2,3-dimethoxyphenyl | H |

I-120

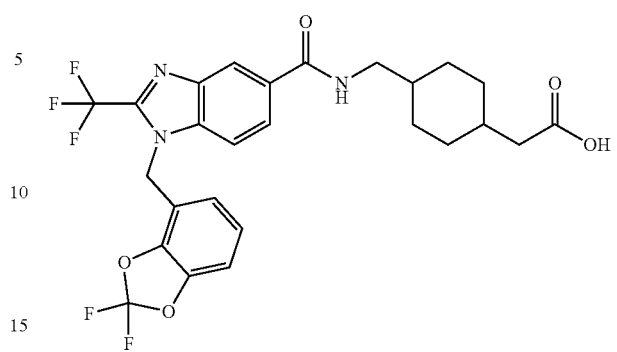

I-121

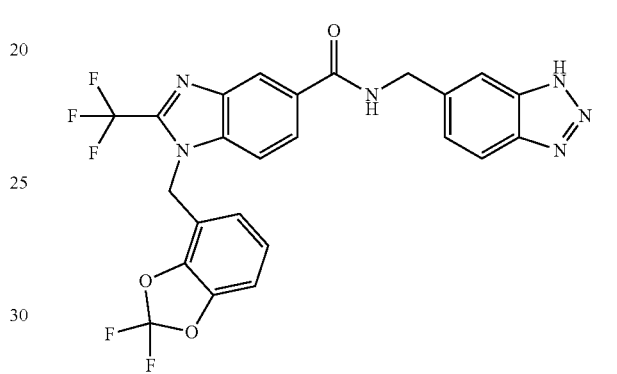

I-122

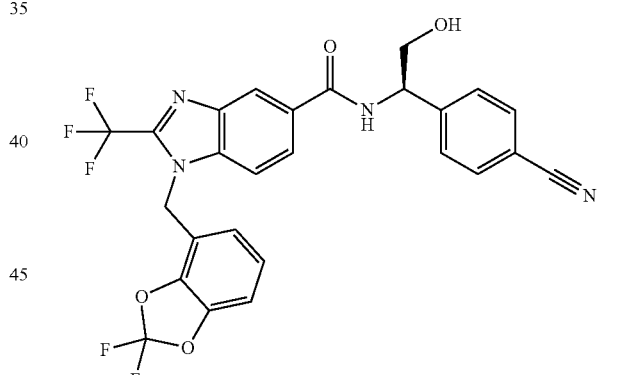

I-123

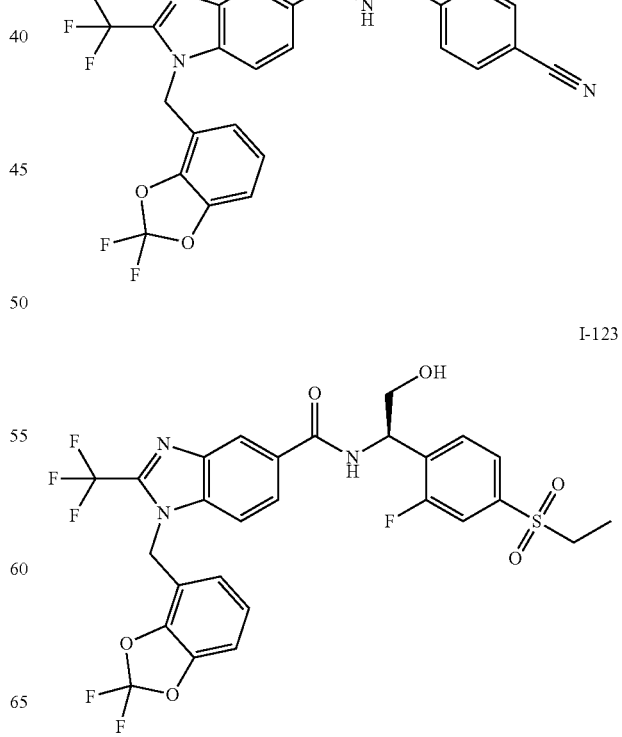

I-124
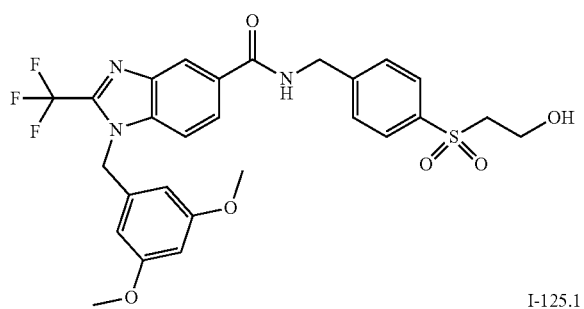
I-125.1
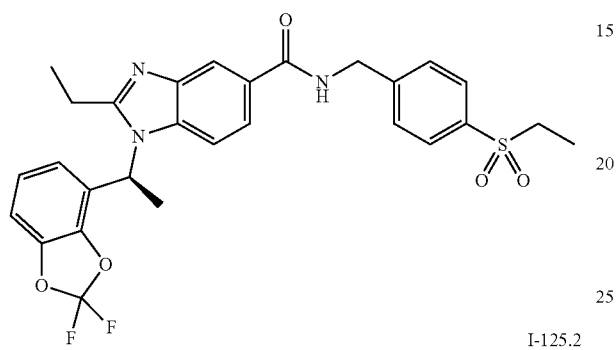
I-125.2
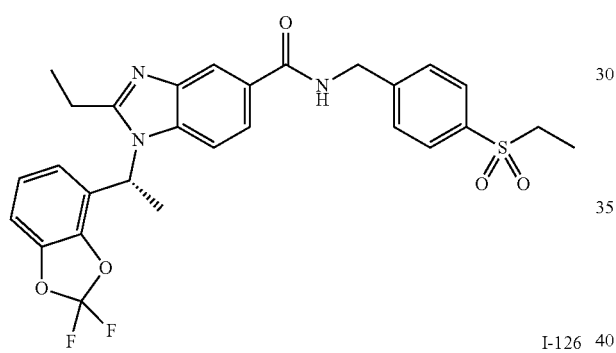
I-126
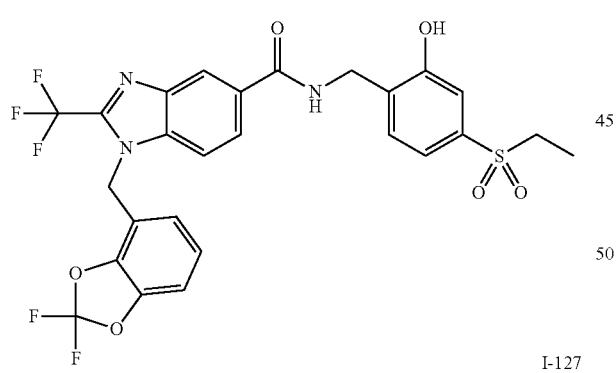
I-127
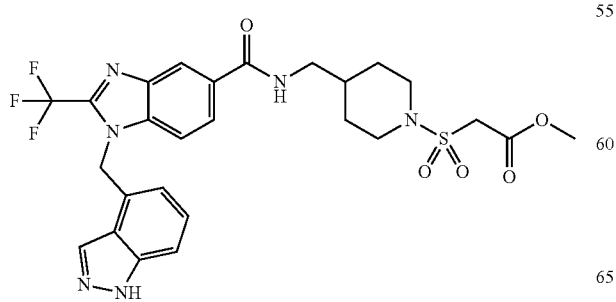
I-128
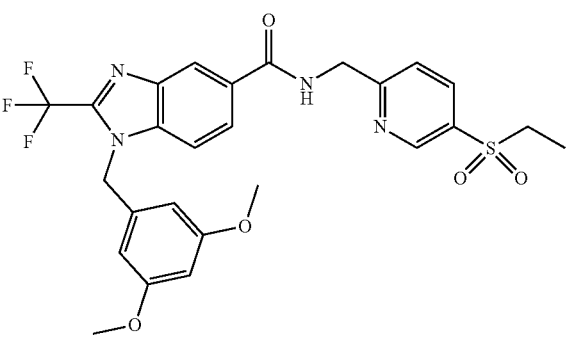
I-129
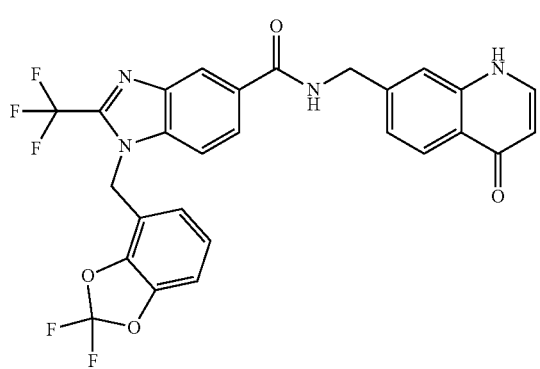
Example 3
(R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide (I-130.1) and (S)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide (I-130.2)
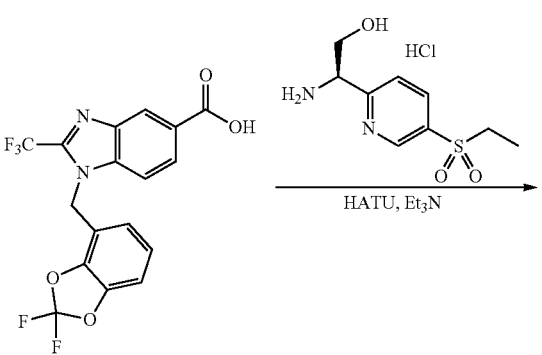

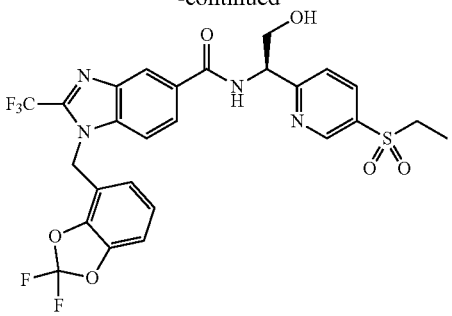

Major

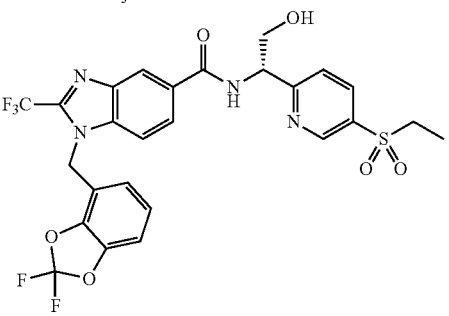

Minor

To a mixture of 1-((2,2-difluorobenzo[d][1,3]dioxol-4-yl)methyl)-2-(trifluoromethyl)-1H-benzo[d]imidazole-5-carboxylic acid (5.4 g, 13.5 mmol) and (R)-2-amino-2-(5-(ethylsulfonyl)pyridin-2-yl)ethanol HCl salt (5.4 g, 20.2 mmol) in anhydrous DCM (120 mL) was added Et$_3$N (8.2 g, 81.0 mmol). Then the mixture solution was cooled to 0° C. and HATU (6.7 g, 17.6 mmol) was added in several portions. The mixture was stirred at 25° C. for 4 h under N$_2$. LC-MS showed that the reaction was completed. The mixture was combined with another 3.6 g batch and diluted with DCM (100 mL), washed with water (2×100 mL) and brine (200 mL). The organic layer was dried over anhydrous Na$_2$SO$_4$, filtered and concentrated under reduced pressure. The residue was purified by column chromatography on silica gel eluting with petroleum ether/EtOAc=1/4 to give the racemic compound (12.4 g, 90%). The racemic compound was separated by SFC separation (AD), basic preparative HPLC separation, then freeze-drying to afford (R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide (I-301.1, 6.73 g, 49%, EE=99.54%) and (S)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide (I-130.2, 1.17 g, 9%, EE=98.84%) as white solids.

Before SFC separation: Isomer SFC t$_R$=4.83 and 5.37 min in 10 min chromatography (Column: AD-H; Method Name: AD_3_IPA_DEA_5_40_25ML, ee=66%)

SFC separation condition:
Instrument: Thar 80
Column: AD 250 mm*30 mm, 10 um
Mobile phase: A: Supercritical CO$_2$, B: IPA (0.05% NH$_3$.H$_2$O), A:B=70:30 at 200 mL/min
Column Temp: 38° C.
Nozzle Pressure: 100 Bar
Nozzle Temp: 60° C.
Evaporator Temp: 20° C.
Trimmer Temp: 25° C.
Wavelength: 220 nm Cpd No I-130.1 (6.73 g, 48.8%, EE=99.54%) as a white solid LC-MS Method 3 t$_R$=0.729 min, MS (ESI) m/z 613.0 [M+H]$^+$ $^1$H NMR (CDCl$_3$ 400 MHz): δ 9.05 (s, 1H), 8.43 (s, 1H), 8.22 (dd, J=2.0, 8.4 Hz, 1H), 7.96 (d, J=8.8 Hz, 1H), 7.86 (d, J=6.8 Hz, 1H), 7.73 (d, J=8.0 Hz, 1H), 7.42 (d, J=8.8 Hz, 1H), 7.10-6.92 (m, 2H), 6.59 (d, J=8.0 Hz, 1H), 5.62 (s, 2H), 5.52-5.40 (m, 1H), 4.35-4.15 (m, 1H), 4.08-3.90 (m, 1H), 3.51-3.44 (m, 1H), 3.18 (q, J=7.6 Hz, 2H), 1.35 (t, J=7.6 Hz, 3H). Isomer SFC t$_R$=5.395 min in 10 min chromatography (Column: AD-3; Method Name: AD_3_IPA_DEA_5_40_25 mL_10 min.met, ee=99.54%)

Basic preparative HPLC Method:
Mobile phase A: water with 0.05% NH$_3$H$_2$O solution
Mobile phase B: MeCN
Flow rate: 120 mL/min.
Detection: UV 220 nm
Column: Phenomenex Gemini 150*25 mm*10 um
Column temperature: 40° C.

| Time in min | % A | % B |
|---|---|---|
| 0.00 | 62 | 38 |
| 19.00 | 32 | 68 |
| 19.20 | 0 | 100 |
| 21.00 | 0 | 100 |

Cpd No I-130.2 (1.17 g, 8.5%, EE=98.84%) as a white solid

LC-MS Method 3 t$_R$=0.728 min, MS (ESI) m/z 613.0 [M+H]$^+$ $^1$H NMR (CDCl$_3$ 400 MHz): δ 9.05 (s, 1H), 8.43 (s, 1H), 8.21 (dd, J=2.4, 8.0 Hz, 1H), 7.96 (d, J=8.4 Hz, 1H), 7.87 (d, J=7.2 Hz, 1H), 7.73 (d, J=8.0 Hz, 1H), 7.42 (d, J=8.8 Hz, 1H), 7.07-6.97 (m, 2H), 6.59 (d, J=8.0 Hz, 1H), 5.62 (s, 2H), 5.51-5.43 (m, 1H), 4.27-4.20 (m, 1H), 4.10-4.04 (m, 1H), 3.55-3.46 (m, 1H), 3.18 (q, J=7.6 Hz, 2H), 1.34 (t, J=7.6 Hz, 3H). Isomer SFC t$_R$=4.840 min in 10 min chromatography (Column: AD-3; Method Name: AD_3_IPA_DEA_5_40_25 mL_10 min.met, ee=98.84%)

Basic Preparative HPLC Method:
Mobile phase A: water with 0.05% NH$_3$H$_2$O solution
Mobile phase B: MeCN
Flow rate: 120 mL/min.
Detection: UV 220 nm
Column: Gemini 150*25 5 u
Column temperature: 40° C.

| Time in min | % A | % B |
|---|---|---|
| 0.00 | 59 | 41 |
| 17.00 | 29 | 71 |
| 17.20 | 0 | 100 |
| 19.00 | 0 | 100 |

A solution of Cpd No I-130.1 (0.5 g) in MeCN (5 mL) was diluted with 5% aq HCl (~20 mL) until the solution became milky and immediately frozen in a dry ice/acetone bath. The resulting solid was lyophilized to afford I-130.1.HCl salt as a tan solid. $^1$H NMR (CD$_3$OD 400 MHz): δ 9.20 (s, 1H), 8.79 (d, 1H), 8.48 (s, 1H), 8.24 (d, 1H), 8.03 (d, 1H), 7.67 (d, 1H), 7.10-7.21 (m, 2H), 6.89 (d, 1H), 5.82 (s, 2H), 5.43 (m, 1H), 4.15 (m, 2H), 3.40 (q, 2H), 1.27 (t, 3H).

Seed crystals were obtained by vapor diffusion of ether into a solution of lyophilized I-130.1.HCl salt (3-5 mg) in MeCN (0.25 mL).

A solution of lyophilized I-130.1.HCl salt (1.80 g) in MeCN (36 mL) was diluted with Et₂O (12 mL) and a seed crystal was added. After standing overnight, the solid was collected by filtration and dried under high vacuum to afford I-130.1.HCl salt (1.39 g) as a white solid, mp 139-142° C. This material gave the X-ray powder diffraction pattern shown in FIG. 1.

XRPD analyses were conducted using a Bruker D8 Advance X-Ray diffractometer operating with a Cu radiation source at 40 kV, 40 mA through a Ni filter with a divergence slit of 0.60 mm/2.5°.

A solution of the free base of I-130.1 (0.30 g) in EtOAc (3 mL) was diluted with hexanes (7 mL) and allowed to stand loosely covered for 5 days. Filtration provided a solid (224 mg) with mp 149-152° C. This material gave the X-ray powder diffraction pattern shown in FIG. 2.

Example 4

(R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide (I-131.1) and (S)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide (I-131.2)

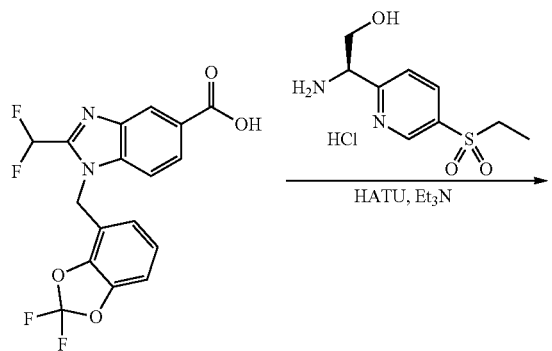

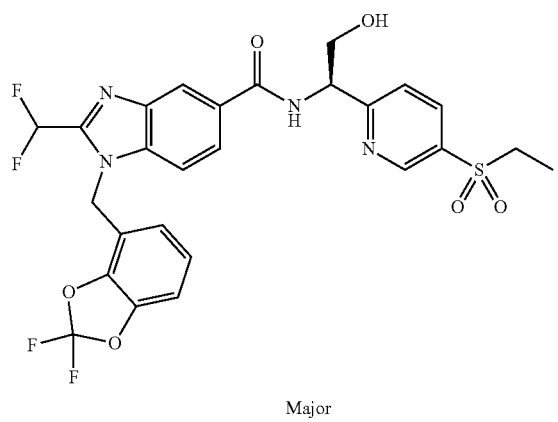

Major

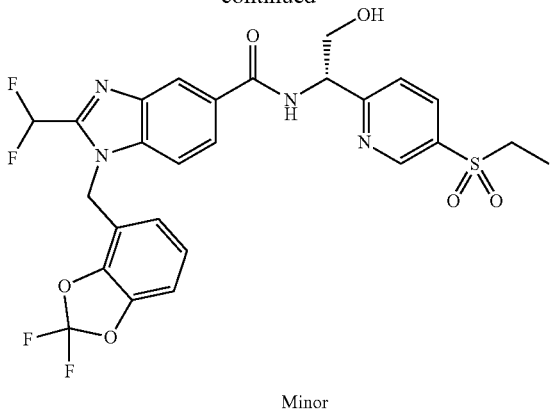

Minor

To a mixture of 1-((2,2-difluorobenzo[d][1,3]dioxol-4-yl)methyl)-2-(difluoromethyl)-1H-benzo[d]imidazole-5-carboxylic acid (8.5 g, 22.25 mmol) and Et₃N (6.7 g, 66.75 mmol) in CH₂Cl₂ (350 mL) was added (R)-2-amino-2-(5-(ethylsulfonyl)pyridin-2-yl)ethanol HCl salt (7.7 g, 28.83 mmol) at 0° C. Then the mixture was stirred at 0° C. for 5 min. HATU (10.1 g, 26.7 mmol) was added in portions. The mixture was stirred at 0-16° C. for 3 h. LC-MS showed that the reaction was completed. The mixture was combined with another 13.2 g batch and washed with water (3×300 mL) and brine (300 mL), dried over anhydrous Na₂SO₄, filtered and concentrated under reduced pressure. The residue was purified by column chromatography on silica gel eluting with petroleum ether/EtOAc=1/4-0/1, separated by SFC (AD), preparative HPLC separation and dry-freezing to afford (R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide (I-131.1, 7.96 g, 28%, neutral preparative HPLC separation) and (S)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide (I-131.2, 1.71 g, 6%, basic preparative HPLC separation) as white solids.

Before SFC separation: Isomer SFC $t_R$=0.556 and 0.760 min in 3 min chromatography (Column: AD-H; Method Name: AD-H_3UM_4_40_4ML_3MIN.M, ee=68%)

SFC separation condition:
Instrument: Thar 80
Column: AD 250 mm*30 mm, 10 um
Mobile phase: A: Supercritical CO₂, B: IPA (0.05% NH₃.H₂O), A:B=60:40 at 200 mL/min
Column Temp: 38° C.
Nozzle Pressure: 100 Bar
Nozzle Temp: 60° C.
Evaporator Temp: 20° C.
Trimmer Temp: 25° C.
Wavelength: 220 nm Cpd No I-131.1 (7.96 g, 25%) as a white solid
LC-MSMethod 3 $t_R$=0.713 min, MS (ESI) m/z 595.1 [M+H]⁺ ¹H NMR (CDCl₃ 400 MHz): δ 9.04 (d, J=2.0 Hz, 1H), 8.37 (s, 1H), 8.21 (dd, J=2.4, 8.0 Hz, 1H), 7.90 (d, J=8.8 Hz, 1H), 7.84 (d, J=6.8 Hz, 1H), 7.72 (d, J=8.4 Hz, 1H), 7.38 (d, J=8.4 Hz, 1H), 7.02 (t, J=52.4 Hz, 1H), 7.04-6.96 (m, 2H), 6.64 (d, J=8.0 Hz, 1H), 5.66 (s, 2H), 5.49-5.46 (m, 1H), 4.23 (dd, J=4.0, 11.2 Hz, 1H), 4.23 (dd, J=4.0, 11.6 Hz, 1H), 3.17 (q, J=7.6 Hz, 2H), 1.34 (t, J=7.6 Hz, 3H). Isomer SFC $t_R$=0.814 min in 3 min chromatography (Column: AD-H; Method Name: AD-H_3UM_4_40_4ML_3MIN.M, ee=99.47%)

Neutral Preparative HPLC Method:

Mobile phase A: water with 10 mM $NH_4HCO_3$ solution

Mobile phase B: MeCN

Flow rate: 120 mL/min.

Detection: UV 220 nm

Column: Phenomenex luna C18 250*50 mm*10 um

Column temperature: 40° C.

| Time in min | % A | % B |
|---|---|---|
| 0.00 | 77 | 23 |
| 21.00 | 38 | 62 |
| 24.00 | 0 | 100 |
| 30.00 | 0 | 100 |

Cpd No I-131.2 (1.71 g, 5%) as a wlite solid

LC-MS Method 3 $t_R$=0.719 min, MS (ESI) m/z 595.0 [M+H]$^+$ $^1$H NMR (CDCl$_3$ 400 MHz): δ 9.04 (s, 1H), 8.36 (s, 1H), 8.18 (d, J=8.4 Hz, 1H), 7.89 (d, J=8.4 Hz, 1H), 7.87-7.84 (m, 1H), 7.71 (d, J=8.0 Hz, 1H), 7.38 (d, J=8.4 Hz, 1H), 7.01 (t, J=52.4 Hz, 1H), 7.03-6.95 (m, 2H), 6.64 (d, J=8.0 Hz, 1H), 5.65 (s, 2H), 5.49-5.45 (m, 1H), 4.25-4.21 (m, 1H), 4.06-4.03 (m, 1H), 3.16 (q, J=7.6 Hz, 2H), 1.33 (t, J=7.6 Hz, 3H). Isomer SFC $t_R$=0.577 min in 3 min chromatography (Column: AD-H; Method Name: AD-H_3UM_4_40_4ML_3MIN.M, ee=95.60%)

Basic Preparative HPLC Method:

Mobile phase A: water with 0.05% $NH_3H_2O$ solution

Mobile phase B: MeCN

Flow rate: 110 mL/min.

Detection: UV 220 nm

Column: Phenomenex Synergi Max-RP 250*50 mm*10 um

Column temperature: 40° C.

| Time in min | % A | % B |
|---|---|---|
| 0.00 | 85 | 15 |
| 25.00 | 35 | 65 |
| 28.00 | 0 | 100 |
| 31.00 | 0 | 100 |

A solution of lyophilized I-131.1.HCl salt (2.03 g) in MeCN (36 mL) was diluted with Et$_2$O (12 mL) and a seed crystal of I-130.1 HCl salt was added. After standing over the weekend, the mixture was placed in the freezer for 2 weeks. The white solid was collected by filtration and dried under high vacuum to afford I-131.1.HCl salt (1.30 g), mp 129-134° C. This material gave the X-ray powder diffraction pattern shown in FIG. 6.

Example 5

(R)-2-cyclobutyl-1-((2,2-difluorobenzo[d][1,3]di-oxol-4-yl)methyl)-N-(1-(5-(ethylsulfonyl)pyridin-2-yl)-2-hydroxyethyl)-1H-benzo[d]imidazole-5-car-boxamide (I-132.1) and (S)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide (I-132.2)

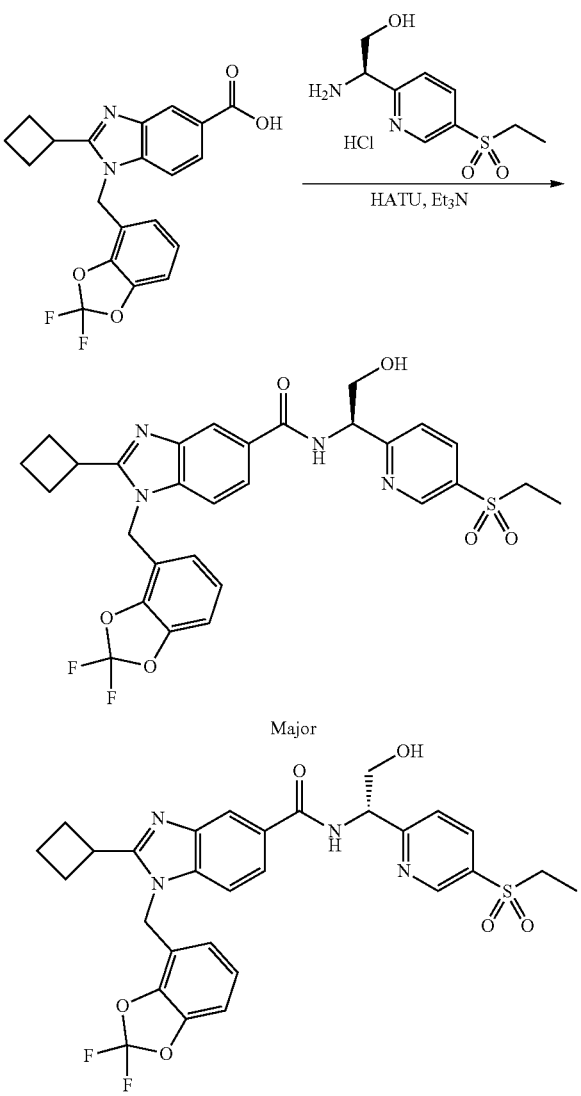

To a mixture of 2-cyclobutyl-1-((2,2-difluorobenzo[d][1,3]dioxol-4-yl)methyl)-1H-benzo[d]imidazole-5-carboxylic acid (3.6 g, 9.32 mmol) in anhydrous CH$_2$Cl$_2$ (150 mL) was added (R)-2-amino-2-(5-(ethylsulfonyl)pyridin-2-yl)ethanol HCl salt (3.2 g, 12.0 mmol), Et$_3$N (2.83 g, 28 mmol) and HATU (4.6 g, 12.12 mmol) in portions at 0° C. under N$_2$. The mixture was stirred at 22° C. for 1 h. LC-MS showed the reaction was completed. The mixture (together with another 5.5 g batch) was added with water (300 mL) and washed with CH$_2$Cl$_2$ (3×300 mL). The combined organic layers were washed with brine (500 mL), dried over anhydrous Na$_2$SO$_4$, filtered and concentrated under reduced pressure. The residue was purified by column chromatography on silica gel eluting with CH$_2$Cl$_2$:MeOH=50:1-25:1 to give 2-cyclobutyl-1-((2,2-difluorobenzo[d][1,3]dioxol-4-yl)methyl)-N-(1-(5-(ethylsulfonyl)pyridine-2-yl)-2-hydroxyethyl)-1H-benzo[d]imidazole-5-carboxamide (11.72 g), which was separated by SFC separation (cellulose-2) to give (R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide (I-132.1, 6.2 g+2.4 g), and (S)-2-cyclobutyl-1-((2,2-difluorobenzo[d][1,3]dioxol-4-yl) methyl)-N-(1-(5-(ethylsulfonyl)pyridin-2-yl)-2-hydroxyethyl)-1H-benzo[d]imidazole-5-carboxamide (I-132.2, 1.6 g) as yellow solids.

I-132.1 (6.2 g) was purified by basic preparative HPLC separation and dry-freezing to afford (R)-2-cyclobutyl-1-((2, 2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide (I-132.1, 4.88 g, 35%) as a white solid.

I-132.2 (1.6 g) was purified by basic preparative HPLC separation and dry-freezing to afford (S)-2-cyclobutyl-1-((2, 2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide (I-132.2, 784 mg, 6%) as a white solid.

I-132.1 (2.4 g) was purified by HCl preparative HPLC separation and dry-freezing to afford (R)-2-cyclobutyl-1-((2, 2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide (I-132.1, 1.29 g, 9%) as a white solid.

Before SFC separation: Isomer SFC $t_R$=7.525 and 10.107 min in 12 min chromatography (Column: CELLULOSE-2; Method Name: CELLULOSE-2_ETOH(DEA)_40_2_12 min.met, ee=67.57%).

SFC Separation Condition:
Instrument: Berger MultiGram™ SFC, Mettler Toledo Co, Ltd
Column: C$_{2\ 250}$ mm*50 mm, 10 um
Mobile phase: A: Supercritical CO$_2$, B: EtOH (0.05% NH$_4$OH), A:B=60:40 at 200 mL/min
Column Temp: 40° C.
Nozzle Pressure: 100 Bar
Nozzle Temp: 60° C.
Evaporator Temp: 20° C.
Trimmer Temp: 25° C.
Wavelength: 220 nm Cpd No I-132.1 (4.88 g, free base) as a white solid LC-MS Method 3 $t_R$=0.649 min, MS (ESI) m/z 599.1 [M+H]$^+$ $^1$H NMR (CDCl$_3$ 400 MHz): δ 9.01 (s, 1H), 8.34 (s, 1H), 8.07-7.97 (m, 2H), 7.84 (d, J=12.4 Hz, 1H), 7.67 (d, J=8.0 Hz, 1H), 7.29 (s, 1H), 7.03 (d, J=7.6 Hz, 1H), 6.97 (t, J=8.0 Hz, 1H), 6.46 (d, J=8.0 Hz, 1H), 5.52-5.35 (m, 1H), 5.35 (s, 2H), 4.60-4.36 (m, 1H), 4.31-4.25 (m, 1H), 4.11-4.05 (m, 1H), 3.76-3.68 (m, 1H), 3.16 (q, J=7.6 Hz, 2H), 2.61-2.50 (m, 2H), 2.48-2.31 (m, 2H), 2.19-2.08 (m, 1H), 2.07-1.98 (m, 1H), 1.33 (t, J=7.2 Hz, 3H). Isomer SFC $t_R$=10.480 min in 14 min chromatography (Column: CELLULOSE-2; Method Name: CELLULOSE-2_ETOH(DEA)_40_2,5M-14 min.met, ee=99.66%).

Basic Preparative HPLC Method
Mobile phase A: water (0.05% ammonia hydroxide v/v)-ACN
Mobile phase B: CH$_3$CN
Flow rate: 150 mL/min.
Detection: UV 220 nm/254 nm
Column: Phenomenex Synergi Max-RP 250*50 mm*10 um
Column temperature: 30° C.

| Time in min | % A | % B |
|---|---|---|
| 0.00 | 70 | 30 |
| 10.00 | 45 | 55 |
| 12.00 | 0 | 100 |
| 13.00 | 0 | 100 |

A solution of the free base of I-132.1 (0.25 g) in EtOAc (3 mL) was diluted with hexanes (3 mL) and allowed stand loosely covered. Filtration and drying under vacuum provided I-132.1 (177 mg) as a solid with mp 96-110° C. This material gave the X-ray powder diffraction pattern shown in FIG. 7.

Cpd No I-132.2 (0.784 g, free base) as a white solid LC-MS Method 3 $t_R$=0.653 min, MS (ESI) m/z 599.2 [M+H]$^+$ $^1$H NMR (CDCl$_3$ 400 MHz): δ 8.91 (s, 1H), 8.37 (s, 1H), 8.16 (d, J=7.6 Hz, 1H), 7.87-7.78 (m, 2H), 7.57 (d, J=8.0 Hz, 1H), 7.23 (d, J=8.4 Hz, 1H), 6.98 (d, J=7.6 Hz, 1H), 6.92 (t, J=8.0 Hz, 1H), 6.42 (d, J=8.0 Hz, 1H), 5.52-5.41 (m, 1H), 5.35-5.20 (m, 2H), 5.15-4.93 (m, 1H), 5.34 (dd, J=3.6, 11.6 Hz, 1H), 4.10-4.02 (m, 1H), 3.71-3.62 (m, 1H), 3.08 (q, J=7.6 Hz, 2H), 2.61-2.52 (m, 2H), 2.49-2.21 (m, 2H), 2.15-1.91 (m, 2H), 1.26 (t, J=7.6 Hz, 3H). Isomer SFC $t_R$=7.466 min in 13 min chromatography (Column: CELLULOSE-2; Method Name: CELLULOSE-2_ETOH(DEA)_40_2,5M-13 min.met, ee=95.17%).

Basic Preparative HPLC Method
Mobile phase A: water (0.05% ammonia hydroxide v/v)-ACN
Mobile phase B: CH3CN
Flow rate: 25 mL/min.
Detection: UV 220 nm/254 nm
Column: Phenomenex Gemini 150*25 mm*10 um
Column temperature: 30° C.

| Time in min | % A | % B |
|---|---|---|
| 0.00 | 59 | 41 |
| 10.00 | 29 | 71 |
| 12.00 | 0 | 100 |
| 13.00 | 0 | 100 |

Cpd No I-132.1 (1.29 g, HCl salt) as a white solid LC-MS Method 3 $t_R$=0.663 min, MS (ESI) m/z 599.1 [M+H]$^+$ $^1$H NMR (CD$_3$OD 400 MHz): δ 9.05 (s, 1H), 8.43-8.36 (m, 1H), 8.35-8.22 (m, 1H), 8.16 (d, J=7.2 Hz, 1H), 7.88 (d, J=8.8 Hz, 1H), 7.83-7.22 (m, 1H), 7.27-7.21 (m, 2H), 7.17 (d, J=7.2 Hz, 1H), 5.88 (s, 2H), 5.43 (t, J=6.0 Hz, 1H), 4.39-4.31 (m, 1H), 4.12-4.03 (m, 2H), 3.29-3.27 (m, 2H), 2.66-2.51 (m, 4H), 2.36-2.26 (m, 1H), 2.17-2.06 (m, 1H), 1.28 (t, J=7.2 Hz, 3H). Isomer SFC $t_R$=9.673 min in 13 min chromatography (Column: CELLULOSE-2; Method Name: CELLULOSE-2_ETOH(DEA)_40_2,5M-13 min.met, ee=99.77%).

HCl Preparative HPLC Method
Mobile phase A: water (0.05% HCl)-ACN
Mobile phase B: CH$_3$CN
Flow rate: 120 mL/min.
Detection: UV 220 nm/254 nm
Column: Phenomenex Synergi Max-RP 250*50 mm*10 um
Column temperature: 30° C.

| Time in min | % A | % B |
| --- | --- | --- |
| 0.00 | 95 | 5 |
| 10.00 | 60 | 40 |
| 12.00 | 0 | 100 |
| 13.00 | 0 | 100 |

The following compounds are prepared using procedures analogous to those in Examples 3, 4 and 5.

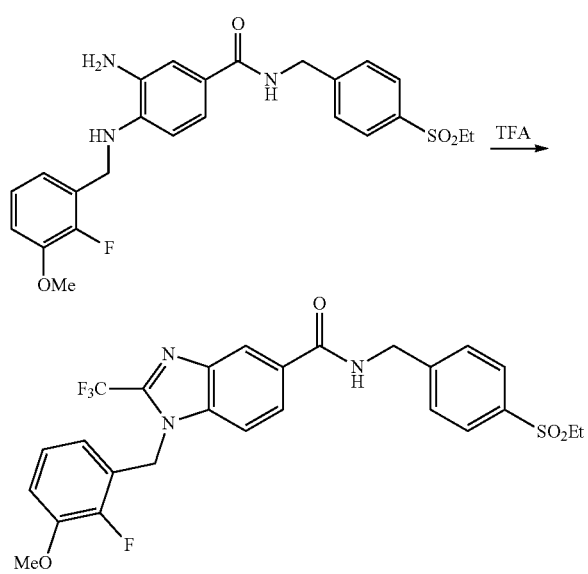

| Cpd No | R¹ | * | $R^b$ |
| --- | --- | --- | --- |
| I-133.1 | c-Pr | R | Et |
| I-133.2 | c-Pr | S | Et |
| I-134.1 | 1-fluorocyclopropyl | R | Et |
| I-134.2 | 1-fluorocyclopropyl | S | Et |
| I-135 | CF₃ | R | Me |

Example 6

N-(4-(ethylsulfonyl)benzyl)-1-(2-fluoro-3-methoxybenzyl)-2-(trifluoromethyl)-1H-benzo[d]imidazole-5-carboxamide (I-136)

A solution of 3-amino-N-(4-(ethylsulfonyl)benzyl)-4-((2-fluoro-3-methoxybenzyl)amino)benzamide (16.5 mg, mol) in TFA (2 mL) was stirred at 70° C. for 3 h. After concentration, the residue was purified by prep HPLC to provide the title compound (6 mg, 31%) as an oil. 1H NMR (d₄-MeOH) δ 1.20 (s, 3H), 3.19 (q, 2H), 3.87 (s, 3H), 4.71 (s, 2H), 5.75 (s, 2H), 6.34-6.42 (m, 1H), 6.96-7.10 (m, 2H), 7.58-7.64 (m, 3H), 7.88 (d, 2H), 7.97 (d, 1H), 8.38 (s, 1H). LC-MS Method 1 $t_R$=1.63 min, m/z=550.

The following compounds are prepared using an analogous procedure

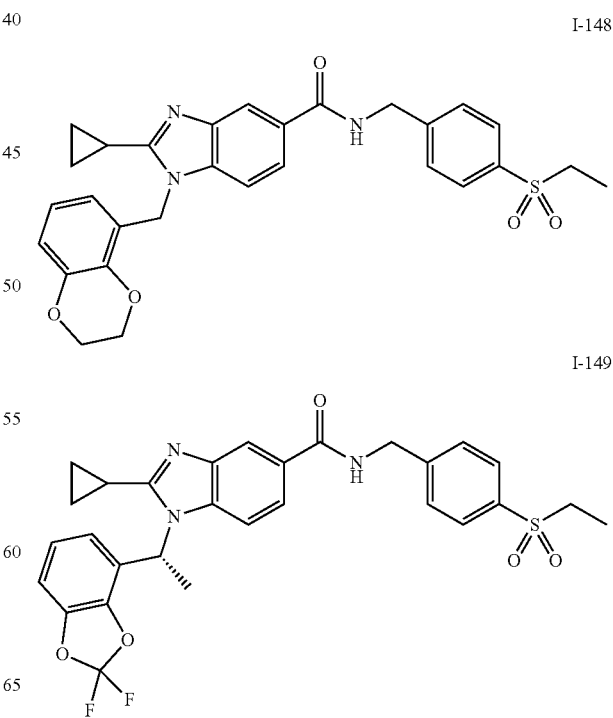

| Cpd No | Cy² |
| --- | --- |
| I-137 | 1-methyl-1H-indazol-7-yl |
| I-138 | 4-methyl-6-(trifluoromethyl)pyrimidin-2-yl |
| I-139 | 2-methyl-2H-indazol-7-yl |
| I-140 | 1,2-dimethyl-1H-benzo[d]imidazol-7-yl |
| I-141 | 1-methyl-1H-indazol-4-yl |
| I-142 | 1H-indazol-7-yl |
| I-143 | 2-methyl-2H-indazol-4-yl |
| I-144 | 6-oxo-1-(2,2,2-trifluoroethyl)-1,6-dihydropyridin-3-yl |
| I-445ᵃ | 1-(t-butoxycarbonyl)piperidin-4-yl |
| I-146 | 1-methyl-2-oxo-1,2-dihydropyridin-3-yl |
| I-147 | benzo[d]oxazol-4-yl |

ᵃThe crude product was treated with Boc₂O to reintroduce the Boc group.

The following compounds are prepared by similar procedures.

125

-continued

I-150

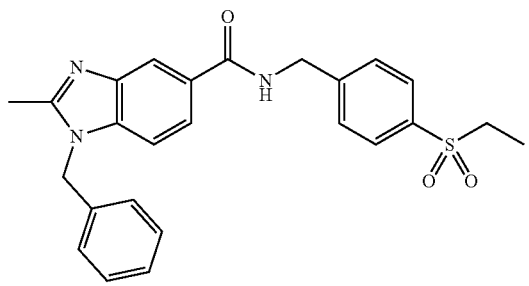

Example 7

1-(benzo[c][1,2,5]oxadiazol-4-ylmethyl)-N-(4-(ethylsulfonyl)benzyl)-2-(trifluoromethyl)-1H-benzo[d]imidazole-5-carboxamide (I-151)

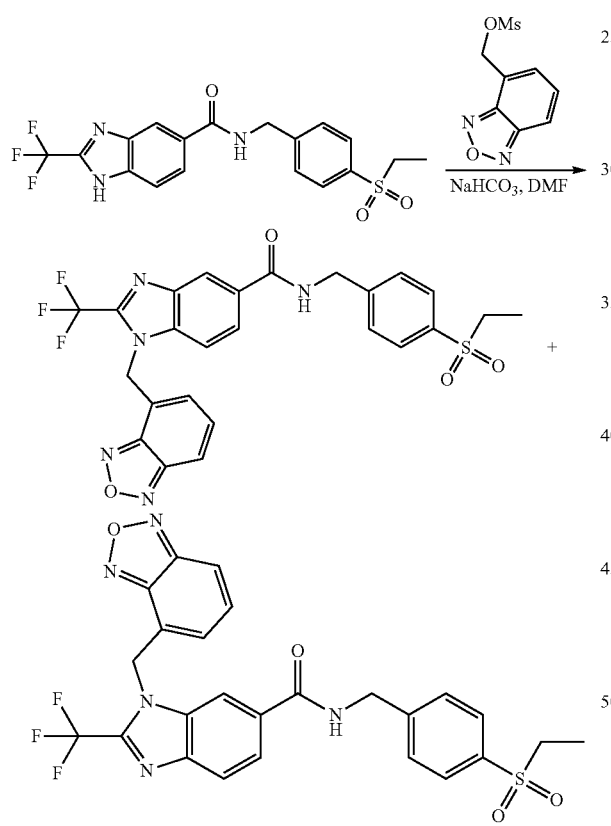

A stirred mixture of N-(4-(ethylsulfonyl)benzyl)-2-(trifluoromethyl)-1H-benzo[d]imidazole-5-carboxamide (37 mg, 90 μmol), benzo[c][1,2,5]oxadiazol-4-ylmethyl methanesulfonate (31 mg, 135 μmol), powdered NaHCO$_3$ (23 mg, 0.27 mmol) and dry DMF (2 mL) was heated at 60° C. for 3 h. The mixture was diluted with EtOAc (90 mL), washed with water (10 mL) and brine (10 mL), and dried over Na$_2$SO$_4$. Removal of the solvent left an oil (111 mg) which was purified by prep HPLC to afford the title compound as a 1:1 mixture with the regioisomer shown. LC-MS Method 1 $t_R$=1.56 min, m/z=545.

126

The following compound is prepared by a similar procedure, also as a mixture of regioisomers.

I-152

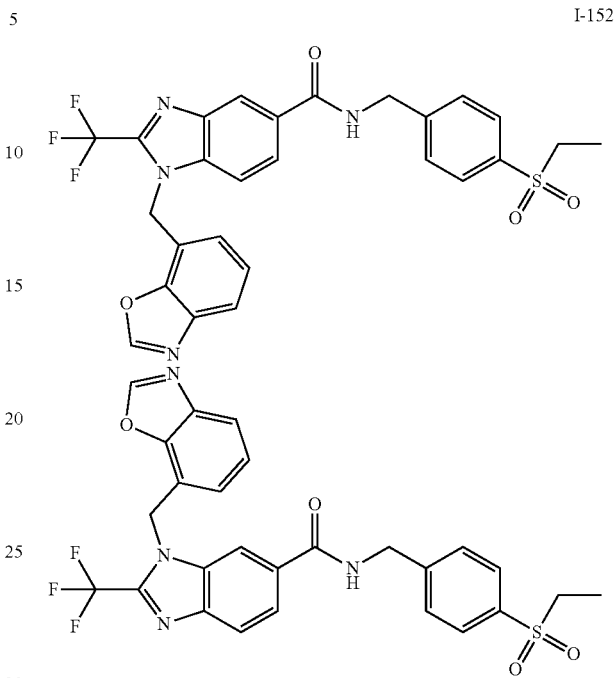

Example 8

2-cyclopropyl-N-(4-(ethylsulfonyl)benzyl)-1-(3-hydroxy-5-(trifluoromethoxy)benzyl)-1H-benzo[d]imidazole-5-carboxamide (I-153)

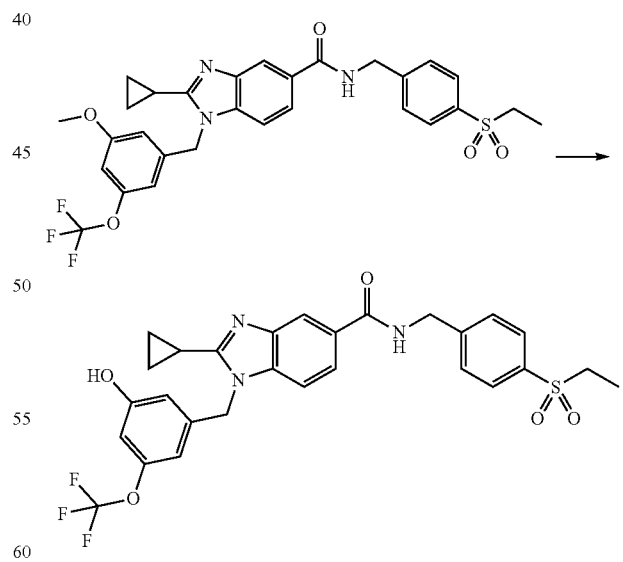

To a stirred, ice-cold solution of 2-cyclopropyl-N-(4-(ethylsulfonyl)benzyl)-1-(3-methoxy-5-(trifluoromethoxy)benzyl)-1H-benzo[d]imidazole-5-carboxamide (28 mg, 48 mol) in CH$_2$Cl$_2$ (2 mL) was added 1M BBr$_3$ in CH$_2$Cl$_2$ (0.25 mL, 0.25 mmol). The mixture was allowed to warm to rt, stirred overnight and treated with MeOH (5 mL). The mixture was concentrated and the residue was purified by prep HPLC to give 2-cyclopropyl-N-(4-(ethylsulfonyl)benzyl)-1-(3-hydroxy-5-(trifluoromethoxy)benzyl)-1H-benzo[d]imidazole-5-carboxamide (11 mg, 40%) as its TFA salt. $^1$H NMR (CD$_3$OD, 400 MHz) δ 8.15 (s, 1H), 8.05 (d, 1H), 7.82 (d, 2H), 7.72 (d, 1H), 7.57 (d, 2H), 6.57-6.65 (m, 2H), 6.54 (s, 1H), 5.72 (s, 2H), 4.66 (s, 2H), 3.10 (q, 2H), 2.37-2.47 (m, 1H), 1.25-1.45 (m, 4H), 1.13 (t, 3H). LC-MS Method 1 $t_R$=1.26 min, m/z=574.

The following compound is prepared from Cpd No I-119 using an analogous procedure:

I-154

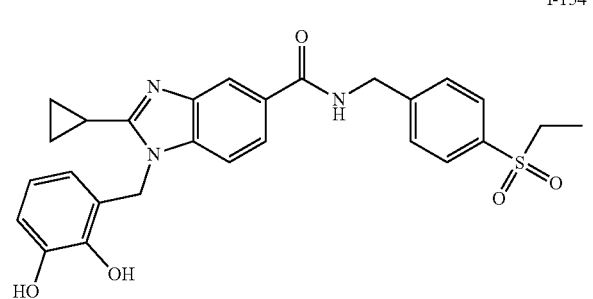

Example 9

N-(4-(ethylsulfonyl)benzyl)-1-((1-(2,2,2-trifluoroethyl)piperidin-4-yl)methyl)-2-(trifluoromethyl)-1H-benzo[d]imidazole-5-carboxamide (I-155)

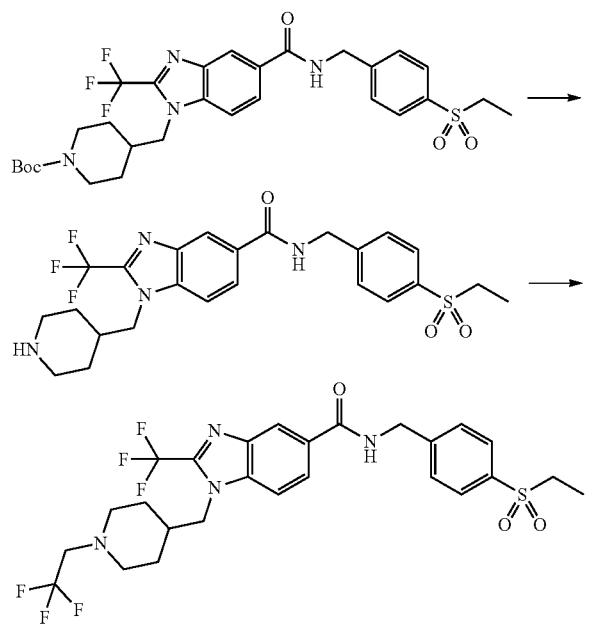

Step 1

A solution of tert-butyl 4-((5-((4-(ethylsulfonyl)benzyl)carbamoyl)-2-(trifluoromethyl)-1H-benzo[d]imidazol-1-yl)methyl)piperidine-1-carboxylate (42 mg, 69 μmol) in 4:1 CH$_2$Cl$_2$/TFA (5 mL) was stirred at rt for 2 h and concentrated to leave crude N-(4-(ethylsulfonyl)benzyl)-1-(piperidin-4-ylmethyl)-2-(trifluoromethyl)-1H-benzo[d]imidazole-5-carboxamide as its TFA salt (53 mg, quant). LC-MS Method 1 $t_R$=0.74 min, m/z=509.

Step 2

To a stirred solution of N-(4-(ethylsulfonyl)benzyl)-1-(piperidin-4-ylmethyl)-2-(trifluoromethyl)-1H-benzo[d]imidazole-5-carboxamide TFA salt (18 mg, 29 μmol) and i-Pr$_2$NEt (21 μL, 0.12 mmol) in MeCN (1 mL) was added 2,2,2-trifluoroethyl trifluoromethanesulfonate (5 μL, 35 μmol). The mixture was stirred overnight at rt and purified by prep HPLC to give the title compound as its TFA salt (8 mg, 39%). 1H NMR (CD$_3$OD, 400 MHz) δ 8.38 (s, 1H), 8.03 (d, 1H), 7.82-7.95 (m, 3H), 7.62 (d, 2H), 4.71 (s, 2H), 4.40 (d, 2H), 3.68 (q, 2H), 3.36 (m, 2H), 3.19 (q, 2H), 2.78 (t, 2H), 2.15-2.30 (m, 1H), 1.60-1.78 (m, 2H), 1.18 (t, 3H). LC-MS Method 1 $t_R$=1.26 min, m/z=591.

The following compounds are prepared using analogous procedures.

I-156

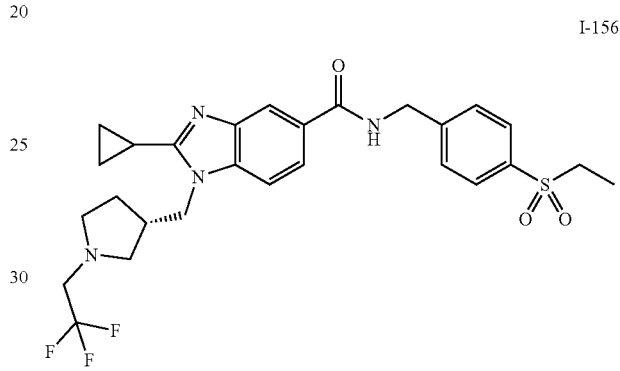

I-157

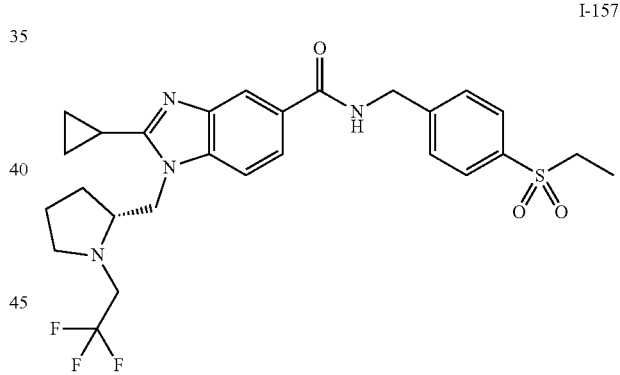

Example 10

N-(4-(ethylsulfonyl)benzyl)-1-((1-(5-fluoropyrimidin-2-yl)piperidin-4-yl)methyl)-2-(trifluoromethyl)-1H-benzo[d]imidazole-5-carboxamide (I-158)

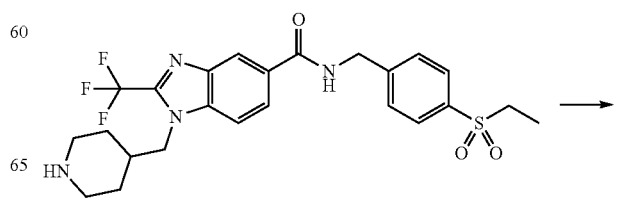

129
-continued

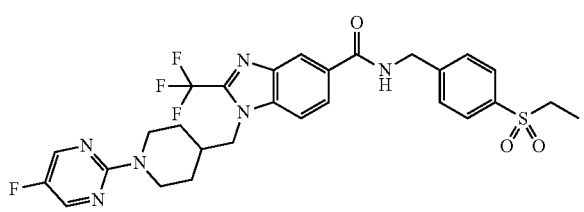

A solution of N-(4-(ethylsulfonyl)benzyl)-1-(piperidin-4-ylmethyl)-2-(trifluoromethyl)-1H-benzo[d]imidazole-5-carboxamide TFA salt (18 mg, 29 μmol), 2-chloro-5-fluoropyrimidine (11.5 mg, 86 μmol) and i-Pr₂NEt (21 μL, 0.12 mmol) in MeCN (1 mL) was heated in the microwave at 100° C. for 3 h. Prep HPLC gave the title compound as its TFA salt (5 mg, 23%). ¹H NMR (CD₃OD, 400 MHz) δ 8.40 (s, 1H), 8.28 (s, 2H), 8.08 (d, 1H), 7.86-7.98 (m, 3H), 7.68 (d, 2H), 4.77 (s, 2H), 4.41 (d, 2H), 3.15-3.40 (m, 4H), 2.78-2.90 (m, 2H), 2.28-2.42 (m, 1H), 1.58-1.68 (m, 2H), 1.35-1.50 (m, 2H), 1.25 (t, 3H). LC-MS Method 1 t$_R$=1.54 min, m/z=605.

The following compounds are prepared using analogous procedures.

I-159

I-160

130

Example 11

2-((1-((2,2-difluorobenzo[d][1,3]dioxol-4-yl)methyl)-2-(trifluoromethyl)-1H-benzo[d]imidazole-5-carboxamido)methyl)-5-(ethylsulfonyl)pyridine 1-oxide (I-161)

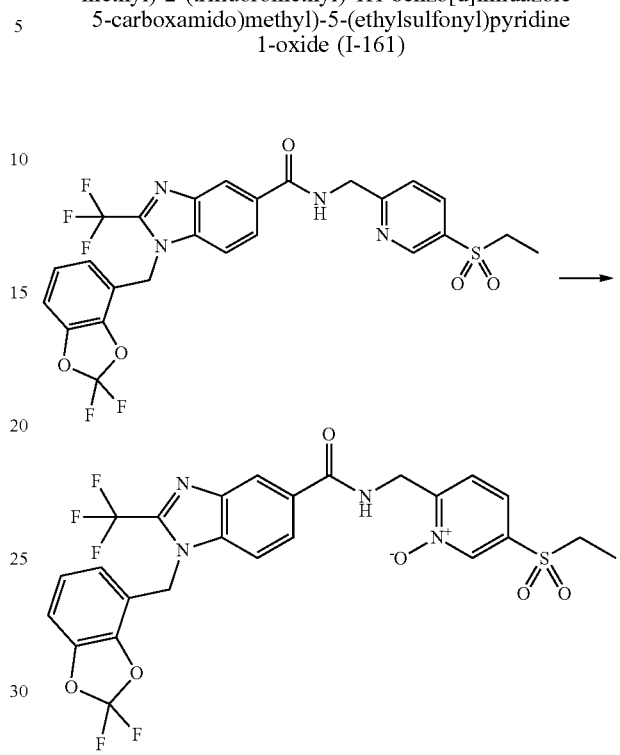

To a stirred solution of 1-((2,2-difluorobenzo[d][1,3]dioxol-4-yl)methyl)-N-((5-(ethylsulfonyl)pyridin-2-yl)methyl)-2-(trifluoromethyl)-1H-benzo[d]imidazole-5-carboxamide (28 mg, 49 μmol) in CH₂Cl₂ (2 mL) was added m-CPBA (16 mg, 65 μmol assuming 70% purity). The mixture was stirred overnight at rt, concentrated and the residue purified by prep HPLC to give the title compound (5.6 mg, 19%). 1H NMR (CD₃OD, 400 MHz) δ 8.78 (s, 1H), 8.46 (s, 1H), 8.03 (d, 1H), 7.93 (d, 1H), 7.75 (d, 1H), 7.68 (d, 1H), 7.08-7.21 (m, 2H), 6.86 (d, 1H), 5.83 (s, 2H), 4.83 (s, 2H), 3.35 (q, 2H), 1.25 (t, 3H). LC-MS Method 1 t$_R$=1.43 min, m/z=599. Starting material (14 mg, 50%) was also recovered.

Example 12

1-((2,2-difluorobenzo[d][1,3]dioxol-4-yl)methyl)-2-(dimethylamino)-N-(4-(ethylsulfonyl)benzyl)-1H-benzo[d]imidazole-5-carboxamide (I-162)

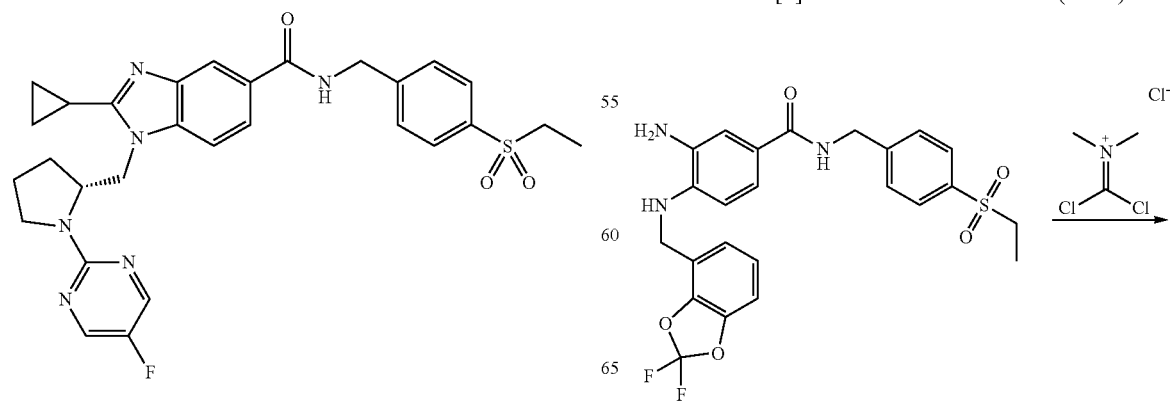

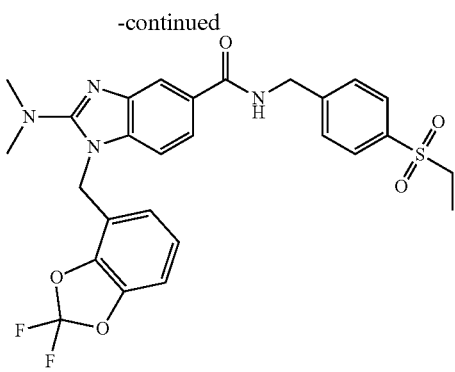

A mixture of 3-amino-4-(((2,2-difluorobenzo[d][1,3]dioxol-4-yl)methyl)amino)-N-(4-(ethylsulfonyl)benzyl)benzamide (52 mg, 0.1 mmol), phosgene iminium chloride (34 mg, 0.21 mmol), i-Pr$_2$NEt (0.3 mL, 1.7 mmol) and 1,2-dichloroethane (1 mL) was stirred at rt for 4 h. The mixture was diluted with EtOAc (90 mL), washed with water (10 mL), satd aq NaHCO$_3$ (5 mL) and brine (5 mL), and dried over Na$_2$SO$_4$. Removal of the solvent left an oil (50 mg). Prep HPLC gave the title compound (5 mg, 7%) as an oil. $^1$H NMR (CD$_3$OD, 400 MHz) δ 7.99 (s, 1H), 7.82-7.88 (m, 3H), 7.62 (d, 2H), 7.47 (d, 1H), 7.15-7.27 (m, 2H), 7.08 (d, 1H), 5.72 (s, 2H), 4.68 (d, 2H), 3.30 (s, 6H), 3.18 (q, 2H), 1.20 (t, 3H). LC-MS Method 1 $t_R$=1.30 min, m/z=557.

Example 13

1-((2,2-difluorobenzo[d][1,3]dioxol-4-yl)methyl)-N-((1-((2-hydroxyethyl)sulfonyl)piperidin-4-yl)methyl)-2-(trifluoromethyl)-1H-benzo[d]imidazole-5-carboxamide (I-163)

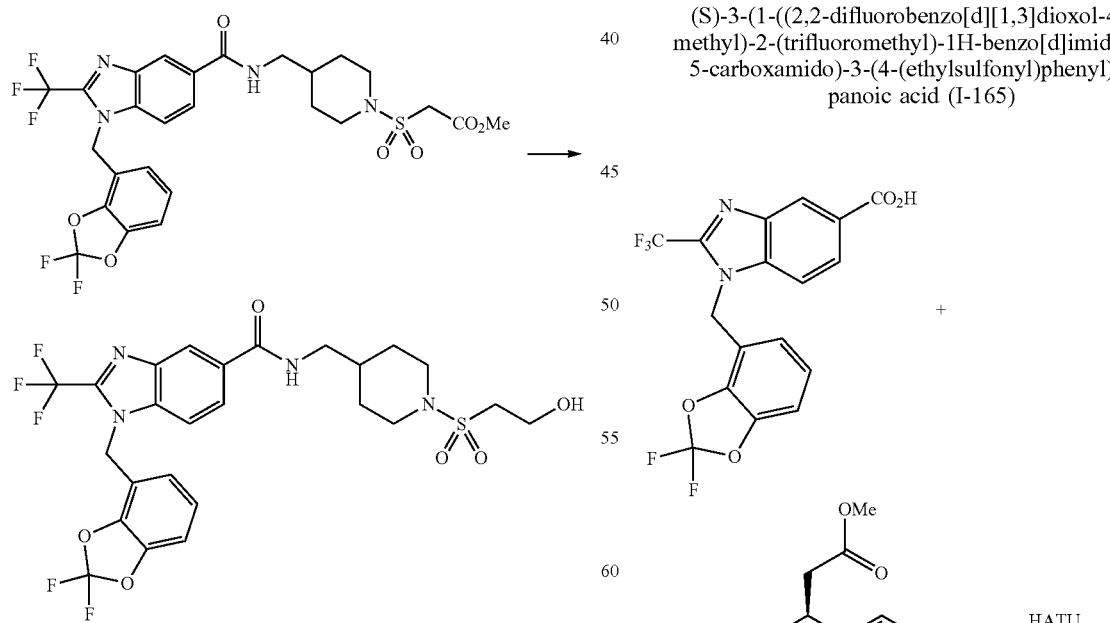

To a mixture of methyl 2-((4-((1-((2,2-difluorobenzo[d][1,3]dioxol-4-yl)methyl)-2-(trifluoromethyl)-1H-benzo[d]imidazole-5-carboxamido)methyl)piperidin-1-yl)sulfonyl)acetate (Cpd No I-74, 25 mg, 0.0396 mmol) in MeOH (1 mL) was added NaBH$_4$ (8 mg, 0.1978 mmol). The mixture was stirred at rt for 2 h under N$_2$. LC-MS showed that 63% of product was observed. The mixture was quenched with satd aq NH$_4$Cl solution (15 mL) and extracted with EtOAc (3×15 mL). The combined organic layers were dried over anhydrous Na$_2$SO$_4$, filtered and concentrated under reduced pressure. The residue was purified by preparative TLC with CH$_2$Cl$_2$/acetone=2/1 and basic preparative HPLC separation, then freeze dried directly to afford 1-((2,2-difluorobenzo[d][1,3]dioxol-4-yl)methyl)-N-((1-((2-hydroxyethyl)sulfonyl)piperidin-4-yl)methyl)-2-(trifluoromethyl)-1H-benzo[d]imidazole-5-carboxamide (I-163, 9.90 mg, 41%) as a white solid. LC-MS Method 3 $t_R$=0.731 min, MS (ESI) m/z 605.0 [M+H]$^+$. $^1$H NMR (CDCl$_3$ 400 MHz): δ 8.26 (s, 1H), 7.90 (d, J=8.8 Hz, 1H), 7.39 (d, J=8.8 Hz, 1H), 7.06-6.96 (m, 2H), 6.57 (d, J=8.0 Hz, 1H), 6.45-6.38 (m, 1H), 5.59 (s, 2H), 4.11-4.04 (m, 2H), 3.83 (d, J=12.4 Hz, 2H), 3.41 (t, J=5.6 Hz, 2H), 3.13 (t, J=5.6 Hz, 2H), 2.90-2.75 (m, 3H), 1.93-1.81 (m, 3H), 1.45-1.32 (m, 2H).

Basic Preparative HPLC Method:
Mobile phase A: water with 0.05% ammonia solution
Mobile phase B: MeCN
Flow rate: 25 mL/min.
Detection: UV 220 nm
Column: Gemini 150*25 5 u
Column temperature: 40° C.

| Time in min | % A | % B |
|---|---|---|
| 0.00 | 65 | 35 |
| 10.00 | 35 | 65 |
| 10.20 | 0 | 100 |
| 12.00 | 0 | 100 |

Example 14

(S)-3-(1-((2,2-difluorobenzo[d][1,3]dioxol-4-yl)methyl)-2-(trifluoromethyl)-1H-benzo[d]imidazole-5-carboxamido)-3-(4-(ethylsulfonyl)phenyl)propanoic acid (I-165)

-continued

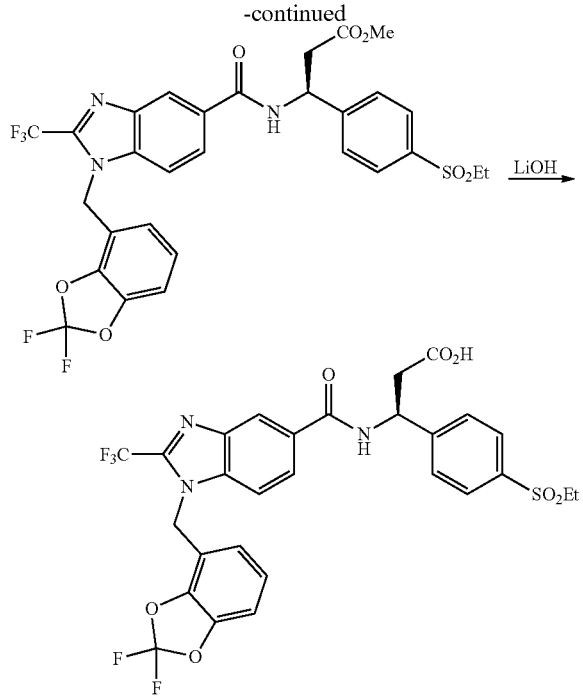

Step 1
Methyl (S)-3-(1-((2,2-difluorobenzo[d][1,3]dioxol-4-yl)methyl)-2-(trifluoromethyl)-1H-benzo[d]imidazole-5-carboxamido)-3-(4-(ethylsulfonyl)phenyl)propanoate is prepared following conditions analogous to those described in Example 2.

Step 2
Hydrolysis of the methyl ester to give I-165 is accomplished under conditions analogous to those described in Preparation 21, Step 2. $^1$H NMR (CDCl$_3$, 400 MHz): δ 8.49 (s, 1H), 8.24 (s, 1H), 7.78 (d, J=8.4 Hz, 1H), 7.57 (d, J=8.0 Hz, 2H), 7.45 (d, J=8.0 Hz, 2H), 7.23 (d, J=8.8 Hz, 1H), 6.90-6.80 (m, 2H), 6.45 (d, J=7.6 Hz, 1H), 5.55-5.41 (m, 3H), 4.85-4.70 (m, 2H), 2.95-2.75 (m, 3H), 1.00 (t, J=7.2 Hz, 3H).

The compounds shown below are prepared following an analogous procedure.

I-166

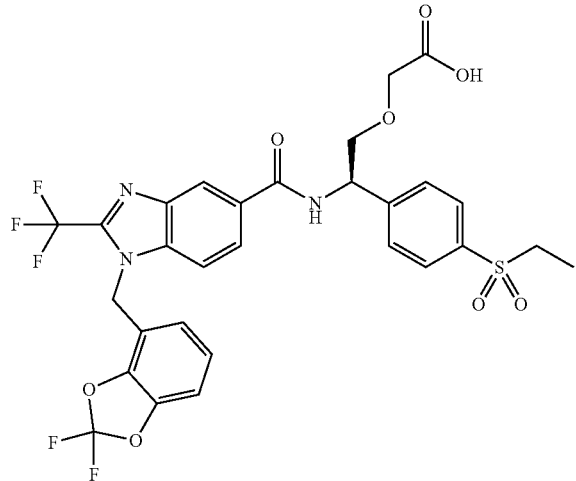

-continued

Precursor of I-169

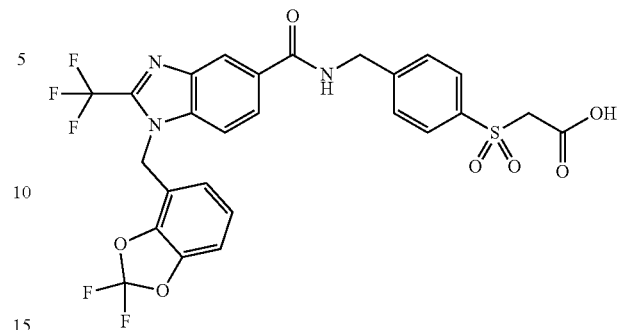

Example 15

(S)-1-((2,2-difluorobenzo[d][1,3]dioxol-4-yl)methyl)-N-(1-(4-(ethylsulfonyl)phenyl)-3-(methylamino)-3-oxopropyl)-2-(trifluoromethyl)-1H-benzo[d]imidazole-5-carboxamide (I-167)

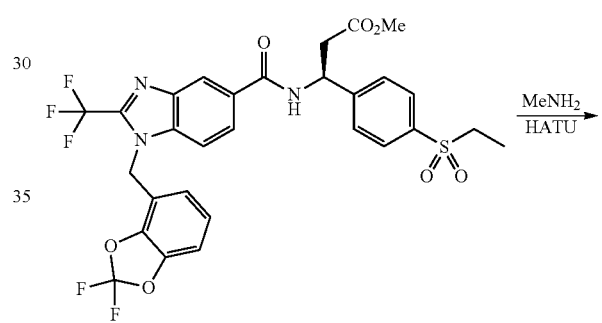

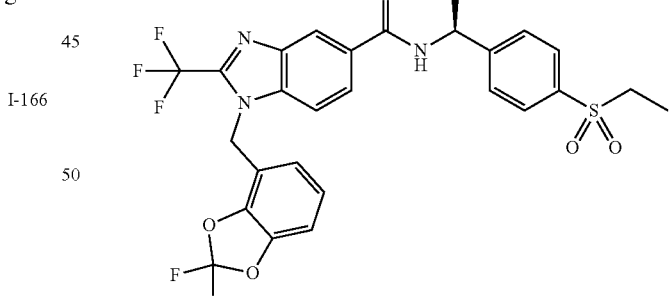

The title compound is prepared from I-165 following a procedure analogous to Example 2. $^1$H NMR (CDCl$_3$, 400 MHz): δ 9.24 (d, J=7.2 Hz, 1H), 8.53 (s, 1H), 7.98 (d, J=8.4 Hz, 1H), 7.85 (d, J=8.4 Hz, 2H), 7.56 (d, J=8.4 Hz, 2H), 7.40 (d, J=8.4 Hz, 1H), 7.06-6.98 (m, 2H), 6.58 (d, J=8.0 Hz, 1H), 5.62 (s, 2H), 5.57-5.51 (m, 2H), 3.09 (q, J=7.6 Hz, 2H), 2.92 (dd, J=4.8, 14.4 Hz, 1H), 2.73 (d, J=4.4 Hz, 3H), 2.63 (dd, J=4.4, 14.8 Hz, 1H), 1.28 (t, J=7.6 Hz, 3H).

The following compounds are prepared by an analogous procedure.

I-168

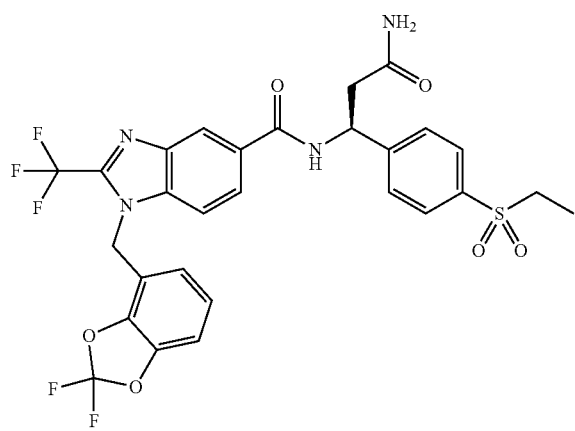

I-169

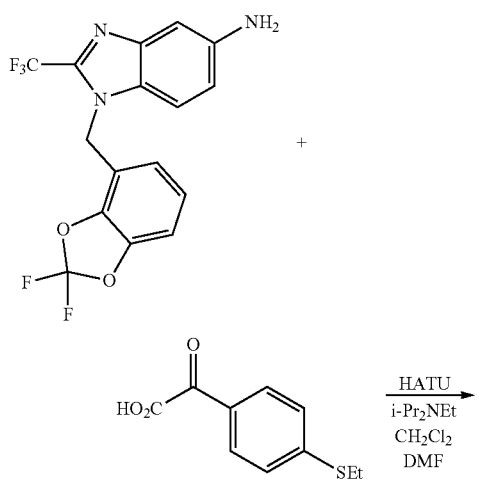

Example 16

N-(1-((2,2-difluorobenzo[d][1,3]dioxol-4-yl)methyl)-2-(trifluoromethyl)-1H-benzo[d]imidazol-5-yl)-2-(4-(ethylsulfonyl)phenyl)-2-hydroxyacetamide (I-170)

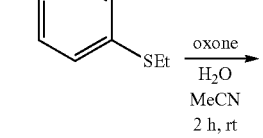

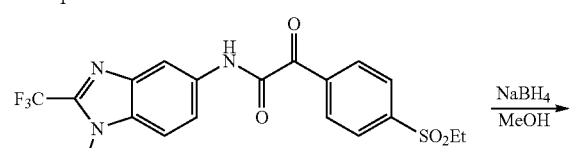

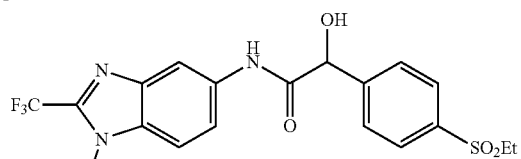

mixture of enantiomers separted via chiral column

Step 1

A procedure analogous to that in Example 1 was followed. LC-MS Method 1 $t_R$=2.03 min, m/z=564 (M+H).

Step 2

A 0.05 M solution of the thioether in 1:1 MeCN/H$_2$O was treated with oxone (3 equivs) and stirred overnight at rt. The mixture was concentrated. The aqueous residue was extracted with EtOAc (2×). The combined EtOAc layer was washed with brine, dried over Na$_2$SO$_4$ and concentrated to leave the crude sulfone. LC-MS Method 1 $t_R$=1.79 min, m/z=596 (M+H).

Step 3

A procedure analogous to that in Example 13 was followed to give I-170. $^1$H NMR (CD$_3$OD, 400 MHz) δ 8.20 (s, 1H), 7.92 (d, 2H), 7.85 (d, 2H), 7.63 (d, 1H), 7.50 (d, 1H), 7.07-7.18 (m, 2H), 6.80 (d, 1H), 5.76 (s, 2H), 5.32 (s, 1H), 3.20 (q, 2H), 1.30 (t, 3H). The enantiomers (I-170.1 and I-170.2) were separated by chromatography on a chiral column.

Example 17

1-((2,2-difluorobenzo[d][1,3]dioxol-4-yl)methyl)-N-((4-methyl-1-(methylsulfonyl)-1,4-diazepan-5-yl)methyl)-2-(trifluoromethyl)-1H-benzo[d]imidazole-5-carboxamide (I-171)

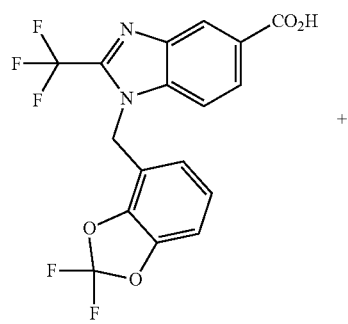

+

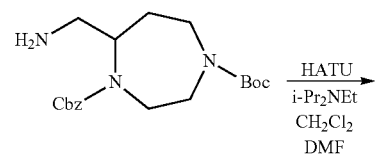

HATU
i-Pr₂NEt
CH₂Cl₂
DMF

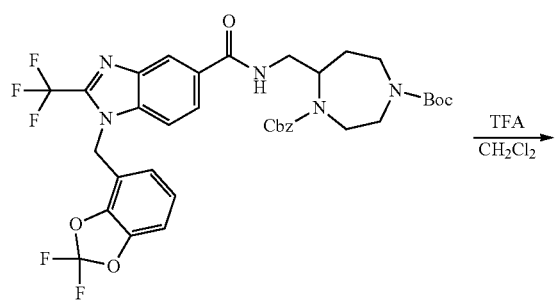

TFA
CH₂Cl₂

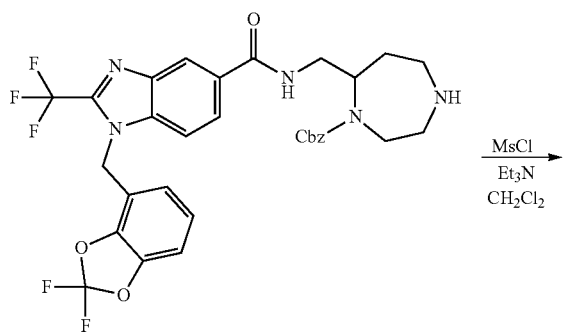

MsCl
Et₃N
CH₂Cl₂

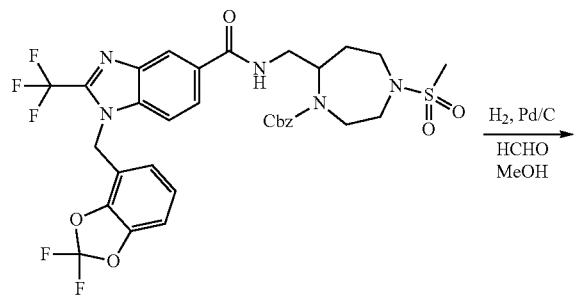

H₂, Pd/C
HCHO
MeOH

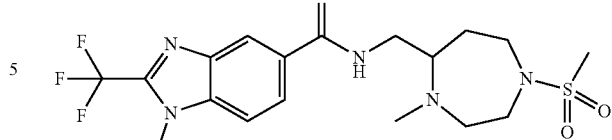

Example 18

1-((2,3-dihydrobenzofuran-4-yl)methyl)-N-(4-(ethylsulfonyl)benzyl)-2-(trifluoromethyl)-1H-benzo[d]imidazole-5-carboxamide (I-172)

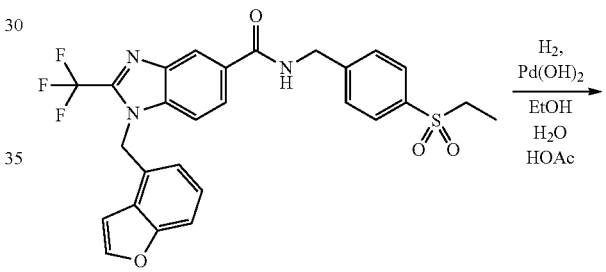

H₂, Pd(OH)₂
EtOH
H₂O
HOAc

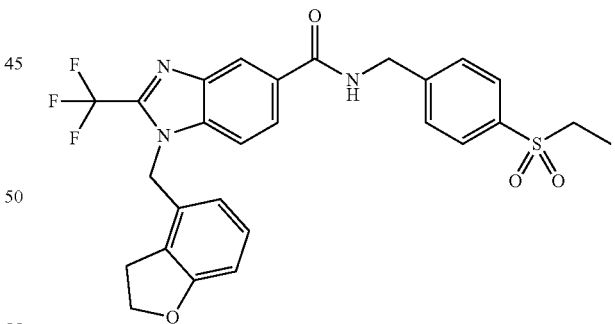

A solution I-95 (8 mg) in 4:2:1 EtOH/H₂O/HOAc (3.5 mL) was stirred under H₂ (1 atm, balloon) in the presence of Pd(OH)₂ (cat qty) overnight at rt. Prep HPLC afforded the title compound (1.1 mg). $^1$H NMR (CD₃OD, 400 MHz) δ 8.40 (s, 1H), 7.94 (d, 1H), 7.87 (d, 2H), 7.64 (d, 2H), 7.50 (d, 1H), 6.99 (t, 1H), 7.68 (d, 2H), 6.19 (d, 1H), 5.66 (s, 2H), 4.73 (d, 2H), 4.55 (t, 2H), 3.19 (q, 2H), 3.05 (t, 2H), 1.20 (t, 3H).

Example 19

Methyl 1-((2,2-difluorobenzo[d][1,3]dioxol-4-yl)methyl)-5-((4-(ethylsulfonyl)benzyl)carbamoyl)-1H-benzo[d]imidazole-2-carboxylate (I-173)

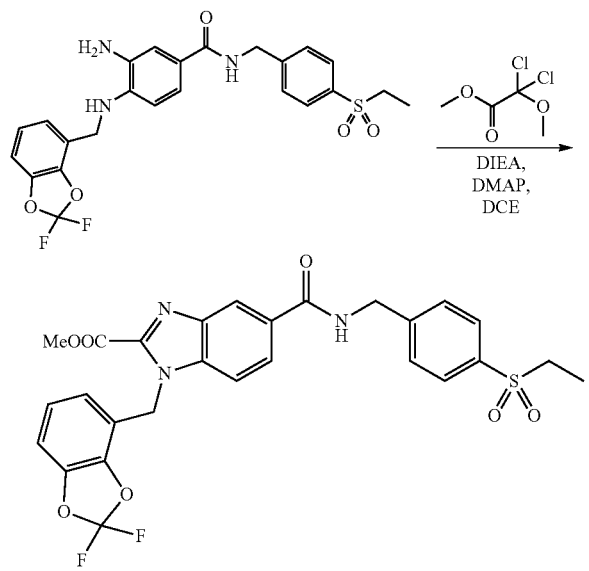

Step 1

To a mixture of 3-amino-4-(((2,2-difluorobenzo[d][1,3]dioxol-4-yl)methyl)amino)-N-(4-(ethylsulfonyl)benzyl)benzamide (47 mg, 0.093 mmol), DIPEA (72 mg, 0.56 mmol) and DMAP (5.7 mg, 0.047 mmol) in DCE (4 mL) was added methyl 2,2-dichloro-2-methoxyacetate (48 mg, 0.28 mmol) at 18° C. After stirring at 18° C. for 0.5 h, 40° C. for 1 h and 60° C. for 0.5 h, LC-MS showed that most was product. The mixture was diluted with H$_2$O (25 mL) and DCM (30 mL). After partition, the organic layer was dried over Na$_2$SO$_4$, filtered, concentrated under reduced pressure, purified by neutral preparative HPLC separation and freeze dried to afford the title compound (11.60 mg, 23%) as a white solid.

LC-MS Method 3 t$_R$=0.725 min, MS (ESI) m/z 572.0 [M+H]$^+$ $^1$H NMR (CDCl$_3$ 400 MHz): δ 8.08 (d, J=2.0 Hz, 1H), 7.87 (d, J=8.0 Hz, 3H), 7.55 (d, J=8.0 Hz, 2H), 7.32 (d, J=8.4 Hz, 1H), 7.00-6.98 (m, 2H), 6.92-6.91 (m, 1H), 6.70-6.69 (m, 1H), 5.58 (s, 2H), 4.77 (d, J=6.0 Hz, 2H), 4.15 (s, 3H), 3.11 (q, J=7.6 Hz, 2H), 1.28 (t, J=7.6 Hz, 3H).

Neutral Preparative HPLC Method:
Mobile phase A: water with 10 mM NH$_4$HCO$_3$ solution
Mobile phase B: CH$_3$CN
Flow rate: 22 mL/min.
Detection: UV 220 nm/254 nm
Column: Phenomenex Synergi C18 150*25*10 um
Column temperature: 30° C.

| Time in min | % A | % B |
|---|---|---|
| 0.00 | 62 | 38 |
| 12.00 | 32 | 68 |
| 12.20 | 0 | 100 |
| 14.50 | 0 | 100 |

Example 20

1-((2,2-difluorobenzo[d][1,3]dioxol-4-yl)methyl)-N-(2-(4-(ethylsulfonyl)phenyl)-1,3-dihydroxypropan-2-yl)-2-(trifluoromethyl)-1H-benzo[d]imidazole-5-carboxamide (I-174)

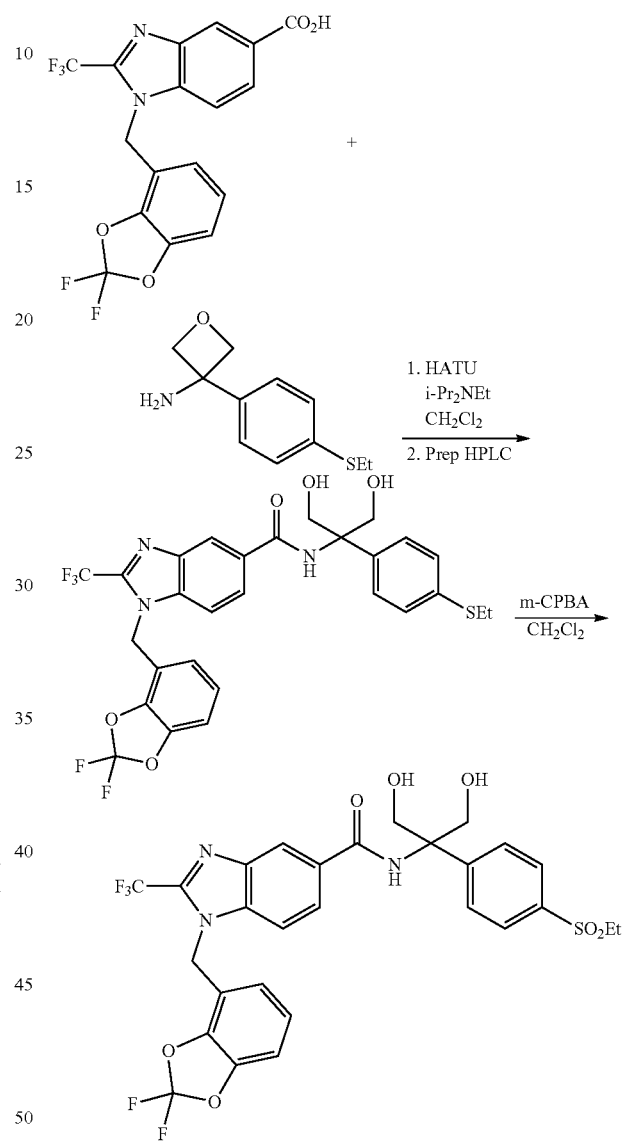

Step 1

To a stirred solution of 1-((2,2-difluorobenzo[d][1,3]dioxol-4-yl)methyl)-2-(trifluoromethyl)-1H-benzo[d]imidazole-5-carboxylic acid (137 mg, 0.34 mmol), 3-(4-(ethylthio)phenyl)oxetan-3-amine HCl salt (126 mg, 0.51 mmol) and i-Pr$_2$NEt (0.25 mL, 1.4 mmol) in CH$_2$Cl$_2$ (5 mL) was added solid HATU (0.26 g, 0.69 mmol). The mixture was stirred for 1 h, diluted with EtOAc (90 mL), washed with 5% aq HCl (10 mL), satd aq NaHCO$_3$ (10 mL) and brine (10 mL), and dried over Na$_2$SO$_4$. Removal of the solvent left an oil (570 mg). Chromatography on a 12 g silica cartridge, eluted with a 0-100% EtOAc in hexanes gradient gave an oil (142 mg). A 23 mg portion of this oil was purified by prep HPLC (MeCN in H$_2$O gradient, 0.1% TFA) to afford crude 1-((2,2-difluorobenzo[d][1,3]dioxol-4-yl)methyl)-N-(2-(4-

(ethylthio)phenyl)-1,3-dihydroxypropan-2-yl)-2-(trifluoromethyl)-1H-benzo[d]imidazole-5-carboxamide (16 mg) as a solid. LC-MS Method 1 $t_R$=1.26 min, m/z=610.

Step 2

To a stirred, ice-cold solution of crude 1-((2,2-difluorobenzo[d][1,3]dioxol-4-yl)methyl)-N-(2-(4-(ethylthio)phenyl)-1,3-dihydroxypropan-2-yl)-2-(trifluoromethyl)-1H-benzo[d]imidazole-5-carboxamide (16 mg, 26 μmol) in CH$_2$Cl$_2$ (2 mL) was added m-CPBA (≤77% pure, 12 mg, ≤53 μmol). The mixture was stirred in the ice bath for 1 h and a second aliquot of m-CPBA (≤77%, 16 mg, ≤70 μmol) was added. The mixture was stirred for 2 h at rt, diluted with CH$_2$Cl$_2$ (40 mL), washed with 1 M aq NaOH (5 mL), dried over Na$_2$SO$_4$ and concentrated to leave an oil (19 mg). Prep HPLC afforded the title compound (10 mg, 59%) as an oil. LC-MS Method 1 $t_R$=1.11 min, m/z=642. $^1$H NMR (CD$_3$OD, 400 MHz): δ 8.43 (s, 1H), 8.02-8.08 (m, 3H), 7.63 (d, 2H), 7.63 (d, 1H), 7.10-7.20 (m, 2H), 6.87 (d, 1H), 5.81 (s, 2H), 5.0 (d, 1H), 4.91 (d, 1H), 4.15 (d, 1H), 4.04 (d, 1H), 3.21 (q, 2H), 1.16 (t, 3H).

LC-MS data

| Cpd No | LC-MS Method | $t_R$ (min) | m/z |
|---|---|---|---|
| I-1 | 1 | 1.80 | 582 (M + H) |
| I-2 | 1 | 1.71 | 568 (M + H) |
| I-3 | 1 | 1.64 | 598 (M + H) |
| I-4 | 1 | 1.68 | 612 (M + H) |
| I-5 | 3 | 0.782 | 582.9 (M + H) |
| I-6 | 1 | 1.83 | 515 (M + H) |
| I-7 | 1 | 1.86 | 576 (M + H) |
| I-8 | 1 | 1.69 | 548 (M + H) |
| I-9 | 1 | 1.28 | 554 (M + H) |
| I-10 | 2 | 1.134 | 575.1 (M + H) |
| I-11.1 | 3 | 0.77 | 612.0 (M + H) |
| I-11.2 | 1 | 1.63 | 612 (M + H) |
| I-12 | 1 | 1.10 | 584 (M + H) |
| I-13 | 1 | 1.31 | 598 (M + H) |
| I-14 | 1 | 1.62 | 608 (M + H) |
| I-15 | 1 | 1.07 | 573 (M + H) |
| I-16 | 1 | 1.23 | 572 (M + H) |
| I-17 | 3 | 0.73 | 593.9 (M + H) |
| I-18 | 1 | 1.55 | 602 (M + H) |
| I-19 | 1 | 1.61 | 616 (M + H) |
| I-20.1 | 3 | 0.745 | 597.9 (M + H) |
| I-20.2 | 3 | 0.747 | 597.8 (M + H) |
| I-21 | 3 | 0.628 | 570.0 (M + H) |
| I-22 | 3 | 0.776 | 584.1 (M + H) |
| I-23.1 | 3 | 0.715 | 579.9 (M + H) |
| I-23.2 | 3 | 0.719 | 579.9 (M + H) |
| I-24 | 3 | 0.734 | 587.9 (M + H) |
| I-25 | 2 | 1.25 | 582.0 (M + H) |
| I-26 | 1 | 1.19 | 554 (M + H) |
| I-27 | 1 | 1.49 | 572 (M + H) |
| I-28 | 1 | 1.47 | 558 (M + H) |
| I-29 | 1 | 1.11 | 542 (M + H) |
| I-30 | 1 | 1.28 | 570 (M + H) |
| I-31 | 1 | 1.20 | 556 (M + H) |
| I-32 | 1 | 1.06 | 528 (M + H) |
| I-33 | 1 | 1.25 | 570 (M + H) |
| I-34 | 1 | 1.14 | 540 (M + H) |
| I-35 | 1 | 1.16 | 555 (M + H) |
| I-36 | 1 | 1.24 | 568 (M + H) |
| I-37 | 1 | 1.62 | 564 (M + H) |
| I-38 | 1 | 1.71 | 578 (M + H) |
| I-39.1 | 1 | 1.57 | 584 (M + H) |
| I-39.2 | 1 | 1.52 | 584 (M + H) |
| I-40 | 1 | 1.71 | 558 (M + H) |
| I-41 | 1 | 1.54 | 588 (M + H) |
| I-42 | 1 | 1.62 | 573 (M + H) |
| I-43 | 1 | 1.67 | 586 (M + H) |
| I-44 | 1 | 1.43 | 614 (M + H) |
| I-45 | 1 | 1.70 | 598 (M + H) |
| I-46 | 1 | 1.60 | 583 (M + H) |
| I-47 | 1 | 1.27 | 570 (M + H) |
| I-48 | 3 | 0.893 | 568.0 (M + H) |
| I-49.1 | 3 | 0.695 | 572.0 (M + H) |
| I-49.2 | 3 | 0.695 | 572.0 (M + H) |
| I-50 | 3 | 0.740 | 549.9 (M + H) |
| I-51 | 3 | 0.758 | 569.1 (M + H) |
| I-52 | 3 | 0.79 | 596.0 (M + H) |
| I-53 | 3 | 0.793 | 625.8 (M + H) |
| I-54 | 3 | 0.758 | 586.0 (M + H) |
| I-55 | 1 | 1.54 | 544 (M + H) |
| I-56 | 1 | 1.30 | 579 (M + H) |
| I-57 | 1 | 1.36 | 579 (M + H) |
| I-58 | 1 | 1.36 | 612 (M + H) |
| I-59 | 3 | 0.917 | 626.0 (M + H) |
| I-60 | 3 | 0.692 | 597.9 (M + H) |
| I-61 | 3 | 0.790 | 615.9 (M + H) |
| I-62 | 2 | 1.128 | 627.1 (M + H) |
| I-63 | 1 | 1.64 | 583 (M + H) |
| I-64 | 1 | 1.12 | 555 (M + H) |
| I-65 | 1 | 1.18 | 569 (M + H) |
| I-66 | 1 | 1.65 | 579 (M + H) |
| I-67 | 1 | 1.56 | 573 (M + H) |
| I-68 | 1 | 1.5 | 559 (M + H) |
| I-69 | 1 | 1.65 | 587 (M + H) |
| I-70 | 3 | 0.737 | 569.0 (M + H) |
| I-71 | 3 | 0.764 | 574.9 (M + H) |
| I-72 | 1 | 1.11 | 547 (M + H) |
| I-73 | 1 | 1.65 | 565 (M + H) |
| I-74 | 3 | 0.773 | 633.0 (M + H) |
| I-75 | 3 | 0.753 | 632.0 (M + H) |
| I-76 | 3 | 0.776 | 632.9 (M + H) |
| I-77 | 3 | 0.763 | 590.0 (M + H) |
| I-78 | 3 | 0.865 | 618.1 (M + H) |
| I-79 | 3 | 0.678 | 604.1 (M + H) |
| I-80 | 1 | 1.66 | 574 (M + H) |
| I-81 | 3 | 0.842 | 576.0 (M + H) |
| I-82 | 1 | 1.46 | 562.2 (M + H) |
| I-83 | 1 | 1.62 | 557 (M + H) |
| I-84 | 1 | 1.59 | 586 (M + H) |
| I-85 | 1 | 1.35 | 527 (M + H) |
| I-86 | 1 | 0.94 | 533 (M + H) |
| I-87 | 1 | 0.78 | 560 (M + H) |
| I-88 | 1 | 1.45 | 532 (M + H) |
| I-89 | 1 | 1.31 | 533 (M + H) |
| I-90 | 1 | 1.35 | 527 (M + H) |
| I-91 | 1 | 1.18 | 569 (M + H) |
| I-92 | 1 | 1.43 | 553 (M + H) |
| I-93.1 | 1 | 1.41 | 541 (M + H) |
| I-93.2 | 1 | 1.59 | 542 (M + H) |
| I-94 | 1 | 1.55 | 545 (M + H) |
| I-95 | 1 | 1.63 | 542 (M + H) |
| I-96 | 1 | 1.75 | 544 (M + H) |
| I-97 | 1 | 1.40 | 542 (M + H) |
| I-98 | 3 | 0.754 | 546.0 (M + H) |
| I-99 | 3 | 0.728 | 560.0 (M + H) |
| I-100 | 1 | 0.79 | 542 (M + H) |
| I-101 | 1 | 1.34 | 574 (M + H) |
| I-102 | 1 | 1.05 | 546 (M + H) |
| I-103 | 1 | 1.05 | 534.5 (M + H) |
| I-104 | 1 | 1.22 | 558 (M + H) |
| I-105 | 1 | 1.17 | 554 (M + H) |
| I-106 | 1 | 1.21 | 558 (M + H) |
| I-107 | 1 | 1.03 | 567 (M + H) |
| I-108 | 1 | 1.00 | 567 (M + H) |
| I-109 | 1 | 1.22 | 558 (M + H) |
| I-110 | 1 | 1.23 | 572 (M + H) |
| I-111 | 1 | 0.89 | 546 (M + H) |
| I-112 | 1 | 0.99 | 499 (M + H) |
| I-113 | 1 | 1.11 | 540 (M + H) |
| I-114 | 1 | 0.94 | 546 (M + H) |
| I-115 | 1 | 1.25 | 588 (M + H) |
| I-116 | 1 | 1.21 | 568 (M + H) |
| I-117 | 1 | 1.45 | 586 (M + H) |
| I-118 | 1 | 1.39 | 544 (M + H) |
| I-119 | 1 | 1.09 | 534 (M + H) |
| I-120 | 3 | 0.9 | 554.1 (M + H) |

| Cpd No | LC-MS Method | $t_R$ (min) | m/z |
|---|---|---|---|
| I-121 | 1 | 1.57 | 531 (M + H) |
| I-122 | 1 | 1.60 | 545 (M + H) |
| I-123 | 3 | 0.89 | 629.9 (M + H) |
| I-124 | 1 | 1.34 | 578.3 (M + H) |
| I-125.1 | 1 | 1.13 | 556 (M + H) |
| I-125.2 | 1 | 1.13 | 556 (M + H) |
| I-126 | 1 | 1.66 | 598 (M + H) |
| I-127 | 3 | 0.663 | 593.0 (M + H) |
| I-128 | 1 | 1.39 | 563.3 (M + H) |
| I-129 | 1 | 1.48 | 557 (M + H) |
| I-130.1 | 3 | 0.729 | 613.0 (M + H) |
| I-130.2 | 3 | 0.754 | 612.9 (M + H) |
| I-131.1 | 3 | 0.713 | 595.1 (M + H) |
| I-131.2 | 3 | 0.704 | 595.0 (M + H) |
| I-132.1 | 3 | 0.649 | 599.1 (M + H) |
| I-132.2 | 3 | 0.653 | 599.2 (M + H) |
| I-133.1 | 3 | 0.660 | 584.9 (M + H) |
| I-133.2 | 3 | 0.664 | 584.9 (M + H) |
| I-134.1 | 3 | 0.846 | 603.0 (M + H) |
| I-134.2 | 3 | 0.846 | 603.0 (M + H) |
| I-135 | 3 | 0.865 | 599.0 (M + H) |
| I-136 | 1 | 1.63 | 550 (M + H) |
| I-137 | 1 | 1.67 | 556 (M + H) |
| I-138 | 1 | 1.66 | 586 (M + H) |
| I-139 | 1 | 1.42 | 556 (M + H) |
| I-140 | 1 | 0.93 | 570 (M + H) |
| I-141 | 1 | 1.44 | 556 (M + H) |
| I-142 | 1 | 1.33 | 542 (M + H) |
| I-143 | 1 | 1.30 | 556 (M + H) |
| I-144 | 1 | 1.33 | 601 (M + H) |
| I-145 | 1 | 0.98 | 553 (M − 56 + H) |
| I-146 | 1 | 1.09 | 533 (M + H) |
| I-147 | 1 | 1.51 | 543 (M + H) |
| I-148 | 1 | 1.01 | 532 (M + H) |
| I-149 | 1 | 1.20 | 568 (M + H) |
| I-150 | 3 | 0.730 | 448.2 (M + H) |
| I-151 | 1 | 1.56 | 544 (M + H) |
| I-152 | 1 | 1.48 | 543 (M + H) |
| I-153 | 1 | 1.26 | 574 (M + H) |
| I-154 | 1 | 1.05 | 506 (M + H) |
| I-155 | 1 | 1.26 | 591 (M + H) |
| I-156 | 1 | 0.88 | 549 (M + H) |
| I-157 | 1 | 1.03 | 549 (M + H) |
| I-158 | 1 | 1.54 | 605 (M + H) |
| I-159 | 1 | 0.93 | 563 (M + H) |
| I-160 | 1 | 0.95 | 563 (M + H) |
| I-161 | 1 | 1.43 | 599 (M + H) |
| I-162 | 1 | 1.30 | 557 (M + H) |
| I-163 | 3 | 0.731 | 605.0 (M + H) |
| I-164.1 | 3 | 0.732 | 604.9 (M + H) |
| I-164.2 | 3 | 0.732 | 604.9 (M + H) |
| I-165 | 3 | 0.748 | 639.9 (M + H) |
| I-166 | 3 | 0.759 | 669.9 (M + H) |
| I-167 | 3 | 0.752 | 652.9 (M + H) |
| I-168 | 3 | 0.739 | 638.9 (M + H) |
| I-169 | 3 | 0.751 | 624.9 (M + H) |
| I-170 | 1 | 1.72 | 598 (M + H) |
| I-170.1 | 3 | 0.785 | 597.9 (M + H) |
| I-170.2 | 3 | 0.779 | 597.9 (M + H) |
| I-171 | 1 | 1.12 | 604 (M + H) |
| I-172 | 1 | 1.53 | 544 (M + H) |
| I-173 | 3 | 0.725 | 572.0 (M + H) |
| I-174 | 1 | 1.11 | 642 (M + H) |

$^1$H NMR data of selected compounds

| Cpd | Solvent | Resonances |
|---|---|---|
| I-11.1 | CDCl$_3$ | 8.56 (s, 1H), 8.04 (d, J = 8.8 Hz, 1H), 7.71 (d, J = 8.0 Hz, 2H), 7.66 (d, J = 7.2 Hz, 1H), 7.58 (d, J = 8.0 Hz, 2H), 7.46 (d, J = 8.8 Hz, 1H), 7.07-7.03 (m, 2H), 6.65 (d, J = 7.6 Hz, 1H), 5.65 (d, J = 4.8 Hz, 2H), 5.42-5.40 (m, 1H), 4.18-4.14 (m, 2H), 3.42-3.40 (brs, 1H), 3.07 (q, J = 7.6 Hz, 2H), 1.28 (t, J = 7.6 Hz, 3H). |
| I-14 | CD$_3$OD | 8.38 (s, 1H), 7.93 (d, 1H), 7.89 (d, 2H), 7.72 (d, 2H), 7.63 (d, 1H), 7.00-7.20 (m, 2H), 6.75 (d, 1H), 5.80 (s, 2H), 5.31 (m, 1H), 3.92 (d, 2H), 3.19 (q, 2H), 2.25 (t, 3H), 1.20 (t, 3H) |

-continued
| Cpd | Solvent | Resonances |
|---|---|---|
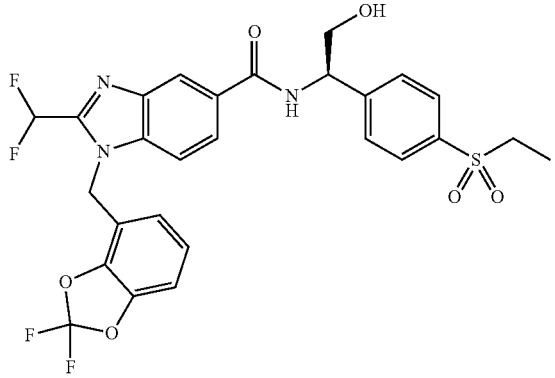
I-17
CD$_3$OD 8.39 (s, 1H), 7.93 (dd, J = 1.2, 8.8 Hz, 1H), 7.89 (d, J = 8.4 Hz, 2H), 7.70 (d, J = 8.4 Hz, 2H), 7.59 (d, J = 8.8 Hz, 1H), 7.23 (t, J = 52.0 Hz, 1H), 7.15-7.09 (m, 2H), 6.85 (d, J = 7.6 Hz, 1H), 5.82 (s, 2H), 5.30 (t, J = 6.0 Hz, 1H), 3.92 (d, J = 6.4 Hz, 2H), 3.19 (q, J = 7.2 Hz, 2H), 1.20 (t, J = 7.2 Hz, 3H).
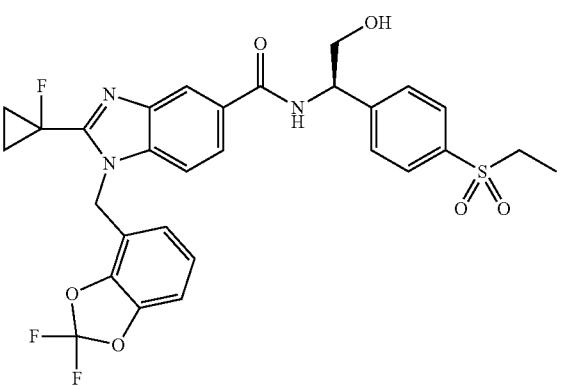
I-18
CD$_3$OD 8.33 (s, 1H), 7.92-7.98 (m, 3H), 7.77 (d, 2H), 7.63 (d, 1H), 7.10-7.25 (m, 2H), 6.92 (d, 1H), 5.92 (s, 2H), 5.38 (m, 1H), 3.99 (d, 2H), 3.23 (q, 2H), 1.57-1.67 (m, 2H), 1.43-1.53 (2H), 1.25 (t, 3H)
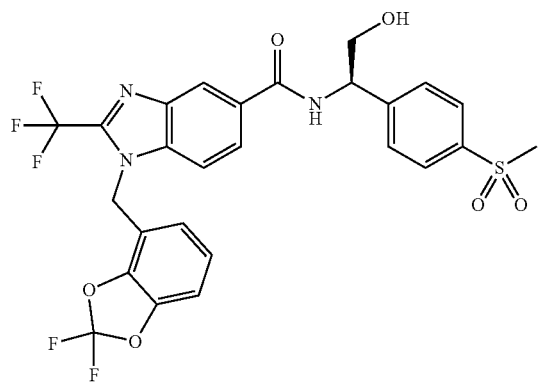
I-20.1
CD$_3$OD 8.43 (s, 1H), 7.95 (d, J = 8.0 Hz, 1H), 7.81 (d, J = 8.4 Hz, 2H), 7.57 (d, J = 8.4 Hz, 2H), 7.45-7.40 (m, 2H), 7.05-6.95 (m, 2H), 6.60 (d, J = 7.6 Hz, 1H), 5.61 (s, 2H), 5.38-5.30 (m, 1H), 4.15-4.00 (m, 2H), 3.00 (s, 3H), 2.96 (s, 1H).

-continued

| Cpd | Solvent | Resonances |
|---|---|---|
| I-24 | CDCl₃ | 8.26 (s, 1H), 7.92 (d, J = 8.4 Hz, 2H), 7.89 (d, J = 8.4 Hz, 1H), 7.60 (d, J = 8.0 Hz, 2H), 7.36 (d, J = 8.4 Hz, 1H), 7.20 (d, J = 8.4 Hz, 1H), 7.01 (t, J = 5.6 Hz, 1H), 6.98 (d, J = 8.0 Hz, 1H), 6.67 (d, J = 8.0 Hz, 1H), 5.69 (s, 2H), 5.34 (t, J = 7.2 Hz, 1H), 4.12-4.02 (m, 2H), 3.04 (s, 3H), 2.42 (brs, 1H), 1.56 (t, J = 4.0 Hz, 2H), 1.52 (t, J = 6.4 Hz, 2H). |
| I-25 | CDCl₃ | 8.39 (d, J = 1.2 Hz, 1H), 7.97 (dd, J = 1.2, 10.0 Hz, 1H), 7.69 (dd, J = 1.6, 6.8 Hz, 2H), 7.45-7.39 (m, 4H), 7.03-6.99 (m, 2H), 6.60 (d, J = 7.2 Hz, 1H), 5.61 (s, 2H), 4.74 (d, J = 6.0 Hz, 2H), 3.07 (q, J = 7.2 Hz, 2H), 1.23 (t, J = 7.2 Hz, 3H). |
| I-27 | CD₃OD | 8.24 (s, 1H), 7.84-7.92 (m, 3H), 7.63 (d, 2H), 7.57 (d, 1H), 7.05-7.17(m, 2H), 6.83 (d, 1H), 5.84 (s, 2H), 4.70 (s, 2H), 3.18 (q, 2H), 1.48-1.60 (m, 2H), 1.35-1.45 (2H), 1.19 (t, 3H) |
| I-37 | CD₃OD | 8.42 (s, 1H), 8.02 (d, 1H), 7.96-7.92 (d, 2H), 7.70 (d, 2H), 7.62 (d, 1H), 7.14 (t, 1H), 7.05-7.12 (m, 2H), 6.80 (d, 1H), 5.82 (s, 2H), 4.78 (s, 2H), 3.23 (q, 2H), 1.23 (t, 3H) |

| Cpd | Solvent | Resonances |
|---|---|---|
| 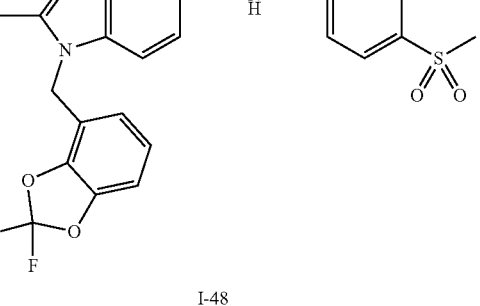 I-48 | CDCl$_3$ | 8.33 (s, 1H), 7.94 (d, J = 8.0 Hz, 1H), 7.89 (d, J = 8.0 Hz, 2H), 7.54 (d, J = 8.0 Hz, 2H), 7.42 (d, J = 8.4 Hz, 1H), 7.05-6.97 (m, 2H), 6.73 (t, J = 5.6 Hz, 1H), 6.59 (d, J = 8.0 Hz, 1H), 5.61 (s, 2H), 4.77 (d, J = 6.0 Hz, 2H), 3.04 (s, 3H). |
| 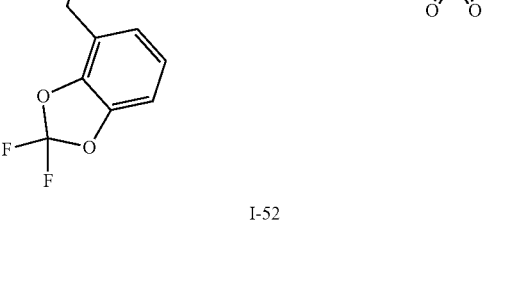 I-52 | CDCl$_3$ | 8.35 (s, 1H), 7.95 (d, J = 8.8 Hz, 1H), 7.84 (d, J = 6.4 Hz, 2H), 7.53 (d, J = 8.4 Hz, 2H), 7.42 (d, J = 8.8 Hz, 1H), 7.03-7.00 (m, 2H), 6.78 (t, J = 8.8 Hz, 1H), 6.59 (d, J = 6.8 Hz, 1H), 5.61 (s, 2H), 4.78 (d, J = 5.6 Hz, 2H), 3.05 (t, J = 8.0 Hz, 2H), 1.76-1.71 (m, 2H), 0.99 (t, J = 7.2 Hz, 3H). |
| 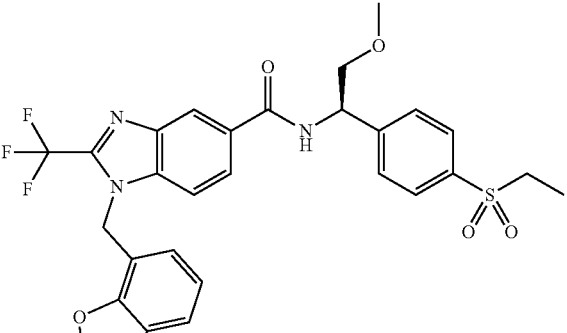 I-59 | CD$_3$OD | $^1$H NMR (CD$_3$OD 400 MHz): δ 9.09 (d, J = 7.6 Hz, 1H), 8.42 (s, 1H), 7.98 (d, J = 9.2 Hz, 1H), 7.90 (d, J = 8.0 Hz, 2H), 7.71 (d, J = 8.4 Hz, 2H), 7.67 (d, J = 8.8 Hz, 1H), 7.18 (d, J = 6.8 Hz, 1H), 7.13 (t, J = 8.0 Hz, 1H), 6.86 (d, J = 7.2 Hz, 1H), 5.84 (s, 2H), 5.46-5.44 (m, 1H), 3.84-3.80 (m, 1H), 3.77-3.73 (m, 1H), 3.42 (s, 3H), 3.20 (q, J = 7.6 Hz, 2H), 1.21 (t, J = 7.6 Hz, 3H). |

-continued
| Cpd | Solvent | Resonances |
|---|---|---|
| 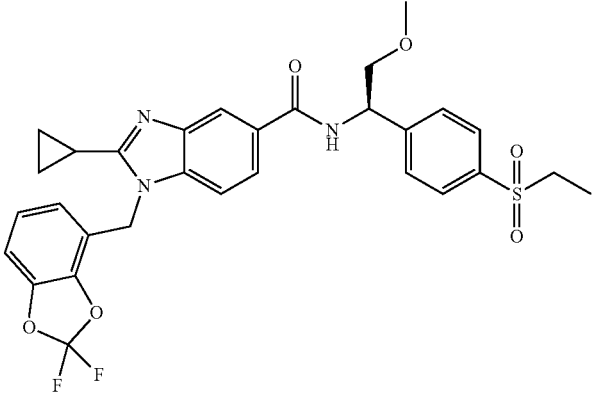 I-60 | CDCl$_3$ | 8.15 (s, 1H), 7.86 (d, J = 8.0 Hz, 2H), 7.79 (d, J = 8.0 Hz, 1H), 7.60 (d, J = 8.0 Hz, 2H), 7.33 (d, J = 8.4 Hz, 1H), 7.15 (d, J = 7.6 Hz, 1H), 7.05-6.95 (m, 2H), 6.63 (d, J = 7.6 Hz, 1H), 5.53 (s, 2H), 5.40-5.33 (m, 1H), 3.85-3.65 (m, 2H), 3.39 (s, 3H), 3.09 (q, J = 7.2 Hz, 2H), 2.05-0.95 (m, 1H), 1.28 (t, J = 7.2 Hz, 5H), 1.18-1.07 (m, 2H). |
| 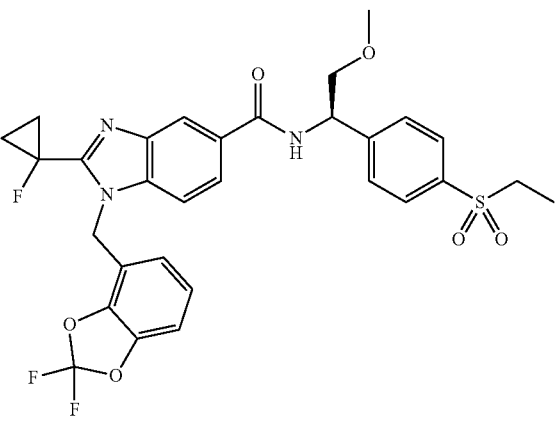 I-61 | CDCl$_3$ | 8.24 (s, 1H), 7.88-7.83 (m, 3H), 7.61 (d, J = 8.4 Hz, 2H), 7.36 (d, J = 8.8 Hz, 1H), 7.15 (d, J = 6.8 Hz, 1H), 7.02 (d, J = 7.6 Hz, 1H), 7.00 (t, J = 7.6 Hz, 1H), 6.66 (d, J = 8.0 Hz, 1H), 5.69 (s, 2H), 5.38 (d, J = 3.2 Hz, 1H), 3.83-3.73 (m, 2H), 3.39 (s, 3H), 3.09 (q, J = 6.8 Hz, 2H), 1.59-1.49 (m, 4H), 1.28 (t, J = 7.2 Hz, 3H). |
| 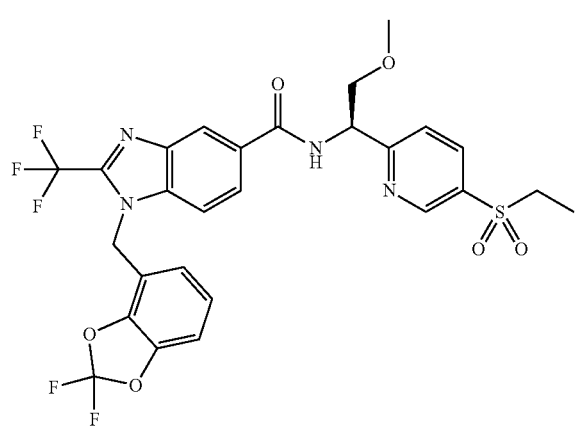 I-62 | CD$_3$OD | 9.04 (d, J = 2.0 Hz, 1H), 8.45 (s, 1H), 8.30 (dd, J = 2.0, 6.0 Hz, 1H), 8.00 (dd, J = 1.2, 8.8 Hz, 1H), 7.78 (d, J = 8.4 Hz, 1H), 7.68 (d, J = 9.2 Hz, 1H), 7.20-7.12 (m, 2H), 6.87 (d, J = 7.6 Hz, 1H), 5.84 (s, 2H), 5.23 (t, J = 6.4 Hz, 1H), 3.94-3.90 (m, 2H), 3.39 (s, 3H), 3.29 (q, J = 7.2 Hz, 2H), 1.26 (t, J = 7.2 Hz, 3H). |

-continued

| Cpd | Solvent | Resonances |
|---|---|---|
| I-63 | CD$_3$OD | 8.99 (s, 1H), 8.44 (s, 1H), 8.27 (d, 1H), 8.03 (d, 1H), 7.64-7.74 (m, 2H), 7.12-7.22 (m, 2H), 6.86 (d, 1H), 5.82 (s, 2H), 4.82 (d, 2H), 3.26 (q, 2H), 1.25 (t, 3H) |
| I-66 | CD$_3$OD | 8.97 (s, 1H), 8.39 (s, 1H), 8.25 (d, 1H), 7.93 (d, 1H), 7.64 (d, 1H), 7.53 (d, 1H), 7.02-7.17 (m, 2H), 6.62 (d, 1H), 5.81 (s, 2H), 4.82 (d, 2H), 3.26 (q, 2H), 2.25 (t, 1H), 1.23 (t, 3H) |
| I-81 | CDCl$_3$ | 8.45 (s, 1H), 7.94 (dd, J = 1.2, 8.8 Hz, 1H), 7.74 (d, J = 8.4 Hz, 2H), 7.56 (d, J = 8.4 Hz, 2H), 7.51 (d, J = 6.8 Hz, 1H), 7.45 (d, J = 8.8 Hz, 1H), 6.80-6.71 (m, 2H), 6.44 (d, J = 6.8 Hz, 1H), 5.97 (dd, J = 1.2, 5.2 Hz, 2H), 5.53 (d, J = 2.8 Hz, 2H), 5.39-5.33 (m, 1H), 4.18-4.03 (m, 2H), 3.21 (brs, 1H), 3.06 (q, J = 7.6 Hz, 2H), 1.25 (t, J = 7.6 Hz, 3H). |
| I-95 | CD$_3$OD | 9.22 (m, 1H), 8.41 (s, 1H), 7.75-7.95 (m, 4H), 7.63 (d, 2H), 7.47 (d, 2H), 7.20 (t, 1H), 6.76 (s, 1H), 6.66 (d, 1H), 5.96 (s, 2H), 4.70 (d, 2H), 3.17 (q, 2H), 1.19 (t, 3H) |

-continued

| Cpd | Solvent | Resonances |
|---|---|---|
| 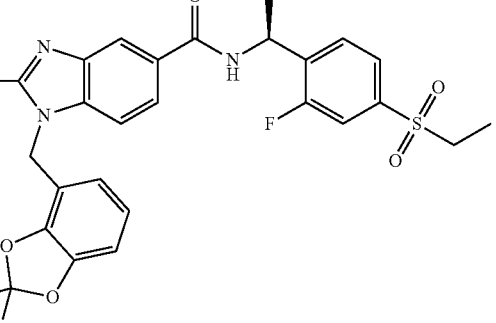<br>I-123 | CDCl$_3$ | 8.51 (s, 1H), 7.99 (d, J = 8.4 Hz, 1H), 7.64 (d, J = 8.8 Hz, 1H), 7.51 (d, J = 6.8 Hz, 2H), 7.42 (d, J = 8.8 Hz, 1H), 7.30 (d, J = 8.0 Hz, 1H), 7.03-7.00 (m, 2H), 6.61 (d, J = 8.0 Hz, 1H), 5.61 (d, J = 2.8 Hz, 2H), 4.13 (s, 2H), 3.61 (s, 1H), 3.05 (q, J = 7.2 Hz, 2H), 1.25 (t, J = 7.2 Hz, 3H). |
| 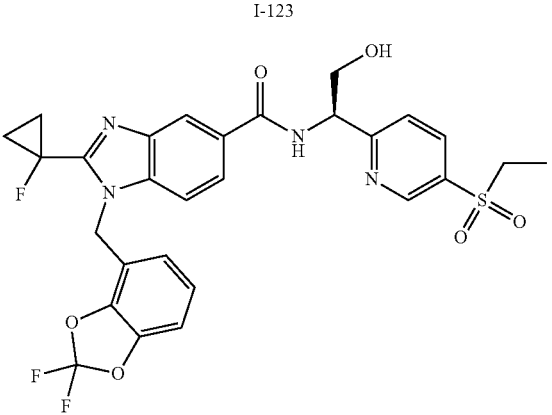<br>I-134.1 | CD$_3$OD | 9.04 (s, 1H), 8.42 (s, 1H), 8.34 (d, J = 8.4 Hz, 1H), 8.16 (d, J = 8.8 Hz, 1H), 7.89 (d, J = 8.8 Hz, 1H), 7.82 (d, J = 8.4 Hz, 1H), 7.23 (t, J = 7.6 Hz, 1H), 7.18 (d, J = 8.0 Hz, 1H), 7.08 (d, J = 8.0 Hz, 1H), 6.05 (s, 2H), 5.40 (t, J = 6.4 Hz, 1H), 4.08 (q, J = 3.2 Hz, 2H), 3.28 (q, J = 7.6 Hz, 2H), 1.87-1.83 (m, 2H), 1.67-1.63 (m, 2H), 1.25 (t, J = 7.2 Hz, 3H). |

BIOLOGICAL ASSAYS

Radio-Ligand RORγ Binding Assay (Assay 1)

Compounds described herein were tested for ability to bind to RORγ in a cell-free competition assay with commercially available radio-ligand (RL), 25-hydroxy [26,27-$^3$H]-cholesterol (PerkinElmer, Cat. #NET674250UC), for a ligand binding site on a recombinant RORγ Ligand Binding Domain (LBD) protein expressed as a 6×His-Glutathione-S-Transferase (GST) fusion. The assay was performed in 96-well SPA plates (PerkinElmer, Cat. #1450-401) in 50 mM HEPES buffer, pH 7.4, containing 150 mM NaCl, 5 mM MgCl$_2$, 10% (v/v) glycerol, 2 mM CHAPS, 0.5 mM β-octylglucopyranoside and 5 mM DTT. Tested compounds were dissolved in DMSO, and semi-log (3.162×) serial dilutions of the compounds were prepared in the same solvent. Two μL of the DMSO solutions were mixed with 28 μL of 8.6 nM 25-hydroxy [26,27-$^3$H]-cholesterol and 50 μL of 24 nM RORγ LBD. The plate was shaken at 700 rpm for 20 min and incubated for 10 min at rt, after which 40 μL of poly-Lys YSi SPA beads (PerkinElmer, Cat. #RPNQ0010) were added to achieve 50 ag of the beads per well. The plate was incubated on an orbital shaker for 20 min and then for 10 min without agitation at rt. SPA signal for tritium beta radiation was registered on PerkinElmer Microbeta plate reader. Percent inhibition values were calculated based on the high signal obtained with DMSO control and the low signal observed with 10 μM standard RORγ inverse agonist T0901317 (SigmaAldrich, Cat. #T2320). The percent inhibition vs. concentration data were fit into a four-parameter model, and IC50 values were calculated from the fit as the concentrations corresponding to the inflection points on the dose-response curves. Inhibitory constants (Ki) were calculated using the following equation, where [RL] is the concentration in the assay and K$_D$ is a dissociation constant of 25-hydroxy [26,27-$^3$H]-cholesterol:

$$K_i = \frac{IC_{50}}{\left(1 + \frac{[RL]}{K_D}\right)}.$$

RORγt 5×RORE Assay in Jurkat Cells (Assay 2)

Compounds described herein were tested for RORγ inverse agonist activity in a cell-based, transcriptional activity assay. Secreted Nanoluc® luciferase was used as a reporter for transcriptional activity of the full-length RORγt in Jurkat cells (ATCC, Cat. #TIB-152). A reporter plasmid was constructed by inserting 5 repeats of the ROR Response Element (RORE) AAAGTAGGTCA (SEQ ID NO: 1) into a commercially available promoterless plasmid pNL1.3[secNluc] (Promega, Cat. #N1021) using KpnI and HindIII restriction sites. The expression plasmid for RORγt was purchased (Geneocopoeia, Cat. #EX-T6988-M02). Jurkat cells (30 million cells) were transfected with 11 ag of EX-T6988-MO2 and 26 ag of the reporter plasmid in OptiMEM® media using Lipofectamine® LTX and Plus™ reagents (Life Technologies, Cat. #15338-100). After 5-6 hrs of incubation at 37° C./5% CO$_2$, the cells were collected, resuspended in phenol-red free RPMI media containing 10% (v/v) delipidated FBS (Hyclone, Cat. #SH30855.03) and dispensed into 96-well clear bottom tissue culture plates (CoStar, Cat. #3603), at 80,000 cells per well. Tested compounds were added to the cells in the same media (final concentration of DMSO was 0.1% (v/v)), and the plates were incubated at 37° C./5% CO$_2$ for 16-18 hrs. Luciferase activity in the conditioned supernatants was determined with NanoGlo® assay reagents (Promega, Cat. #N1130). Percent inhibition values were calculated based on the fully inhibited and non-inhibited (DMSO) controls, and the values were regressed against concentrations of the tested compounds to derive IC50 values using a four-parameter non-linear fitting model.

The results of assays 1 and 2 are shown in Table 3 below.

TABLE 3

| Cpd No | Assay 1 Ki (nM) | Assay 2 IC$_{50}$ (nM) |
| --- | --- | --- |
| I-1 | +++ | +++ |
| I-2 | +++ | +++ |
| I-3 | +++ | +++ |
| I-4 | +++ | +++ |
| I-5 | +++ | +++ |
| I-6 | +++ | + |
| I-7 | ++ | nt |
| I-8 | ++ | nt |
| I-9 | +++ | +++ |
| I-10 | +++ | + |
| I-11.1 | +++ | +++ |
| I-11.2 | +++ | +++ |
| I-12 | +++ | +++ |
| I-13 | +++ | +++ |
| I-14 | +++ | +++ |
| I-15 | +++ | +++ |
| I-16 | +++ | +++ |
| I-17 | +++ | +++ |
| I-18 | +++ | +++ |
| I-19 | +++ | +++ |
| I-20.1 | +++ | +++ |
| I-20.2 | +++ | +++ |
| I-21 | +++ | +++ |
| I-22 | +++ | +++ |
| I-23.1 | +++ | +++ |
| I-23.2 | +++ | ++ |
| I-24 | +++ | +++ |
| I-25 | +++ | +++ |
| I-26 | +++ | +++ |
| I-27 | +++ | +++ |
| I-28 | +++ | +++ |
| I-29 | +++ | +++ |
| I-30 | +++ | +++ |
| I-31 | +++ | +++ |
| I-32 | +++ | + |
| I-33 | +++ | +++ |
| I-34 | +++ | +++ |
| I-35 | +++ | +++ |
| I-36 | +++ | +++ |
| I-37 | +++ | +++ |
| I-38 | +++ | +++ |
| I-39.1 | +++ | +++ |
| I-39.2 | +++ | +++ |
| I-40 | +++ | +++ |
| I-41 | +++ | +++ |
| I-42 | +++ | +++ |
| I-43 | +++ | +++ |
| I-44 | +++ | +++ |
| I-45 | +++ | +++ |
| I-46 | +++ | +++ |
| I-47 | +++ | +++ |
| I-48 | +++ | +++ |
| I-49.1 | +++ | +++ |
| I-49.2 | +++ | +++ |
| I-50 | +++ | +++ |
| I-51 | +++ | ++ |
| I-52 | +++ | +++ |
| I-53 | +++ | ++ |
| I-54 | +++ | +++ |
| I-55 | +++ | ++ |
| I-56 | ++ | nt |
| I-57 | +++ | +++ |
| I-58 | +++ | ++ |
| I-59 | +++ | +++ |
| I-60 | +++ | +++ |
| I-61 | +++ | +++ |
| I-62 | +++ | +++ |
| I-63 | +++ | +++ |
| I-64 | +++ | +++ |
| I-65 | +++ | +++ |
| I-66 | +++ | +++ |
| I-67 | +++ | +++ |
| I-68 | +++ | +++ |
| I-69 | +++ | +++ |
| I-70 | +++ | +++ |
| I-71 | +++ | +++ |
| I-72 | +++ | +++ |
| I-73 | +++ | +++ |
| I-74 | +++ | +++ |
| I-75 | +++ | +++ |
| I-76 | +++ | +++ |
| I-77 | +++ | +++ |
| I-78 | +++ | +++ |
| I-79 | +++ | ++ |
| I-80 | +++ | ++ |
| I-81 | +++ | +++ |
| I-82 | +++ | + |
| I-83 | +++ | ++ |
| I-84 | +++ | ++ |
| I-85 | +++ | + |
| I-86 | + | nt |
| I-87 | ++ | nt |
| I-88 | +++ | +++ |
| I-89 | +++ | ++ |
| I-90 | +++ | +++ |
| I-91 | ++ | nt |
| I-92 | +++ | ++ |
| I-93.1 | +++ | +++ |
| I-93.2 | +++ | +++ |
| I-94 | +++ | ++ |
| I-95 | +++ | +++ |
| I-96 | +++ | + |
| I-97 | +++ | +++ |
| I-98 | +++ | +++ |
| I-99 | +++ | ++ |
| I-100 | +++ | ++ |
| I-101 | +++ | + |
| I-102 | +++ | +++ |
| I-103 | +++ | ++ |
| I-104 | +++ | + |
| I-105 | ++ | nt |
| I-106 | +++ | ++ |
| I-107 | + | nt |
| I-108 | + | nt |
| I-109 | +++ | +++ |
| I-110 | ++ | + |
| I-111 | + | nt |
| I-112 | ++ | nt |
| I-113 | +++ | +++ |
| I-114 | + | nt |
| I-115 | +++ | +++ |
| I-116 | +++ | +++ |
| I-117 | + | nt |
| I-118 | +++ | + |
| I-119 | +++ | +++ |
| I-120 | +++ | ++ |
| I-121 | ++ | nt |
| I-122 | +++ | +++ |
| I-123 | +++ | +++ |
| I-124 | +++ | + |
| I-125.1 | +++ | + |
| I-125.2 | +++ | +++ |
| I-126 | +++ | +++ |
| I-127 | +++ | +++ |

TABLE 3-continued

| Cpd No | Assay 1 Ki (nM) | Assay 2 IC$_{50}$ (nM) |
|---|---|---|
| I-128 | +++ | + |
| I-129 | ++ | nt |
| I-130.1 | +++ | +++ |
| I-130.2 | +++ | +++ |
| I-131.1 | +++ | +++ |
| I-131.2 | +++ | ++ |
| I-132.1 | +++ | +++ |
| I-132.2 | +++ | +++ |
| I-133.1 | +++ | +++ |
| I-133.2 | ++ | nt |
| I-134.1 | +++ | +++ |
| I-134.2 | +++ | +++ |
| I-135 | ++ | nt |
| I-136 | +++ | +++ |
| I-137 | +++ | +++ |
| I-138 | +++ | ++ |
| I-139 | +++ | +++ |
| I-140 | ++ | nt |
| I-141 | + | ++ |
| I-142 | ++ | nt |
| I-143 | +++ | ++ |
| I-144 | ++ | nt |
| I-145 | ++ | nt |
| I-146 | ++ | nt |
| I-147 | +++ | ++ |
| I-148 | +++ | + |
| I-149 | +++ | +++ |
| I-150 | ++ | + |
| I-151 | +++ | +++ |
| I-152 | +++ | +++ |
| I-153 | +++ | +++ |
| I-154 | +++ | + |
| I-155 | ++ | nt |
| I-156 | + | nt |
| I-157 | + | nt |
| I-158 | +++ | + |
| I-159 | + | nt |
| I-160 | ++ | nt |
| I-161 | +++ | +++ |
| I-162 | +++ | +++ |
| I-163 | +++ | +++ |
| I-164.1 | +++ | +++ |
| I-164.2 | +++ | +++ |
| I-165 | +++ | + |
| I-166 | +++ | + |
| I-167 | +++ | +++ |
| I-168 | +++ | +++ |
| I-169 | +++ | +++ |
| I-170 | +++ | +++ |
| I-170.1 | +++ | +++ |
| I-170.2 | +++ | +++ |
| I-171 | ++ | nt |
| I-172 | +++ | +++ |
| I-173 | +++ | ++ |
| I-174 | +++ | nt | nt = not tested;
+ means >1000 nM;
++ means 100 nM-1000 nM;
+++ means <100 nM.

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of the Formula VI:

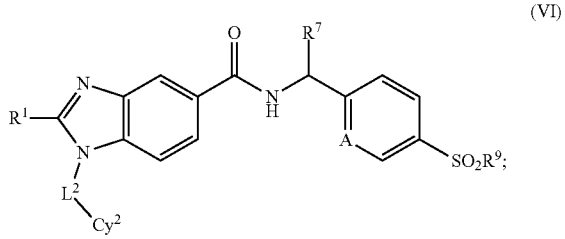

(VI)

or a pharmaceutically acceptable salt thereof, wherein
A is N or CH;
$R^1$ is $(C_1-C_4)$alkyl, halo$(C_1-C_4)$alkyl, or cycloalkyl optionally substituted with 1 to 3 halo;
$L^2$ is $CH_2$ or CHMe;
$Cy^2$ is bi-cyclic heterocyclyl or bi-cyclic heteroaryl, each of which are optionally substituted with 1 to 3 groups independently selected from halo, $(C_1-C_4)$alkyl, and $(C_1-C_4)$alkoxy, wherein said $(C_1-C_4)$alkyl and $(C_1-C_4)$alkoxy are optionally substituted with 1 to 3 halo;
$R^7$ is hydrogen or —$CH_2OH$; and
$R^9$ is —NH$(C_1-C_4)$alkyl, $(C_1-C_4)$alkyl, or $(C_1-C_4)$alkyl substituted with OH.

2. The compound of claim 1, wherein the compound is of the Formula VIII:

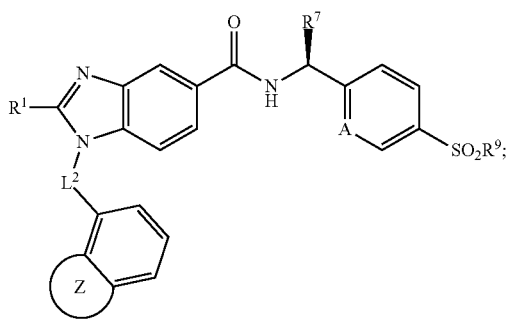

(VIII)

or a pharmaceutically acceptable salt thereof, wherein Z is a 5- or 6-membered heterocyclyl ring having one or more heteroatoms selected from oxygen or nitrogen; and wherein Z is optionally substituted with $(C_1-C_4)$alkyl or 1 to 3 halo.

3. The compound of claim 2, wherein the compound is of the Formula XI:

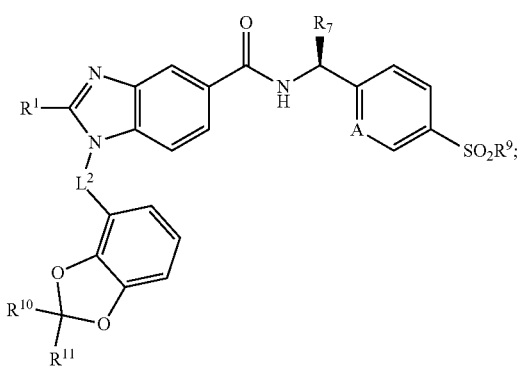

(XI)

or a pharmaceutically acceptable salt thereof, wherein $R^{10}$ and $R^{11}$ are each independently hydrogen or halo.

4. The compound of claim 3, wherein $R^1$ is halo$(C_1-C_4)$alkyl, cyclopropyl, or cyclobutyl, wherein said cyclopropyl and cyclobutyl are each optionally substituted with 1 to 3 halo.

5. The compound of claim 3, wherein $L^2$ is $CH_2$.

6. The compound of claim 3, wherein $R^7$ is —$CH_2OH$; and A is N.

7. The compound of claim 3, wherein $R^{10}$ and $R^{11}$ are each fluoro.

8. The compound of claim 3, wherein the compound is of the formula:

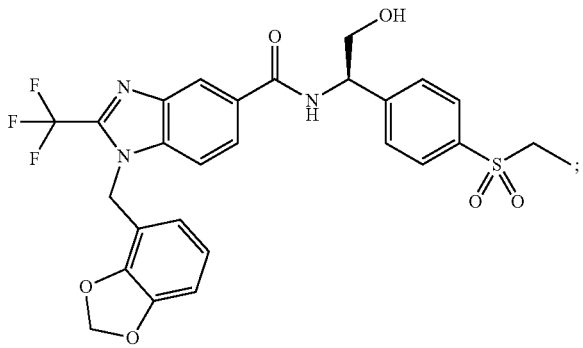 [SMILES: CCS(=O)(=O)c1ccc([C@H](CO)NC(=O)c2ccc3c(c2)nc(C(F)(F)F)n3Cc2cccc3c2OCO3)cc1]

or a pharmaceutically acceptable salt thereof.

9. A compound of the formula:

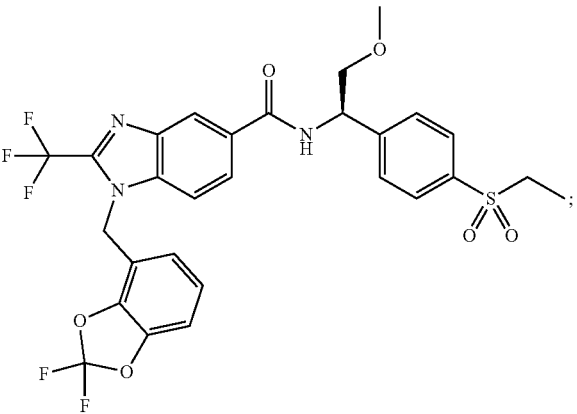 [SMILES: CCS(=O)(=O)c1ccc([C@H](COC)NC(=O)c2ccc3c(c2)nc(C(F)(F)F)n3Cc2cccc3c2OC(F)(F)O3)cc1]

or a pharmaceutically acceptable salt thereof.

10. The compound of claim 3, wherein the compound is of the formula:

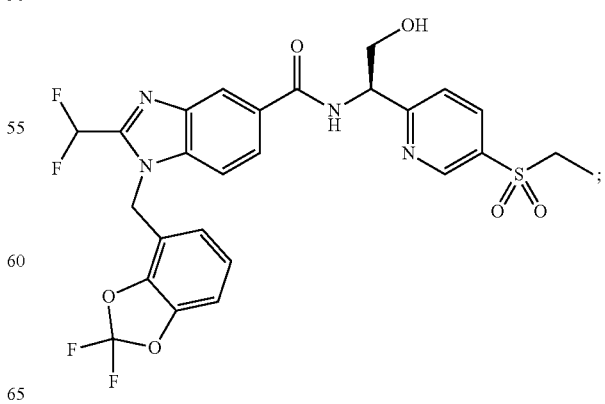

or a pharmaceutically acceptable salt thereof.

11. The compound of claim 3, wherein the compound is of the formula:

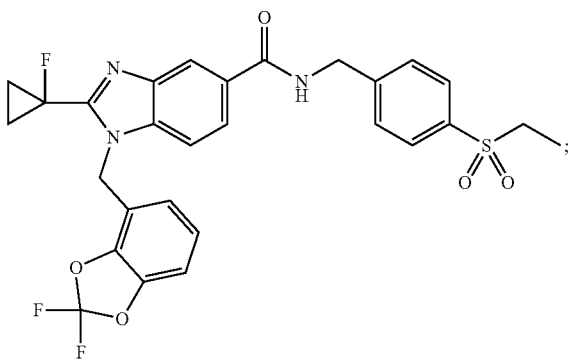 [SMILES: CCS(=O)(=O)c1ccc(CNC(=O)c2ccc3c(c2)nc(C2(F)CC2)n3Cc2cccc3c2OC(F)(F)O3)cc1]

or a pharmaceutically acceptable salt thereof.

12. A compound of the formula:

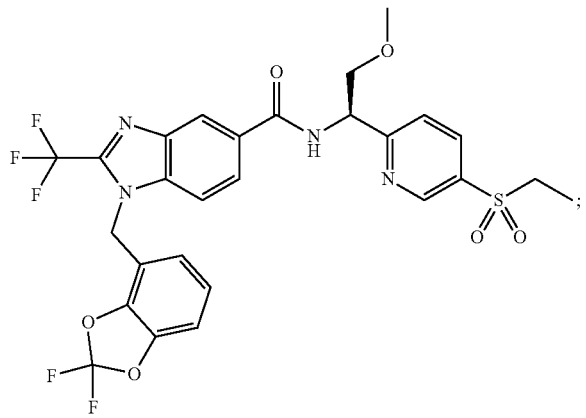 [SMILES: CCS(=O)(=O)c1ccc([C@H](COC)NC(=O)c2ccc3c(c2)nc(C(F)(F)F)n3Cc2cccc3c2OC(F)(F)O3)nc1]

or a pharmaceutically acceptable salt thereof.

13. A compound of the formula:

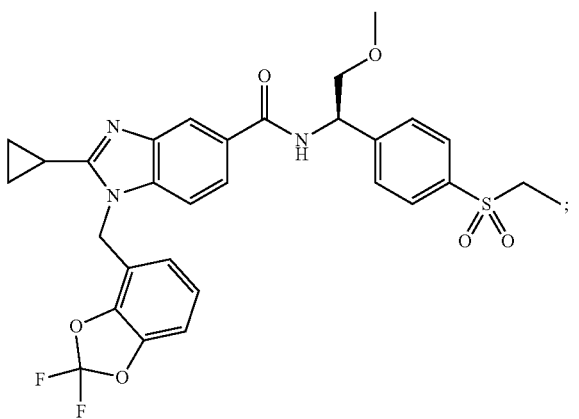 [SMILES: CCS(=O)(=O)c1ccc([C@H](COC)NC(=O)c2ccc3c(c2)nc(C2CC2)n3Cc2cccc3c2OC(F)(F)O3)cc1]

or a pharmaceutically acceptable salt thereof.

14. A compound selected from:

N-(1-((2,2-difluorobenzo[d][1,3]dioxol-4-yl)methyl)-2-(trifluoromethyl)-1H-benzo[d]imidazol-5-yl)-2-(4-(ethylsulfonyl)phenyl)acetamide;

N-(1-((2,2-difluorobenzo[d][1,3]dioxol-4-yl)methyl)-2-(trifluoromethyl)-1H-benzo[d]imidazol-5-yl)-2-(4-(methylsulfonyl)phenyl)acetamide;

N-(1-((2,2-difluorobenzo[d][1,3]dioxol-4-yl)methyl)-2-(trifluoromethyl)-1H-benzo[d]imidazol-5-yl)-2-(4-((2-hydroxyethyl)sulfonyl)phenyl)acetamide;

N-(1-((2,2-difluorobenzo[d][1,3]dioxol-4-yl)methyl)-2-(trifluoromethyl)-1H-benzo[d]imidazol-5-yl)-2-(4-((2-methoxyethyl)sulfonyl)phenyl)acetamide;

N-(1-((2,2-difluorobenzo[d][1,3]dioxol-4-yl)methyl)-2-(trifluoromethyl)-1H-benzo[d]imidazol-5-yl)-2-(4-(N-methylsulfamoyl)phenyl)acetamide;

2-(4-cyanophenyl)-N-(1-((2,2-difluorobenzo[d][1,3]dioxol-4-yl)methyl)-2-(trifluoromethyl)-1H-benzo[d]imidazol-5-yl)acetamide;

ethyl 2-(4-(2-((1-((2,2-difluorobenzo[d][1,3]dioxol-4-yl)methyl)-2-(trifluoromethyl)-1H-benzo[d]imidazol-5-yl)amino)-2-oxoethyl)phenyl)acetate;

2-(4-(2-((1-((2,2-difluorobenzo[d][1,3]dioxol-4-yl)methyl)-2-(trifluoromethyl)-1H-benzo[d]imidazol-5-yl)amino)-2-oxoethyl)phenyl)acetic acid;

N-(2-cyclopropyl-1-((2,2-difluorobenzo[d][1,3]dioxol-4-yl)methyl)-1H-benzo[d]imidazol-5-yl)-2-(4-(ethylsulfonyl)phenyl)acetamide;

N-(1-((2,2-difluorobenzo[d][1,3]dioxol-4-yl)methyl)-2-(trifluoromethyl)-1H-benzo[d]imidazol-5-yl)-2-(1-(methylsulfonyl)piperidin-4-yl)acetamide;

(R)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide;

(S)-1-((2,2-difluorobenzo[d][1,3]dioxol-4-yl)methyl)-N-(1-(4-(ethylsulfonyl)phenyl)-2-hydroxyethyl)-2-(trifluoromethyl)-1H-benzo[d]imidazole-5-carboxamide;

(R)-2-cyclopropyl-1-((2,2-difluorobenzo[d][1,3]dioxol-4-yl)methyl)-N-(1-(4-(ethylsulfonyl)phenyl)-2-hydroxyethyl)-1H-benzo[d]imidazole-5-carboxamide;

(R)-2-cyclobutyl-1-((2,2-difluorobenzo[d][1,3]dioxol-4-yl)methyl)-N-(1-(4-(ethylsulfonyl)phenyl)-2-hydroxyethyl)-1H-benzo[d]imidazole-5-carboxamide;

(R)-1-((2,2-difluorobenzo[d][1,3]dioxol-4-yl)methyl)-2-(1,1-difluoroethyl)-N-(1-(4-(ethylsulfonyl)phenyl)-2-hydroxyethyl)-1H-benzo[d]imidazole-5-carboxamide;

1-((2,2-difluorobenzo[d][1,3]dioxol-4-yl)methyl)-N—((R)-1-(4-(ethylsulfonyl)phenyl)-2-hydroxyethyl)-2-((R)-tetrahydrofuran-2-yl)-1H-benzo[d]imidazole-5-carboxamide;

(R)-1-((2,2-difluorobenzo[d][1,3]dioxol-4-yl)methyl)-2-ethyl-N-(1-(4-(ethylsulfonyl)phenyl)-2-hydroxyethyl)-1H-benzo[d]imidazole-5-carboxamide;

(R)-1-((2,2-difluorobenzo[d][1,3]dioxol-4-yl)methyl)-2-(difluoromethyl)-N-(1-(4-(ethylsulfonyl)phenyl)-2-hydroxyethyl)-1H-benzo[d]imidazole-5-carboxamide;

(R)-1-((2,2-difluorobenzo[d][1,3]dioxol-4-yl)methyl)-N-(1-(4-(ethylsulfonyl)phenyl)-2-hydroxyethyl)-2-(1-fluorocyclopropyl)-1H-benzo[d]imidazole-5-carboxamide;

(R)-1-((2,2-difluorobenzo[d][1,3]dioxol-4-yl)methyl)-N-(1-(4-(ethylsulfonyl)phenyl)-2-hydroxyethyl)-2-(1-fluorocyclobutyl)-1H-benzo[d]imidazole-5-carboxamide;

(R)-1-((2,2-difluorobenzo[d][1,3]dioxol-4-yl)methyl)-N-(2-hydroxy-1-(4-(methylsulfonyl)phenyl)ethyl)-2-(trifluoromethyl)-1H-benzo[d]imidazole-5-carboxamide;

(S)-1-((2,2-difluorobenzo[d][1,3]dioxol-4-yl)methyl)-N-(2-hydroxy-1-(4-(methylsulfonyl)phenyl)ethyl)-2-(trifluoromethyl)-1H-benzo[d]imidazole-5-carboxamide;

(R)-2-cyclopropyl-1-((2,2-difluorobenzo[d][1,3]dioxol-4-yl)methyl)-N-(2-hydroxy-1-(4-(methylsulfonyl)phenyl)ethyl)-1H-benzo[d]imidazole-5-carboxamide;
(R)-2-cyclobutyl-1-((2,2-difluorobenzo[d][1,3]dioxol-4-yl)methyl)-N-(2-hydroxy-1-(4-(methylsulfonyl)phenyl)ethyl)-1H-benzo[d]imidazole-5-carboxamide;
(R)-1-((2,2-difluorobenzo[d][1,3]dioxol-4-yl)methyl)-2-(difluoromethyl)-N-(2-hydroxy-1-(4-(methylsulfonyl)phenyl)ethyl)-1H-benzo[d]imidazole-5-carboxamide;
(S)-1-((2,2-difluorobenzo[d][1,3]dioxol-4-yl)methyl)-2-(difluoromethyl)-N-(2-hydroxy-1-(4-(methylsulfonyl)phenyl)ethyl)-1H-benzo[d]imidazole-5-carboxamide;
(R)-1-((2,2-difluorobenzo[d][1,3]dioxol-4-yl)methyl)-2-(1-fluorocyclopropyl)-N-(2-hydroxy-1-(4-(methylsulfonyl)phenyl)ethyl)-1H-benzo[d]imidazole-5-carboxamide;
1-((2,2-difluorobenzo[d][1,3]dioxol-4-yl)methyl)-N-(4-(ethylsulfonyl)benzyl)-2-(trifluoromethyl)-1H-benzo[d]imidazole-5-carboxamide;
2-cyclopropyl-1-((2,2-difluorobenzo[d][1,3]dioxol-4-yl)methyl)-N-(4-(ethylsulfonyl)benzyl)-1H-benzo[d]imidazole-5-carboxamide;
1-((2,2-difluorobenzo[d][1,3]dioxol-4-yl)methyl)-N-(4-(ethylsulfonyl)benzyl)-2-(1-fluorocyclopropyl)-1H-benzo[d]imidazole-5-carboxamide;
1-((2,2-difluorobenzo[d][1,3]dioxol-4-yl)methyl)-N-(4-(ethylsulfonyl)benzyl)-2-(methoxymethyl)-1H-benzo[d]imidazole-5-carboxamide;
1-((2,2-difluorobenzo[d][1,3]dioxol-4-yl)methyl)-2-ethyl-N-(4-(ethylsulfonyl)benzyl)-1H-benzo[d]imidazole-5-carboxamide;
2-(tert-butyl)-1-((2,2-difluorobenzo[d][1,3]dioxol-4-yl)methyl)-N-(4-(ethylsulfonyl)benzyl)-1H-benzo[d]imidazole-5-carboxamide;
1-((2,2-difluorobenzo[d][1,3]dioxol-4-yl)methyl)-N-(4-(ethylsulfonyl)benzyl)-2-isopropyl-1H-benzo[d]imidazole-5-carboxamide;
1-((2,2-difluorobenzo[d][1,3]dioxol-4-yl)methyl)-N-(4-(ethylsulfonyl)benzyl)-2-methyl-1H-benzo[d]imidazole-5-carboxamide;
1-((2,2-difluorobenzo[d][1,3]dioxol-4-yl)methyl)-N-(4-(ethylsulfonyl)benzyl)-2-isobutyl-1H-benzo[d]imidazole-5-carboxamide;
2-cyclopropyl-1-((2,2-difluorobenzo[d][1,3]dioxol-4-yl)methyl)-N-(4-(methylsulfonyl)benzyl)-1H-benzo[d]imidazole-5-carboxamide;
2-cyclopropyl-1-((2,2-difluorobenzo[d][1,3]dioxol-4-yl)methyl)-N-(4-(N-methylsulfamoyl)benzyl)-1H-benzo[d]imidazole-5-carboxamide;
2-cyclobutyl-1-((2,2-difluorobenzo[d][1,3]dioxol-4-yl)methyl)-N-(4-(ethylsulfonyl)benzyl)-1H-benzo[d]imidazole-5-carboxamide;
1-((2,2-difluorobenzo[d][1,3]dioxol-4-yl)methyl)-2-(difluoromethyl)-N-(4-(ethylsulfonyl)benzyl)-1H-benzo[d]imidazole-5-carboxamide;
1-((2,2-difluorobenzo[d][1,3]dioxol-4-yl)methyl)-2-(1,1-difluoroethyl)-N-(4-(ethylsulfonyl)benzyl)-1H-benzo[d]imidazole-5-carboxamide;
1-((2,2-difluorobenzo[d][1,3]dioxol-4-yl)methyl)-N-(4-(ethylsulfonyl)benzyl)-2-(tetrahydrofuran-2-yl)-1H-benzo[d]imidazole-5-carboxamide;
1-((2,2-difluorobenzo[d][1,3]dioxol-4-yl)methyl)-2-(1-fluorocyclopropyl)-N-(4-(methylsulfonyl)benzyl)-1H-benzo[d]imidazole-5-carboxamide;
1-((2,2-difluorobenzo[d][1,3]dioxol-4-yl)methyl)-2-(1-fluorocyclopropyl)-N-(4-((2-hydroxyethyl)sulfonyl)benzyl)-1H-benzo[d]imidazole-5-carboxamide;
1-((2,2-difluorobenzo[d][1,3]dioxol-4-yl)methyl)-2-(1-fluorocyclopropyl)-N-(4-(N-methylsulfamoyl)benzyl)-1H-benzo[d]imidazole-5-carboxamide;
1-((2,2-difluorobenzo[d][1,3]dioxol-4-yl)methyl)-N-(4-(ethylsulfonyl)benzyl)-2-(1-fluorocyclobutyl)-1H-benzo[d]imidazole-5-carboxamide;
1-((2,2-difluorobenzo[d][1,3]dioxol-4-yl)methyl)-2-(difluoromethyl)-N-(4-((2-hydroxyethyl)sulfonyl)benzyl)-1H-benzo[d]imidazole-5-carboxamide;
1-((2,2-difluorobenzo[d][1,3]dioxol-4-yl)methyl)-N-(4-((2-hydroxyethyl)sulfonyl)benzyl)-2-(trifluoromethyl)-1H-benzo[d]imidazole-5-carboxamide;
1-((2,2-difluorobenzo[d][1,3]dioxol-4-yl)methyl)-N-(4-(N-methylsulfamoyl)benzyl)-2-(trifluoromethyl)-1H-benzo[d]imidazole-5-carboxamide;
2-cyclopropyl-1-((2,2-difluorobenzo[d][1,3]dioxol-4-yl)methyl)-N-(4-((2-hydroxyethyl)sulfonyl)benzyl)-1H-benzo[d]imidazole-5-carboxamide;
1-((2,2-difluorobenzo[d][1,3]dioxol-4-yl)methyl)-N-(4-(methylsulfonyl)benzyl)-2-(trifluoromethyl)-1H-benzo[d]imidazole-5-carboxamide;
(S)-1-((2,2-difluorobenzo[d][1,3]dioxol-4-yl)methyl)-N-(4-(ethylsulfonyl)benzyl)-2-(1-methoxyethyl)-1H-benzo[d]imidazole-5-carboxamide;
(R)-1-((2,2-difluorobenzo[d][1,3]dioxol-4-yl)methyl)-N-(4-(ethylsulfonyl)benzyl)-2-(1-methoxyethyl)-1H-benzo[d]imidazole-5-carboxamide;
1-((2,2-difluorobenzo[d][1,3]dioxol-4-yl)methyl)-2-(difluoromethyl)-N-(4-(methylsulfonyl)benzyl)-1H-benzo[d]imidazole-5-carboxamide;
1-((2,2-difluorobenzo[d][1,3]dioxol-4-yl)methyl)-N-(4-sulfamoylbenzyl)-2-(trifluoromethyl)-1H-benzo[d]imidazole-5-carboxamide;
1-((2,2-difluorobenzo[d][1,3]dioxol-4-yl)methyl)-N-(4-(propylsulfonyl)benzyl)-2-(trifluoromethyl)-1H-benzo[d]imidazole-5-carboxamide;
methyl 2-((4-((1-((2,2-difluorobenzo[d][1,3]dioxol-4-yl)methyl)-2-(trifluoromethyl)-1H-benzo[d]imidazole-5-carboxamido)methyl)phenyl)sulfonyl)acetate;
1-((2,2-difluorobenzo[d][1,3]dioxol-4-yl)methyl)-N-(4-(ethylsulfonyl)benzyl)-2-(2-methoxypropan-2-yl)-1H-benzo[d]imidazole-5-carboxamide;
1-((2,2-difluorobenzo[d][1,3]dioxol-4-yl)methyl)-N-(4-(ethylsulfonyl)benzyl)-2-methoxy-1H-benzo[d]imidazole-5-carboxamide;
2-((1S,2R)-2-cyanocyclopropyl)-1-((2,2-difluorobenzo[d][1,3]dioxol-4-yl)methyl)-N-(4-(ethylsulfonyl)benzyl)-1H-benzo[d]imidazole-5-carboxamide;
2-((1R,2R)-2-cyanocyclopropyl)-1-((2,2-difluorobenzo[d][1,3]dioxol-4-yl)methyl)-N-(4-(ethylsulfonyl)benzyl)-1H-benzo[d]imidazole-5-carboxamide;
methyl (1R,2R)-2-(1-((2,2-difluorobenzo[d][1,3]dioxol-4-yl)methyl)-5-((4-(ethylsulfonyl)benzyl)carbamoyl)-1H-benzo[d]imidazol-2-yl)cyclopropane-1-carboxylate;
(R)-1-((2,2-difluorobenzo[d][1,3]dioxol-4-yl)methyl)-N-(1-(4-(ethylsulfonyl)phenyl)-2-methoxyethyl)-2-(trifluoromethyl)-1H-benzo[d]imidazole-5-carboxamide;
(R)-2-cyclopropyl-1-((2,2-difluorobenzo[d][1,3]dioxol-4-yl)methyl)-N-(1-(4-(ethylsulfonyl)phenyl)-2-methoxyethyl)-1H-benzo[d]imidazole-5-carboxamide;
(R)-1-((2,2-difluorobenzo[d][1,3]dioxol-4-yl)methyl)-N-(1-(4-(ethylsulfonyl)phenyl)-2-methoxyethyl)-2-(1-fluorocyclopropyl)-1H-benzo[d]imidazole-5-carboxamide;

(R)-1-((2,2-difluorobenzo[d][1,3]dioxol-4-yl)methyl)-N-(1-(5-(ethylsulfonyl)pyridin-2-yl)-2-methoxyethyl)-2-(trifluoromethyl)-1H-benzo[d]imidazole-5-carboxamide;

1-((2,2-difluorobenzo[d][1,3]dioxol-4-yl)methyl)-N-((5-(ethylsulfonyl)pyridin-2-yl)methyl)-2-(trifluoromethyl)-1H-benzo[d]imidazole-5-carboxamide;

2-cyclopropyl-1-((2,2-difluorobenzo[d][1,3]dioxol-4-yl)methyl)-N-((5-(ethylsulfonyl)pyridin-2-yl)methyl)-1H-benzo[d]imidazole-5-carboxamide;

2-cyclobutyl-1-((2,2-difluorobenzo[d][1,3]dioxol-4-yl)methyl)-N-((5-(ethylsulfonyl)pyridin-2-yl)methyl)-1H-benzo[d]imidazole-5-carboxamide;

1-((2,2-difluorobenzo[d][1,3]dioxol-4-yl)methyl)-2-(1,1-difluoroethyl)-N-((5-(ethylsulfonyl)pyridin-2-yl)methyl)-1H-benzo[d]imidazole-5-carboxamide;

1-((2,2-difluorobenzo[d][1,3]dioxol-4-yl)methyl)-N-((5-(ethylsulfonyl)pyridin-2-yl)methyl)-2-(1-fluorocyclopropyl)-1H-benzo[d]imidazole-5-carboxamide;

1-((2,2-difluorobenzo[d][1,3]dioxol-4-yl)methyl)-2-(1-fluorocyclopropyl)-N-((5-(methylsulfonyl)pyridin-2-yl)methyl)-1H-benzo[d]imidazole-5-carboxamide;

1-((2,2-difluorobenzo[d][1,3]dioxol-4-yl)methyl)-N-((5-(ethylsulfonyl)pyridin-2-yl)methyl)-2-(1-fluorocyclobutyl)-1H-benzo[d]imidazole-5-carboxamide;

1-((2,2-difluorobenzo[d][1,3]dioxol-4-yl)methyl)-N-((5-(methylsulfonyl)pyridin-2-yl)methyl)-2-(trifluoromethyl)-1H-benzo[d]imidazole-5-carboxamide;

1-((2,2-difluorobenzo[d][1,3]dioxol-4-yl)methyl)-N-((1-(methylsulfonyl)piperidin-4-yl)methyl)-2-(trifluoromethyl)-1H-benzo[d]imidazole-5-carboxamide;

2-cyclopropyl-1-((2,2-difluorobenzo[d][1,3]dioxol-4-yl)methyl)-N-((1-(methylsulfonyl)piperidin-4-yl)methyl)-1H-benzo[d]imidazole-5-carboxamide;

1-((2,2-difluorobenzo[d][1,3]dioxol-4-yl)methyl)-2-(1-fluorocyclopropyl)-N-((1-(methylsulfonyl)piperidin-4-yl)methyl)-1H-benzo[d]imidazole-5-carboxamide;

methyl 2-(4-((1-((2,2-difluorobenzo[d][1,3]dioxol-4-yl)methyl)-2-(trifluoromethyl)-1H-benzo[d]imidazole-5-carboxamido)methyl)piperidin-1-yl)sulfonyl)acetate;

1-((2,2-difluorobenzo[d][1,3]dioxol-4-yl)methyl)-N-((1-((2-(methylamino)-2-oxoethyl)sulfonyl)piperidin-4-yl)methyl)-2-(trifluoromethyl)-1H-benzo[d]imidazole-5-carboxamide;

methyl 2-(1-((2,2-difluorobenzo[d][1,3]dioxol-4-yl)methyl)-2-(trifluoromethyl)-1H-benzo[d]imidazole-5-carboxamido)-2-(1-(methylsulfonyl)piperidin-4-yl)acetate;

1-((2,2-difluorobenzo[d][1,3]dioxol-4-yl)methyl)-N-((1-(N-methylsulfamoyl)piperidin-4-yl)methyl)-2-(trifluoromethyl)-1H-benzo[d]imidazole-5-carboxamide;

N-((1-((2-amino-2-oxoethyl)sulfonyl)piperidin-4-yl)methyl)-1-((2,2-difluorobenzo[d][1,3]dioxol-4-yl)methyl)-2-(trifluoromethyl)-1H-benzo[d]imidazole-5-carboxamide;

2-cyclopropyl-1-((2,2-difluorobenzo[d][1,3]dioxol-4-yl)methyl)-N-((1-((2-(methylamino)-2-oxoethyl)sulfonyl)piperidin-4-yl)methyl)-1H-benzo[d]imidazole-5-carboxamide;

(R)-1-((2,3-dihydrobenzofuran-7-yl)methyl)-N-(1-(4-(ethylsulfonyl)phenyl)-2-hydroxyethyl)-2-(trifluoromethyl)-1H-benzo[d]imidazole-5-carboxamide;

(R)-1-(benzo[d][1,3]dioxol-4-ylmethyl)-N-(1-(4-(ethylsulfonyl)phenyl)-2-hydroxyethyl)-2-(trifluoromethyl)-1H-benzo[d]imidazole-5-carboxamide;

1-((6,7-dihydro-5H-pyrrolo[2,1-c][1,2,4]triazol-3-yl)methyl)-N-(4-(ethylsulfonyl)benzyl)-2-(trifluoromethyl)-1H-benzo[d]imidazole-5-carboxamide;

N-(4-(ethylsulfonyl)benzyl)-1-((2-methyl-5,6,7,8-tetrahydroimidazo[1,2-a]pyridin-8-yl)methyl)-2-(trifluoromethyl)-1H-benzo[d]imidazole-5-carboxamide;

N-(4-(ethylsulfonyl)benzyl)-1-((2-oxo-1,2-dihydroquinolin-4-yl)methyl)-2-(trifluoromethyl)-1H-benzo[d]imidazole-5-carboxamide;

1-(benzofuran-4-ylmethyl)-N-(4-(ethylsulfonyl)benzyl)-2-(trifluoromethyl)-1H-benzo[d]imidazole-5-carboxamide;

1-((2,3-dihydrobenzofuran-7-yl)methyl)-N-(4-(ethylsulfonyl)benzyl)-2-(trifluoromethyl)-1H-benzo[d]imidazole-5-carboxamide;

1-((1H-indazol-4-yl)methyl)-N-(4-(ethylsulfonyl)benzyl)-2-(trifluoromethyl)-1H-benzo[d]imidazole-5-carboxamide;

1-(benzo[d][1,3]dioxol-4-ylmethyl)-N-(4-(ethylsulfonyl)benzyl)-2-(trifluoromethyl)-1H-benzo[d]imidazole-5-carboxamide;

1-((1H-pyrrolo[2,3-c]pyridin-4-yl)methyl)-N-(4-(ethylsulfonyl)benzyl)-2-(trifluoromethyl)-1H-benzo[d]imidazole-5-carboxamide;

(R)-2-cyclopropyl-1-((2,2-dimethyl-2,3-dihydrobenzofuran-7-yl)methyl)-N-(1-(4-(ethylsulfonyl)phenyl)-2-hydroxyethyl)-1H-benzo[d]imidazole-5-carboxamide;

(R)-2-cyclopropyl-1-((2,3-dihydrobenzofuran-7-yl)methyl)-N-(1-(4-(ethylsulfonyl)phenyl)-2-hydroxyethyl)-1H-benzo[d]imidazole-5-carboxamide;

2-cyclopropyl-1-((2,2-difluorobenzo[d][1,3]dioxol-5-yl)methyl)-N-(4-(ethylsulfonyl)benzyl)-1H-benzo[d]imidazole-5-carboxamide;

(S)-2-cyclopropyl-1-(1-(2,2-difluorobenzo[d][1,3]dioxol-4-yl)ethyl)-N-(4-(ethylsulfonyl)benzyl)-1H-benzo[d]imidazole-5-carboxamide;

2-cyclopropyl-1-((2,2-dimethyl-2,3-dihydrobenzofuran-7-yl)methyl)-N-(4-(ethylsulfonyl)benzyl)-1H-benzo[d]imidazole-5-carboxamide;

2-(4-((1-((2,2-difluorobenzo[d][1,3]dioxol-4-yl)methyl)-2-(trifluoromethyl)-1H-benzo[d]imidazole-5-carboxamido)methyl)cyclohexyl)acetic acid;

N-((1H-benzo[d][1,2,3]triazol-6-yl)methyl)-1-((2,2-difluorobenzo[d][1,3]dioxol-4-yl)methyl)-2-(trifluoromethyl)-1H-benzo[d]imidazole-5-carboxamide;

(R)—N-(1-(4-cyanophenyl)-2-hydroxyethyl)-1-((2,2-difluorobenzo[d][1,3]dioxol-4-yl)methyl)-2-(trifluoromethyl)-1H-benzo[d]imidazole-5-carboxamide;

(R)-1-((2,2-difluorobenzo[d][1,3]dioxol-4-yl)methyl)-N-(1-(4-(ethylsulfonyl)-2-fluorophenyl)-2-hydroxyethyl)-2-(trifluoromethyl)-1H-benzo[d]imidazole-5-carboxamide;

(S)-1-(1-(2,2-difluorobenzo[d][1,3]dioxol-4-yl)ethyl)-2-ethyl-N-(4-(ethylsulfonyl)benzyl)-1H-benzo[d]imidazole-5-carboxamide;

(R)-1-(1-(2,2-difluorobenzo[d][1,3]dioxol-4-yl)ethyl)-2-ethyl-N-(4-(ethylsulfonyl)benzyl)-1H-benzo[d]imidazole-5-carboxamide;

1-((2,2-difluorobenzo[d][1,3]dioxol-4-yl)methyl)-N-(4-(ethylsulfonyl)-2-hydroxybenzyl)-2-(trifluoromethyl)-1H-benzo[d]imidazole-5-carboxamide;

methyl 2-((4-((1-((1H-indazol-4-yl)methyl)-2-(trifluoromethyl)-1H-benzo[d]imidazole-5-carboxamido)methyl)piperidin-1-yl)sulfonyl)acetate;

1-((2,2-difluorobenzo[d][1,3]dioxol-4-yl)methyl)-N-((4-oxo-1,4-dihydroquinolin-7-yl)methyl)-2-(trifluoromethyl)-1H-benzo[d]imidazole-5-carboxamide;

(R)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide;

(S)-1-((2,2-difluorobenzo[d][1,3]dioxol-4-yl)methyl)-N-(1-(5-(ethylsulfonyl)pyridin-2-yl)-2-hydroxyethyl)-2-(trifluoromethyl)-1H-benzo[d]imidazole-5-carboxamide;

(R)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide;

(S)-1-((2,2-difluorobenzo[d][1,3]dioxol-4-yl)methyl)-2-(difluoromethyl)-N-(1-(5-(ethylsulfonyl)pyridin-2-yl)-2-hydroxyethyl)-1H-benzo[d]imidazole-5-carboxamide;

(R)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide;

(S)-2-cyclobutyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide;

(R)-2-cyclopropyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide;

(S)-2-cyclopropyl-1-((2,2-difluorobenzo[d][1,3]dioxol-4-yl)methyl)-N-(1-(5-(ethylsulfonyl)pyridin-2-yl)-2-hydroxyethyl)-1H-benzo[d]imidazole-5-carboxamide;

(R)-1-((2,2-difluorobenzo[d][1,3]dioxol-4-yl)methyl)-N-(1-(5-(ethylsulfonyl)pyridin-2-yl)-2-hydroxyethyl)-2-(1-fluorocyclopropyl)-1H-benzo[d]imidazole-5-carboxamide;

(S)-1-((2,2-difluorobenzo[d][1,3]dioxol-4-yl)methyl)-N-(1-(5-(ethylsulfonyl)pyridin-2-yl)-2-hydroxyethyl)-2-(1-fluorocyclopropyl)-1H-benzo[d]imidazole-5-carboxamide;

(R)-1-((2,2-difluorobenzo[d][1,3]dioxol-4-yl)methyl)-N-(2-hydroxy-1-(5-(methylsulfonyl)pyridin-2-yl)ethyl)-2-(trifluoromethyl)-1H-benzo[d]imidazole-5-carboxamide;

N-(4-(ethylsulfonyl)benzyl)-1-((1-methyl-1H-indazol-7-yl)methyl)-2-(trifluoromethyl)-1H-benzo[d]imidazole-5-carboxamide;

N-(4-(ethylsulfonyl)benzyl)-1-((2-methyl-2H-indazol-7-yl)methyl)-2-(trifluoromethyl)-1H-benzo[d]imidazole-5-carboxamide;

1-((1,2-dimethyl-1H-benzo[d]imidazol-7-yl)methyl)-N-(4-(ethylsulfonyl)benzyl)-2-(trifluoromethyl)-1H-benzo[d]imidazole-5-carboxamide;

N-(4-(ethylsulfonyl)benzyl)-1-((1-methyl-1H-indazol-4-yl)methyl)-2-(trifluoromethyl)-1H-benzo[d]imidazole-5-carboxamide;

1-((1H-indazol-7-yl)methyl)-N-(4-(ethylsulfonyl)benzyl)-2-(trifluoromethyl)-1H-benzo[d]imidazole-5-carboxamide;

N-(4-(ethylsulfonyl)benzyl)-1-((2-methyl-2H-indazol-4-yl)methyl)-2-(trifluoromethyl)-1H-benzo[d]imidazole-5-carboxamide;

1-(benzo[d]oxazol-4-ylmethyl)-N-(4-(ethylsulfonyl)benzyl)-2-(trifluoromethyl)-1H-benzo[d]imidazole-5-carboxamide;

2-cyclopropyl-1-((2,3-dihydrobenzo[b][1,4]dioxin-5-yl)methyl)-N-(4-(ethylsulfonyl)benzyl)-1H-benzo[d]imidazole-5-carboxamide;

(R)-2-cyclopropyl-1-(1-(2,2-difluorobenzo[d][1,3]dioxol-4-yl)ethyl)-N-(4-(ethylsulfonyl)benzyl)-1H-benzo[d]imidazole-5-carboxamide;

1-(benzo[c][1,2,5]oxadiazol-4-ylmethyl)-N-(4-(ethylsulfonyl)benzyl)-2-(trifluoromethyl)-1H-benzo[d]imidazole-5-carboxamide;

1-(benzo[d]oxazol-7-ylmethyl)-N-(4-(ethylsulfonyl)benzyl)-2-(trifluoromethyl)-1H-benzo[d]imidazole-5-carboxamide;

2-((1-((2,2-difluorobenzo[d][1,3]dioxol-4-yl)methyl)-2-(trifluoromethyl)-1H-benzo[d]imidazole-5-carboxamido)methyl)-5-(ethylsulfonyl)pyridine 1-oxide;

1-((2,2-difluorobenzo[d][1,3]dioxol-4-yl)methyl)-2-(dimethylamino)-N-(4-(ethylsulfonyl)benzyl)-1H-benzo[d]imidazole-5-carboxamide;

1-((2,2-difluorobenzo[d][1,3]dioxol-4-yl)methyl)-N-((1-((2-hydroxyethyl)sulfonyl)piperidin-4-yl)methyl)-2-(trifluoromethyl)-1H-benzo[d]imidazole-5-carboxamide;

(R)-1-((2,2-difluorobenzo[d][1,3]dioxol-4-yl)methyl)-N-(2-hydroxy-1-(1-(methylsulfonyl)piperidin-4-yl)ethyl)-2-(trifluoromethyl)-1H-benzo[d]imidazole-5-carboxamide;

(S)-1-((2,2-difluorobenzo[d][1,3]dioxol-4-yl)methyl)-N-(2-hydroxy-1-(1-(methylsulfonyl)piperidin-4-yl)ethyl)-2-(trifluoromethyl)-1H-benzo[d]imidazole-5-carboxamide;

(S)-3-(1-((2,2-difluorobenzo[d][1,3]dioxol-4-yl)methyl)-2-(trifluoromethyl)-1H-benzo[d]imidazole-5-carboxamido)-3-(4-(ethylsulfonyl)phenyl)propanoic acid;

(R)-2-(2-(1-((2,2-difluorobenzo[d][1,3]dioxol-4-yl)methyl)-2-(trifluoromethyl)-1H-benzo[d]imidazole-5-carboxamido)-2-(4-(ethylsulfonyl)phenyl)ethoxy)acetic acid;

(S)-1-((2,2-difluorobenzo[d][1,3]dioxol-4-yl)methyl)-N-(1-(4-(ethylsulfonyl)phenyl)-3-(methylamino)-3-oxopropyl)-2-(trifluoromethyl)-1H-benzo[d]imidazole-5-carboxamide;

(S)—N-(3-amino-1-(4-(ethylsulfonyl)phenyl)-3-oxopropyl)-1-((2,2-difluorobenzo[d][1,3]dioxol-4-yl)methyl)-2-(trifluoromethyl)-1H-benzo[d]imidazole-5-carboxamide;

1-((2,2-difluorobenzo[d][1,3]dioxol-4-yl)methyl)-N-(4-((2-(methylamino)-2-oxoethyl)sulfonyl)benzyl)-2-(trifluoromethyl)-1H-benzo[d]imidazole-5-carboxamide;

N-(1-((2,2-difluorobenzo[d][1,3]dioxol-4-yl)methyl)-2-(trifluoromethyl)-1H-benzo[d]imidazol-5-yl)-2-(4-(ethylsulfonyl)phenyl)-2-hydroxyacetamide;

(R)—N-(1-((2,2-difluorobenzo[d][1,3]dioxol-4-yl)methyl)-2-(trifluoromethyl)-1H-benzo[d]imidazol-5-yl)-2-(4-(ethylsulfonyl)phenyl)-2-hydroxyacetamide;

1-((2,2-difluorobenzo[d][1,3]dioxol-4-yl)methyl)-N-((4-methyl-1-(methylsulfonyl)-1,4-diazepan-5-yl)methyl)-2-(trifluoromethyl)-1H-benzo[d]imidazole-5-carboxamide;

1-((2,3-dihydrobenzofuran-4-yl)methyl)-N-(4-(ethylsulfonyl)benzyl)-2-(trifluoromethyl)-1H-benzo[d]imidazole-5-carboxamide;

methyl 1-((2,2-difluorobenzo[d][1,3]dioxol-4-yl)methyl)-5-((4-(ethylsulfonyl)benzyl)carbamoyl)-1H-benzo[d]imidazole-2-carboxylate; and 1-((2,2-difluorobenzo[d][1,3]dioxol-4-yl)methyl)-N-(2-(4-(ethylsulfonyl)phenyl)-1,3-dihydroxypropan-2-yl)-2-(trifluoromethyl)-1H-benzo[d]imidazole-5-carboxamide;

or a pharmaceutically acceptable salt of any of the foregoing.

15. A composition comprising the compound of claim 1, or a pharmaceutically acceptable salt thereof; and a pharmaceutically acceptable carrier.

16. A composition comprising the compound of claim 8, or a pharmaceutically acceptable salt thereof; and a pharmaceutically acceptable carrier.

17. A composition comprising the compound of claim 9, or a pharmaceutically acceptable salt thereof; and a pharmaceutically acceptable carrier.

18. A composition comprising the compound of claim 10, or a pharmaceutically acceptable salt thereof; and a pharmaceutically acceptable carrier.

19. A composition comprising the compound of claim 11, or a pharmaceutically acceptable salt thereof; and a pharmaceutically acceptable carrier.

20. A composition comprising the compound of claim 12, or a pharmaceutically acceptable salt thereof; and a pharmaceutically acceptable carrier.

21. A composition comprising the compound of claim 13, or a pharmaceutically acceptable salt thereof; and a pharmaceutically acceptable carrier.

22. A composition comprising the compound of claim 14, or a pharmaceutically acceptable salt thereof; and a pharmaceutically acceptable carrier.

\* \* \* \* \*